US012679807B2

(12) United States Patent
Breslin et al.

(10) Patent No.: US 12,679,807 B2
(45) Date of Patent: Jul. 14, 2026

(54) MODIFIED ISOINDOLINONES AS GLUCOSYLCERAMIDE SYNTHASE INHIBITORS

(71) Applicant: MERCK SHARP & DOHME LLC, Rahway, NJ (US)

(72) Inventors: Michael J. Breslin, Drexel Hill, PA (US); Mark E. Fraley, North Wales, PA (US); H. Marie Loughran, Perkasie, PA (US); James J. Mulhearn, Elkins Park, PA (US); Anthony J. Roecker, Harleysville, PA (US); Kathy M. Schirripa, Harleysville, PA (US); Shawn J. Stachel, Perkasie, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 490 days.

(21) Appl. No.: 18/252,425

(22) PCT Filed: Nov. 18, 2021

(86) PCT No.: PCT/US2021/059809

§ 371 (c)(1),
(2) Date: May 10, 2023

(87) PCT Pub. No.: WO2022/115301

PCT Pub. Date: Jun. 2, 2022

(65) Prior Publication Data

US 2024/0076291 A1 Mar. 7, 2024

Related U.S. Application Data

(60) Provisional application No. 63/117,542, filed on Nov. 24, 2020.

(51) Int. Cl.

| | |
|---|---|
| *C07D 209/34* | (2006.01) |
| *A61K 45/06* | (2006.01) |
| *A61P 25/16* | (2006.01) |
| *C07D 401/12* | (2006.01) |
| *C07D 403/04* | (2006.01) |
| *C07D 403/12* | (2006.01) |
| *C07D 403/14* | (2006.01) |
| *C07D 405/04* | (2006.01) |
| *C07D 405/06* | (2006.01) |
| *C07D 405/14* | (2006.01) |
| *C07D 413/10* | (2006.01) |
| *C07D 413/12* | (2006.01) |
| *C07D 417/10* | (2006.01) |
| *C07D 417/12* | (2006.01) |
| *C07D 471/04* | (2006.01) |
| *C07D 471/08* | (2006.01) |
| *C07D 491/04* | (2006.01) |

(52) U.S. Cl.

CPC ............ *C07D 209/34* (2013.01); *A61K 45/06* (2013.01); *A61P 25/16* (2018.01); *C07D 401/12* (2013.01); *C07D 403/04* (2013.01); *C07D 403/12* (2013.01); *C07D 403/14* (2013.01); *C07D 405/04* (2013.01); *C07D 405/06* (2013.01); *C07D 405/14* (2013.01); *C07D 413/10* (2013.01); *C07D 417/10* (2013.01); *C07D 417/12* (2013.01); *C07D 471/04* (2013.01); *C07D 471/08* (2013.01); *C07D 491/04* (2013.01); *C07D 413/12* (2013.01)

(58) Field of Classification Search

None

See application file for complete search history.

(56) References Cited

U.S. PATENT DOCUMENTS

| | | | | |
|---|---|---|---|---|
| 2012/0083495 | A1 | 4/2012 | Heemskerk et al. | |
| 2012/0157440 | A1 | 6/2012 | Butler | |
| 2018/0222905 | A1 | 8/2018 | Geneste et al. | |
| 2019/0175596 | A1 * | 6/2019 | de Maeyer ......... | A61K 31/4439 |

FOREIGN PATENT DOCUMENTS

| | | | | |
|---|---|---|---|---|
| WO | 2004080423 A2 | 9/2004 | | |
| WO | WO-2005100351 A1 * | 10/2005 | .............. | A61P 43/00 |
| WO | 2007139464 | 12/2007 | | |
| WO | 2016013976 A1 | 1/2016 | | |

* cited by examiner

*Primary Examiner* — Jennifer A Berrios
*Assistant Examiner* — Sophia Reilly
(74) *Attorney, Agent, or Firm* — Patricia A. Shatynski; John C. Todaro

(57) ABSTRACT

The present invention relates to compounds of Formula (I): and pharmaceutically acceptable salts or prodrug thereof. The present invention also relates to compositions comprising at least one compound of Formula (I), and methods of using the compounds of Formula (I) for treatment or prophylaxis of lysosomal storage diseases, neurodegenerative disease, cystic disease, cancer, or a diseases or disorders associated with elevated levels of glucosylceramide (GlcCer), glucosylsphingosine (GlcSph) and/or other glucosylceramide-based glycosphingolipids (GSLs).

(I)

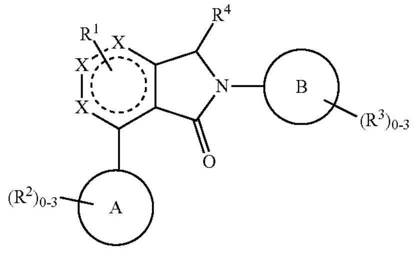

14 Claims, No Drawings

MODIFIED ISOINDOLINONES AS GLUCOSYLCERAMIDE SYNTHASE INHIBITORS

CROSS-REFERENCE TO RELATED APPLICATIONS

This application is a U.S. National Stage application of International Patent Application No. PCT/US21/059809, filed Nov. 18, 2021, which claims priority to U.S. Provisional Patent Application No. 63/117,542, filed Nov. 24, 2020.

FIELD OF THE INVENTION

The present invention is directed to a class of modified isoindolinone compounds, their salts, pharmaceutical compositions comprising them and their use in the treatment of human disease. In particular, the invention is directed to a class of glucosylceramide synthase (GCS) inhibitors, and hence are useful in the treatment of lysosomal storage diseases, neurodegenerative disease, cystic disease, cancer, or diseases or disorders associated with elevated levels of glucosylceramide (GlcCer), glucosylsphingosine (GlcSph) and/or other glucosylceramide-based glycosphingolipids (GSLs), either alone or in combination with enzyme replacement therapy

BACKGROUND OF THE INVENTION

Glucosylceramide synthase (GCS) is a ubiquitously expressed, Golgi membrane-bound, 394 amino acid enzyme that glycosylates ceramide to form glucosylceramide (GlcCer), the first step in the biosynthesis of an extensive family of glycosphingolipids (GSLs) that are integral components of cellular structure and function (Ichikawa, S. et al. Proc. Natl. Acad. Sci. USA, 1996, 93, 4638). Inhibitors of GCS have been proposed and/or investigated for use in the treatment for a variety of diseases, including lysosomal storage diseases such as Niemann-Pick type C, Fabry, Tay-Sachs, and Sandhoff, among others (Platt, F. M., Nat. Rev. 2018, 17, 133). Gaucher's disease (GD) is lysosomal storage disorder resulting from the accumulation of GlcCer due to loss-of-function mutations in the GBA1 gene, which encodes glucocerbrosidase (GCase), a lysosomal hydrolase that metabolizes GlcCer and GlcSph. Eliglustat (Cerdelga®) is a GCS inhibitor (GCSi) approved for the treatment of type 1 GD (Balwani, M., et al., Mol. Genet. Metab. 2016, 117, 95). Mutations in GBA1 also represent a prevalent genetic risk factor for Parkinson's disease (PD) (Sidransky, E. et al., Lancet Neurol. 2012, 11, 986).

In laboratory models, reduction of GCase activity through mutations or chemical inhibition has been shown to elevate levels of glycolipids and accelerate formation of α-synuclein aggregates, a pathological hallmark of PD (Mazzulli, J. R. et al., Cell 2011, 146, 37; Manning-Boğ, A. B. et al., Neurotoxicology 2009, 30, 1127). Conversely, GCSi's have been shown to lower GSL levels and attenuate α-synuclein formation in similar models. As an example, eliglustat has been shown to reverse the formation of pathological α-synuclein aggregates in GD and PD patient-derived induced pluripotert stem cell (iPSC) neurons (Zunke, F. et al., Neuron 2018, 97, 92). Furthermore, a brain penetrant, GCSi has been shown to reduce central α-synuclein accumulation and attenuate cognitive impairment in a GBA-mutant mouse model (Sardi, S. P. et al., Proc. Natl. Acad. Sci. 2017, 114, 2699). These recent data support the proposal that GCSi's may be useful for the treatment of PD and related diseases, such as dementia with Lewy bodies. Additional proposed therapies for GCSi's include other diseases associated with elevated GSL levels, such as polycystic kidney disease, renal hypertrophy and diabetic nephropathy, diabetes mellitus and obesity, and hyperglycemia or hyperinsulemia, and cancers where GSL synthesis is abnormal, or overexpression of GCS disrupts ceramide-induced apoptosis.

SUMMARY OF THE INVENTION

In one aspect, the present invention provides compounds of formula I or pharmaceutically acceptable salts thereof:

I

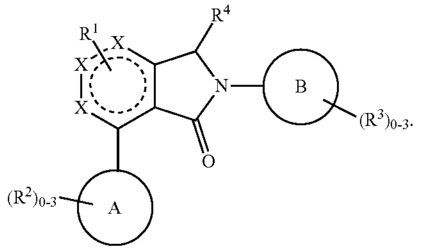

The invention is further directed to methods of treating a patient (preferably a human) for diseases or disorders in which elevated levels of glucosylceramide (GlcCer), glucosyl sphingosine (GlcSph), and/or other glucosylceramide-based glycosphingolipids (GSLs) are involved. The invention further involves use of the compounds as GCS inhibitors for the preparation of a medicament for the treatment and/or prevention of diseases associated with inhibiting GCS, which includes metabolic diseases, such as lysosomal storage diseases, neurodegenerative disease, such as Parkinson's disease (PD) and dementia with Lewy bodies (DLB), cystic disease, and cancer. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

Other embodiments, aspects and features of the present invention are either further described in or will be apparent from the ensuing description, examples and appended claims.

DETAILED DESCRIPTION OF THE INVENTION

The present invention includes compounds of formula I

I

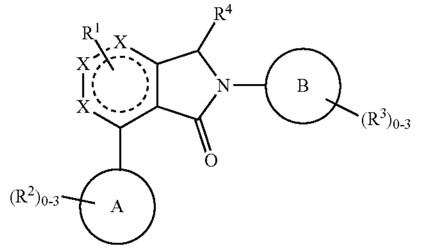

or a pharmaceutically acceptable salt thereof, wherein $R^1$ is hydrogen, C1-C4 alkyl, C1-C4 fluoroalkyl, hydroxy, —C1-C4alkylOH, or halo;

Each X is independently —$CR^a$—, or N;

$R^a$ is hydrogen, C1-C4 alkyl, C1-C4 fluoroalkyl, hydroxy, or halo;

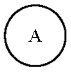

is aryl(C0-C4 alkyl), heteroaryl(C0-C4 alkyl), aryl(C2-C6 alkenyl), heteroaryl(C2-C6 alkenyl), aryl(C2-C6 alkynyl), heteroaryl(C2-C6 alkynyl), arylcarbonylamino, heteroarylcarbonylamino, heterocycloalkyloxycarbonylamino, cycloalkyloxycarbonylamino, heteroaryloxy(C1-C4alkyl), heteroaryl(C1-C4alkyl)oxy(C0-C4alkyl), heteroarylamino (C1-C4alkyl), arylamino(C1-C4alkyl), or heteroaryl(C1-C4alkoxy);

each $R^2$ is independently selected from halo, cyano, C1-C4 fluoroalkyl, —(C1-C4 alkyl)OH, hydroxy, C1-C4 alkyl, oxo, heteroaryl, aryl, —(C0-C4 alkyl)O (C1-C4 fluoroalkyl) and —(C0-C4 alkyl)O(C1-C4 alkyl), wherein each $R^2$ is substituted with 0, 1, or 2 $R^5$ substituents, each $R^5$ is independently C1-C6alkyl, halo, hydroxy, or —(C1-C4 alkyl)OH;

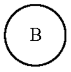

is C1-C6 alkyl, cycloalkylC0-C4 alkyl, hetrocycloalkylC0-C4 alkyl, arylC0-C4alkyl, heteroarylC0-C4alkyl, —C1-C8alkylOH, or —(C0-C4 alkyl)O(C1-C4 alkyl);

each $R^3$ is independently selected from C1-C4 alkyl, halo, hydroxy, C1-C4 fluoroalkyl, C1-C4 alkoxy, —(C0-C4 alkyl)cycloalkyl, —(C0-C4 alkyl)heterocycloalkyl, —(C0-C4 alkyl)O(C1-C4 alkyl), and —(C1-C4 alkyl) OH; and $R^4$ is hydrogen, C1-C4 alkyl, hydroxy, or cycloalkyl.

In a first embodiment of the invention, $R^1$ is hydrogen, C1-C4 alkyl, hydroxy, —C1-C4alkylOH, or halo; and the other groups are as provided in the general formula above.

In a second embodiment of the invention, $R^1$ is methyl, ethyl, propyl, isopropyl, trifluoromethyl, —OH, fluoro, chloro, or bromo, and the other groups are as provided in the general formula above.

In a third embodiment of the invention IV is hydrogen, methyl, —OH, fluoro or chloro and the other groups are as provided in the general formula above.

In a fourth embodiment of the invention, each $R^2$ is independently selected from fluoro, chloro, bromo, cyano, trifluromethyl, 2,2,2-trifluroethyl, methoxy, ethoxy, propoxy, hydroxy, methyl, ethyl, propyl, isopropyl, butyl, oxo, phenyl, azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, isoquinolinyl, and oxazolyl, —(C0-C4 alkyl)O(C1-C4 fluoroalkyl) and wherein each $R^2$ is substituted with 0, 1, or 2 $R^5$ substituents and the other groups are as provided in the general formula above, or as in the first through third embodiments.

In a fifth embodiment of the invention, each $R^2$ independently is selected from fluoro, chloro, bromo, cyano, trifluromethyl, trifluoroethyl, 2,2,2-trifluoroethyl, methoxy, ethoxy, 2,2,2-trifluoroethoxy, trifluoroethoxy, hydroxy, methyl, ethyl, propyl, butyl, isobutyl, oxo, phenyl, benzofuranyl, benzofurazanyl, benzopyrazolyl, benzotriazolyl, imidazolyl, indolinyl, indolyl, indolazinyl, indazolyl, isoindolyl, isoquinolyl, isothiazolyl, isoxazolyl, oxadiazolyl, oxazolyl, oxazoline, isoxazoline, pyranyl, pyrazinyl, pyrazolyl, pyrrolyl, pyridazinyl, pyridyl, pyrimidyl, pyrimidinyl, pyrrolyl, tetrazolyl, triazolyl, and oxazolyl, wherein each $R^2$ is substituted with 0, 1, or 2 $R^5$ substituents and the other groups are as provided in the general formula above, or as in the first through third embodiments.

In a sixth embodiment of the invention each $R^2$ independently is selected from fluoro, chloro, bromo, cyano, trifluromethyl, methoxy, ethoxy, 2,2,2-trifluoroethoxy, trifluoroethoxy, hydroxy, methyl, oxo, and a five to 6-membered hetero-aromatic ring having 1, 2, or 3 heteroatoms selected from O, S, or N, wherein each $R^2$ is substituted with 0, 1, or 2 $R^5$ substituents and the other groups are as provided in the general formula above, or as in the first through third embodiments.

In a seventh embodiment, each $R^2$ independently is selected from fluoro, chloro, bromo, cyano, trifluromethyl, methoxy, ethoxy, 2,2,2-trifluoroethoxy, trifluoroethoxy, hydroxy, methyl, oxo, isothiazolyl, isoxazolyl, oxadiazolyl, oxazolyl, pyrazolyl, pyridazinyl, pyridyl, triazolyl, and oxazolyl, wherein each $R^2$ is substituted with 0, 1, or 2 $R^5$ substituents, wherein $R^2$ is independently substituted with 0, 1, 2, or 3 $R^5$ substituents and the other groups are as provided in the general formula above, or as in the first through third embodiments.

In an eighth embodiment, each $R^5$ independently is selected from methyl, ethyl, propyl, isopropyl, butyl, hydroxymethyl, hydroxyethyl, hydroxypropyl, methoxy, ethoxy, and propoxy and the other groups are as provided in the general formula above, or as in the first through seventh embodiments.

In a ninth embodiment of the invention, each $R^5$ independently is selected from methyl, ethyl, and hydroxymethyl and the other groups are as provided in the general formula above, or as in the first through third embodiments.

In a tenth embodiment of the invention,

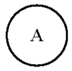

is aryl(C0-C4 alkyl), heteroaryl(C0-C4 alkyl), aryl(C2-C6 alkenyl), heteroaryl(C2-C6 alkenyl), heteroaryl(C2-C6 alkynyl), arylcarbonylamino, heteroarylcarbonylamino, heterocycloalkyloxycarbonylamino, cycloalkyloxycarbonylamino, heteroaryloxy(C1-C4alkyl), heteroaryl(C1-C4alkyl)oxy(C0-C4alkyl), heteroarylamino(C1-C4alkyl), or heteroaryl(C1-C4alkoxy), wherein each said aryl is independently phenyl, 2,3-dihydro-1H-indenyl, or naphthyl, wherein each said heteroaryl is independently azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, 2,3-dihydro-1H-cyclopenta[b]quinolinyl, 2,3-dihydrofuro[2,3-b]pyridinyl, 1H-pyrrolo[2,3-b]pyridinyl, 2,3-dihydro[1,4]dioxino[2,3-b]pyridinyl, 6,7-dihydro-[1,3]dioxolo[4,5-b]pyridyl, pyrazolo[1,5-c]pyridyl, pyrazolo[4,3-b]pyridyl, or oxazolyl, wherein each said heterocycloalkyl is independently decahydroisoquinoline, 2,3-dihydro-1H-benzo[d]imidazolyl, isoindolinyl, dioxaspiro[4.5]decane), 2,5-diazabicyclo[2.2.1]heptyl, quinuclidinyl, 2,3-dihydro-1H-benzo[d]imidazolyl, indazolyl, benzo[d][1,3]dioxolyl, 1,2,3,4-tetrahydroisoquinolinyl, 2,3-dihydobenzofuranyl, oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, or pyrrolidinone, and oxides thereof and all isomers thereof, wherein each said cycloalkyl is independently cyclopropyl, cyclobutyl, cyclopentyl, cyclohexyl, cycloheptyl, bicyclo[2.2.2]octanyl, bicyclo[1.1.1]pentanyl, bicyclo[2.2.1]heptanyl, [1.1.1]-bicyclo pentane, 1-decalinyl, spiro[2.4]heptyl, spiro[2.2]pentyl, spiro[4.5]decanyl, 2,3-dihydro-1H-indenyl, or norbornyl, and the other groups are as provided in the general formula above, or as in the first through ninth embodiments.

In an eleventh embodiment of the invention,

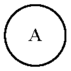

is phenyl, 2,3-dihydro-1H-benzo[d]imidazolyl, indazolyl, benzo[d][1,3]dioxolyl, isoindolinyl, 1,2,3,4-tetrahydroisoquinolinyl, quinoxalinyl, phenylcarbonylamino, (benzo[d][1,3]dioxolyl)carbonylamino, quinuclidinyloxycarbonylamino, pyridyl, pyridylcarbonylamino, pyrazolyl, quinolinylcarbonylamino, (2,3-dihydro-1H-cyclopenta[b]quinolinyl)carbonylamino, (2,3-dihydrofuro[2,3-b]pyridinyl)carbonylamino, (dihydrobenzofuranyl)carbonylamino, (indolyl)carbonylamino, (indazolyl)carbonylamino, (2,3-dihydrobenzofuranyl)cabonylamino, (1H-pyrrolo[2,3-b]pyridinyl)carbonylamino, (2,3-dihydro[1,4]dioxino[2,3-b]pyridinyl)carbonylamino, (2,3-dihydro-1H-indenyl)carbonylamino, (6,7-dihydro-5H-cyclopenta[b]pyridyl)ethenyl, (6,7-dihydro-5H-cyclopenta[b]pyridyl)carbonylamino, (benzo[d]thiazolyl)carbonylamino, (6,7-dihydro-5H-cyclopenta[b]pyridyl)ethenyl, (6,7-dihydro-5H-cyclopenta[b]pyridyl)ethyl, (6,7-dihydro-5H-cyclopenta[b]pyridyl)oxymethyl, (6,7-dihydro-5H-cyclopenta[b]pyridyl)methoxy, (6,7-dihydro-5H-cyclopenta[b]pyridyl)ethynyl, phenylethenyl, ([1,3]dioxolo[4,5-b]pyridyl)ethenyl, ([1,3]dioxolo[4,5-b]pyridyl)ethyl, ([1,3]dioxolo[4,5-b]pyridyl)carbonylamino, ([1,3]dioxolo[4,5-b]pyridyl)oxymethyl, ([1,3]dioxolo[4,5-b]pyridyl)methoxy, ([1,3]dioxolo[4,5-b]pyridyl)aminomethyl, (pyrazolo[1,5-a]pyridyl)carbonylamino, (pyrazolo[4,3-b]pyridyl)carbonylamino, or naphthyridinylcarbonylamino and the other groups are as provided in the general formula above, or as in the first through ninth embodiments.

In a twelfth embodiment of the invention,

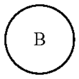

is C1-C6 alkyl, cycloalkylC0-C4 alkyl, hetrocycloalkylC0-C4 alkyl, arylC0-C4alkyl, heteroarylC0-C4alkyl, —C1-C8alkylOH, or —(C0-C4 alkyl)O(C1-C4 alkyl); wherein each said aryl is independently phenyl, 2,3-dihydro-1H-indenyl, or naphthyl, wherein each said heteroaryl is independently azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, 2,3-dihydro-1H-cyclopenta[b]quinolinyl, 2,3-dihydrofuro[2,3-b]pyridinyl, 1H-pyrrolo[2,3-b]pyridinyl, 2,3-dihydro[1,4]dioxino[2,3-b]pyridinyl, 6,7-dihydro-5H-cyclopenta[b]pyridyl, [1,3]dioxolo[4,5-b]pyridyl, pyrazolo[1,5-a]pyridyl, pyrazolo[4,3-b]pyridyl, or oxazolyl, wherein each said heterocycloalkyl is independently decahydroisoquinoline, 2,3-dihydro-1H-benzo[d]imidazolyl, isoindolinyl, dioxaspiro[4.5]decane), 2,5-diazabicyclo[2.2.1]heptyl, quinuclidinyl, 2,3-dihydro-1H-benzo[d]imidazolyl, indazolyl, benzo[d][1,3]dioxolyl, 1,2,3,4-tetrahydroisoquinolinyl, 2,3-dihydobenzofuranyl, oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, or pyrrolidinone, and oxides thereof and all isomers thereof, wherein each said cycloalkyl is independently cyclopropyl, cyclobutyl, cyclopentyl, cyclohexyl, cycloheptyl, bicyclo[2.2.2]octanyl, bicyclo[1.1.1]pentanyl, bicyclo[2.2.1]heptanyl, [1.1.1]-bicyclo pentane, 1-decalinyl, spiro[2.4]heptyl, spiro[2.2]pentyl, spiro[4.5]decanyl, 2,3-dihydro-1H-indenyl, or norbornyl, and the other groups are as provided in the general formula above, or as in the first through eleventh embodiments.

In a thirteenth embodiment of the invention,

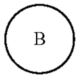

is 2-hydroxy-2-methylpropyl, 1-methyl-2-hydroxy-2-methylpropyl, cyclopentylethyl, 1-ethyl-2-hydroxy-2-methylpropyl, 2-hydroxyethyl, oxetanylmethyl, quinuclidinylethyl, cyclopropyl-2-methylpropyl, cyclopropylmethyl, methylisobutyl, cyclobutylmethyl, 1-cyclopropylethyl, cyclohexyl, quinuclidinyl, phenyl, isobutyl, or oxetanylmethyl and the other groups are as provided in the general formula above, or as in the first through eleventh embodiments.

In a fourteenth embodiment, each $R^3$ is independently selected from C1-C4 alkyl, halo, hydroxy, C1-C4 fluoroalkyl, C1-C4 alkoxy, —(C0-C4 alkyl)cycloalkyl, —(C0-C4 alkyl)heterocycloalkyl, —(C0-C4 alkyl)O(C1-C4 alkyl), and —(C1-C4 alkyl)OH, wherein each said heterocycloalkyl is independently decahydroisoquinoline, 2,3-dihydro-1H-benzo[d]imidazolyl, isoindolinyl, dioxaspiro[4.5]decane), 2,5-diazabicyclo[2.2.1]heptyl, quinuclidinyl, 2,3-dihydro-1H-benzo[d]imidazolyl, indazolyl, benzo[d][1,3]dioxolyl, 1,2,3,4-tetrahydroisoquinolinyl, 2,3-dihydobenzofuranyl, oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, or pyrrolidinone, and oxides thereof and all isomers thereof, wherein each said cycloalkyl is independently cyclopropyl, cyclobutyl, cyclopentyl, cyclohexyl, cycloheptyl, bicyclo[2.2.2]octanyl, bicyclo[1.1.1]pentanyl, bicyclo[2.2.1]heptanyl, [1.1.1]-bicyclo pentane, 1-decalinyl, spiro[2.4]heptyl, spiro[2.2]pentyl, spiro[4.5]decanyl, 2,3-dihydro-1H-indenyl, or norbornyl, and the other groups are as provided in the general formula above, or as in the first through thirteenth embodiments.

In a fifteenth embodiment, each $R^3$ independently is selected from trifluoromethyl, methyl, ethyl, hydroxy, methoxy, 2-hydroxy-propyl, hydroxymethyl, cyclopropyl, methoxymethyl and fluoro and the other groups are as provided in the general formula above, or as in the first through thirteenth embodiments.

In a sixteenth embodiment, one X is N, and the other two X are each —CW— and the other groups are as provided in the general formula above, or as in the first through fifteenth embodiments.

In a seventeenth embodiment, each X is —$CR^a$—, and the other groups are as provided in the general formula above, or as in the first through fifteenth embodiments.

In an eighteenth embodiment of the invention, at least one X is N, and the other groups are as provided in the general formula above, or as in the first through fifteenth embodiments.

In a nineteenth embodiment of the invention, two X are each N, and the other groups are as provided in the general formula above, or as in the first through fifteenth embodiments.

In a twentieth embodiment of the invention, $R^a$ is hydrogen, methyl, hydroxy, F, or Cl and the other groups are as provided in the general formula above, or as in the first through nineteenth embodiments.

In a twenty-first embodiment of the invention, $R^4$ is hydrogen, methyl, ethyl, propyl, butyl, hydroxy, cyclopropyl or cyclobutyl and the other groups are as provided in the general formula above, or as in the first through twentieth embodiments.

In a twenty-second embodiment of the invention, $R^4$ is hydrogen or methyl, and the other groups are as provided in the general formula above, or as in the first through eleventh and nineteenth embodiments.

In a twenty-third embodiment of the invention, each X is —$CR^a$—,

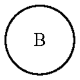

is 2-hydroxy-2-methylpropyl and $R^3$ is cyclopropyl or methyl and the other groups are as provided in the general formula above, or as in the first through eleventh and the twentieth through twenty-second embodiments.

In a twenty-fourth embodiment of the invention,

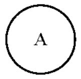

is aryl, heteroaryl, heterocycloalkyl, or cycloalkyl and the other groups are as provided in the general formula above, or as in the first through ninth and the twelfth through twenty-third embodiments.

In a twenty-fifth embodiment,

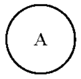

is aryl, heteroaryl, heterocycloalkyl, or cycloalkyl, wherein each said aryl is phenyl, 2,3-dihydro-1H-indenyl, or naphthyl, wherein said heteroaryl is azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, 2,3-dihydro-1H-cyclopenta[b]quinolinyl, 2,3-dihydrofuro[2,3-b]pyridinyl, 1H-pyrrolo[2,3-b]pyridinyl, 2,3-dihydro[1,4]dioxino[2,3-b]pyridinyl, 6,7-dihydro-[1,3]dioxolo[4,5-b]pyridyl, pyrazolo[1,5-c]pyridyl, pyrazolo[4,3-b]pyridyl, or oxazolyl, wherein said heterocycloalkyl is independently decahydroisoquinoline, 2,3-dihydro-1H-benzo[d]imidazolyl, isoindolinyl, dioxaspiro[4.5]decane), 2,5-diazabicyclo[2.2.1]heptyl, quinuclidinyl, 2,3-dihydro-1H-benzo[d]imidazolyl, indazolyl, benzo[d][1,3]dioxolyl, 1,2,3,4-tetrahydroisoquinolinyl, 2,3-dihydobenzofuranyl, oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, or pyrrolidinone, and oxides thereof and all isomers thereof, and wherein each said cycloalkyl is independently cyclopropyl, cyclobutyl, cyclopentyl, cyclohexyl, cycloheptyl, bicyclo[2.2.2]octanyl, bicyclo[1.1.1]pentanyl, bicyclo[2.2.1]heptanyl, [1.1.1]-bicyclo pentane, 1-decalinyl, spiro[2.4]heptyl, spiro[2.2]pentyl, spiro[4.5]decanyl, 2,3-dihydro-1H-indenyl, or norbornyl, and the other groups are as provided in the general formula above, or as in the first through ninth and the twelfth through twenty-third embodiments.

In a twenty-sixth embodiment of the invention

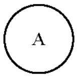

is phenyl, 2,3-dihydro-1H-benzo[d]imidazolyl, indazolyl, benzo[d][1,3]dioxolyl, isoindolinyl, 1,2,3,4-tetrahydroisoquinolinyl, quinoxalinyl, pyridyl, or pyrazolyl, and the other groups are as provided in the general formula above, or as in the first through ninth and the twelfth through twenty-third embodiments.

Non-limiting examples of the Compounds of Formula I include compounds 1-181 or a pharmaceutically acceptable salt thereof, as set forth in the Examples:

(R)-2-(1-Cyclopropyl-2-hydroxy-2-methylpropyl)-7-(4-(5-methyl-1,3,4-oxadiazol-2-yl)phenyl)isoindolin-1-one;
2-(1-Cyclopropyl-2-hydroxy-2-methylpropyl)-7-(4-(5-methyl-1,3,4-oxadiazol-2-yl)phenyl)isoindolin-1-one;
(R)-2-(1-Cyclopropyl-2-hydroxy-2-methylpropyl)-6-fluoro-7-(4-(5-methyl-1,3,4-oxadiazol-2-yl)phenyl)isoindolin-1-one;
(S)-2-(1-Cyclopropyl-2-hydroxy-2-methylpropyl)-6-fluoro-7-(4-(5-methyl-1,3,4-oxadiazol-2-yl)phenyl)isoindolin-1-one;
2-(1-Cyclopropyl-2-hydroxy-2-methylpropyl)-6-fluoro-7-(4-(5-methyl-1,3,4-oxadiazol-2-yl)phenyl)isoindolin-1-one;
2-(1-Cyclopropyl-2-hydroxy-2-methylpropyl)-5-fluoro-7-(4-(5-methyl-1,3,4-oxadiazol-2-yl)phenyl)isoindolin-1-one;
(R)-2-(1-Cyclopropyl-2-hydroxy-2-methylpropyl)-5-fluoro-7-(4-(5-methyl-1,3,4-oxadiazol-2-yl)phenyl)isoindolin-1-one;
2-(1-cyclopropyl-2-hydroxy-2-methylpropyl)-7-(2,4-difluorostyryl)isoindolin-1-one;
(R)-(E)-2-(1-cyclopropyl-2-hydroxy-2-methylpropyl)-7-(2,4-difluorostyryl)isoindolin-1-one;
(S)-(E)-2-(1-cyclopropyl-2-hydroxy-2-methylpropyl)-7-(2,4-difluorostyryl)isoindolin-1-one;
7-(4-(1,3,4-oxadiazol-2-yl)phenyl)-2-(1-cyclopropyl-2-hydroxy-2-methylpropyl)isoindolin-1-one;
(R)-7-(4-(1,3,4-oxadiazol-2-yl)phenyl)-2-(1-cyclopropyl-2-hydroxy-2-methylpropyl)isoindolin-1-one;
(R)-5-(2-(1-cyclopropyl-2-hydroxy-2-methylpropyl)-3-oxoisoindolin-4-yl)-1,3-dimethyl-1,3-dihydro-2H-benzo[d]imidazol-2-one;
5-(2-(1-cyclopropyl-2-hydroxy-2-methylpropyl)-3-oxoisoindolin-4-yl)-1,3-dimethyl-1,3-dihydro-2H-benzo[d]imidazol-2-one;
(R)-2-(1-cyclopropyl-2-hydroxy-2-methylpropyl)-7-(2-(2,2,2-trifluoroethoxy)phenyl)isoindolin-1-one;
2-(1-cyclopropyl-2-hydroxy-2-methylpropyl)-7-(2-(2,2,2-trifluoroethoxy)phenyl)isoindolin-1-one;
3-(2-(1-cyclopropyl-2-hydroxy-2-methylpropyl)-3-oxoisoindolin-4-yl)-5-methoxybenzonitrile;
(R)-3-(2-(1-cyclopropyl-2-hydroxy-2-methylpropyl)-3-oxoisoindolin-4-yl)-5-methoxybenzonitrile;
2-(1-cyclopropyl-2-hydroxy-2-methylpropyl)-7-(3-fluoro-4-(5-methyl-1,3,4-oxadiazol-2-yl)phenyl)isoindolin-1-one;
(R)-2-(1-cyclopropyl-2-hydroxy-2-methylpropyl)-7-(3-fluoro-4-(5-methyl-1,3,4-oxadiazol-2-yl)phenyl)isoindolin-1-one;
7-(3-chloro-5-methoxyphenyl)-2-(1-cyclopropyl-2-hydroxy-2-methylpropyl)isoindolin-1-one;
(R)-7-(3-chloro-5-methoxyphenyl)-2-(1-cyclopropyl-2-hydroxy-2-methylpropyl)isoindolin-1-one;
(R)-2-(1-cyclopropyl-2-hydroxy-2-methylpropyl)-7-(6-fluoro-3-methyl-1H-indazol-5-yl)isoindolin-1-one;
2-(1-cyclopropyl-2-hydroxy-2-methylpropyl)-7-(6-fluoro-3-methyl-1H-indazol-5-yl)isoindolin-1-one;
(R)-2-(1-cyclopropyl-2-hydroxy-2-methylpropyl)-7-(1-methyl-1H-indazol-5-yl)isoindolin-1-one;
2-(1-cyclopropyl-2-hydroxy-2-methylpropyl)-7-(1-methyl-1H-indazol-5-yl)isoindolin-1-one;
(R)-2-(1-cyclopropyl-2-hydroxy-2-methylpropyl)-7-(3-(5-methyl-1,3,4-oxadiazol-2-yl)phenyl)isoindolin-1-one;
2-(1-cyclopropyl-2-hydroxy-2-methylpropyl)-7-(3-(5-methyl-1,3,4-oxadiazol-2-yl)phenyl)isoindolin-1-one;
(R)-2-(1-cyclopropyl-2-hydroxy-2-methylpropyl)-7-(3-(2,2,2-trifluoroethoxy)phenyl)isoindolin-1-one;
2-(1-cyclopropyl-2-hydroxy-2-methylpropyl)-7-(3-(2,2,2-trifluoroethoxy)phenyl)isoindolin-1-one;
(R)-2-(1-cyclopropyl-2-hydroxy-2-methylpropyl)-7-(4-(1-methyl-1H-pyrazol-4-yl)phenyl)isoindolin-1-one;
2-(1-cyclopropyl-2-hydroxy-2-methylpropyl)-7-(4-(1-methyl-1H-pyrazol-4-yl)phenyl)isoindolin-1-one;
(R)-2-(1-cyclopropyl-2-hydroxy-2-methylpropyl)-7-(2,2-difluorobenzo[d][1,3]dioxol-4-yl)isoindolin-1-one;
2-(1-cyclopropyl-2-hydroxy-2-methylpropyl)-7-(2,2-difluorobenzo[d][1,3]dioxol-4-yl)isoindolin-1-one;
(R)-7-(4-(2H-1,2,3-triazol-2-yl)phenyl)-2-(1-cyclopropyl-2-hydroxy-2-methylpropyl)isoindolin-1-one;
7-(4-(2H-1,2,3-triazol-2-yl)phenyl)-2-(1-cyclopropyl-2-hydroxy-2-methylpropyl)isoindolin-1-one;
(R)-2-(1-cyclopropyl-2-hydroxy-2-methylpropyl)-7-(4-(6-methylpyridazin-3-yl)phenyl)isoindolin-1-one;
2-(1-cyclopropyl-2-hydroxy-2-methylpropyl)-7-(4-(6-methylpyridazin-3-yl)phenyl)isoindolin-1-one;
(S)-2-(1-cyclopropyl-2-hydroxy-2-methylpropyl)-7-(4-(6-methylpyridazin-3-yl)phenyl)isoindolin-1-one;
2-(1-cyclopropyl-2-hydroxy-2-methylpropyl)-7-(4-(6-methylpyridazin-3-yl)phenyl)isoindolin-1-one;
(R)-2-(1-cyclopropyl-2-hydroxy-2-methylpropyl)-7-(3,4-dimethoxyphenyl)isoindolin-1-one;
(S)-2-(1-cyclopropyl-2-hydroxy-2-methylpropyl)-7-(3,4-dimethoxyphenyl)isoindolin-1-one;
2-(1-cyclopropyl-2-hydroxy-2-methylpropyl)-7-(3,4-dimethoxyphenyl)isoindolin-1-one;
(R)-2-(1-cyclopropyl-2-hydroxy-2-methylpropyl)-7-(2,6-dimethylpyridin-4-yl)isoindolin-1-one;
(S)-2-(1-cyclopropyl-2-hydroxy-2-methylpropyl)-7-(2,6-dimethylpyridin-4-yl)isoindolin-1-one;
2-(1-cyclopropyl-2-hydroxy-2-methylpropyl)-7-(2,6-dimethylpyridin-4-yl)isoindolin-1-one;
2-((R)-1-cyclopropyl-2-hydroxy-2-methylpropyl)-6-fluoro-7-(2-(2,2,2-trifluoroethoxy)phenyl)isoindolin-1-one;
2-((S)-1-cyclopropyl-2-hydroxy-2-methylpropyl)-6-fluoro-7-(2-(2,2,2-trifluoroethoxy)phenyl)isoindolin-1-one;
2-(1-cyclopropyl-2-hydroxy-2-methylpropyl)-6-fluoro-7-(2-(2,2,2-trifluoroethoxy)phenyl)isoindolin-1-one;
(R)-2-(1-cyclopropyl-2-hydroxy-2-methylpropyl)-6-fluoro-7-(3-fluoro-4-(5-methyl-1,3,4-oxadiazol-2-yl)phenyl)isoindolin-1-one;
2-(1-cyclopropyl-2-hydroxy-2-methylpropyl)-6-fluoro-7-(3-fluoro-4-(5-methyl-1,3,4-oxadiazol-2-yl)phenyl)isoindolin-1-one;
(R)-2-(1-cyclopropyl-2-hydroxy-2-methylpropyl)-5-fluoro-7-(2-(2,2,2-trifluoroethoxy)phenyl)isoindolin-1-one;
(S)-2-(1-cyclopropyl-2-hydroxy-2-methylpropyl)-5-fluoro-7-(2-(2,2,2-trifluoroethoxy)phenyl)isoindolin-1-one;

2-(1-cyclopropyl-2-hydroxy-2-methylpropyl)-5-fluoro-7-(2-(2,2,2-trifluoroethoxy)phenyl)isoindolin-1-one;
(R)-2-(1-cyclopropyl-2-hydroxy-2-methylpropyl)-5-fluoro-7-(4-(1-methyl-1H-pyrazol-4-yl)phenyl)isoindolin-1-one;
2-(1-cyclopropyl-2-hydroxy-2-methylpropyl)-5-fluoro-7-(4-(1-methyl-1H-pyrazol-4-yl)phenyl)isoindolin-1-one;
(R)-2-(1-cyclopropyl-2-hydroxy-2-methylpropyl)-6-fluoro-2'-methyl-[4,5'-biisoindoline]-1',3-dione;
2-(1-cyclopropyl-2-hydroxy-2-methylpropyl)-6-fluoro-2'-methyl-[4,5'-biisoindoline]-1',3-dione;
(R)-2-(1-cyclopropyl-2-hydroxy-2-methylpropyl)-5-fluoro-7-(4-(3-methylisoxazol-5-yl)phenyl)isoindolin-1-one;
2-(1-cyclopropyl-2-hydroxy-2-methylpropyl)-5-fluoro-7-(4-(3-methylisoxazol-5-yl)phenyl)isoindolin-1-one;
(R)-2-(1-cyclopropyl-2-hydroxy-2-methylpropyl)-5-fluoro-7-(2-fluoro-4-(5-methyl-1,3,4-oxadiazol-2-yl)phenyl)isoindolin-1-one;
2-(1-cyclopropyl-2-hydroxy-2-methylpropyl)-5-fluoro-7-(2-fluoro-4-(5-methyl-1,3,4-oxadiazol-2-yl)phenyl)isoindolin-1-one;
(R)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one;
(S)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one;
(R)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one;
(R)-2-(1-cyclopropyl-2-hydroxy-2-methylpropyl)-4-(4-(1-methyl-1H-pyrazol-4-yl)phenyl)-1,2-dihydro-3H-pyrrolo[3,4-c]pyridin-3-one;
2-(1-cyclopropyl-2-hydroxy-2-methylpropyl)-4-(4-(1-methyl-1H-pyrazol-4-yl)phenyl)-1,2-dihydro-3H-pyrrolo[3,4-c]pyridin-3-one;
(R)-3-(2-(1-cyclopropyl-2-hydroxy-2-methylpropyl)-3-oxo-2,3-dihydro-1H-pyrrolo[3,4-c]pyridin-4-yl)-5-methoxybenzonitrile;
(S)-3-(2-(1-cyclopropyl-2-hydroxy-2-methylpropyl)-3-oxo-2,3-dihydro-1H-pyrrolo[3,4-c]pyridin-4-yl)-5-methoxybenzonitrile;
3-(2-(1-cyclopropyl-2-hydroxy-2-methylpropyl)-3-oxo-2,3-dihydro-1H-pyrrolo[3,4-c]pyri din-4-yl)-5-methoxybenzonitrile;
(R)-2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one;
(S)-2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one;
2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one;
(R)-2-(1-cyclopropyl-2-hydroxy-2-methylpropyl)-7-(4-(1-methyl-1H-pyrazol-4-yl)phenyl)-2,3-dihydro-1H-pyrrolo[3,4-c]pyridin-1-one;
2-(1-cyclopropyl-2-hydroxy-2-methylpropyl)-7-(4-(1-methyl-1H-pyrazol-4-yl)phenyl)-2,3-dihydro-1H-pyrrolo[3,4-c]pyridin-1-one;
(R)-6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one;
(S)-6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one;
6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one;
(R)-6-(1-cyclopropyl-2-hydroxy-2-methylpropyl)-4-(4-(1-methyl-1H-pyrazol-4-yl)phenyl)-6,7-dihydro-5H-pyrrolo[3,4-b]pyridin-5-one;
6-(1-cyclopropyl-2-hydroxy-2-methylpropyl)-4-(4-(1-methyl-1H-pyrazol-4-yl)phenyl)-6,7-dihydro-5H-pyrrolo[3,4-b]pyridin-5-one;
(R)-6-(1-cyclopropyl-2-hydroxy-2-methylpropyl)-4-(2-fluoro-5-methyl-4-(1-methyl-1H-pyrazol-4-yl)phenyl)-6,7-dihydro-5H-pyrrolo[3,4-b]pyridin-5-one;
6-(1-cyclopropyl-2-hydroxy-2-methylpropyl)-4-(2-fluoro-5-methyl-4-(1-methyl-1H-pyrazol-4-yl)phenyl)-6,7-dihydro-5H-pyrrolo[3,4-b]pyridin-5-one;
(R)-2-(1-cyclopropyl-2-hydroxy-2-methylpropyl)-4-fluoro-7-(4-(5-methyl-1,3,4-oxadiazol-2-yl)phenyl)isoindolin-1-one;
2-(1-cyclopropyl-2-hydroxy-2-methylpropyl)-4-fluoro-7-(4-(5-methyl-1,3,4-oxadiazol-2-yl)phenyl)isoindolin-1-one;
(R)-4-chloro-2-(1-cyclopropyl-2-hydroxy-2-methylpropyl)-7-(4-(1-methyl-1H-pyrazol-4-yl)phenyl)isoindolin-1-one;
4-chloro-2-(1-cyclopropyl-2-hydroxy-2-methylpropyl)-7-(4-(1-methyl-1H-pyrazol-4-yl)phenyl)isoindolin-1-one;
(R)-4-chloro-2-(1-cyclopropyl-2-hydroxy-2-methylpropyl)-7-(4-(5-methyl-1,3,4-oxadiazol-2-yl)phenyl)isoindolin-1-one;
4-chloro-2-(1-cyclopropyl-2-hydroxy-2-methylpropyl)-7-(4-(5-methyl-1,3,4-oxadiazol-2-yl)phenyl)isoindolin-1-one;
(R)-5-chloro-2-(1-cyclopropyl-2-hydroxy-2-methylpropyl)-7-(4-(5-methyl-1,3,4-oxadiazol-2-yl)phenyl)isoindolin-1-one;
(S)-5-chloro-2-(1-cyclopropyl-2-hydroxy-2-methylpropyl)-7-(4-(5-methyl-1,3,4-oxadiazol-2-yl)phenyl)isoindolin-1-one;
5-chloro-2-(1-cyclopropyl-2-hydroxy-2-methylpropyl)-7-(4-(5-methyl-1,3,4-oxadiazol-2-yl)phenyl)isoindolin-1-one;
(R)-6-chloro-2-(1-cyclopropyl-2-hydroxy-2-methylpropyl)-7-(4-(5-methyl-1,3,4-oxadiazol-2-yl)phenyl)isoindolin-1-one;
6-chloro-2-(1-cyclopropyl-2-hydroxy-2-methylpropyl)-7-(4-(5-methyl-1,3,4-oxadiazol-2-yl)phenyl)isoindolin-1-one;
(R)-4-chloro-2-(1-cyclopropyl-2-hydroxy-2-methylpropyl)-6-fluoro-7-(4-(5-methyl-1,3,4-oxadiazol-2-yl)phenyl)isoindolin-1-one;
4-chloro-2-(1-cyclopropyl-2-hydroxy-2-methylpropyl)-6-fluoro-7-(4-(5-methyl-1,3,4-oxadiazol-2-yl)phenyl)isoindolin-1-one;
(R)-7-(4-(5-methyl-1,3,4-oxadiazol-2-yl)phenyl)-2-(1,1,1-trifluoro-3-hydroxy-3-methylbutan-2-yl)isoindolin-1-one;
(S)-7-(4-(5-methyl-1,3,4-oxadiazol-2-yl)phenyl)-2-(1,1,1-trifluoro-3-hydroxy-3-methylbutan-2-yl)isoindolin-1-one;
7-(4-(5-methyl-1,3,4-oxadiazol-2-yl)phenyl)-2-(1,1,1-trifluoro-3-hydroxy-3-methylbutan-2-yl)isoindolin-1-one;
(R)-7-(4-(1-methyl-1H-pyrazol-4-yl)phenyl)-2-(1,1,1-trifluoro-3-hydroxy-3-methylbutan-2-yl)isoindolin-1-one;
(S)-7-(4-(1-methyl-1H-pyrazol-4-yl)phenyl)-2-(1,1,1-trifluoro-3-hydroxy-3-methylbutan-2-yl)isoindolin-1-one;
7-(4-(1-methyl-1H-pyrazol-4-yl)phenyl)-2-(1,1,1-trifluoro-3-hydroxy-3-methylbutan-2-yl)isoindolin-1-one;

(R)-6-fluoro-7-(4-(5-methyl-1,3,4-oxadiazol-2-yl)phenyl)-2-(1,1,1-trifluoro-3-hydroxy-3-methylbutan-2-yl)isoindolin-1-one;
(S)-6-fluoro-7-(4-(5-methyl-1,3,4-oxadiazol-2-yl)phenyl)-2-(1,1,1-trifluoro-3-hydroxy-3-methylbutan-2-yl)isoindolin-1-one;
6-fluoro-7-(4-(5-methyl-1,3,4-oxadiazol-2-yl)phenyl)-2-(1,1,1-tri fluoro-3-hydroxy-3-methylbutan-2-yl)isoindolin-1-one;
(R)-2-(1-cyclopropyl-2-hydroxy-2-methylpropyl)-5,6-difluoro-7-(4-(5-methyl-1,3,4-oxadiazol-2-yl)phenyl)isoindolin-1-one;
2-(1-cyclopropyl-2-hydroxy-2-methylpropyl)-5,6-difluoro-7-(4-(5-methyl-1,3,4-oxadiazol-2-yl)phenyl)isoindolin-1-one;
(R)-2-(3-hydroxy-3-methylbutan-2-yl)-7-(2-(2,2,2-trifluoroethoxy)phenyl)isoindolin-1-one;
2-(3-hydroxy-3-methylbutan-2-yl)-7-(2-(2,2,2-trifluoroethoxy)phenyl)isoindolin-1-one;
(cis)-2-(2-(3-hydroxycyclopentyl)ethyl)-7-(2-(2,2,2-trifluoroethoxy)phenyl)isoindolin-1-one;
(trans)-2-(2-(3-hydroxycyclopentyl)ethyl)-7-(2-(2,2,2-trifluoroethoxy)phenyl)isoindolin-1-one;
2-(2-(3-hydroxycyclopentyl)ethyl)-7-(2-(2,2,2-trifluoroethoxy)phenyl)isoindolin-1-one;
2-[(1R)-1-ethyl-2-hydroxy-2-methyl-propyl]-7-[4-(5-methyl-1,3,4-oxadiazol-2-yl)phenyl]isoindolin-1-one;
2-[(1-ethyl-2-hydroxy-2-methyl-propyl]-7-[4-(5-methyl-1,3,4-oxadiazol-2-yl)phenyl]isoindolin-1-one;
(R)-2-(1-cyclopropyl-2-hydroxyethyl)-7-(2-(2,2,2-trifluoroethoxy)phenyl)isoindolin-1-one;
2-(1-cyclopropyl-2-hydroxyethyl)-7-(2-(2,2,2-trifluoroethoxy)phenyl)isoindolin-1-one;
(R)-2-(1-cyclopropyl-2-hydroxyethyl)-7-(4-(5-methyl-1,3,4-oxadiazol-2-yl)phenyl)isoindolin-1-one;
2-(1-cyclopropyl-2-hydroxyethyl)-7-(4-(5-methyl-1,3,4-oxadiazol-2-yl)phenyl)isoindolin-1-one;
(R)-2-(cyclopropyl(3-hydroxyoxetan-3-yl)methyl)-7-(4-(5-methyl-1,3,4-oxadiazol-2-yl)phenyl)isoindolin-1-one;
(S)-2-(cyclopropyl(3-hydroxyoxetan-3-yl)methyl)-7-(4-(5-methyl-1,3,4-oxadiazol-2-yl)phenyl)isoindolin-1-one;
2-(cyclopropyl(3-hydroxyoxetan-3-yl)methyl)-7-(4-(5-methyl-1,3,4-oxadiazol-2-yl)phenyl)isoindolin-1-one;
(R)-7-(4-fluorophenyl)-2-(2-(quinuclidin-3-yl)ethyl)isoindolin-1-one;
(S)-7-(4-fluorophenyl)-2-(2-(quinuclidin-3-yl)ethyl)isoindolin-1-one;
7-(4-fluorophenyl)-2-(2-(quinuclidin-3-yl)ethyl)isoindolin-1-one;
(R)-2-(2-(quinuclidin-3-yl)ethyl)-7-(1,3,5-trimethyl-1H-pyrazol-4-yl)isoindolin-1-one;
(S)-2-(2-(quinuclidin-3-yl)ethyl)-7-(1,3,5-trimethyl-1H-pyrazol-4-yl)isoindolin-1-one;
2-(2-(quinuclidin-3-yl)ethyl)-7-(1,3,5-trimethyl-1H-pyrazol-4-yl)isoindolin-1-one;
(R)-7-(2-methylpyridin-4-yl)-2-(2-(quinuclidin-3-yl)ethyl)isoindolin-1-one;
(S)-7-(2-methylpyridin-4-yl)-2-(2-(quinuclidin-3-yl)ethyl)isoindolin-1-one;
7-(2-methylpyridin-4-yl)-2-(2-(quinuclidin-3-yl)ethyl)isoindolin-1-one;
(R)-2-(1-cyclopropyl-2-hydroxy-2-methylpropyl)-7-(1,3-dimethyl-1H-indazol-5-yl)-6-fluoroisoindolin-1-one;
2-(1-cyclopropyl-2-hydroxy-2-methylpropyl)-7-(1,3-dimethyl-1H-indazol-5-yl)-6-fluoroisoindolin-1-one;
2-(1-cyclopropyl-2-hydroxy-2-methylpropyl)-7-(1,3-dimethyl-1H-indazol-5-yl)-4-fluoroisoindolin-1-one;
(R)-2-(1-cyclopropyl-2-hydroxy-2-methylpropyl)-7-(1,3-dimethyl-1H-indazol-5-yl)-4-fluoroisoindolin-1-one;
2-(1-cyclopropyl-2-methoxy-2-methylpropyl)-7-(4-(5-methyl-1,3,4-oxadiazol-2-yl)phenyl)isoindolin-1-one;
(R)-2-(1-cyclopropyl-2-methoxy-2-methylpropyl)-7-(4-(5-methyl-1,3,4-oxadiazol-2-yl)phenyl)isoindolin-1-one;
2-(1-cyclopropyl-2-hydroxy-2-methylpropyl)-4-hydroxy-7-(4-(5-methyl-1,3,4-oxadiazol-2-yl)phenyl)isoindolin-1-one;
(R)-2-(1-cyclopropyl-2-hydroxy-2-methylpropyl)-4-hydroxy-7-(4-(5-methyl-1,3,4-oxadiazol-2-yl)phenyl)isoindolin-1-one;
2-(1-cyclopropyl-2-hydroxy-2-methylpropyl)-6-fluoro-4-hydroxy-7-(4-(5-methyl-1,3,4-oxadiazol-2-yl)phenyl)isoindolin-1-one;
(R)-2-(1-cyclopropyl-2-hydroxy-2-methylpropyl)-6-fluoro-4-hydroxy-7-(4-(5-methyl-1,3,4-oxadiazol-2-yl)phenyl)isoindolin-1-one;
2-(1-cyclopropyl-2-hydroxy-2-methylpropyl)-4-hydroxy-7-(4-(1-methyl-1H-pyrazol-4-yl)phenyl)isoindolin-1-one;
(R)-2-(1-cyclopropyl-2-hydroxy-2-methylpropyl)-4-hydroxy-7-(4-(1-methyl-1H-pyrazol-4-yl)phenyl)isoindolin-1-one;
2-(1-cyclopropyl-2-hydroxy-2-methylpropyl)-5-methyl-7-(4-(5-methyl-1,3,4-oxadiazol-2-yl)phenyl)isoindolin-1-one;
(R)-2-(1-cyclopropyl-2-hydroxy-2-methylpropyl)-5-methyl-7-(4-(5-methyl-1,3,4-oxadiazol-2-yl)phenyl)isoindolin-1-one;
2-(1-cyclopropyl-2-hydroxy-2-methylpropyl)-3-methyl-7-(4-(5-methyl-1,3,4-oxadiazol-2-yl)phenyl)isoindolin-1-one;
(R)-2-((R)-1-cyclopropyl-2-hydroxy-2-methylpropyl)-3-methyl-7-(4-(5-methyl-1,3,4-oxadiazol-2-yl)phenyl)isoindolin-1-one;
(S)-2-((R)-1-cyclopropyl-2-hydroxy-2-methylpropyl)-3-methyl-7-(4-(5-methyl-1,3,4-oxadiazol-2-yl)phenyl)isoindolin-1-one;
2-(1-Cyclopropyl-2-hydroxy-2-methylpropyl)-4-hydroxy-7-(4-(5-methyl-1,3,4-oxadiazol-2-yl)phenyl)isoindolin-1-one;
(R)-2-(1-Cyclopropyl-2-hydroxy-2-methylpropyl)-4-hydroxy-7-(4-(5-methyl-1,3,4-oxadiazol-2-yl)phenyl)isoindolin-1-one;
2-(1-Cyclopropyl-2-hydroxy-2-methylpropyl)-5-methyl-7-(4-(5-methyl-1,3,4-oxadiazol-2-yl)phenyl)isoindolin-1-one;
(R)-2-(1-Cyclopropyl-2-hydroxy-2-methylpropyl)-5-methyl-7-(4-(5-methyl-1,3,4-oxadiazol-2-yl)phenyl)isoindolin-1-one;
2-(1-Cyclopropyl-2-hydroxy-2-methylpropyl)-3-methyl-7-(4-(5-methyl-1,3,4-oxadiazol-2-yl)phenyl)isoindolin-1-one;
(R)-2-((R)-1-Cyclopropyl-2-hydroxy-2-methylpropyl)-3-methyl-7-(4-(5-methyl-1,3,4-oxadiazol-2-yl)phenyl)isoindolin-1-one;
(S)-2-((R)-1-Cyclopropyl-2-hydroxy-2-methylpropyl)-3-methyl-7-(4-(5-methyl-1,3,4-oxadiazol-2-yl)phenyl)isoindolin-1-one;
2-(1-Cyclopropyl-2-hydroxy-2-methylpropyl)-2'-methyl-[4,5'-biisoindoline]-1',3-dione;
(R)-2-(1-Cyclopropyl-2-hydroxy-2-methylpropyl)-2'-methyl-[4,5'-biisoindoline]-1',3-dione;
2-(1-Cyclopropyl-2-hydroxy-2-methylpropyl)-7-(4-(5-methyloxazol-2-yl)phenyl)isoindolin-1-one;
(R)-2-(1-Cyclopropyl-2-hydroxy-2-methylpropyl)-7-(4-(5-methyloxazol-2-yl)phenyl)isoindolin-1-one;

2-(1-cyclopropyl-2-hydroxy-2-methylpropyl)-7-(6-(5-methyl-1,3,4-oxadiazol-2-yl)pyridin-3-yl)isoindolin-1-one;
(R)-2-(1-cyclopropyl-2-hydroxy-2-methylpropyl)-7-(6-(5-methyl-1,3,4-oxadiazol-2-yl)pyri din-3-yl)isoindolin-1-one;
2-(1-cyclopropyl-2-hydroxy-2-methylpropyl)-7-(5-fluoro-6-(5-methyl-1,3,4-oxadiazol-2-yl)pyri din-3-yl)isoindolin-1-one;
(R)-2-(1-cyclopropyl-2-hydroxy-2-methylpropyl)-7-(5-fluoro-6-(5-methyl-1,3,4-oxadiazol-2-yl)pyridin-3-yl)isoindolin-1-one;
2-(1-cyclopropyl-2-hydroxy-2-methylpropyl)-7-(3-methoxy-4-(5-methyl-1,3,4-oxadiazol-2-yl)phenyl)isoindolin-1-one;
(R)-2-(1-cyclopropyl-2-hydroxy-2-methylpropyl)-7-(3-methoxy-4-(5-methyl-1,3,4-oxadiazol-2-yl)phenyl)isoindolin-1-one;
2-(1-cyclopropyl-2-hydroxy-2-methylpropyl)-7-(2-fluoro-4-(5-methyl-1,3,4-oxadiazol-2-yl)phenyl)isoindolin-1-one;
(R)-2-(1-cyclopropyl-2-hydroxy-2-methylpropyl)-7-(2-fluoro-4-(5-methyl-1,3,4-oxadiazol-2-yl)phenyl)isoindolin-1-one;
7-(4-(1H-1,2,3-triazol-1-yl)phenyl)-2-(1-cyclopropyl-2-hydroxy-2-methylpropyl)isoindolin-1-one;
(R)-7-(4-(1H-1,2,3-triazol-1-yl)phenyl)-2-(1-cyclopropyl-2-hydroxy-2-methylpropyl)isoindolin-1-one;
2-(1-cyclopropyl-2-hydroxy-2-methylpropyl)-7-(2-fluoro-5-methyl-4-(5-methyl-1,3,4-oxadiazol-2-yl)phenyl)isoindolin-1-one;
(R)-2-(1-cyclopropyl-2-hydroxy-2-methylpropyl)-7-(2-fluoro-5-methyl-4-(5-methyl-1,3,4-oxadiazol-2-yl)phenyl)isoindolin-1-one;
2-(1-cyclopropyl-2-hydroxy-2-methylpropyl)-7-(3-methyl-4-(5-methyl-1,3,4-oxadiazol-2-yl)phenyl)isoindolin-1-one;
(R)-2-(1-cyclopropyl-2-hydroxy-2-methylpropyl)-7-(3-methyl-4-(5-methyl-1,3,4-oxadiazol-2-yl)phenyl)isoindolin-1-one;
2-(1-cyclopropyl-2-hydroxy-2-methylpropyl)-7-(2-fluoro-3-methyl-4-(5-methyl-1,3,4-oxadiazol-2-yl)phenyl)isoindolin-1-one;
(R)-2-(1-cyclopropyl-2-hydroxy-2-methylpropyl)-7-(2-fluoro-3-methyl-4-(5-methyl-1,3,4-oxadiazol-2-yl)phenyl)isoindolin-1-one;
2-(1-cyclopropyl-2-hydroxy-2-methylpropyl)-7-(2-(2,2,2-trifluoroethoxy)pyri din-3-yl)isoindolin-1-one;
(R)-2-(1-cyclopropyl-2-hydroxy-2-methylpropyl)-7-(2-(2,2,2-trifluoroethoxy)pyri din-3-yl)isoindolin-1-one;
7-(2-(1-cyclopropyl-2-hydroxy-2-methylpropyl)-3-oxoisoindolin-4-yl)-2-methyl-1,4-dihydroisoquinolin-3(2H)-one;
(R)-7-(2-(1-cyclopropyl-2-hydroxy-2-methylpropyl)-3-oxoisoindolin-4-yl)-2-methyl-1,4-dihydroisoquinolin-3(2H)-one;
2-(1-cyclopropyl-2-hydroxy-2-methylpropyl)-7-(2-methoxyquinoxalin-6-yl)isoindolin-1-one;
(R)-2-(1-cyclopropyl-2-hydroxy-2-methylpropyl)-7-(2-methoxyquinoxalin-6-yl)isoindolin-1-one;
2-(1-cyclopropyl-2-hydroxy-2-methylpropyl)-7-(4-(5-ethyl-1,3,4-oxadiazol-2-yl)phenyl)isoindolin-1-one;
(R)-2-(1-cyclopropyl-2-hydroxy-2-methylpropyl)-7-(4-(5-ethyl-1,3,4-oxadiazol-2-yl)phenyl)isoindolin-1-one;
2-(1-cyclopropyl-2-hydroxy-2-methylpropyl)-7-(4-(oxazol-2-yl)phenyl)isoindolin-1-one;
(R)-2-(1-cyclopropyl-2-hydroxy-2-methylpropyl)-7-(4-(oxazol-2-yl)phenyl)isoindolin-1-one;
2-(1-cyclopropyl-2-hydroxy-2-methylpropyl)-7-(4-(3-methyl-1,2,4-oxadiazol-5-yl)phenyl)isoindolin-1-one;
(R)-2-(1-cyclopropyl-2-hydroxy-2-methylpropyl)-7-(4-(3-methyl-1,2,4-oxadiazol-5-yl)phenyl)isoindolin-1-one;
2-(1-cyclopropyl-2-hydroxy-2-methylpropyl)-7-(1-methyl-1H-indazol-3-yl)isoindolin-1-one;
(R)-2-(1-cyclopropyl-2-hydroxy-2-methylpropyl)-7-(1-methyl-1H-indazol-3-yl)isoindolin-1-one;
2-(1-cyclopropyl-2-hydroxy-2-methylpropyl)-7-(1-methyl-3-(trifluoromethyl)-1H-indazol-5-yl)isoindolin-1-one;
(R)-2-(1-cyclopropyl-2-hydroxy-2-methylpropyl)-7-(1-methyl-3-(trifluoromethyl)-1H-indazol-5-yl)isoindolin-1-one;
2-(1-cyclopropyl-2-hydroxy-2-methylpropyl)-7-(3-(5-methyl-1,2,4-oxadiazol-3-yl)phenyl)isoindolin-1-one;
(R)-2-(1-cyclopropyl-2-hydroxy-2-methylpropyl)-7-(3-(5-methyl-1,2,4-oxadiazol-3-yl)phenyl)isoindolin-1-one;
7-(3-(1,2,4-oxadiazol-3-yl)phenyl)-2-(1-cyclopropyl-2-hydroxy-2-methylpropyl)isoindolin-1-one;
(R)-7-(3-(1,2,4-oxadiazol-3-yl)phenyl)-2-(1-cyclopropyl-2-hydroxy-2-methylpropyl)isoindolin-1-one;
7-(4-(1,2,4-oxadiazol-3-yl)phenyl)-2-(1-cyclopropyl-2-hydroxy-2-methylpropyl)isoindolin-1-one;
(R)-7-(4-(1,2,4-oxadiazol-3-yl)phenyl)-2-(1-cyclopropyl-2-hydroxy-2-methylpropyl)isoindolin-1-one;
6-(2-(1-cyclopropyl-2-hydroxy-2-methylpropyl)-3-oxoisoindolin-4-yl)-1-methylindolin-2-one;
(R)-6-(2-(1-cyclopropyl-2-hydroxy-2-methylpropyl)-3-oxoisoindolin-4-yl)-1-methylindolin-2-one;
(R)-5-(2-(1-cyclopropyl-2-hydroxy-2-methylpropyl)-3-oxoisoindolin-4-yl)-1-methylindolin-2-one;
2-(1-cyclopropyl-2-hydroxy-2-methylpropyl)-7-(1,3-dimethyl-1H-indazol-5-yl)isoindolin-1-one;
(R)-2-(1-cyclopropyl-2-hydroxy-2-methylpropyl)-7-(1,3-dimethyl-1H-indazol-5-yl)isoindolin-1-one;
2-(1-cyclopropyl-2-hydroxy-2-methylpropyl)-7-(1,6-dimethyl-1H-indazol-5-yl)isoindolin-1-one;
(R)-2-(1-cyclopropyl-2-hydroxy-2-methylpropyl)-7-(1,6-dimethyl-1H-indazol-5-yl)isoindolin-1-one;
2-(1-cyclopropyl-2-hydroxy-2-methylpropyl)-7-(4-(5-methyl-1,2,4-oxadiazol-3-yl)phenyl)isoindolin-1-one;
(R)-2-(1-cyclopropyl-2-hydroxy-2-methylpropyl)-7-(4-(5-methyl-1,2,4-oxadiazol-3-yl)phenyl)isoindolin-1-one;
2-(1-cyclopropyl-2-hydroxy-2-methylpropyl)-7-(1-(pyridin-4-yl)-1H-pyrazol-4-yl)isoindolin-1-one;
(R)-2-(1-cyclopropyl-2-hydroxy-2-methylpropyl)-7-(1-(pyridin-4-yl)-1H-pyrazol-4-yl)isoindolin-1-one;
2-(1-cyclopropyl-2-hydroxy-2-methylpropyl)-7-(4-(3-methylisoxazol-5-yl)phenyl)isoindolin-1-one;
(R)-2-(1-cyclopropyl-2-hydroxy-2-methylpropyl)-7-(4-(3-methylisoxazol-5-yl)phenyl)isoindolin-1-one;
2-[(1-cyclopropyl-2-hydroxy-2-methyl-propyl]-7-[4-(2-methyloxazol-5-yl)phenyl]isoindolin-1-one;
2-[(1R)-1-cyclopropyl-2-hydroxy-2-methyl-propyl]-7-[4-(2-methyloxazol-5-yl)phenyl]isoindolin-1-one;
4-chloro-6-[2-[(1-cyclopropyl-2-hydroxy-2-methyl-propyl]-3-oxo-isoindolin-4-yl]pyridine-2-carbonitrile;
4-chloro-6-[2-[(1R)-1-cyclopropyl-2-hydroxy-2-methyl-propyl]-3-oxo-isoindolin-4-yl]pyridine-2-carbonitrile;
7-(6-chloro-4-methoxypyridin-2-yl)-2-(1-cyclopropyl-2-hydroxy-2-methylpropyl)isoindolin-1-one;
(R)-7-(6-chloro-4-methoxypyridin-2-yl)-2-(1-cyclopropyl-2-hydroxy-2-methylpropyl)isoindolin-1-one;
2-[(1R)-1-cyclopropyl-2-hydroxy-2-methyl-propyl]-7-[4-(1-methyltriazol-4-yl)phenyl]isoindolin-1-one;

2-[1-cyclopropyl-2-hydroxy-2-methyl-propyl]-7-[4-(1-methyltriazol-4-yl)phenyl]isoindolin-1-one;

(R)-2-(1-cyclopropyl-2-hydroxy-2-methylpropyl)-7-(4-(isothiazol-4-yl)phenyl)isoindolin-1-one;

2-(1-cyclopropyl-2-hydroxy-2-methylpropyl)-7-(4-(isothiazol-4-yl)phenyl)isoindolin-1-one;

2-[(1R)-1-cyclopropyl-2-hydroxy-2-methyl-propyl]-7-[4-[3-(hydroxymethyl)-4-methyl-isoxazol-5-yl]phenyl] isoindolin-1-one;

2-[(1-cyclopropyl-2-hydroxy-2-methyl-propyl]-7-[4-[3-(hydroxymethyl)-4-methyl-isoxazol-5-yl]phenyl]isoindolin-1-one;

6-(2-(1-cyclopropyl-2-hydroxy-2-methylpropyl)-3-oxoisoindolin-4-yl)-4-methoxypicolinonitrile;

(R)-6-(2-(1-cyclopropyl-2-hydroxy-2-methylpropyl)-3-oxoisoindolin-4-yl)-4-methoxypicolinonitrile;

N-(2-(Dicyclopropylmethyl)-3-oxoisoindolin-4-yl)-2-ethoxybenzamide; 2-Ethoxy-N-(2-(3-hydroxy-3-methylbutan-2-yl)-3-oxoisoindolin-4-yl)benzamide;

(R)-2-Ethoxy-N-(2-(3-hydroxy-3-methylbutan-2-yl)-3-oxoisoindolin-4-yl)benzamide;

2-ethoxy-N-(2-(1-hydroxy-3-methylbutan-2-yl)-3-oxoisoindolin-4-yl)benzamide;

(R)-2-ethoxy-N-(2-(1-hydroxy-3-methylbutan-2-yl)-3-oxoisoindolin-4-yl)benzamide;

N-(2-(1-cyclobutyl-2-hydroxyethyl)-3-oxoisoindolin-4-yl)-2-ethoxybenzamide;

(S)-N-(2-(1-cyclobutyl-2-hydroxyethyl)-3-oxoisoindolin-4-yl)-2-ethoxybenzamide;

(R)-N-(2-(1-cyclobutyl-2-hydroxyethyl)-3-oxoisoindolin-4-yl)-2-ethoxybenzamide;

N-(2-(1-cyclopropyl-2-hydroxyethyl)-3-oxoisoindolin-4-yl)-2-ethoxybenzamide;

(R)-N-(2-(1-cyclopropyl-2-hydroxyethyl)-3-oxoisoindolin-4-yl)-2-ethoxybenzamide;

2-ethoxy-N-(2-(2-hydroxycyclohexyl)-3-oxoisoindolin-4-yl)benzamide;

2-ethoxy-N-(24(1R,2S)-2-hydroxycyclohexyl)-3-oxoisoindolin-4-yl)benzamide;

N-(2-(cyclopropylmethyl)-3-oxoisoindolin-4-yl)-2-ethoxybenzamide;

2-ethoxy-N-(24(1-hydroxycyclobutyl)methyl)-3-oxoisoindolin-4-yl)benzamide;

2-ethoxy-N-(24(3-hydroxyoxetan-3-yl)methyl)-3-oxoisoindolin-4-yl)benzamide;

2-Ethoxy-N-(3-oxo-2-(quinuclidin-3-yl)isoindolin-4-yl) benzamide;

(R)-2-Ethoxy-N-(3-oxo-2-(quinuclidin-3-yl)isoindolin-4-yl)benzamide;

(S)-2-Ethoxy-N-(3-oxo-2-(quinuclidin-3-yl)isoindolin-4-yl) benzamide;

2-Ethoxy-N-(3-oxo-2-(quinuclidin-2-ylmethyl)isoindolin-4-yl)benzamide; (108)

(R)-2-Ethoxy-N-(3-oxo-2-(quinuclidin-2-ylmethyl)isoindolin-4-yl)benzamide;

(S)-2-Ethoxy-N-(3-oxo-2-(quinuclidin-2-ylmethyl)isoindolin-4-yl)benzamide; carboxamide;

2-chloro-N-(2-(1-cyclopropyl-2-hydroxy-2-methylpropyl)-3-oxoisoindolin-4-yl)-6-fluoro-3-methylbenzamide;

(R)-2-chloro-N-(2-(1-cyclopropyl-2-hydroxy-2-methylpropyl)-3-oxoisoindolin-4-yl)-6-fluoro-3-methylbenzamide;

(S)-2-chloro-N-(2-(1-cyclopropyl-2-hydroxy-2-methylpropyl)-3-oxoisoindolin-4-yl)-6-fluoro-3-methylbenzamide;

6-chloro-N-(2-(1-cyclopropyl-2-hydroxy-2-methylpropyl)-3-oxoisoindolin-4-yl)-2-fluoro-3-methylbenzamide;

(R)-6-chloro-N-(2-(1-cyclopropyl-2-hydroxy-2-methylpropyl)-3-oxoisoindolin-4-yl)-2-fluoro-3-methylbenzamide;

(S)-6-chloro-N-(2-(1-cyclopropyl-2-hydroxy-2-methylpropyl)-3-oxoisoindolin-4-yl)-2-fluoro-3-methylbenzamide;

N-(2-(1-cyclopropyl-2-hydroxy-2-methylpropyl)-3-oxoisoindolin-4-yl)-2,3-difluoro-6-methoxybenzamide;

(R)-N-(2-(1-cyclopropyl-2-hydroxy-2-methylpropyl)-3-oxoisoindolin-4-yl)-2,3-difluoro-6-methoxybenzamide;

(S)-N-(2-(1-cyclopropyl-2-hydroxy-2-methylpropyl)-3-oxoisoindolin-4-yl)-2,3-difluoro-6-methoxybenzamide;

2-chloro-N-(2-(1-cyclopropyl-2-hydroxy-2-methylpropyl)-3-oxoisoindolin-4-yl)-3-methylbenzamide;

(R)-2-chloro-N-(2-(1-cyclopropyl-2-hydroxy-2-methylpropyl)-3-oxoisoindolin-4-yl)-3-methylbenzamide;

(S)-2-chloro-N-(2-(1-cyclopropyl-2-hydroxy-2-methylpropyl)-3-oxoisoindolin-4-yl)-3-methylbenzamide;

N-(2-(1-cyclopropyl-2-hydroxy-2-methylpropyl)-3-oxoisoindolin-4-yl)-2,3-dihydro-1H-indene-4-carboxamide;

(R)-N-(2-(1-cyclopropyl-2-hydroxy-2-methylpropyl)-3-oxoisoindolin-4-yl)-2,3-dihydro-1H-indene-4-carboxamide;

(S)-N-(2-(1-cyclopropyl-2-hydroxy-2-methylpropyl)-3-oxoisoindolin-4-yl)-2,3-dihydro-1H-indene-4-carboxamide;

2-chloro-N-(2-(1-cyclopropyl-2-hydroxy-2-methylpropyl)-3-oxoisoindolin-4-yl)-3,6-difluorobenzamide;

(R)-2-chloro-N-(2-(1-cyclopropyl-2-hydroxy-2-methylpropyl)-3-oxoisoindolin-4-yl)-3,6-difluorobenzamide;

(S)-2-chloro-N-(2-(1-cyclopropyl-2-hydroxy-2-methylpropyl)-3-oxoisoindolin-4-yl)-3,6-difluorobenzamide;

N-(2-(1-cyclopropyl-2-hydroxy-2-methylpropyl)-3-oxoisoindolin-4-yl)-3-fluoro-2-(trifluoromethyl)benzamide;

(R)-N-(2-(1-cyclopropyl-2-hydroxy-2-methylpropyl)-3-oxoisoindolin-4-yl)-3-fluoro-2-(trifluoromethyl)benzamide;

(S)-N-(2-(1-cyclopropyl-2-hydroxy-2-methylpropyl)-3-oxoisoindolin-4-yl)-3-fluoro-2-(trifluoromethyl)benzamide;

N-(2-(dicyclopropylmethyl)-3-oxoisoindolin-4-yl)-6-methyl-[1,3]dioxolo[4,5-b]pyridine-7-carboxamide;

6-chloro-N-(2-(dicyclopropylmethyl)-3-oxoisoindolin-4-yl)-[1,3]dioxolo[4,5-b]pyridine-7-carboxamide;

N-(2-(1-cyclopropyl-2-hydroxy-2-methylpropyl)-3-oxoisoindolin-4-yl)-3-fluoro-2-methylbenzamide;

(R)-N-(2-(1-cyclopropyl-2-hydroxy-2-methylpropyl)-3-oxoisoindolin-4-yl)-3-fluoro-2-methylbenzamide;

(S)-N-(2-(1-cyclopropyl-2-hydroxy-2-methylpropyl)-3-oxoisoindolin-4-yl)-3-fluoro-2-methylbenzamide;

N-(2-(1-cyclopropyl-2-hydroxy-2-methylpropyl)-3-oxoisoindolin-4-yl)-2-methyl-3-(trifluoromethyl)benzamide;

(R)-N-(2-(1-cyclopropyl-2-hydroxy-2-methylpropyl)-3-oxoisoindolin-4-yl)-2-methyl-3-(trifluoromethyl)benzamide;

(S)-N-(2-(1-cyclopropyl-2-hydroxy-2-methylpropyl)-3-oxoisoindolin-4-yl)-2-methyl-3-(trifluoromethyl)benzamide;

N-(2-(dicyclopropylmethyl)-3-oxoisoindolin-4-yl)-6,7-dihydro-5H-cyclopenta[b]pyridine-4-carboxamide;

6-chloro-2-fluoro-N-(2-(1-hydroxy-3-methylbutan-2-yl)-3-oxoisoindolin-4-yl)-3-methylbenzamide;

(R)-6-chloro-2-fluoro-N-(2-(1-hydroxy-3-methylbutan-2-yl)-3-oxoisoindolin-4-yl)-3-methylbenzamide;

2,6-dichloro-3-fluoro-N-(2-(3-hydroxy-3-methylbutan-2-yl)-3-oxoisoindolin-4-yl)benzamide;

(R)-2,6-dichloro-3-fluoro-N-(2-(3-hydroxy-3-methylbutan-2-yl)-3-oxoisoindolin-4-yl)benzamide;

2,6-dichloro-3-fluoro-N-(2-(1-hydroxy-3-methylbutan-2-yl)-3-oxoisoindolin-4-yl)benzamide;

(R)-2,6-dichloro-3-fluoro-N-(2-(1-hydroxy-3-methylbutan-2-yl)-3-oxoisoindolin-4-yl)benzamide;
3-chloro-N-(2-(1-hydroxy-3-methylbutan-2-yl)-3-oxoisoindolin-4-yl)-6-(trifluoromethyl)picolinamide;
(R)-3-chloro-N-(2-(1-hydroxy-3-methylbutan-2-yl)-3-oxoisoindolin-4-yl)-6-(trifluoromethyl)picolinamide;
N-(2-(dicyclopropylmethyl)-3-oxoisoindolin-4-yl)-1-methyl-1H-indole-4-carboxamide;
N-(2-(3-hydroxy-3-methylbutan-2-yl)-3-oxoisoindolin-4-yl)-3-(trifluoromethyl)quinoline-4-carboxamide;
(R)-N-(2-(3-hydroxy-3-methylbutan-2-yl)-3-oxoisoindolin-4-yl)-3-(trifluoromethyl)quinoline-4-carboxamide;
N-(2-(cyclopropylmethyl)-3-oxoisoindolin-4-yl)-2,3-dihydro-1H-cyclopenta[b]quinoline-9-carboxamide;
3-chloro-N-(2-(3-hydroxy-3-methylbutan-2-yl)-3-oxoisoindolin-4-yl)-6-(trifluoromethyl)picolinamide;
(R)-3-chloro-N-(2-(3-hydroxy-3-methylbutan-2-yl)-3-oxoisoindolin-4-yl)-6-(trifluoromethyl)picolinamide;
N-(2-(cyclopropylmethyl)-3-oxoisoindolin-4-yl)-3-(trifluoromethyl)quinoline-4-carboxamide;
N-(2-(1-cyclopropyl-2-hydroxy-2-methylpropyl)-3-oxoisoindolin-4-yl)benzo[d]thiazole-7-carboxamide;
(R)-N-(2-(1-cyclopropyl-2-hydroxy-2-methylpropyl)-3-oxoisoindolin-4-yl)benzo[d]thiazole-7-carboxamide;
(S)-N-(2-(1-cyclopropyl-2-hydroxy-2-methylpropyl)-3-oxoisoindolin-4-yl)benzo[d]thiazole-7-carboxamide;
6-chloro-N-(2-(1-hydroxy-3-methylbutan-2-yl)-3-oxoisoindolin-4-yl)-3-(trifluoromethyl)picolinamide;
(R)-6-chloro-N-(2-(1-hydroxy-3-methylbutan-2-yl)-3-oxoisoindolin-4-yl)-3-(trifluoromethyl)picolinamide;
N-(2-(dicyclopropylmethyl)-3-oxoisoindolin-4-yl)-2-methyl-2H-indazole-4-carboxamide;
(S)-N-(2-(1-cyclopropylethyl)-3-oxoisoindolin-4-yl)-6-methyl-[1,3]dioxolo[4,5-b]pyridine-7-carboxamide;
N-(2-(1-cyclopropylethyl)-3-oxoisoindolin-4-yl)-6-methyl-[1,3]dioxolo[4,5-b]pyridine-7-carboxamide;
N-(2-(cyclopropylmethyl)-3-oxoisoindolin-4-yl)-3-fluoro-6-methoxy-1,5-naphthyridine-4-carboxamide;
N-(2-(1-cyclopropyl-2-methoxyethyl)-3-oxoisoindolin-4-yl)-6,7-dihydro-5H-cyclopenta[b]pyridine-4-carboxamide;
(R)-N-(2-(1-cyclopropyl-2-methoxyethyl)-3-oxoisoindolin-4-yl)-6,7-dihydro-5H-cyclopenta[b]pyridine-4-carboxamide;
(S)-N-(2-(1-cyclopropyl-2-methoxyethyl)-3-oxoisoindolin-4-yl)-6,7-dihydro-5H-cyclopenta[b]pyridine-4-carboxamide;
6-chloro-N-(2-(1-cyclopropylethyl)-3-oxoisoindolin-4-yl)-[1,3]dioxolo[4,5-b]pyridine-7-carboxamide;
(S)-6-chloro-N-(2-(1-cyclopropylethyl)-3-oxoisoindolin-4-yl)-[1,3]dioxolo[4,5-b]pyridine-7-carboxamide;
(R)-2-ethoxy-N-(2-(3-hydroxy-3-methylbutan-2-yl)-3-oxoisoindolin-4-yl)nicotinamide;
2-ethoxy-N-(2-(3-hydroxy-3-methylbutan-2-yl)-3-oxoisoindolin-4-yl)nicotinamide;
3,5-dichloro-N-(2-(cyclopropylmethyl)-3-oxoisoindolin-4-yl)isonicotinamide;
(S)-N-(2-(1-cyclopropylethyl)-3-oxoisoindolin-4-yl)-6,7-dihydro-5H-cyclopenta[b]pyridine-4-carboxamide;
N-(2-(1-cyclopropylethyl)-3-oxoisoindolin-4-yl)-6,7-dihydro-5H-cyclopenta[b]pyridine-4-carboxamide;
N-(2-(dicyclopropylmethyl)-3-oxoisoindolin-4-yl)-1H-pyrrolo[2,3-b]pyridine-4-carboxamide;
N-(2-(dicyclopropylmethyl)-3-oxoisoindolin-4-yl)-7-fluoro-1-oxo-2,3-dihydro-1H-indene-4-carboxamide;
N-(6-chloro-2-(cyclopropylmethyl)-3-oxoisoindolin-4-yl)-6,7-dihydro-5H-cyclopenta[b]pyridine-4-carboxamide;
N-(2-(cyclopropylmethyl)-3-oxoisoindolin-4-yl)-6-fluoroquinoline-4-carboxamide;
N-(2-(dicyclopropylmethyl)-3-oxoisoindolin-4-yl)-2,3-dihydrobenzofuran-7-carboxamide;
N-(2-(cyclopropylmethyl)-3-oxoisoindolin-4-yl)-6,7-dihydro-5H-cyclopenta[b]pyridine-4-carboxamide;
N-(7-chloro-2-(cyclopropylmethyl)-3-oxoisoindolin-4-yl)-6,7-dihydro-5H-cyclopenta[b]pyridine-4-carboxamide;
N-(2-(Cyclopropylmethyl)-6-methyl-3-oxoisoindolin-4-yl)-6,7-dihydro-5H-cyclopenta[b]pyridine-4-carboxamide;
N-(2-(cyclopropylmethyl)-7-hydroxy-3-oxoisoindolin-4-yl)-6,7-dihydro-5H-cyclopenta[b]pyridine-4-carboxamide;
N-(2-(Cyclopropylmethyl)-6-methyl-3-oxoisoindolin-4-yl)-6,7-dihydro-5H-cyclopenta[b]pyridine-4-carboxamide;
N-(2-(Cyclopropylmethyl)-7-hydroxy-3-oxoisoindolin-4-yl)-6,7-dihydro-5H-cyclopenta[b]pyridine-4-carboxamide;
Quinuclidin-3-yl(2-(4-fluorophenyl)-3-oxoisoindolin-4-yl) carbamate;
N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide;
(R)-N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide;
(S)-N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide;
N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide;
(R)-N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide;
(S)-N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide;
N-(2-(1-cyclopropyl-2-hydroxy-2-methylpropyl)-3-oxoisoindolin-4-yl)-2-methoxy-3,5-dimethylisonicotinamide;
(R)-N-(2-(1-cyclopropyl-2-hydroxy-2-methylpropyl)-3-oxoisoindolin-4-yl)-2-methoxy-3,5-dimethylisonicotinamide;
(S)-N-(2-(1-cyclopropyl-2-hydroxy-2-methylpropyl)-3-oxoisoindolin-4-yl)-2-methoxy-3,5-dimethylisonicotinamide;
5-chloro-N-(2-(1-cyclopropyl-2-hydroxy-2-methylpropyl)-3-oxoisoindolin-4-yl)-2-methoxy-3-methylisonicotinamide;
(R)-5-chloro-N-(2-(1-cyclopropyl-2-hydroxy-2-methylpropyl)-3-oxoisoindolin-4-yl)-2-methoxy-3-methylisonicotinamide;
(S)-5-Chloro-N-(2-(1-cyclopropyl-2-hydroxy-2-methylpropyl)-3-oxoisoindolin-4-yl)-2-methoxy-3-methylisonicotinamide;
5-Chloro-N-(2-(1-cyclopropyl-2-hydroxy-2-methylpropyl)-3-oxoisoindolin-4-yl)-2,3-dihydrofuro[2,3-b]pyridine-4-carboxamide;
(R)-5-Chloro-N-(2-(1-cyclopropyl-2-hydroxy-2-methylpropyl)-3-oxoisoindolin-4-yl)-2,3-dihydrofuro[2,3-b]pyridine-4-carboxamide;
(5)-5-Chloro-N-(2-(1-cyclopropyl-2-hydroxy-2-methylpropyl)-3-oxoisoindolin-4-yl)-2,3-dihydrofuro[2,3-b]pyridine-4-carboxamide;
N-(2-(1-cyclopropyl-2-hydroxy-2-methylpropyl)-3-oxoisoindolin-4-yl)pyrazolo[1,5-c]pyridine-4-carboxamide;

(R)-N-(2-(1-cyclopropyl-2-hydroxy-2-methylpropyl)-3-oxoisoindolin-4-yl)pyrazolo[1,5-c]pyridine-4-carboxamide;

6-chloro-N-(2-(1-cyclopropyl-2-hydroxy-2-methylpropyl)-3-oxoisoindolin-4-yl)-[1,3]dioxolo[4,5-b]pyridine-7-carboxamide;

(R)-6-chloro-N-(2-(1-cyclopropyl-2-hydroxy-2-methylpropyl)-3-oxoisoindolin-4-yl)-[1,3]dioxolo[4,5-b]pyridine-7-carboxamide;

(S)-6-chloro-N-(2-(1-cyclopropyl-2-hydroxy-2-methylpropyl)-3-oxoisoindolin-4-yl)-[1,3]dioxolo[4,5-b]pyridine-7-carboxamide;

N-(2-(1-cyclopropyl-2-hydroxy-2-methylpropyl)-3-oxoisoindolin-4-yl)-6,7-dihydro-5H-cyclopenta[b]pyridine-4-carboxamide;

(R)-N-(2-(1-cyclopropyl-2-hydroxy-2-methylpropyl)-3-oxoisoindolin-4-yl)-6,7-dihydro-5H-cyclopenta[b]pyridine-4-carboxamide;

(S)-N-(2-(1-cyclopropyl-2-hydroxy-2-methylpropyl)-3-oxoisoindolin-4-yl)-6,7-dihydro-5H-cyclopenta[b]pyridine-4-carboxamide;

N-(2-(1-cyclopropyl-2-hydroxy-2-methylpropyl)-3-oxoisoindolin-4-yl)-2-methoxy-3-methylisonicotinamide;

(R)-N-(2-(1-cyclopropyl-2-hydroxy-2-methylpropyl)-3-oxoisoindolin-4-yl)-2-methoxy-3-methylisonicotinamide;

N-(2-(1-cyclopropyl-2-hydroxy-2-methylpropyl)-3-oxoisoindolin-4-yl)-2-methyl-2H-indazole-4-carboxamide;

(R)-N-(2-(1-cyclopropyl-2-hydroxy-2-methylpropyl)-3-oxoisoindolin-4-yl)-2-methyl-2H-indazole-4-carboxamide;

(S)-N-(2-(1-cyclopropyl-2-hydroxy-2-methylpropyl)-3-oxoisoindolin-4-yl)-2-methyl-2H-indazole-4-carboxamide;

N-(2-(1-cyclopropyl-2-hydroxy-2-methylpropyl)-6-fluoro-3-oxoisoindolin-4-yl)-2-methyl-2H-indazole-4-carboxamide;

(R)-N-(2-(1-cyclopropyl-2-hydroxy-2-methylpropyl)-6-fluoro-3-oxoisoindolin-4-yl)-2-methyl-2H-indazole-4-carboxamide;

N-(2-(1-cyclopropyl-2-hydroxy-2-methylpropyl)-3-oxoisoindolin-4-yl)-2,3-dihydrofuro[2,3-b]pyridine-4-carboxamide;

(R)-N-(2-(1-cyclopropyl-2-hydroxy-2-methylpropyl)-3-oxoisoindolin-4-yl)-2,3-dihydrofuro[2,3-b]pyridine-4-carboxamide;

(S)-N-(2-(1-cyclopropyl-2-hydroxy-2-methylpropyl)-3-oxoisoindolin-4-yl)-2,3-dihydrofuro[2,3-b]pyridine-4-carboxamide;

N-(2-(1-cyclopropyl-2-hydroxy-2-methylpropyl)-3-oxoisoindolin-4-yl)-2,3-dihydro-[1,4]dioxino[2,3-b]pyridine-8-carboxamide;

(R)-N-(2-(1-cyclopropyl-2-hydroxy-2-methylpropyl)-3-oxoisoindolin-4-yl)-2,3-dihydro-[1,4]dioxino[2,3-b]pyridine-8-carboxamide;

(S)-N-(2-(1-cyclopropyl-2-hydroxy-2-methylpropyl)-3-oxoisoindolin-4-yl)-2,3-dihydro-[1,4]dioxino[2,3-b]pyridine-8-carboxamide;

N-(2-(1-cyclopropyl-2-hydroxy-2-methylpropyl)-3-oxoisoindolin-4-yl)-2,3-dimethoxyisonicotinamide;

(R)-N-(2-(1-cyclopropyl-2-hydroxy-2-methylpropyl)-3-oxoisoindolin-4-yl)-2,3-dimethoxyisonicotinamide;

(S)-N-(2-(1-cyclopropyl-2-hydroxy-2-methylpropyl)-3-oxoisoindolin-4-yl)-2,3-dimethoxyisonicotinamide;

N-(2-(1-cyclopropyl-2-methoxy-2-methylpropyl)-3-oxoisoindolin-4-yl)-6,7-dihydro-5H-cyclopenta[b]pyridine-4-carboxamide;

(R)-N-(2-(1-cyclopropyl-2-methoxy-2-methylpropyl)-3-oxoisoindolin-4-yl)-6,7-dihydro-5H-cyclopenta[b]pyridine-4-carboxamide;

(S)-N-(2-(1-cyclopropyl-2-methoxy-2-methylpropyl)-3-oxoisoindolin-4-yl)-6,7-dihydro-5H-cyclopenta[b]pyridine-4-carboxamide;

N-(2-(1-hydroxycyclobutyl)methyl)-3-oxoisoindolin-4-yl)-6,7-dihydro-5H-cyclopenta[b]pyridine-4-carboxamide;

2-chloro-N-(2-(1-cyclopropyl-2-hydroxy-2-methylpropyl)-1-oxo-2,3-dihydro-1H-pyrrolo[3,4-c]pyridin-7-yl)-6-fluoro-3-methylbenzamide;

(R)-2-chloro-N-(2-(1-cyclopropyl-2-hydroxy-2-methylpropyl)-1-oxo-2,3-dihydro-1H-pyrrolo[3,4-c]pyridin-7-yl)-6-fluoro-3-methylbenzamide;

N-(2-(1-cyclopropyl-2-hydroxy-2-methylpropyl)-3-oxoisoindolin-4-yl)-5-methyl-2,3-dihydrofuro[2,3-b]pyridine-4-carboxamide;

(R)-N-(2-(1-cyclopropyl-2-hydroxy-2-methylpropyl)-3-oxoisoindolin-4-yl)-5-methyl-2,3-dihydrofuro[2,3-b]pyridine-4-carboxamide;

(S)-N-(2-(1-cyclopropyl-2-hydroxy-2-methylpropyl)-3-oxoisoindolin-4-yl)-5-methyl-2,3-dihydrofuro[2,3-b]pyridine-4-carboxamide;

N-(2-(1-cyclopropyl-2-hydroxy-2-methylpropyl)-3-oxoisoindolin-4-yl)-6-methyl-[1,3]dioxolo[4,5-b]pyridine-7-carboxamide;

(R)-N-(2-(1-cyclopropyl-2-hydroxy-2-methylpropyl)-3-oxoisoindolin-4-yl)-6-methyl-[1,3]dioxolo[4,5-b]pyridine-7-carboxamide;

(S)-N-(2-(1-cyclopropyl-2-hydroxy-2-methylpropyl)-3-oxoisoindolin-4-yl)-6-methyl-[1,3]dioxolo[4,5-b]pyridine-7-carboxamide;

quinuclidin-3-yl(2-(4-fluorophenyl)-3-oxoisoindolin-4-yl)(methyl)carbamate;

(R)-quinuclidin-3-yl(2-(4-fluorophenyl)-3-oxoisoindolin-4-yl)(methyl)carbamate;

(S)-quinuclidin-3-yl(2-(4-fluorophenyl)-3-oxoisoindolin-4-yl)(methyl)carbamate;

N-(2-(1-Cyclopropyl-2-hydroxy-2-methylpropyl)-3-oxoisoindolin-4-yl)-5-methyl-2,3-dihydrofuro[2,3-b]pyridine-4-carboxamide;

(R)-N-(2-(1-Cyclopropyl-2-hydroxy-2-methylpropyl)-3-oxoisoindolin-4-yl)-5-methyl-2,3-dihydrofuro[2,3-b]pyridine-4-carboxamide;

(S)-N-(2-(1-Cyclopropyl-2-hydroxy-2-methylpropyl)-3-oxoisoindolin-4-yl)-5-methyl-2,3-dihydrofuro[2,3-b]pyridine-4-carboxamide;

N-(2-(1-Cyclopropyl-2-hydroxy-2-methylpropyl)-3-oxoisoindolin-4-yl)-6-methyl-[1,3]dioxolo[4,5-b]pyridine-7-carboxamide;

(R)-N-(2-(1-Cyclopropyl-2-hydroxy-2-methylpropyl)-3-oxoisoindolin-4-yl)-6-methyl-[1,3]dioxolo[4,5-b]pyridine-7-carboxamide;

(S)-N-(2-(1-Cyclopropyl-2-hydroxy-2-methylpropyl)-3-oxoisoindolin-4-yl)-6-methyl-[1,3]dioxolo[4,5-b]pyridine-7-carboxamide;

Quinuclidin-3-yl(2-(4-fluorophenyl)-3-oxoisoindolin-4-yl)(methyl)carbamate;

(R)-Quinuclidin-3-yl(2-(4-fluorophenyl)-3-oxoisoindolin-4-yl)(methyl)carbamate;

(S)-Quinuclidin-3-yl(2-(4-fluorophenyl)-3-oxoisoindolin-4-yl)(methyl)carbamate;

2-(1-Cyclopropyl-2-hydroxy-2-methylpropyl)-7-(2-(6,7-dihydro-5H-cyclopenta[b]pyridin-4-yl)vinyl)isoindolin-1-one;

(R)-(E)-2-(1-Cyclopropyl-2-hydroxy-2-methylpropyl)-7-(2-(6,7-dihydro-5H-cyclopenta[b]pyridin-4-yl)vinyl)isoindolin-1-one;

(S)-(E)-2-(1-Cyclopropyl-2-hydroxy-2-methylpropyl)-7-(2-(6,7-dihydro-5H-cyclopenta[b]pyridin-4-yl)vinyl)isoindolin-1-one;

2-(1-Cyclopropyl-2-hydroxy-2-methylpropyl)-7-((6,7-dihydro-5H-cyclopenta[b]pyridin-4-yl)ethynyl)isoindolin-1-one;

(R)-2-(1-Cyclopropyl-2-hydroxy-2-methylpropyl)-7-((6,7-dihydro-5H-cyclopenta[b]pyridin-4-yl)ethynyl)isoindolin-1-one;

(S)-2-(1-Cyclopropyl-2-hydroxy-2-methylpropyl)-7-((6,7-dihydro-5H-cyclopenta[b]pyridin-4-yl)ethynyl)isoindolin-1-one;

2-(1-Cyclopropyl-2-hydroxy-2-methylpropyl)-7-(2-(6,7-dihydro-5H-cyclopenta[b]pyridin-4-yl)ethyl)isoindolin-1-one;

(R)-2-(1-Cyclopropyl-2-hydroxy-2-methylpropyl)-7-(2-(6,7-dihydro-5H-cyclopenta[b]pyridin-4-yl)ethyl)isoindolin-1-one;

(S)-2-(1-Cyclopropyl-2-hydroxy-2-methylpropyl)-7-(2-(6,7-dihydro-5H-cyclopenta[b]pyridin-4-yl)ethyl)isoindolin-1-one;

7-(2-(6-Chloro-[1,3]dioxolo[4,5-b]pyridin-7-yl)vinyl)-2-(1-cyclopropyl-2-hydroxy-2-methylpropyl)isoindolin-1-one;

(R)-(E)-7-(2-(6-Chloro-[1,3]dioxolo[4,5-b]pyridin-7-yl)vinyl)-2-(1-cyclopropyl-2-hydroxy-2-methylpropyl)isoindolin-1-one;

(S)-(E)-7-(2-(6-Chloro-[1,3]dioxolo[4,5-b]pyridin-7-yl)vinyl)-2-(1-cyclopropyl-2-hydroxy-2-methylpropyl)isoindolin-1-one;

2-(1-Cyclopropyl-2-hydroxy-2-methylpropyl)-7-(2-(6-methyl-[1,3]dioxolo[4,5-b]pyridin-7-yl)vinyl)isoindolin-1-one;

(R)-(E)-2-(1-Cyclopropyl-2-hydroxy-2-methylpropyl)-7-(2-(6-methyl-[1,3]dioxolo[4,5-b]pyridin-7-yl)vinyl)isoindolin-1-one;

(S)-(E)-2-(1-Cyclopropyl-2-hydroxy-2-methylpropyl)-7-(2-(6-methyl-[1,3]dioxolo[4,5-b]pyridin-7-yl)vinyl)isoindolin-1-one;

2-(1-Cyclopropyl-2-hydroxy-2-methylpropyl)-7-(2-(6-methyl-[1,3]dioxolo[4,5-b]pyridin-7-yl)ethyl)isoindolin-1-one;

(R)-2-(1-Cyclopropyl-2-hydroxy-2-methylpropyl)-7-(2-(6-methyl-[1,3]dioxolo[4,5-b]pyridin-7-yl)ethyl)isoindolin-1-one;

(S)-2-(1-Cyclopropyl-2-hydroxy-2-methylpropyl)-7-(2-(6-methyl-[1,3]dioxolo[4,5-b]pyridin-7-yl)ethyl)isoindolin-1-one;

7-(((6-chloro-[1,3]dioxolo[4,5-b]pyridin-7-yl)oxy)methyl)-2-(1-cyclopropyl-2-hydroxy-2-methylpropyl)isoindolin-1-one;

(R)-7-(((6-chloro-[1,3]dioxolo[4,5-b]pyridin-7-yl)oxy)methyl)-2-(1-cyclopropyl-2-hydroxy-2-methylpropyl)isoindolin-1-one;

(S)-7-(((6-chloro-[1,3]dioxolo[4,5-b]pyridin-7-yl)oxy)methyl)-2-(1-cyclopropyl-2-hydroxy-2-methylpropyl)isoindolin-1-one;

2-(1-Cyclopropyl-2-hydroxy-2-methylpropyl)-7-(((6-methyl-[1,3]dioxolo[4,5-b]pyridin-7-yl)amino)methyl)isoindolin-1-one;

(R)-2-(1-Cyclopropyl-2-hydroxy-2-methylpropyl)-7-(((6-methyl-[1,3]dioxolo[4,5-b]pyridin-7-yl)amino)methyl)isoindolin-1-one;

(S)-2-(1-Cyclopropyl-2-hydroxy-2-methylpropyl)-74(6-methyl-[1,3]dioxolo[4,5-b]pyridin-7-yl)amino)methyl)isoindolin-1-one;

7-((6-chloro-[1,3]dioxolo[4,5-b]pyridin-7-yl)methoxy)-2-(1-cyclopropyl-2-hydroxy-2-methylpropyl)isoindolin-1-one;

(R)-7-((6-chloro-[1,3]dioxolo[4,5-b]pyridin-7-yl)methoxy)-2-(1-cyclopropyl-2-hydroxy-2-methylpropyl)isoindolin-1-one;

(S)-7-((6-chloro-[1,3]dioxolo[4,5-b]pyridin-7-yl)methoxy)-2-(1-cyclopropyl-2-hydroxy-2-methylpropyl)isoindolin-1-one;

2-(1-cyclopropyl-2-hydroxy-2-methylpropyl)-7-((6,7-dihydro-5H-cyclopenta[b]pyridin-4-yl)methoxy)isoindolin-1-one;

(R)-2-(1-cyclopropyl-2-hydroxy-2-methylpropyl)-7-((6,7-dihydro-5H-cyclopenta[b]pyridin-4-yl)methoxy)isoindolin-1-one;

(S)-2-(1-cyclopropyl-2-hydroxy-2-methylpropyl)-7-((6,7-dihydro-5H-cyclopenta[b]pyridin-4-yl)methoxy)isoindolin-1-one;

2-(1-Cyclopropyl-2-hydroxy-2-methylpropyl)-7-(2-(6-methyl-[1,3]dioxolo[4,5-b]pyridin-7-yl)ethyl)isoindolin-1-one;

(R)-2-(1-Cyclopropyl-2-hydroxy-2-methylpropyl)-7-(2-(6-methyl-[1,3]dioxolo[4,5-b]pyridin-7-yl)ethyl)isoindolin-1-one;

(S)-2-(1-Cyclopropyl-2-hydroxy-2-methylpropyl)-7-(2-(6-methyl-[1,3]dioxolo[4,5-b]pyridin-7-yl)ethyl)isoindolin-1-one;

5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one;

(R)-5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one;

(S)-5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one;

2-(1-cyclopropyl-2-hydroxy-2-methylpropyl)-4,5-difluoro-7-(4-(5-methyl-1,3,4-oxadiazol-2-yl)phenyl)isoindolin-1-one; or (R)-2-(1-cyclopropyl-2-hydroxy-2-methylpropyl)-4,5-difluoro-7-(4-(5-methyl-1,3,4-oxadiazol-2-yl)phenyl)isoindolin-1-one.

Other embodiments of the present invention include the following:

(a) A pharmaceutical composition comprising a compound of formula I or a pharmaceutically acceptable salt thereof and a pharmaceutically acceptable carrier.

(b) The pharmaceutical composition of (a), further comprising a second therapeutic agent.

(c) A pharmaceutical combination that is (i) a compound of formula I or a pharmaceutically acceptable salt thereof, and (ii) a second therapeutic agent wherein the compound of formula I and the second therapeutic agent are each employed in an amount that renders the combination effective for treatment or prophylaxis of lysosomal storage diseases, kidney disease, neurodegenerative disease, diabetes related diseases, or cancers where GSL synthesis is abnormal or overexpression of GCS disrupts ceramide-induced apoptosis.

(d) A compound of formula I, or a pharmaceutically acceptable salt thereof, for use in therapy.

(e) A compound of formula I, or a pharmaceutically acceptable salt thereof, for use in the treatment of lysosomal storage diseases, kidney disease, neurodegenerative disease, diabetes related diseases, or cancers where GSL synthesis is abnormal or overexpression GCS of disrupts ceramide-induced apoptosis.

(f) A use of a compound of formula I or a pharmaceutically acceptable salt thereof, in the preparation of a medicament for modulating glucosylceraide (GlcCer), Glocosylsphingosine (GlcSph) and/or other glucosylceramide-based gycosphingolipids (GSLs) in a subject in need thereof.

(g) A use of a compound of formula I or a pharmaceutically acceptable salt thereof, in the preparation of a medicament for treatment or prophylaxis of lysosomal storage diseases, kidney disease, neurodegenerative disease, diabetes related diseases, or cancers where GSL synthesis is abnormal or overexpression of GCS disrupts ceramid-induced apoptosis in a subject in need thereof.

(h) A use of a compound of formula I or a pharmaceutically acceptable salt thereof, in the preparation of a medicament for treatment of lysosomal storage diseases, kidney disease, neurodegenerative disease, diabetes related diseases, or cancers where GSL synthesis is abnormal or overexpression of GCS disrupts ceramide-induced apoptosis in a subject in need thereof.

(i) The method of (f), wherein the compound of formula I or a pharmaceutically acceptable salt thereof, is administered in combination with an effective amount of at least one second therapeutic agent.

(j) A method of modulating glucosylceraide (GlcCer), Glocosylsphingosine (GlcSph) and/or other glucosylceramide-based gycosphingolipids (GSLs) activity in a subject in need thereof, which comprises administering to the subject the pharmaceutical composition of (a) or (b), or the combination of (c).

(k) A method of treating cognitive impairments associated with cardiometabolic diseases, kidney disease, or diabetes and/or reducing the likelihood or severity of symptoms of cognitive impairments associated with lysosomal storage diseases, kidney disease, neurodegenerative disease, diabetes related diseases, or cancers where GSL synthesis is abnormal or overexpression of GCS disrupts ceramid-induced apoptosis in a subject in need thereof, which comprises administering to the subject the pharmaceutical composition of (a) or (b), or the combination of (c).

In the embodiments of the compounds and salts provided above, it is to be understood that each embodiment may be combined with one or more other embodiments, to the extert that such a combination provides a stable compound or salt and is consistert with the description of the embodiments. It is further to be understood that the embodiments of compositions and methods provided as (a) through (k) above are understood to include all embodiments of the compounds and/or salts, including such embodiments as result from combinations of embodiments.

Additional embodiments of the invention include the pharmaceutical compositions, combinations, uses and methods set forth in (a) through (k) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt as appropriate.

The present invention also includes a compound of the present invention for use (i) in, (ii) as a medicament for, or (iii) in the preparation of a medicament for: (a) preventing or treating lysosomal storage diseases, kidney disease, neurodegenerative disease, diabetes related diseases, or cancers where GSL synthesis is abnormal or overexpression of GCS disrupts ceramid-induced apoptosis or (c) use in medicine. In these uses, the compounds of the present invention can optionally be employed in combination with one or more second therapeutic agents.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

It is further to be understood that the embodiments of compositions and methods provided as (a) through (k) above are understood to include all embodiments of the compounds, including such embodiments as result from combinations of embodiments.

Examples of lysosomal storage diseases include, but are not limited to, Niemann-Pick type C, Fabry, Tay-Sachs, Sandhoff, Gaucher's disease, and Type 1 Gaucher's disease.

Examples of neurodegenerative diseases, include but are not limited to, Parkinson's disease (PD), dementia with Lewy bodies.

Examples of kidney diseases, include but are not limited to, polycystic kidney disease, renal hypertrophy.

Examples of diabetes related diseases, include but are not limited to, diabetes mellitus, obesity, hyperglycemia and hyperinsulemia.

Examples of cancers where GSL synthesis is abnormal or overexpression of GCS disrupts ceramide-induced apoptosis include leukemia, papillary renal, and thyroid carcinomas.

The present invention also relates to processes for the preparation of the compounds of Formula I which are described in the following and by which the compounds of the invention are obtainable. Exemplifying the invention is the use of the compounds disclosed in the Examples and herein.

The invention also relates to the use of compounds of the invention for the preparation of a medicament for the treatment and/or prophylaxis of the above-mentioned diseases.

The compounds of the Formula I and their physiologically acceptable salts can be administered to animals, preferably to mammals, and in particular to humans, as pharmaceuticals by themselves, in mixtures with one another or in the form of pharmaceutical preparations. A subject of the present invention therefore also are the compounds of the Formula I and their physiologically acceptable salts for use as pharmaceuticals, their use for modulating glycosphingolipids (GSLs), for normalizing an elevated GSLs level and in particular their use in the therapy and prophylaxis of the abovementioned syndromes as well as their use for preparing medicaments for these purposes.

Furthermore, a subject of the present invention is pharmaceutical preparations (or pharmaceutical compositions) which comprise as active component an effective dose of at least one compound of the Formula I and/or a physiologically acceptable salt thereof and a customary pharmaceutically acceptable carrier, i.e., one or more pharmaceutically acceptable carrier substances and/or additives.

Thus, a subject of the invention is, for example, said compound and its physiologically acceptable salts for use as a pharmaceutical, pharmaceutical preparations which comprise as active component an effective dose of said compound and/or a physiologically acceptable salt thereof and a customary pharmaceutically acceptable carrier, and the uses of said compound and/or a physiologically acceptable salt thereof in the therapy or prophylaxis of the abovementioned syndromes as well as their use for preparing medicaments for these purposes.

As noted above, additional embodiments of the present invention are each directed to a method for the treatment a disease, disorder, or condition, or one or more symptoms thereof ("indications") in which glucosylceramide synthase (GCS) is involved and for which the inhibition of GCS is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of GCS activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which GCS is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, dementia with Lewy bodies, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjogren's syndrome, Delvic's disease, inflammatory myopathies, and ankylosing spondylitis.

Additional indications include papillary renal and thyroid carcinomas in a subject in whom glucoxylceramide (GlcCer), Glucosylsphingosine (GlcSph) and/or other glucosylceramide-based glycosphingolipids (GSLs) are amplified or elevated. Diseases associated with elevated GSL levels include polycystic kidney disease, renal hypertrophy, diabetic nephropathy, diabetes mellitus, obesity, hyperglycemia, and hyperinsulemia.

The compounds of the present invention may be useful in treatment of cancers where GSL synthesis is abnormal or overexpression of GCS disrupts ceramid-induced apoptosis.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

One or more additional pharmacologically active agents may be administered in combination with a compound of Formula (I) (or a pharmaceutically acceptable salt thereof). An additional active agent (or agents) is intended to mean a pharmaceutically active agent (or agents) that is active in the body, including pro-drugs that convert to pharmaceutically active form after administration, which are different from the compound of Formula (I). The additional active agents also include free-acid, free-base and pharmaceutically acceptable salts of said additional active agents. Generally, any suitable additional active agent or agents, including chemotherapeutic agents or therapeutic antibodies, may be used in any combination with the compound of Formula (I) in a single dosage formulation (e.g., a fixed dose drug combination), or in one or more separate dosage formulations which allows for concurrent or sequential administration of the active agents (co-administration of the separate active agents) to subjects. In addition, the compounds of Formula (I) (or pharmaceutically acceptable salts thereof) can be administered in combination with radiation therapy, hormone therapy, surgery or immunotherapy.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefore, contemporaneously or sequentially with a compound of Formula (I). When a compound of Formula (I) is used contemporaneously with one or more other drugs, a pharmaceutical composition in unit dosage form containing such other drugs and the compound of Formula (I) is preferred. However, the combination therapy may also include therapies in which the compound of Formula (I) and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA, PD-1 (programmed cell death protein 1) and PDL-1 (programmed death-ligand 1) antagonists, Leucine-rich repeat kinase 2 (LRRK2) inhibitors, dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

Non-limiting examples of LRRK2 inhibitors include: DNL201 and DNL151 (Denali Therapeutics Inc.), LRRK2-IN-1, CZC-54252, CZC25146, TTT-3002, HG-10-102-1, JH-II-127, GSK2578215A, GNE-7915, GNE0877, GNE-9605, PF-06447475, MLi-2, and PF-06685360 (also known as PFE-360). Additional examples include the LRRK2 inhibitors disclosed in U.S. Pat. No. 9,233,977, WO2016/036586, U.S. Pat. Nos. 9,416,126, 9,493,440, 9,688,654, 9,440,952, 9,718,818, 9,809,568, WO2019/074810, WO2019/074809, and WO2020/092136.

The invention further relates to a method of treating cancer in a human patient comprising administration of a compound of the invention (i.e., a compound of Formula (I)) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™, Regeneron Pharmaceuticals, Inc., Tarrytown, NY, USA), atezolizumab (TECENTRIQ™, Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated, or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanthin and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanthin, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above-mentioned pathological conditions.

In the treatment, prevention, control, amelioration, or reduction of risk of conditions which require inhibition of GCS activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one aspect, the present invention provides a kit comprising a therapeutically effective amount of at least one Compound of Formula (I), or a pharmaceutically acceptable salt or prodrug of said compound and a pharmaceutically acceptable carrier, vehicle or diluent.

In another aspect the present invention provides a kit comprising an amount of at least one Compound of Formula (I), or a pharmaceutically acceptable salt or prodrug of said compound and an amount of at least one additional therapeutic agent listed above, wherein the amounts of the two or more active ingredients result in a desired therapeutic effect. In one embodiment, the one or more Compounds of Formula (I) and the one or more additional therapeutic agents are provided in the same container. In one embodiment, the one or more Compounds of Formula (I) and the one or more additional therapeutic agents are provided in separate containers.

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "haloalkyl," "—O-alkyl," etc.

As used herein, the term "administration" and variants thereof (e.g., "administering" a compound) in reference to a compound of the invention means providing the compound to the individual in need of treatment. When a compound of the invention is provided in combination with one or more other active agents (e.g., L-DOPA), "administration" and its variants are each understood to include concurrent and sequential administration of the compound or salt and other agents.

A "subject" (alternatively referred to herein as "patient") is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. The term also includes herein the amount of active compound sufficient to modulate GSC activity and thereby elicit the response being sought (i.e., a "therapeutically effective amount"). When the active compound (i.e., active ingredient) is administered as the salt, references to the amount of active ingredient are to the free acid or free base form of the compound.

The terms "treating" or "treatment" as used herein with respect to lysosomal storage diseases, neurodegenerative disease, cystic disease, cancer, or a diseases or disorders associated with elevated levels of glucosylceramide (GlcCer), glucosylsphingosine (GlcSph) and/or other glucosylceramide-based glycosphingolipids (GSLs), includes inhibiting the severity of the diseases i.e., arresting or reducing the development of the diseases or its clinical symptoms; or relieving the diseases, i.e., causing regression of the severity of the diseases or their clinical symptoms.

The terms "preventing," or "prophylaxis," as used herein with respect to the cardiometabolic diseases including high blood pressure, heart failure, kidney disease, and diabetes, refers to reducing the likelihood or severity of the diseases.

The term "$C_0$" or "C0" as employed in expressions such as "$C_{0-6}$ alkyl" and C0-6alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

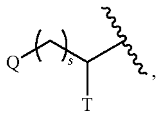

wherein s is an integer equal to zero, 1 or 2, the structure is

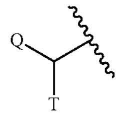

when s is zero.

The term “alkyl,” as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term “carbonyl” means a functional group composed of a carbon atom double-bonded to an oxygen atom, C═O.

“Cycloalkyl” or “$C_{3-12}$ cycloalkyl” means any univalent radical derived from a monocyclic or bicyclic ring system having 3 to 12 ring carbons atoms; said ring system may be (a) a $C_3$ to a $C_8$ monocyclic, saturated ring, or (b) a bicyclic saturated ring. Here, the point of attachment for a “cycloalkyl” to the rest of the molecule is on the saturated ring. Bicyclic cycloalkyl ring systems include fused ring systems, where two rings share two atoms (e.g. decalin), spiro ring systems where two rings share one atom (e.g. spiro[4.5]decanyl) and bridge groups (e.g., norbornane).

Additional examples within the above meaning include, but are not limited to univalent radicals of cyclopropyl, cyclobutyl, cyclopentyl, cyclohexyl, cycloheptyl, bicyclo[2.2.2]octanyl, bicyclo[1.1.1]pentanyl, bicyclo[2.2.1]heptanyl, [1.1.1]-bicyclo pentane, 1-decalinyl, spiro[2.4]heptyl, spiro[2.2]pentyl, 2,3-dihydro-1H-indenyl, and norbornyl.

The term “$C_{3-8}$ cycloalkyl” (or “$C_3$-$C_8$ cycloalkyl”) means a cyclic ring of an alkane having three to eight total carbon atoms (i.e., cyclopropyl, cyclobutyl, cyclopentyl, cyclohexyl, cycloheptyl, or cyclooctyl). The terms “$C_{3-7}$ cycloalkyl”, “$C_{3-6}$ cycloalkyl”, “$C_{5-7}$ cycloalkyl” and the like have analogous meanings.

The term “heteroalkyl” refers to an alkyl group where 1, 2, or 3 of the carbon atoms is substituted by a heteroatom independently chosen from N, O, or S.

The term “alkoxy” refers to an alkyl (carbon and hydrogen chain) group singularly bonded to oxygen (R—O). Non-limiting examples of alkoxy are methoxy ($CH_3O$—), ethoxy ($CH_3CH_2O$—) and butoxy ($CH_3CH_2CH_2O$—).

“Aryl” means a monocyclic, bicyclic or tricyclic carbocyclic aromatic ring or ring system containing 5-14 carbon atoms, wherein at least one of the rings is aromatic. Examples of aryl include phenyl, 2,3-dihydro-1H-indenyl, and naphthyl. In on embodiment of the present invention, aryl is phenyl and 2,3-dihydro-1H-indenyl.

The term “fluoroalkyl” means an alkyl group in which one or more fluorines, for example 1 to 6 fluorines, have been substituted for hydrogen.

The term “halogen” or “halo” includes fluorine, chlorine, bromine, and iodine.

“Haloalkyl” refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes —CFβ, —$CF_2CF_3$, —$CHFCH_3$, and the like.

The term “heteroaryl”, as used herein, represents a stable monocyclic, bicyclic or tricyclic ring system containing 5-14 carbon atoms and containing at least one ring heteroatom selected from N, S (including SO and $SO_2$) and O, wherein at least one of the heteroatom containing rings is aromatic. In the case of a heteroaryl ring system where one or more of the rings are saturated and contain one or more N atoms, the N can be in the form of quaternary amine. Bicyclic heteroaryl ring systems include fused ring systems, where two rings share two atoms, and spiro ring systems, where two rings share one atom. Heteroaryl groups within the scope of this definition include but are not limited to: azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, and isoquinolinyl, and oxazolyl. If the heteroaryl contains nitrogen atoms, it is understood that the corresponding N-oxides thereof are also encompassed by this definition.

The term “heterocycloalkyl,” as used herein, refers to a non-aromatic saturated monocyclic or multicyclic ring system comprising 3 to about 14 ring atoms, wherein from 1 to 4 of the ring atoms are independently O, S, or N, and the remainder of the ring atoms are carbon atoms. There are no adjacent oxygen and/or sulfur atoms present in the ring system. A heterocycloalkyl group can be joined via a ring carbon or ring nitrogen atom. Said ring system may be (a) a saturated monocyclic ring or a partially unsaturated ring, or (b) a bicyclic ring system having at one saturated ring with at least one ring atom that is independently O, S, or N. The other ring of the bicyclic system (b) may be saturated or partially unsaturated. For a bicyclic system, the rings are fused across two adjacent ring carbon atoms (e.g., decahydroisoquinoline, 2,3-dihydro-1H-benzo[d]imidazolyl, isoindolinyl), at one ring carbon atom (e.g., 1,4-dioxaspiro[4.5]decane), or are bridged groups (e.g., 2,5-diazabicyclo[2.2.1]heptyl, quinuclidinyl).

In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof and all isomers thereof.

"Oxo" means an oxygen atom connected to another atom by a double bond and is represented by "═O" herein.

By "pharmaceutically acceptable" is meant that the ingredients of the pharmaceutical composition must be compatible with each other and not deleterious to the recipient thereof.

Where any amine is present in the compound, the N atom may be optionally in the form of a quaternary amine having one or more appropriate additional substitutions, as further described herein.

When any variable (e.g., n, $R^a$, $R^b$, etc.) occurs more than one time in any constituent or in Formula (I), its definition on each occurrence is independent of its definition at every other occurrence. Also, combinations of substituents and/or variables are permissible only if such combinations result in stable compounds.

When any ring atom is specified as being optionally substituted with, or in a specified form, for example, S substituted with oxo groups, or N in the form of a N-oxide, this does not preclude the substitution of any ring atom with the other listed optional substituents when not substituted with oxo groups or in the form of a N-oxide.

"Celite®" (Fluka) diatomite is diatomaceous earth, and can be referred to as "celite".

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

By "stable compound" or "stable structure" is meant a compound that is sufficiently robust to survive isolation to a useful degree of purity from a reaction mixture, and formulation into an efficacious therapeutic agent. The compounds of the present invention are limited to stable compounds embraced by Formula (I).

The term "compound" refers to the compound and, in certain embodiments, to the extert they are stable, any hydrate or solvate thereof. A hydrate is the compound complexed with water, and a solvate is the compound complexed with an organic solvent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

Under standard nomenclature used throughout this disclosure, the terminal portion of the designated side chain is preceded by the adjacent functionality toward the point of attachment. For example, a C1-5 alkylcarbonylamino C1-6 alkyl substituent is equivalent to

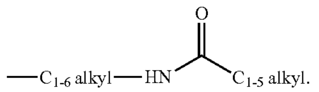

Structural representations of compounds having substituents terminating with a methyl group may display the terminal methyl group either using the characters "CH3", e.g. "—CH3" or using a straight line representing the presence of the methyl group, e.g. "—", i.e.,

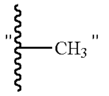 and 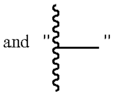

have equivalent meanings.

For variable definitions containing terms having repeated terms, e.g., (CRiRj)r, where r is the integer 2, Ri is a defined variable, and Rj is a defined variable, the value of Ri may differ in each instance in which it occurs, and the value of Rj may differ in each instance in which it occurs. For example, if Ri and Rj are independently selected from the group consisting of methyl, ethyl, propyl and butyl, then (CRiRj)2 can be

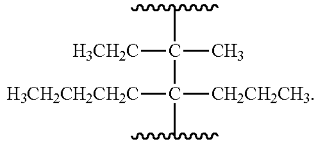

Unless expressly stated to the contrary, all ranges cited herein are inclusive. For example, a heteroaromatic ring described as containing from "1 to 4 heteroatoms" means the ring can contain, 1, 2, 3 or r heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. Similarly, $C_1$-$C_6$ when used with a chain, for example an alkyl chains means that the chain can contain 1, 2, 3, 4, 5, or 6 carbon atoms. It also includes all ranges contained therein including $C_1$-$C_5$, $C_1$-$C_4$, $C_1$-$C_3$, $C_1$-$C_2$, $C_2$-$C_6$, $C_3$-$C_6$, $C_4$-$C_6$, $C_5$-$C_6$, and all other possible combinations.

In choosing compounds of the present invention, one of ordinary skill in the art will recognize that the various substituents, i.e. $R^1$, $R^A$, etc., are to be chosen in conformity with well-known principles of chemical structure connectivity and stability.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a compound of Formula (I) or a pharmaceutically acceptable salt of the compound. The transformation may occur by various mechanisms (e.g., by metabolic or chemical processes), such as, for example, through hydrolysis in blood. For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of Formula (I) contains an alcohol functional group, a prodrug can be formed by the replacement of one or more of the hydrogen atoms of the alcohol groups with a group such as, for example, ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino ($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a compound of Formula (I) incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$) alkyl, ($C_3$-$C_7$) cycloalkyl, benzyl, a natural a aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$)alkyl and $Y^3$ is ($C_1$-$C_6$) alkyl; carboxy ($C_1$-$C_6$)alkyl; amino($C_1$-$C_4$)alkyl or mono-N— or di-N,N—($C_1$-$C_6$)alkylaminoalkyl; —C($Y^4$)$Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$ alkyl, —O—($C_{1-4}$ alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compound of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the compound of Formula (I) may be atropisomers (e.g., substituted biaryls) and are considered as part of this invention. Enantiomers can also be directly separated using chiral chromatographic techniques.

It is also possible that the compound of Formula (I) may exist in different tautomeric forms, and all such forms are embraced within the scope of the invention. For example, all keto-enol and imine-enamine forms of the compounds are included in the invention.

Unless otherwise indicated, all stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a compound of Formula (I) incorporates a double bond or a fused ring, both the cis- and trans-forms, as well as mixtures, are embraced within the scope of the invention.

When a substituent on a chiral carbon atom is depicted without specific stereochemistry (by using a straight line bond to a chiral center), it is to be understood that both the alpha and beta configurations of said substituent group are to be considered part of the present invention. For example, the compound of the present invention, which is drawn as follows:

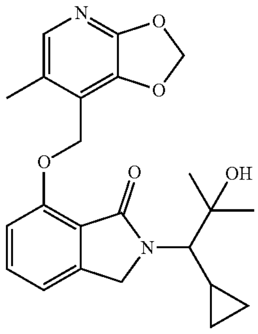

, is understood to encompass both stereoisomers at the indicated chiral center located at the carbon atom attached to the carboxamide portion of the compound, the structures of which are as follows:

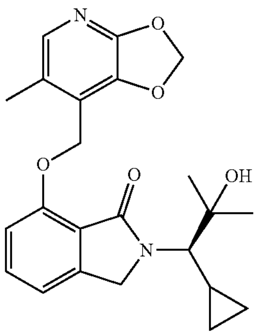

and

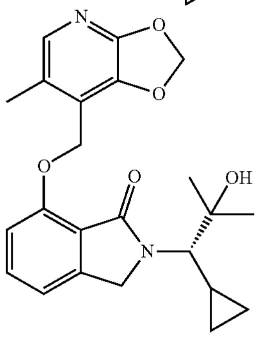

.

In the Examples section below, compounds of the present invention that have been purified as individual stereoisomers are sometimes depicted in non-stereospecific form but identified using one or more of the terms: "diastereomer 1," "diastereomer 2," "isomer 1," "isomer 2," "first eluding enantiomer", "enantiomer A" and "enantiomer B." In this instance, the absolute stereochemistry of each isolated diastereomer and enantiomeric center has not been determined and the terms used above are used to represent each individual purified stereochemically pure compound.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUP AC 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1H$) and deuterium ($^2H$). Protium is the predominant hydrogen isotope found in nature. Enriching for deuterium may provide certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

In another embodiment, the Compounds of Formula (I) are in substantially purified form.

Methods of Synthesis

General Procedures

The compounds of the present invention can be prepared according to the following general schemes and specific examples, or modifications thereof, using readily available starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following schemes.

Unless otherwise specifically indicated, all reagents are commercially available, known in the literature, or readily synthesized by one skilled in the art. The general route applied to the synthesis of compounds of Formula (I) is described in the Schemes that follow. In some instances, the order of carrying out the reaction steps in the schemes may be varied to facilitate the reaction or to avoid unwanted reaction products. Additionally, various protecting group strategies familiar to one skilled in the art of organic synthesis may be employed to facilitate the reaction or to avoid unwanted reaction products.

In some cases, the final product may be further modified, for example, by manipulation of substituents. These manipulations may include, but are not limited to, reduction, oxidation, alkylation, acylation, and hydrolysis reactions which are commonly known to those skilled in the art.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC/MS).

The following examples are provided so that the invention might be more fully understood. These examples are illustrative only and should not be construed as limiting the invention in any way. Wherein a racemic mixture is produced, the enantiomers may be separated using SFC reverse or normal phase chiral resolution conditions either after isolation of the final product or at a suitable Intermediate, followed by processing of the single isomers individually. It is understood that alternative methodologies may also be employed in the synthesis of these key intermediates and examples. Asymmetric methodologies (e.g. chiral catalysis, auxiliaries) may be used where possible and appropriate. The exact choice of reagents, solvents, temperatures, and other reaction conditions, depends upon the nature of the intended product.

The following abbreviations are used throughout the text:

Me: methyl
Et: ethyl
Ac: acetyl
Bn: benzyl
DMF: N,N-dimethylformamide
THF: tetrahydrofuran
TEA: triethylamine
MS: mass spectrometry
EtOAc: ethyl acetate
° C.: degrees Celsius
ATP: adenosine triphosphate
OAc: acetate
TFA: trifluoroacetic acid
FA: formic acid
Boc: tert-butoxycarbonyl
$Boc_2O$: di-tert-butyl dicarbonate
NBS: N-bromosuccinimide
HATU: O-(7-azabenzotriazol-1-yl)-N,N,N'N'-tetramethyluronium hexafluorophosphate
min: minutes
h: hours
HPLC: high performance liquid chromatography
SFC: supercritical fluid chromatography
TLC: thin layer chromatography
dtbpf: 1,1'-bis(di-tert-butylphosphino)ferrocene
LDA: lithium diisopropylamide
DCM: dichloromethane
XPhos: 2-dicyclohexylphosphino-2',4',6'-triisopropylbiphenyl
Addp: 1,1'-(azodicarbonyl)dipiperidine
AIBN: azobisisobutyronitrile
BPO: benzoyl peroxide
DPPA: diphenylphosphoryl azide
dppf: 1,1'-Bis(diphenylphosphino)ferrocene
ACN: acetonitrile
DEA: diethylamine
DIEA: N,N-diisopropylethylamine
DMAP: 4-dimethylaminopyridine
PMB: 4-methoxybenzyl
XantPhos: 4,5-Bis(diphenylphosphino)-9,9-dimethylxanthene
$Pd_2(dba)_3$: Tris(dibenzylideneacetone)dipalladium(0)
Josiphos: (R)-1-[(SP)-2-(Diphenylphosphino)ferrocenyl]ethyldicyclohexylphosphine RockPhos Pd G3: [(2-Di-tert-butylphosphino-3-methoxy-6-methyl-2',4',6'-triisopropyl-1,1'-biphenyl)-2-(2-aminobiphenyl)]palladium(II) methanesulfonate
TBS: tert-butyldimethylsilyl
BISPIN: Bis(pinacolato)diboron
PE: polyethylene
ELSD: evaporative light scattering detector
NIS: N-Iodosuccinimide
DMA: dimethylacetamide
SEM: [2-(Trimethylsilyl)ethoxy]methyl acetal
ESI: Electrospray ionization
NMR: nuclear magnetic resonance
UDP: uridine diphosphate
DMSO: dimethylsulfoxide
HEPES: 4-(2-hydroxyethyl)-1-piperazineethanesulfonic acid
DOPC: 1,2-dioleoyl-sn-glycero-3-phosphatidylcholine Reaction Schemes The compounds of the present invention can be prepared readily according to the following Schemes and specific Examples, or modifications thereof, using readily available commercial starting materials, reagents and conventional synthetic procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Reaction Scheme A illustrates the preparation of the intermediate amines of the type A-3. Substituted Boc-protected amino esters of the type A-1 can be treated with methyl Grignard reagent to afford tertiary alcohol A-2. Boc deprotection under acidic conditions yields substituted amino alcohol intermediates of the present invention as formula A-3. In some cases, various protecting group strategies familiar to one skilled in the art of organic synthesis may be employed to allow preparation of a particular compound of the present invention.

Scheme A

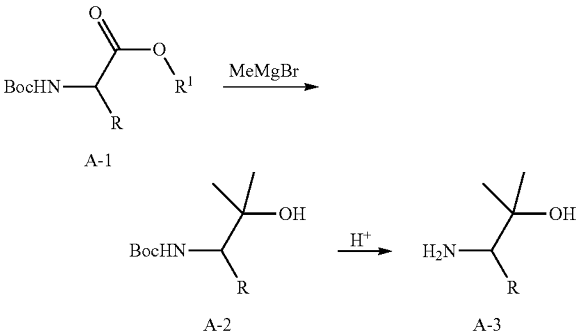

A-1
A-2
A-3

As illustrated in Scheme B, in general, amine intermediates of the invention can be prepared starting with the addition of a ketone B-2 to the enolate of B-1, formed by deprotonation using a strong base, such as LDA, to provide tertiary alcohol B-3. Cleavage of the benzyl ester can be achieved by under standard hydrogenation conditions to produce the corresponding carboxylic acid B-4. Heating B-4 under Curtius rearrangement conditions results in a cyclized product B-5 that can be ring opened with base at elevated temperature to yield intermediates of the present invention as formula B-6.

Scheme B

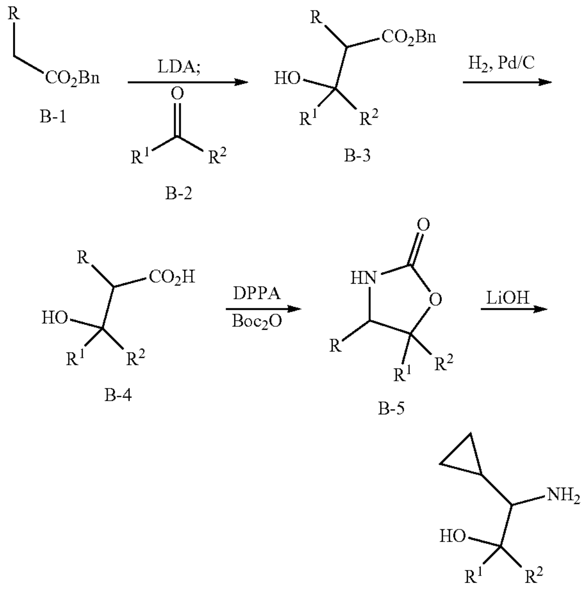

B-1
B-2
B-3
B-4
B-5
B-6

As illustrated in Scheme C, in general, intermediates of the invention can be prepared by deprotonation of an amide intermediate C-1 with strong base, such as sodium hydride, followed by alkylation with an appropriately functionalized alkyl halide to provide intermediates of the present invention as formula C-2.

Scheme C

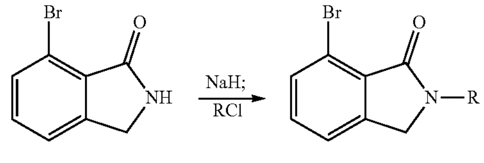

C-1
C-2

As illustrated in Scheme D, in general, intermediates of the invention can be prepared by radical bromination of a functionalized methyl 2-bromo-6-methylbenzoate D-1 to give the corresponding benzylic bromide D-2. In turn, bromide D-2 can be displaced with a primary amine. Cyclization via amide formation can then be affected with base, such as potassium carbonate, at elevated temperature to yield intermediates of the present invention as formula D-3.

Scheme D

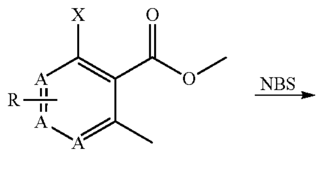

D-1

-continued

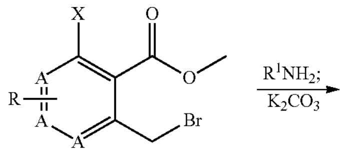

D-2

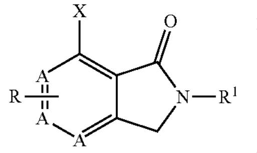

D-3 where A = CH and/or N
X = Br, Cl

As illustrated in Scheme E, in general, intermediates of the invention can be prepared by palladium-mediated iodination of an appropriated substituted 2-methylbenzoic acid E-1 to afford E-2. Esterification utilizing carbonate base and methyl iodide can generate the corresponding methyl ester E-3. Radical bromination provides the corresponding benzylic bromide, E-4. Bromide displacement with a primary amine and subsequent amide formation with base at elevated temperature affords intermediates of the present invention as formula E-5.

Scheme E

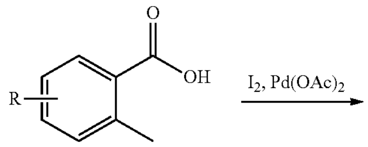

E-1

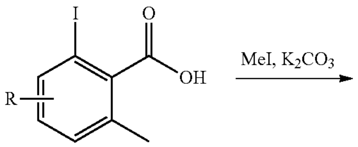

E-2

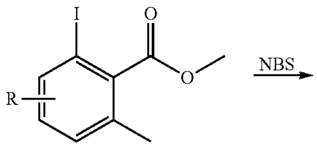

E-3

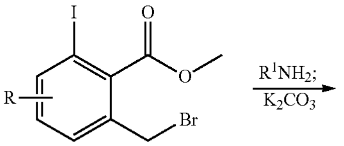

E-4

-continued

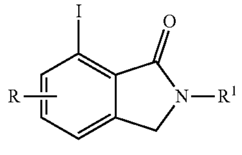

E-5

Reaction Scheme F illustrates the preparation of the intermediate bromides of the type F-3. In general, the hydroxyl group of substituted isoindolinones F-1 can be protected, with a SEM group, for example, to provide F-2, which can undergo deprotonation with a strong base, such as sodium hydride, and subsequent methylation with iodomethane to provide intermediates of the present invention as formula F-3.

Scheme F

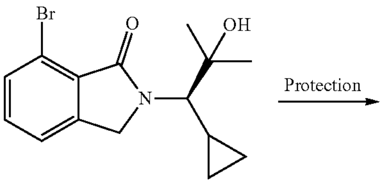

F-1

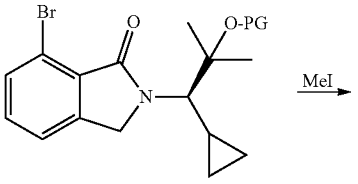

F-2

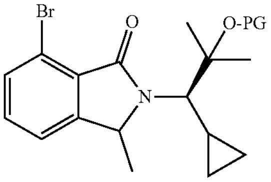

F-3 where PG = Protecting group

Reaction Scheme G illustrates the preparation of intermediate G-2. Alcohol G-1 can be methylated with trimethyloxonium tetrafluoroborate to provide G-2.

Scheme G

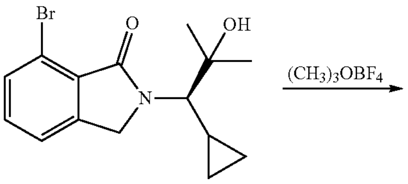

G-1

-continued

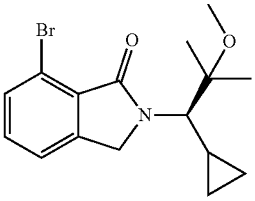

G-2

Reaction Scheme H illustrates the preparation of the intermediate bromides II-2 or boronic acids/esters II-3. In general, aryl acid chlorides or methyl ketone intermediates H-1 can be transformed via known methods to afford oxazole heterocycles of type II-2. Additionally, aryl halides can be transformed via Palladium-catalyzed cyanation or suzuki reactions to produce Intermediates of the type II-2. Palladium-catalyzed borylation of bromide II-2 at elevated temperatures provides intermediates of the present invention of formula II-3.

Scheme H

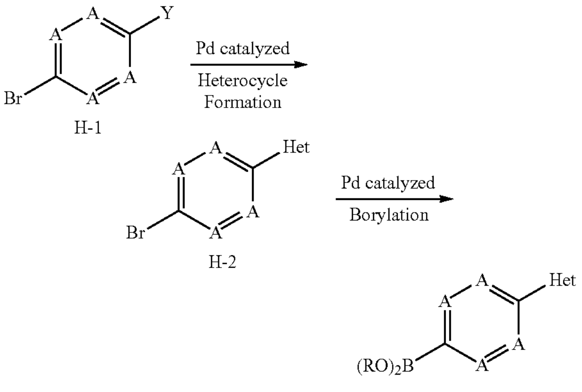

H-1 H-2 H-3 where A = CH and/or N
Y = aryl acid chloride/Me ketone: oxazole formation

As illustrated in Scheme I, in general, compounds of the invention can be prepared by a palladium-catalyzed Suzuki coupling reaction between an appropriately functionalized boronic ester or acid (either commercially available or of the type as described by Scheme H) and intermediate D-3 to yield compounds of the present invention as formula I-2.

Scheme I

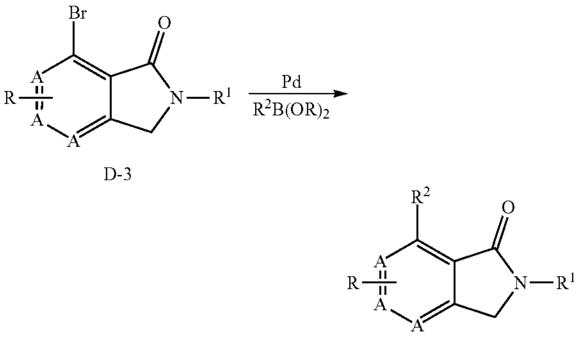

D-3 I-2

-continued where A = CH and/or N

As illustrated in Scheme J, in general, compounds of the invention can be prepared by reversing the coupling partners in the palladium-catalyzed Suzuki coupling reaction between an appropriately functionalized boronic ester or acid 0.1-1 and aryl halides (either commercially available or of the type as described by Scheme H) to yield compounds of the present invention as formula J-2.

Scheme J

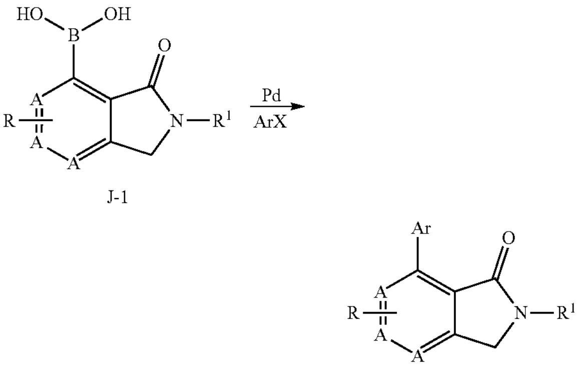

J-1 J-2 where A = CH and/or N
X = aryl halide

As illustrated in Scheme K, in general, compounds of the invention can be prepared by an cyclization of appropriately functionalized methyl or ethyl 2-(bromomethyl)benzoate intermediate K-1 by initial displacement of the benzylic bromide with a primary amine followed by amide formation, with or without base, at elevated temperature to afford intermediates of the present invention as formula K-2.

Scheme K

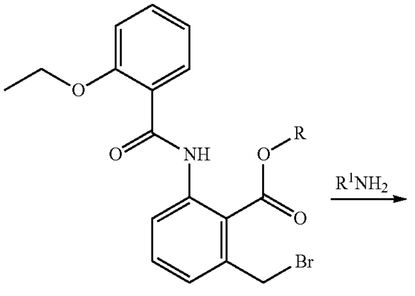

K-1

-continued

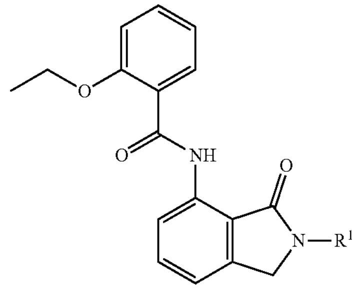

K-2

As illustrated in Scheme L, in general, compounds of the invention can be prepared by amide or carbamate bond formation between an appropriately functionalized 7-aminoisoindolin-1-one intermediate L-1 and a pre-formed acid chloride or carbonochloridate in the presence of a tertiary amine base, such as triethylamine, to yield compounds of the present invention as formula L-2.

Scheme L

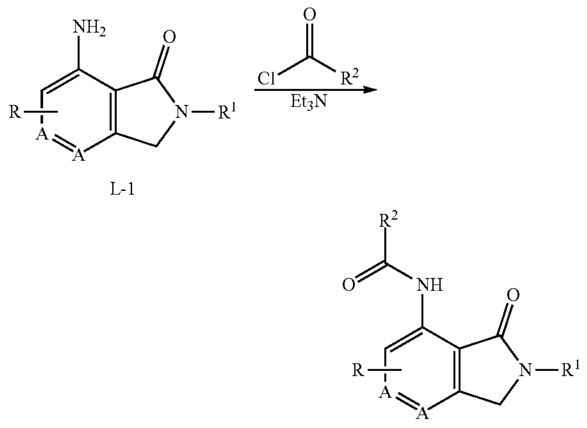

L-1

L-2 where A = CH and/or N

As illustrated in Scheme M, in general, compounds of the invention can be prepared by subjecting an appropriately functionalized halogenated isoindolin-1-one intermediate M-1 to palladium-catalyzed C—N bond forming cross-coupling conditions with a primary amide to yield compounds of the present invention as formula M-2.

Scheme M

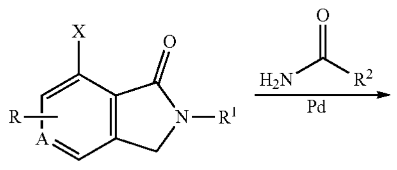

M-1

-continued

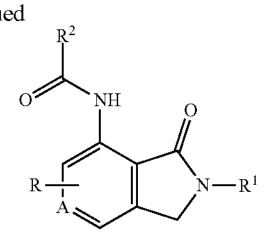

M-2 where A = CH and/or N
X = Br or Cl

As illustrated in Scheme N, in general, compounds of the invention can be prepared by subjecting an appropriately functionalized 7-bromoisoindolin-1-one intermediate N-1 to palladium-catalyzed C—C bond forming cross-coupling conditions with an alkene, alkyne or boronic acid or ester to yield compounds of the present invention as formula N-2 where alkenes or alkynes can be further reduced to the alkane to yield compounds of the present invention as formula N-3.

Scheme N

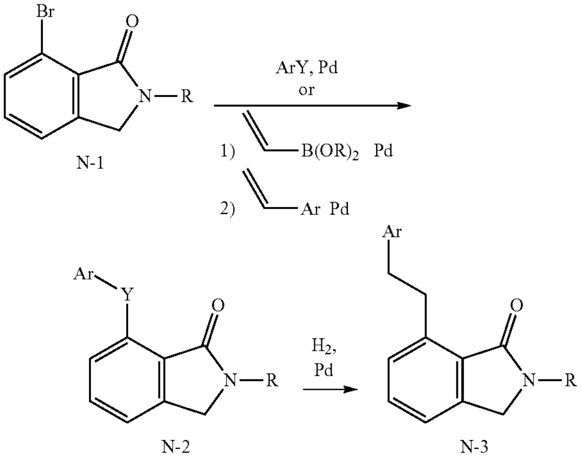

N-1

N-2

N-3 where Y = trans alkene
or alkyne

As illustrated in Scheme O, in general, compounds of the invention can be prepared by subjecting appropriately functionalized 7-bromoisoindolin-1-one intermediate O-1 to palladium-catalyzed C—C bond forming Suzuki coupling conditions with an appropriately protected hydroxymethyl or methylamine $BF_3K$ salt to afford intermediate O-1. Deprotection of intermediate O-1 under acidic conditions followed by a palladium-catalyzed C—N or C—O bond forming reaction with an aryl iodide yields compounds of the present invention as formula O-2.

Scheme O

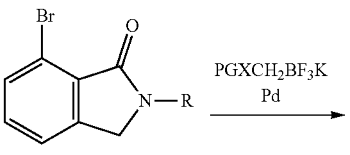

N-1

-continued

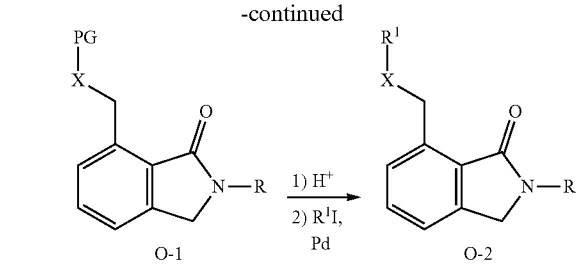

O-1 O-2 where X = NH or O
PG = Protecting Group

As illustrated in Scheme P, in general, compounds of the invention can be prepared by subjecting functionalized 7-hydroxyisoindolin-1-one intermediate P-1 to Mitsunobu reaction conditions with an appropriately functionalized primary alcohol to yield compounds of the present invention as formula P-2.

Scheme P

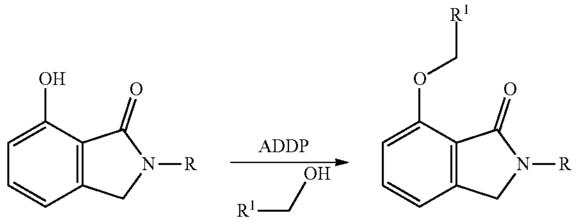

P-1 P-2

Specific embodiments of the compounds of the invention, and methods of making them, are described in the Intermediates and Examples herein.

Intermediate I-1

I-1

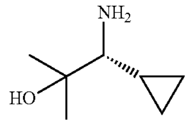

(R)-1-Amino-1-cyclopropyl-2-methylpropan-2-ol (I-1)

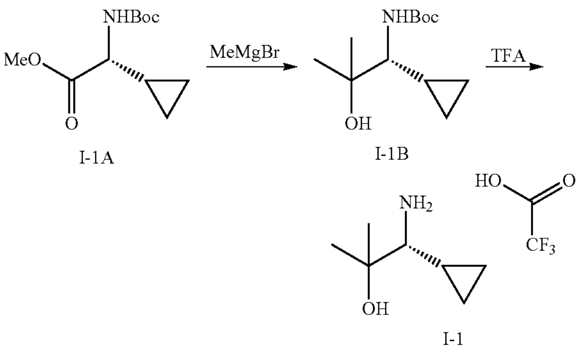

I-1A I-1B I-1

Step A: tert-Butyl (R)-(1-cyclopropyl-3-hydroxy-3-methyl-2-oxobutyl)carbamate (I-1B)

To a solution of methyl (R)-2-((tert-butoxycarbonyl) amino)-2-cyclopropylacetate (I-1A, 240 g, 1.1 mol) in THF (1.5 L) at 0° C. was added 3M MeMgBr (methylmagnesium bromide) in diethyl ether (1.2 L, 3.7 mmol). The mixture was stirred for 4 h at ambient temp. The excess Grignard was quenched with ice and aqueous sat. $NH_4C_1$ solution (10 L) was added. The reaction was extracted with EtOAc and dried over $Na_2SO_4$ (sodium sulfate) and concentrated to provide compound I-1B. $^1$HNMR (400 MHz, Chloroform-d): δ 4.90 (br.s, 1H), 2.83-2.88 (m, 1H), 2.57 (bs, 1H), 1.28 (s, 9H), 1.24 (s, 3H), 1.23 (s, 3H), 0.88-0.90 (m, 1H), 0.60-0.62 (m, 1H), 0.05-0.44 (m, 2H).

Step B: (R)-1-Amino-1-cyclopropyl-2-methylpropan-2-ol (I-1)

To a solution of tert-butyl (R)-(1-cyclopropyl-3-hydroxy-3-methyl-2-oxobutyl)carbamate (I-1B, 190 g, 0.82 mol) in DCM (1.1 L) at 5° C. was added dropwise TFA (1.1 L). The reaction mixture was warmed to ambient temp and stirred for 2 h. The mixture was concentrated to give compound I-1 as a TFA salt. $^1$H NMR (300 MHz, Chloroform-d) δ 4.82 (bs, 1H), 2.90 (t, J=8.9 Hz, 1H), 1.30 (s, 3H), 1.27 (s, 3H), 0.90 (m, 1H), 0.65 (m, 1H), 0.50-0.29 (m, 2H).

Intermediate I-2 shown in Table 1 was made in an analogous manner as intermediate I-1

TABLE 1

| Intermediate Number | Structure | Compound Name | Observed Mass (M + 1) |
|---|---|---|---|
| I-2 | 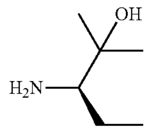 | (R)-3-amino-2-methylpentan-2-ol | NA |

Intermediate I-3

I-3

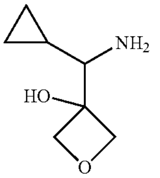

(R and S)-3-(Amino(cyclopropyl)methyl)oxetan-3-ol (I-3)

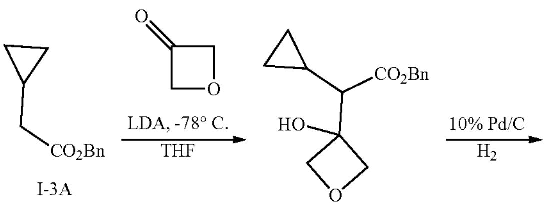

I-3A I-3B

-continued

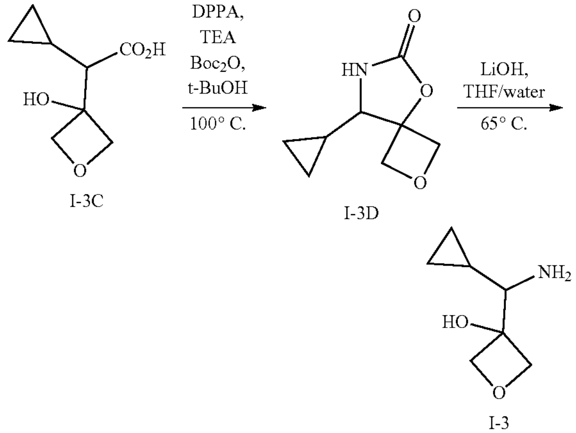

I-3C

I-3D

I-3

Step A: Benzyl (R and S)-2-cyclopropyl-2-(3-hydroxyoxetan-3-yl)acetate (I-3B)

To a solution of 2M LDA in THF/heptane/ethylbenzene (1.3 mL, 2.6 mmol) in 2.0 mL THF was added a solution of benzyl 2-cyclopropylacetate (0.25 g, 1.3 mmol) in 2.0 mL THF dropwise at −78° C. The mixture was stirred for 1 h while cooled at −78° C. To this solution was added oxetan-3-one (0.11 g, 1.6 mmol) dropwise at −78° C. and the mixture was stirred for 2 h while cooled at −78° C. The excess LDA was quenched with aqueous saturated $NH_4C_1$ solution and diluted with EtOAc. The layers were separated, and the organic layer was washed with brine, dried over $Na_2SO_4$, and concentrated. The residue was purified by silica gel chromatography (0-100% EtOAc/Hex gradient) to afford compound I-3B. MS: m/z=263.2 (M+1).

Step B: (R and S)-2-Cyclopropyl-2-(3-hydroxyoxetan-3-yl)acetic acid (I-3C)

To a solution of benzyl (R and S)-2-cyclopropyl-2-(3-hydroxyoxetan-3-yl)acetate (I-3B, 130 mg, 0.496 mmol) in EtOAc (2.47 mL) under nitrogen was added 10 wt % Pd/C (11 mg, 0.099 mmol) at ambient temp. The reaction was hydrogenated under a balloon of hydrogen gas for 2 h to obtain compound I-3C.

Step C: (R and S)-8-Cyclopropyl-2,5-dioxa-7-azaspiro[3.4]octan-6-one (I-3D)

To a solution of (R and S)-2-cyclopropyl-2-(3-hydroxyoxetan-3-yl)acetic acid (I-3C, 83 mg, 0.48 mmol) and di-tert-butyl dicarbonate (0.11 mL, 0.48 mmol) in t-butanol (2.4 mL) was added triethylamine (0.13 mL, 0.96 mmol) and diphenylphosphoryl azide (0.16 mL, 0.72 mmol). The reaction mixture was heated at 100° C. for 2 h then concentrated. The residue was purified by silica gel chromatography (0-100% EtOAc/Hexane gradient, ELSD) to provide compound I-3D. $^1$H NMR (500 MHz, DMSO-$d_6$) δ 7.94 (s, 1H), 5.06 (d, J=7.8 Hz, 1H), 4.70-4.60 (m, 3H), 3.38 (d, J=8.4 Hz, 1H), 2.50 (d, J=3.4 Hz, 7H), 0.94 (ddt, J=13.0, 8.2, 4.1 Hz, 1H), 0.53 (ddtt, J=40.4, 23.7, 9.1, 4.5 Hz, 3H), 0.18 (dq, J=9.2, 4.8 Hz, 1H).

Step D: (R and S)-3-(amino(cyclopropyl)methyl)oxetan-3-ol (I-3)

To a solution of (R and S)-8-cyclopropyl-2,5-dioxa-7-azaspiro[3.4]octan-6-one (I-3D, 40 mg, 0.24 mmol) in THF (1.2 mL) and water (1.2 mL) was added LiOH (lithium hydroxide, 40 mg, 1.7 mmol). The mixture was heated at 65° C. for 16 h, and then additional LiOH (11 mg, mmol) was added and the reaction heated at 65° C. for 16 h more. The reaction was concentrated to afford compound I-3.

Intermediate I-4

I-4

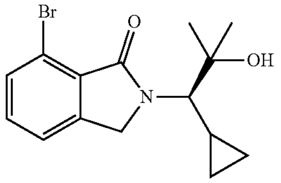

(R)-7-Bromo-2-(1-cyclopropyl-2-hydroxy-2-methylpropyl)isoindolin-1-one (I-4)

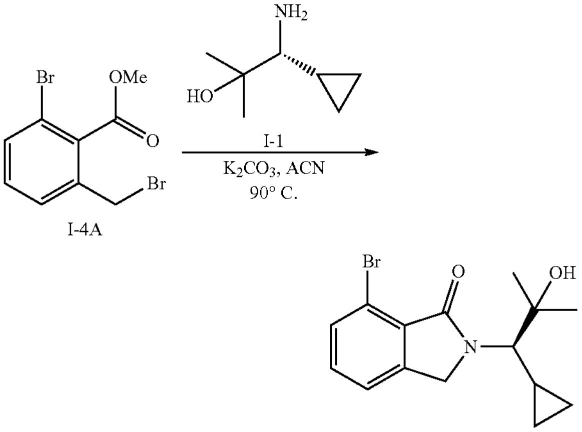

I-4A

I-4

To a solution of (R)-1-amino-1-cyclopropyl-2-methylpropan-2-ol (I-1, 100 g, 0.26 mol) in ACN (0.50 L) was added methyl 2-bromo-6-(bromomethyl)benzoate (94 g, 0.31 mol) and $K_2CO_3$ (potassium carbonate, 70 g, 0.51 mol). The mixture was heated at 90° C. for 12 h. The reaction was diluted with water (1.0 L), extracted with ethyl acetate (1.0 L, 0.50 L) and the combined organic layers were washed with brine (1.0 L) and dried over with $Na_2SO_4$ and concentrated. The residue was purified by silica gel chromatography (0-50% EtOAc/Hexane gradient) to provide compound I-4. MS: m/z=324.1, 326.1 (M+1). $^1$H NMR (400 MHz, DMSO-$d_6$): δ=7.64 (d, J=7.6 Hz, 2H), 7.49 (t, J=7.6 Hz, 1H), 4.83 (d, J=18.8 Hz, 1H), 4.76 (s, 1H), 4.55 (d, J=18.8 Hz, 1H), 3.23 (d, J=10.4 Hz, 1H), 1.40-1.43 (m, 1H), 1.33 (s, 3H), 1.01 (s, 3H), 0.73-0.75 (m, 1H), 0.50-0.53 (m, 1H), 0.37-0.39 (m, 1H), −0.13–−0.11 (m, 1H).

Intermediates I-5 through I-12, found in Table 2, were made in a similar manner as that disclosed for intermediate I-4 where the resulting intermediate may have been synthesized from chiral or racemic amines or separated by chiral chromatography.

TABLE 2

| Intermediate Number | Structure | Compound Name | Observed Mass (M + 1) |
|---|---|---|---|
| I-5 | 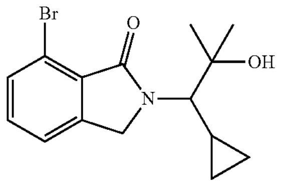 [SMILES: CC(C)(O)C(C1CC1)N1Cc2cccc(Br)c2C1=O] | (R and S)-7-bromo-2-(1-cyclopropyl-2-hydroxy-2-methylpropyl)isoindolin-1-one | 324.1, 326.1 |
| I-6 | 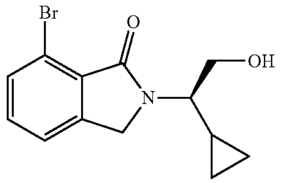 [SMILES: O=C1c2c(Br)cccc2CN1[C@@H](CO)C1CC1] | (R)-7-bromo-2-(1-cyclopropyl-2-hydroxyethyl)isoindolin-1-one | 296.1, 298.1 |
| I-7 | 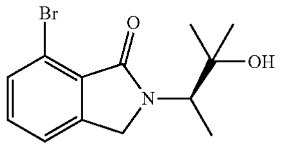 [SMILES: C[C@@H](N1Cc2cccc(Br)c2C1=O)C(C)(C)O] | (R)-7-bromo-2-(3-hydroxy-3-methylbutan-2-yl)isoindolin-1-one | 298.2, 300.2 |
| I-8 | 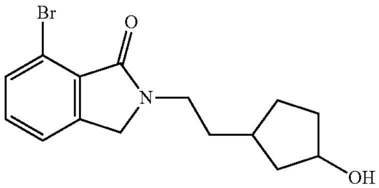 [SMILES: O=C1c2c(Br)cccc2CN1CCC1CCC(O)C1] | (cis and trans racemic)-7-bromo-2-(2-(3-hydroxycyclopentyl)ethyl)isoindolin-1-one | 324.2, 326.2 |
| I-9 | 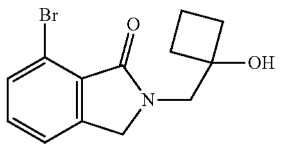 [SMILES: O=C1c2c(Br)cccc2CN1CC1(O)CCC1] | 7-bromo-2-((1-hydroxycyclobutyl)methyl)isoindolin-1-one | 296.0, 298.0 |
| I-10 | 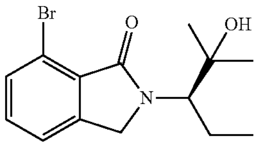 [SMILES: CC[C@@H](N1Cc2cccc(Br)c2C1=O)C(C)(C)O] | (R)-7-bromo-2-(2-hydroxy-2-methylpentan-3-yl)isoindolin-1-one | 312.0, 314.0 |
| I-11 | 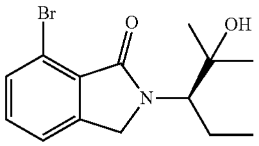 [SMILES: CC[C@@H](N1Cc2cccc(Br)c2C1=O)C(C)(C)O] | (R or S)-7-bromo-2-(1,1,1-trifluoro-3-hydroxy-3-methylbutan-2-yl)isoindolin-1-one | 384.1, 386.1 |
| I-12 | 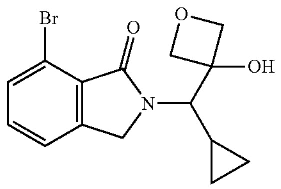 [SMILES: O=C1c2c(Br)cccc2CN1C(C1CC1)C1(O)COC1] | (R or S)-7-bromo-2-(cyclopropyl(3-hydroxyoxetan-3-yl)methyl)isoindolin-1-one | 338.1, 340.1 |

Intermediate I-13

I-13

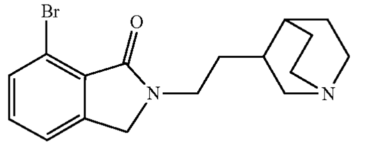

(R and S)-7-Bromo-2-(2-(quinuclidin-3-yl)ethyl) isoindolin-1-one (I-13)

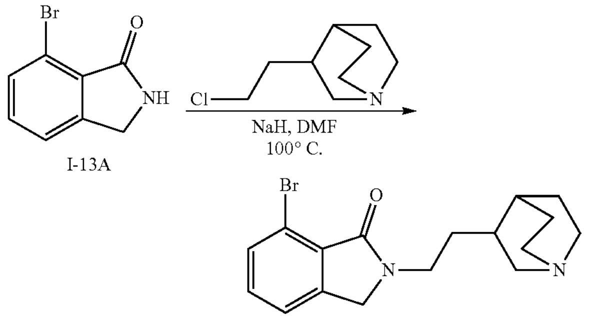

I-13A

I-13

To a solution of 7-bromoisoindolin-1-one (0.10 g, 0.47 mmol) in DMF (2.4 mL) at ambient temp was added 60 wt % NaH in mineral oil (sodium hydride, 57 mg, 1.4 mmol). The reaction was stirred for 5 min, at which point (R and S)-3-(2-chloroethyl)quinuclidine hydrochloride (0.15 g, 0.71 mmol) was added. The reaction was sealed and heated at 100° C. for 6 h. The reaction was cooled to ambient temp, and the excess NaH was quenched with water (5 ml), and then extracted with EtOAc (5 ml×3). The combined organic layers were concentrated, and the residue was purified by prep HPLC (30 cm×150 cm C18, 30 min, 0-95% acetonitrile-water gradient, 0.05% TFA added) to give compound I-13. MS: m/z=349.3 (M+1).

Intermediate I-14

I-14

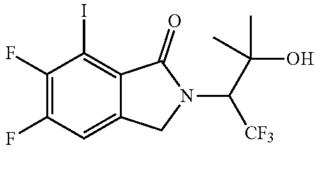

(R and S)-5,6-difluoro-7-iodo-2-(1,1,1-trifluoro-3-hydroxy-3-methylbutan-2-yl)isoindolin-1-one (I-14)

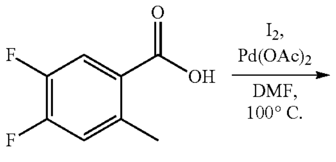

I-14A

-continued

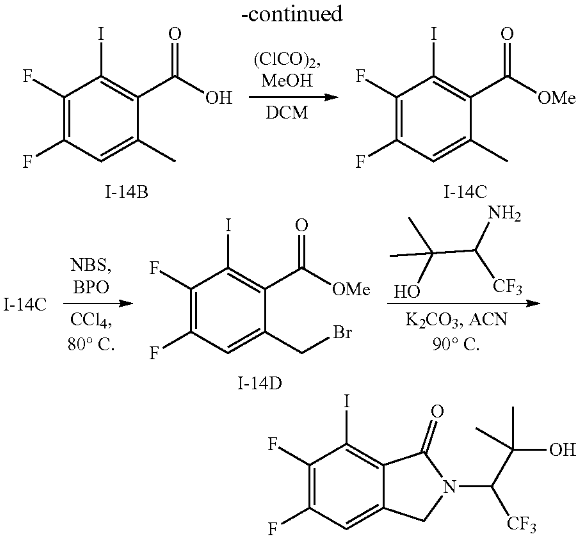

I-14B

I-14C

I-14C

I-14D

I-14

Step A: 3,4-Difluoro-2-iodo-6-methylbenzoic acid (I-14B)

To a solution of 4,5-difluoro-2-methylbenzoic acid (I-14A, 0.93 g, 5.4 mmol) in DMF (15 mL) were added $Pd(OAc)_2$ (palladium(II) acetate, 60 mg, 0.27 mmol), 12 (1.6 g, 6.5 mmol), and $PhI(OAc)_2$ ((diacetoxyiodo)benzene, 2.1 g, 6.5 mmol) at ambient temp under nitrogen atmosphere. The reaction mixture was heated at 100° C. for 16 h. The resulting solution was cooled to ambient temp and diluted with 1N aq. HCl (30 mL), then extracted with EtOAc (3×50 mL). The combined organic layers were dried over $Na_2SO_4$ and concentrated. The residue was purified by prep HPLC (C18, 20-75% ACN/water gradient, 0.1% TFA added) to afford compound I-14B. $^1H$ NMR (500 MHz, Chloroform-d) δ 7.07 (dd, J=10.2, 7.2 Hz, 1H), 2.44 (s, 3H).

Step B: Methyl 3,4-difluoro-2-iodo-6-methylbenzoateoate (I-14C)

To a solution of 3,4-difluoro-2-iodo-6-methylbenzoic acid (I-14B, 1.0 g, 3.5 mmol) in DCM (35 mL) cooled at 0° C. under nitrogen atmosphere were added $(ClCO)_2$ (2M oxalyl chloride in DCM, 6.9 mL, 14 mmol) and DMF (catalytic, 5 drops). The mixture solution was cooled at 0° C. for 2 h under nitrogen atmosphere then added dropwise to $CH_3OH$ (210 mL) at 0° C. After stirring for 10 minutes the reaction was concentrated to provide compound I-14C. $^1H$ NMR (500 MHz, Chloroform-d) δ 7.06-6.99 (m, 1H), 3.96 (s, 3H), 2.32 (s, 3H).

Step C: methyl 6-(bromomethyl)-3,4-difluoro-2-iodobenzoate (I-14D)

To a solution of methyl 3,4-difluoro-2-iodo-6-methylbenzoate (I-14C, 1.1 g, 0.3.5 mmol) in $CCl_4$ (35 mL) were added NBS (0.74 g, 4.2 mmol) and benzoyl peroxide (84 mg, 0.35 mmol) at ambient temperature. The reaction mixture was heated at 80° C. for 16 h. The resulting mixture was concentrated, and the residue was purified by a silica gel column chromatography (0-10% EtOAc/Hexane gradient)

to provide compound I-14D. $^1$H NMR (500 MHz, Chloroform-d) δ 7.32-7.26 (m, 1H), 4.44 (s, 2H), 4.01 (s, 3H).

Step D: (R and S)-5,6-Difluoro-7-iodo-2-(1,1,1-trifluoro-3-hydroxy-3-methylbutan-2-yl)isoindolin-1-one (I-14)

A mixture of methyl 6-(bromomethyl)-3,4-difluoro-2-iodobenzoate (I-14D, 200 mg, 0.51 mmol), (R and S)-3-amino-4,4,4-trifluoro-2-methylbutan-2-ol oxalate (I-74, 140 mg, 0.56 mmol), and potassium carbonate (210 mg, 1.5 mmol) in acetonitrile (5.1 mL) was heated at 90° C. for 16 h. The cooled reaction was diluted with water (15 mL) and extracted with EtOAc (3×10 mL). The combined organic layers were dried over $Na_2SO_4$ and concentrated. The residue was purified by silica gel column chromatography (0-60% EtOAc/hexane gradient) to afford the racemic mixture of compound I-14. The racemic mixture was purified by Chiral-Prep-HPLC (ES Industries AD-H, 30 mm×250 mm, 5 um; 20% MeOH (0.1% DEA) isocratic gradient). The second product-containing fractions were isolated to give the chiral compound I-14. MS (ESI): m/z=436.0 (M+1). $^1$H-NMR (300 MHz, Chloroform-d): δ 7.32-2.27 (m, 1H), 5.01-4.88 (m, 2H), 4.48-4.42 (m, 1H), 1.60 (s, 3H), 1.28 (s, 3H). $^{19}$F-NMR (282 MHz, Chloroform-d): δ-63.87 (s, 1F), −116.94 (d, 1F), −126.89 (d, 1F).

Intermediates I-15 through I-19 as shown in Table 3, were synthesized in an analogous manner as described for intermediate I-14 where the resulting intermediate may have been synthesized from chiral or racemic material or separated by chiral chromatography.

TABLE 3

| Intermediate Number | Structure | Compound Name | Observed Mass (M + 1) |
|---|---|---|---|
| I-15 | 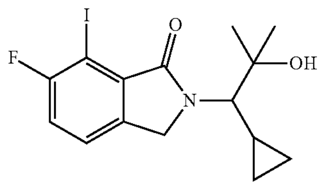 [SMILES: CC(C)(O)C(C1CC1)N1Cc2ccc(F)c(I)c2C1=O] | (R or S)-2-(1-cyclopropyl-2-hydroxy-2-methylpropyl)-6-fluoro-7-iodoisoindolin-1-one | 390.0 |
| I-16 | 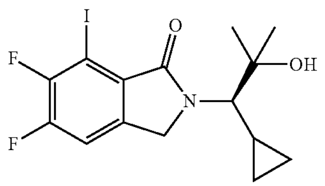 [SMILES: CC(C)(O)[C@@H](C1CC1)N1Cc2cc(F)c(F)c(I)c2C1=O] | (R)-2-(1-cyclopropyl-2-hydroxy-2-methylpropyl)-5,6-difluoro-7-iodoisoindolin-1-one | 408.0 |
| I-17 | 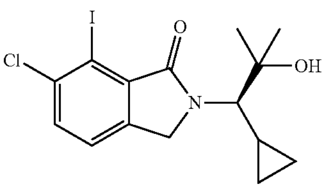 [SMILES: CC(C)(O)[C@@H](C1CC1)N1Cc2ccc(Cl)c(I)c2C1=O] | (R)-6-chloro-2-(1-cyclopropyl-2-hydroxy-2-methylpropyl)-7-iodoisoindolin-1-one | 406.0 |
| I-18 | 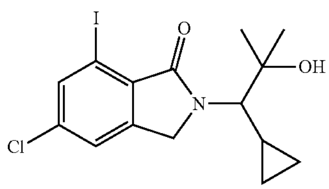 [SMILES: CC(C)(O)C(C1CC1)N1Cc2cc(Cl)cc(I)c2C1=O] | (R or S)-5-chloro-2-(1-cyclopropyl-2-hydroxy-2-methylpropyl)-7-iodoisoindolin-1-one | 406.0 |
| I-19 | 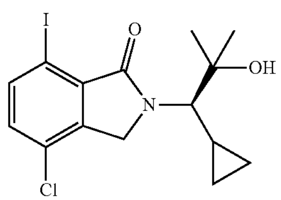 [SMILES: CC(C)(O)[C@@H](C1CC1)N1Cc2c(Cl)ccc(I)c2C1=O] | (R)-4-chloro-2-(1-cyclopropyl-2-hydroxy-2-methylpropyl)-7-iodoisoindolin-1-one | 406.0 |

TABLE 3-continued

| Intermediate Number | Structure | Compound Name | Observed Mass (M + 1) |
|---|---|---|---|
| I-75 | 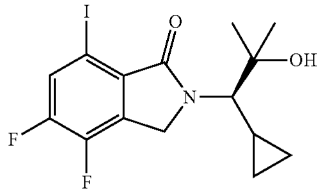 [SMILES: CC(C)(O)[C@@H](C1CC1)N1Cc2c(F)c(F)cc(I)c2C1=O] | (R)-2-(1-cyclopropyl-2-hydroxy-2-methylpropyl)-4,5-difluoro-7-iodoisoindolin-1-one | 408.1 |

Intermediate I-20

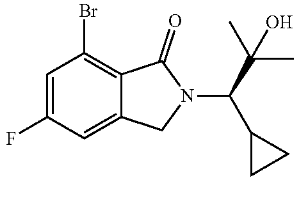

I-20

(R)-7-Bromo-2-(1-cyclopropyl-2-hydroxy-2-methylpropyl)-5-fluoroisoindolin-1-one (I-20)

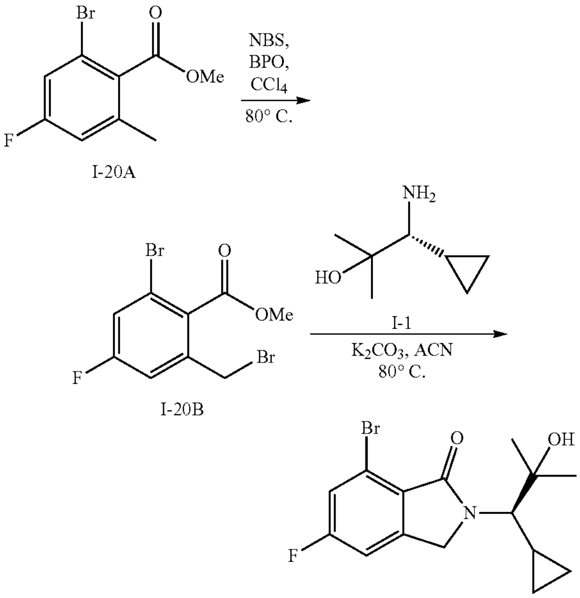

I-20A

I-20B

I-20

Step A: Methyl 2-bromo-6-(bromomethyl)-4-fluorobenzoate (I-20B)

To a solution of methyl 2-bromo-4-fluoro-6-methylbenzoate (I-20A, 110 g, 0.37 mol) in $CCl_4$ (0.60 L) were added NBS (87 g, 0.49 mol) and benzoyl peroxide (12 g, 0.037 mol) at ambient temp. The reaction solution was heated at 80° C. for 12 h. The resulting cooled mixture was diluted with water (500 mL) and extracted with DCM (200 mL, 100 mL). The combined organic layers were washed with brine (200 mL), dried over $Na_2SO_4$ and filtered. The filtrate was concentrated to afford compound I-20B. $^1$H-NMR (400 MHz, $CDCl_3$) δ 7.42 (q, J=5.2 Hz, 1H), 7.09 (t, J=7.6 Hz, 1H), 4.48 (s, 2H), 4.02 (s, 3H)

Step B: (R)-7-Bromo-2-(1-cyclopropyl-2-hydroxy-2-methylpropyl)-5-fluoroisoindolin-1-one (I-20)

To a solution of methyl 2-bromo-6-(bromomethyl)-4-fluorobenzoate (I-20B, 32 g, 0.087 mol) in ACN (0.19 L) were added (R)-1-amino-1-cyclopropyl-2-methylpropan-2-ol 2,2,2-trifluoroacetate (32 g, 0.079 mol) and $K_2CO_3$ (22 g, 0.16 mol) at ambient temp. The reaction solution was heated at 80° C. for 12 h. The resulting mixture was poured into water (200 mL) and extracted with ethyl acetate (150 mL, 100 mL, 50 mL). The combined organic layers were washed with brine (150 mL), dried over with $Na_2SO_4$ and concentrated. The residue was purified by a silica gel column chromatography (0-50% EtOAc/Hexane gradient) to provide compound I-MS: m/z=390.1 (M+1). $^1$H-NMR (400 MHz, DMSO-$d_6$) δ 7.62-7.64 (m, 1H), 7.46 (t, J=8.4 Hz, 1H), 4.76 (t, J=8.8 Hz, 2H), 4.48 (d, J=18.8 Hz, 1H), 3.24 (d, J=10.4 Hz, 1H), 1.40-1.42 (m, 1H), 1.33 (s, 3H), 1.01 (s, 3H), 0.74-0.76 (m, 1H), 0.50-0.52 (m, 1H), 0.37-0.39 (m, 1H), −0.13∼−0.11 (m, 1H).

Intermediates I-21 through I-23 found in Table 4 were synthesis in an analogous manner to that depicted for Intermediate I-20 where the resulting intermediate may have been synthesized from chiral or racemic material or separated by chiral chromatography.

TABLE 4

| Intermediate Number | Structure | Compound Name | Observed Mass (M + 1) |
|---|---|---|---|
| I-21 | 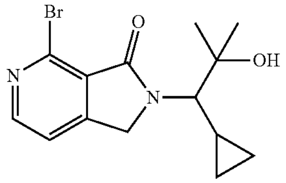 [SMILES: CC(C)(O)C(C1CC1)N1Cc2ccnc(Br)c2C1=O] | (R or S)-4-bromo-2-(1-cyclopropyl-2-hydroxy-2-methylpropyl)-1H-pyrrolo[3,4-c] pyridin-3(2H)-one | 325.0, 327.0 |
| I-22 | 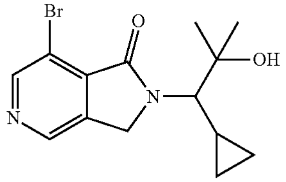 [SMILES: CC(C)(O)C(C1CC1)N1Cc2cncc(Br)c2C1=O] | (R or S)-7-bromo-2-(1-cyclopropyl-2-hydroxy-2-methylpropyl)-2,3-dihydro-1H-pyrrolo[3,4-c]pyridin-1-one | 325.0, 327.0 |
| I-23 | 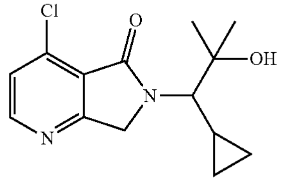 | (R or S)-4-chloro-6-(1-cyclopropyl-2-hydroxy-2-methylpropyl)-6,7-dihydro-5H-pyrrolo[3,4-b]pyridin-5-one | 281.2 |

Intermediate I-24

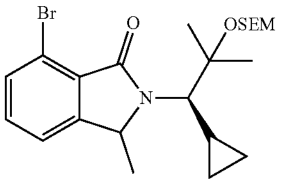

I-24

(R or S)-7-Bromo-2-((R)-1-cyclopropyl-2-methyl-2-((2-(trimethylsilyl)ethoxy)methoxy)propyl)-3-methylisoindolin-1-one (I-24)

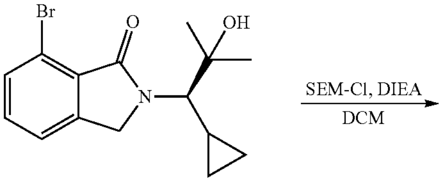

I-4

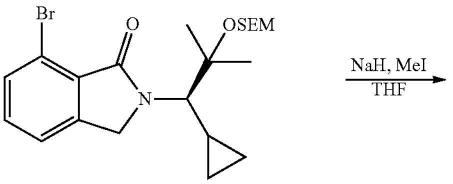

I-24B

-continued

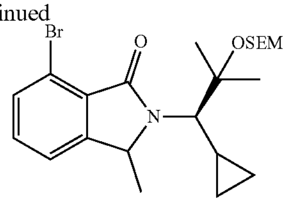

I-24

Step A: (R)-7-Bromo-2-(1-cyclopropyl-2-methyl-2-((2-(trimethylsilyl)ethoxy)methoxy)propyl)isoindolin-1-one (I-24B)

To a solution of (R)-7-bromo-2-(1-cyclopropyl-2-hydroxy-2-methylpropyl)isoindolin-1-one (I-4, 0.20 g, 0.62 mmol) in DCM (1.0 mL) were added DIEA (0.24 g, 1.8 mmol) and (2-(chloromethoxy)ethyl)trimethylsilane (0.21 g, 1.2 mmol) at 0° C. The reaction was stirred for 16 h at ambient temp. The resulting mixture was diluted with water (10 ml) and extracted with EtOAc (3×20 mL). The combined organic layers were washed with brine (20 mL), dried over $Na_2SO_4$ and concentrated. The residue was purified by silica gel column chromatography (0-40% EtOAc/Hexane gradient) to provide compound I-24B. MS: m/z=454.05 and 456.05 (M+1).

Step B: (R or S)-7-Bromo-2-((R)-1-cyclopropyl-2-methyl-2-((2-(trimethylsilyl)ethoxy)methoxy)propyl)-3-methylisoindolin-1-one (I-24)

60 wt % sodium hydride in mineral oil (66 mg, 1.6 mmol) was added to a solution of (R)-7-bromo-2-(1-cyclopropyl-2-methyl-2-((2-(trimethylsilyl)ethoxy)methoxy)propyl) isoindolin-1-one (I-24B, 0.25 g, 0.55 mmol) in THF (1.5 mL) cooled at 0° C. The reaction was stirred for 2 h at ambient temp. Iodomethane (0.39 g, 2.8 mmol) was added and the reaction was stirred for 16 h at ambient temp. The excess NaH was quenched by the addition of water (30 mL) and extracted with EtOAc (3×40 mL). The combined organic layers were washed with brine (20 mL), dried over $Na_2SO_4$ and concentrated. The residue was purified by silica gel column chromatography (0-20% EtOAc/Hexane gradient) to provide compound I-24. MS: m/z=468.3 and 470.3 (M+1).

Intermediate 25

I-25

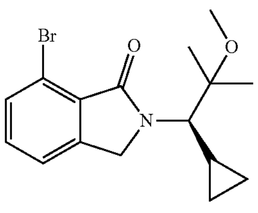

(R)-7-Bromo-2-(1-cyclopropyl-2-methoxy-2-methylpropyl)isoindolin-1-one (I-25)

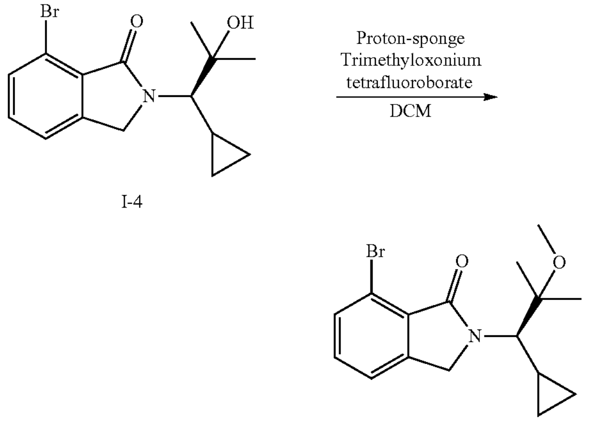

I-4

I-25

To a solution of (R)-7-bromo-2-(1-cyclopropyl-2-hydroxy-2-methylpropyl)isoindolin-1-one (I-4, 0.20 g, 0.62 mmol) in DCM (4.0 mL) were added 1,8-bis(dimethylamino)naphthalene (0.13 mg, 0.62 mmol) and trimethyloxonium tetrafluoroborate (0.18 g, 1.2 mmol) and the mixture was stirred at ambient temp for 16 h under nitrogen. The reaction was concentrated, and the residue was purified by prep TLC (2:1 EtOAc/Hexanes) to give compound I-25. MS: m/z=348.10, 340.10 (M+1). $^1$H-NMR (300 MHz, Chloroform-d): δ 7.63-7.60 (m, 1H), 7.44-7.35 (m, 2H), 4.82-4.55 (m, 2H), 3.55-3.50 (m, 1H), 3.26 (s, 3H), 1.60-1.50 (m, 1H), 1.42 (s, 3H), 1.18 (s, 3H), 0.88-0.82 (m, 2H), 0.59-0.54 (m, 1H), 0.42-0.39 (m, 1H).

Intermediate I-26

I-26

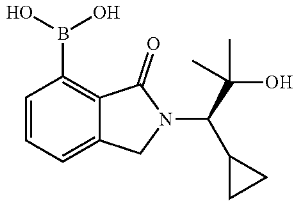

(R)-(2-(1-Cyclopropyl-2-hydroxy-2-methylpropyl)-3-oxoisoindolin-4-yl)boronic acid (I-26)

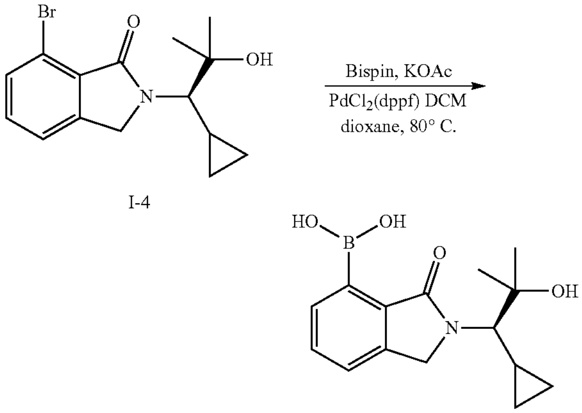

I-4

I-26

A solution of (R)-7-bromo-2-(1-cyclopropyl-2-hydroxy-2-methylpropyl)isoindolin-1-one (0.30 g, 0.92 mmol), BISPIN (0.47 g, 1.8 mmol), $PdCl_2$(dppf)-$CH_2Cl_2$ adduct ([1,1'-Bis(diphenylphosphino)ferrocene]palladium(II) dichloride-dichloromethane adduct, 38 mg, mmol) and potassium acetate (0.23 g, 2.3 mmol) under nitrogen in dioxane (4.6 mL) was heated at 80° C. for 3 h. The reaction was diluted with water (20 mL) and extracted with ethyl acetate (20 mL, 20 mL). The combined organic layers were washed with brine (20 mL), dried over $Na_2SO_4$ and concentrated. The residue was purified by silica gel chromatography (0-100% EtOAc/Hexane gradient) to provide compound I-26. MS: m/z=290.3 (M+1).

Intermediate I-27

I-27

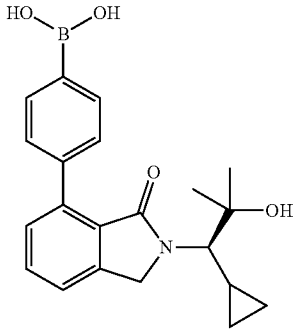

(R)-(4-(2-(1-Cyclopropyl-2-hydroxy-2-methylpropyl)-3-oxoisoindolin-4-yl)phenyl)boronic acid (I-27)

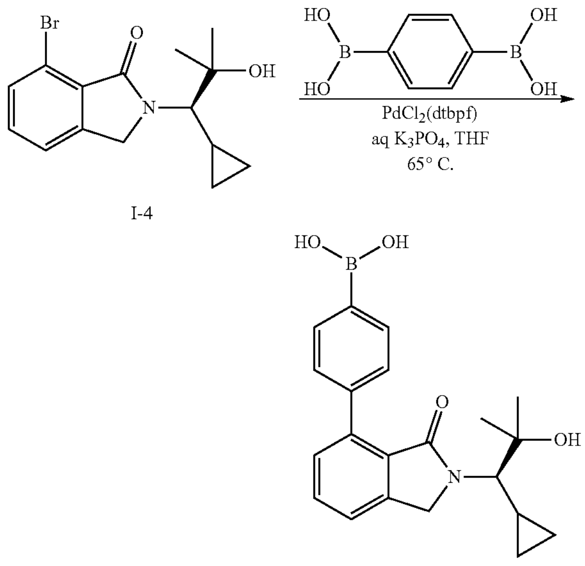

I-4

I-27

A solution of (R)-7-bromo-2-(1-cyclopropyl-2-hydroxy-2-methylpropyl)isoindolin-1-one (I-4, 0.40 g, 1.2 mmol), 1,4-phenylenediboronic acid (0.61 g, 3.7 mmol), 1,1'-bis(di-t-butylphosphino)ferrocene palladium(II) dichloride (38 mg, 0.046 mmol) and $K_3PO_4$ (1.0 mL, 3.1 mmol) in THF (6.2 mL) under nitrogen was heated at 65° C. for 16 h. The reaction was diluted with water (20 mL) and acidified with 1N aq HCl. The aqueous layer was extracted with ethyl acetate (2×20 mL) and the combined organic layers were washed with brine (20 mL), dried over $Na_2SO_4$ and concentrated to afford compound I-27. MS: m/z=366.4 (M+1).

Intermediate I-28

I-28

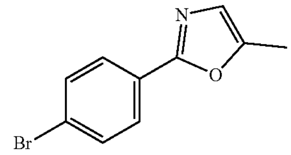

2-(4-Bromophenyl)-5-methyloxazole (I-28)

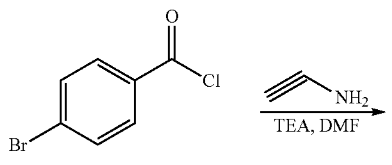

I-28A

-continued

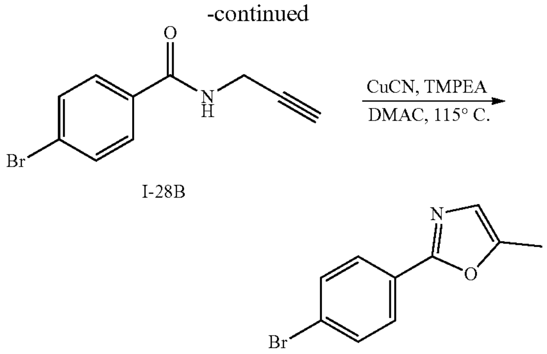

I-28B

I-28

Step A: 4-Bromo-N-(prop-2-yn-1-yl)benzamide (I-28B)

To a stirred solution of 4-bromobenzoyl chloride (0.22 g, 1.0 mmol) in DCM (2.0 mL) was added prop-2-yn-1-amine (66 mg, 1.2 mmol) and triethylamine (0.14 mL, 1.0 mmol) at 0° C. and the resulting mixture was stirred at ambient temp for 3 h. The reaction mixture was partitioned between ethyl acetate (40 mL) and brine (5 mL). The organic layer was dried over $Na_2SO_4$ and concentrated. The residue was purified by purified by prep TLC (50% EtOAc/PE) to give compound I-28B. MS: m/z=236.0 and 238.0 (M−1). $^1$H-NMR (400 MHz, DMSO-$d_6$): δ 9.05-9.02 (m, 1H), 7.83-7.80 (m, 2H), 7.72-7.69 (m, 2H), 4.07-4.05 (m, 2H), 3.15-3.14 (m, 1H).

Step B: 2-(4-Bromophenyl)-5-methyloxazole (I-28)

A mixture of 4-bromo-N-(prop-2-yn-1-yl) benzamide (I-28B, 0.15 g, 0.63 mmol), copper(I) cyanide (73 mg, 0.82 mmol) and 2-(3,4,5-trimethoxyphenyl) ethanamine (0.60 g, 2.8 mmol) in DMA (2.0 mL) was heated at 115° C. for 16 h. The reaction mixture was diluted with ethyl acetate (40 mL), the organic layer was washed with brine (5 mL), dried over $Na_2SO_4$ and concentrated. The residue was purified by purified by prep TLC (50% EtOAc/PE) to give compound I-28. MS: m/z=238.0 and 240.0 (M+1). $^1$H-NMR (400 MHz, DMSO-$d_6$): δ 7.94-7.80 (m, 2H), 7.77-7.70 (m, 2H), 7.02-7.00 (m, 1H), 2.39 (s, 3H).

Intermediate I-29

I-29

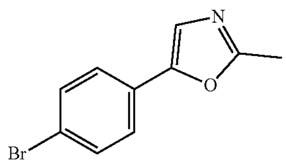

5-(4-Bromophenyl)-2-methyloxazole (I-29)

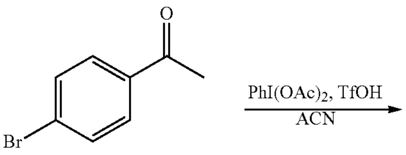

I-29A

-continued

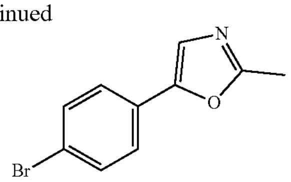

I-29

To a stirred solution of 1-(4-bromophenyl)ethanone (I-29A, 1.0 g, 5.0 mmol) in acetonitrile (2.0 mL) was added trifluoromethanesulfonic acid (1.3 mL, 15 mmol), and the mixture was stirred at ambient temp for 10 min. (Diacetoxyiodo)benzene (1.8 mL, 7.5 mmol) in ACN (2.0 mL) was then added and the resulting mixture was heated at 80° C. for 1.5 h. The residue obtained after removing the solvent was diluted with DCM (200 mL), and the organic layer was washed with saturated aqueous $NaHCO_3$ solution (50 ml), dried over $MgSO_4$, and concentrated. The residue was purified by silica gel column chromatography (0-17% EtOAc/PE gradient) to provide compound I-29. MS: m/z=237.9, 239.9 (M+1). $^1H$ NMR (300 MHz, $CDCl_3$) δ 7.82 (s, 1H), 7.61-7.50 (m, 4H), 2.53 (s, 3H).

Intermediate I-30

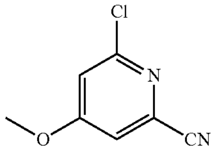

6-Chloro-4-methoxypicolinonitrile (I-30)

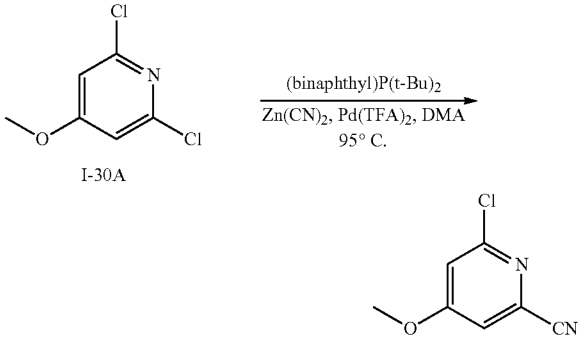

I-30A

I-30

Argon was bubbled through a mixture of 2,6-dichloro-4-methoxypyridine (I-30A, 0.18 g, mmol), zinc cyanide (0.038 mL, 0.60 mmol) and rac-2-(di-t-butylphosphino)-1,1'-binaphthyl (36 mg, 0.089 mmol) in DMA (2.0 mL) for 10 min. Then palladium (II) trifluoroacetate (16 mg, 0.050 mmol) was added and the mixture was heated at 95° C. for 16 h. The reaction mixture was diluted with ethyl acetate (30 mL), then washed with brine (3×5 mL). Subsequently, the organic layer was washed with saturated aqueous $NaHCO_3$ solution (50 ml), dried over $Na_2SO_4$ and concentrated. The residue was purified by preparative TLC (developed by PE/EtOAc 3:1) to provide compound I-30. MS: m/z=169.00 (M+1).

Intermediate I-31

I-31

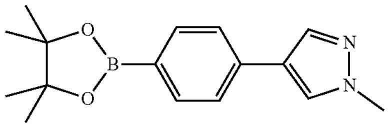

1-Methyl-4-(4-(4,4,5,5-tetramethyl-1,3,2-dioxaborolan-2-yl)phenyl)-1H-pyrazole (I-31)

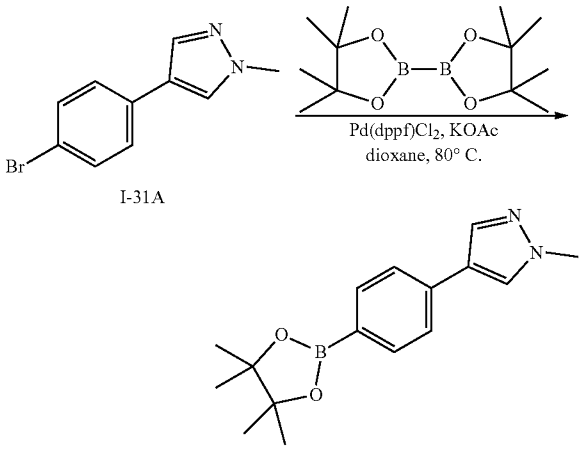

I-31A

I-31

A mixture of 4-(4-bromophenyl)-1-methyl-1H-pyrazole (I-31A, 0.50 g, 2.1 mmol), 4,4,4',4',5,5,5',5'-octamethyl-2,2'-bi(1,3,2-dioxaborolane) (0.64 g, 2.5 mmol), potassium acetate (0.36 mL, 5.7 mmol) and [1,1'-bis(diphenylphosphino)ferrocene]dichloropalladium (II) (0.15 g, mmol) in dioxane (5.0 mL) under nitrogen was heated at 80° C. for 16 h. The reaction mixture was cooled down to ambient temperature, diluted with water (50 mL) and extracted with ethyl acetate (3×50 mL). The combined organic layers were washed with brine (3×50 mL), dried over $Na_2SO_4$ and concentrated. The residue was purified by silica gel column chromatography (0-50% EtOAc/PE gradient) to provide compound I-31. MS: m/z=285.3 (M+1). $^1H$-NMR (400 MHz, Chloroform-d): δ 7.83-7.81 (m, 3H), 7.68 (s, 1H), 7.51-7.48 (m, 2H), 3.97 (s, 3H), 1.37 (s, 12H).

Intermediate compounds I-32 and I-33 as shown in Table 5, were synthesized in a process analogous to that depicted for intermediate I-31.

TABLE 5

| Intermediate Number | Structure | Compound Name | Observed Mass (M + 1) |
|---|---|---|---|
| 32 | 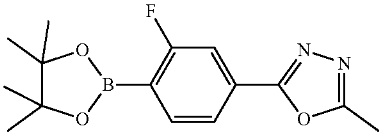 | 2-(3-fluoro-4-(4,4,5,5-tetramethyl-1,3,2-dioxaborolan-2-yl)phenyl)-5-methyl-1,3,4-oxadiazole | 305.2 |
| 33 | 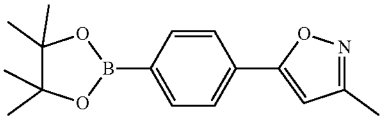 | 3-methyl-5-(4-(4,4,5,5-tetramethyl-1,3,2-dioxaborolan-2-yl)phenyl)isoxazole | 286.1 |

Intermediate I-34

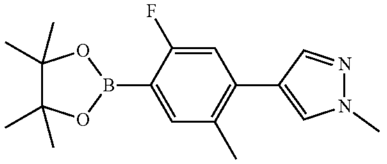

(I-34)

4-(5-Fluoro-2-methyl-4-(4,4,5,5-tetramethyl-1,3,2-dioxaborolan-2-yl)phenyl)-1-methyl-1H-pyrazole (I-34)

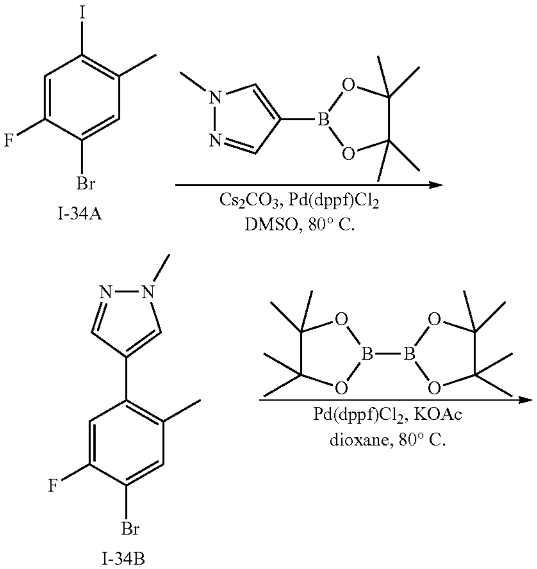

-continued

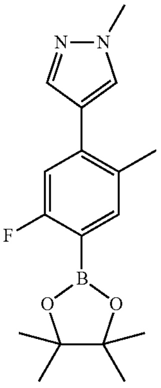

I-34

Step A: 4-(4-Bromo-5-fluoro-2-methylphenyl)-1-methyl-1H-pyrazole (I-34B)

A deoxygenated mixture of 1-bromo-2-fluoro-4-iodobenzene (I-34A, 0.50 g, 1.7 mmol), 1-methyl-4-(4,4,5,5-tetramethyl-1,3,2-dioxaborolan-2-yl)-1H-pyrazole (0.24 g, 1.2 mmol), [1,1'-bis(diphenylphosphino)ferrocene]dichloropalladium (II) (0.12 g, 0.17 mmol), and cesium carbonate (1.6 g, 5.0 mmol) in DMSO (5.0 mL) was heated at 80° C. for 1 h. The reaction mixture was diluted with ethyl acetate (80 mL), then washed with brine (5×5 mL) dried over $Na_2SO_4$ and concentrated. The residue was purified by silica gel column chromatography (10-40% EtOAc/Hexane gradient) to provide compound I-34B. MS: m/z=269.1, 271.1 (M+1). $^1$H-NMR (300 MHz, Chloroform-d): δ 7.63 (s, 1H), 7.49 (s, 1H), 7.44-7.42 (m, 1H), 7.11-7.08 (m, 1H), 3.99 (s, 3H), 2.36 (s, 3H). $^{19}$F-NMR (282 MHz, Chloroform-d): 6-112.71 (s, 1F).

Step B: 4-(5-Fluoro-2-methyl-4-(4,4,5,5-tetramethyl-1,3,2-dioxaborolan-2-yl)phenyl)-1-methyl-1H-pyrazole (I-34)

A deoxygenated mixture of 4,4,4',4',5,5,5',5'-octamethyl-2,2'-bi(1,3,2-dioxaborolane) (0.33 g, 1.3 mmol), 4-(4-bromo-5-fluoro-2-methylphenyl)-1-methyl-1H-pyrazole (I-34B, 0.29 g, 1.1 mmol), [1,1'-bis(diphenylphosphino)ferrocene]dichloropalladium (II) (79 mg, 0.11 mmol) and potassium acetate (0.29 g, 2.9 mmol) in 1,4-dioxane (3.0 mL) was heated at 80° C. for 16 h. The reaction mixture was diluted with ethyl acetate (30 mL), then washed with brine (3×5 mL), dried over $Na_2SO_4$ and concentrated. The residue was purified by prep TLC (1:3 EtOAc/PE) to give compound I-34. MS: m/z=317.1 (M+1). $^1$H-NMR (400 MHz, Chloroform-d): δ 7.69 (s, 1H), 7.62-7.60 (m, 1H), 7.55 (s, 1H), 7.06-7.02 (m, 1H), 4.00 (s, 3H), 2.40 (s, 3H), 1.40 (s, 12H). $^{19}$F-NMR (376 MHz, Chloroform-d): δ-107.88 (s, 1F).

Intermediate I-35

I-35

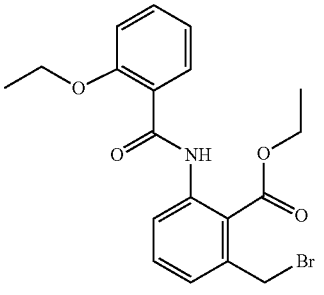

Ethyl 2-(bromomethyl)-6-(2-ethoxybenzamido)benzoate (I-35)

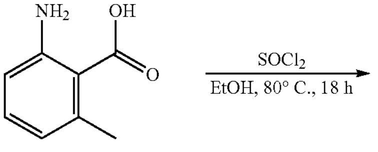

I-35A

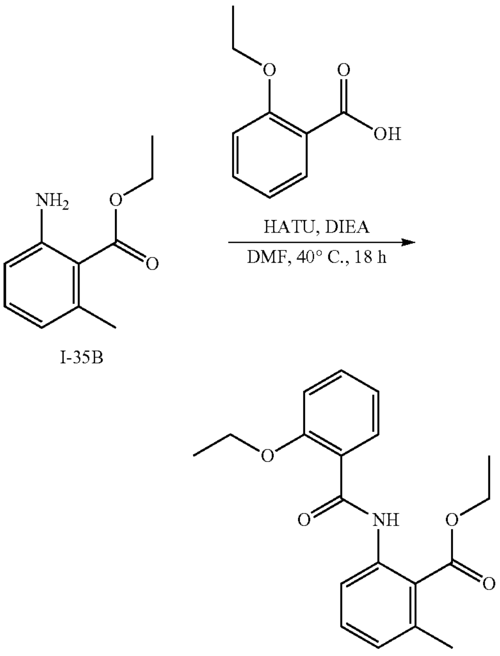

I-35B

I-35C

-continued

I-35C

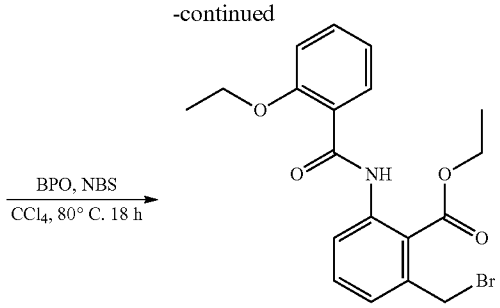

I-35

Step A: Ethyl 2-amino-6-methylbenzoate (I-35B)

To a solution of 2-amino-6-methylbenzoic acid (I-35A, 1.0 g, 6.6 mmol) in EtOH (10 mL) was added sulfurous dichloride (0.79 g, 6.6 mmol) and the mixture was heated at 80° C. for 18 h. The resulting mixture was concentrated. The residue was diluted with EtOAc (50 mL). The resulting mixture was washed with aq. saturated $NaHCO_3$ solution (3×20 mL). The organic layer was dried over anhydrous $Na_2SO_4$ and concentrated. The residue was purified by silica gel column chromatography (0-20% EtOAc/Hexane gradient) to provide compound I-35B. MS: m/z=180.1 (M+1).

Step B: Ethyl 2-(2-ethoxybenzamido)-6-methylbenzoate

A mixture of methyl ethyl 2-amino-6-methylbenzoate (I-35B, 0.10 g, 0.56 mmol), DIEA (0.22 g, 1.7 mmol), 2-ethoxybenzoic acid (0.11 g, 0.67 mmol) and HATU (0.26 g, 0.67 mmol) in DMF (1 mL) was heated at 40° C. for 18 h. The reaction mixture was diluted with water (10 mL), extracted with EtOAc (3×5 mL). The combined organic layers were washed with brine (3×5 mL), dried over $Na_2SO_4$ and concentrated. The residue was purified by silica gel column chromatography (0-20% EtOAc/PE gradient) to provide compound I-35C. MS: m/z=328.2 (M+1).

Step C: Ethyl 2-(bromomethyl)-6-(2-ethoxybenzamido)benzoate (I-35)

To a solution of ethyl 2-(2-ethoxybenzamido)-6-methylbenzoate (I-35C, 2.0 g, 6.1 mmol) in $CCl_4$ (61 mL) were added NBS (1.1 g, 6.1 mmol) and BPO (0.80 g, 3.1 mmol) and the reaction mixture was heated at 80° C. for 18 h. The resulting mixture was concentrated, and the residue was purified by silica gel column chromatography (0-20% EtOAc/PE gradient) to provide compound I-35. MS: m/z=406, 408 (M+1). $^1$H NMR (300 MHz, DMSO-$d_6$) δ 10.42 (s, 1H), 7.96-7.84 (m, 2H), 7.59-7.45 (m, 2H), 7.36-7.25 (m, 1H), 7.22 (d, J=8.4 Hz, 1H), 7.12-7.05 (m, 1H), 4.84 (s, 2H), 4.40-4.25 (m, 4H), 1.41-1.48 (m, 3H), 1.27-1.22 (m, 3H).

Intermediate I-36 shown in Table 6, was made in accordance with an analogous method to that described for intermediate I-35.

TABLE 6

| Intermediate Number | Structure | Compound Name | Observed Mass (M + 1) |
|---|---|---|---|
| I-36 | 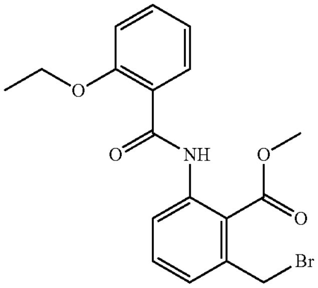 [SMILES: CCOc1ccccc1C(=O)Nc1cccc(CBr)c1C(=O)OC] | methyl 2-(bromomethyl)-6-(2-ethoxybenzamido)benzoate | 392, 394 |

Intermediate I-37

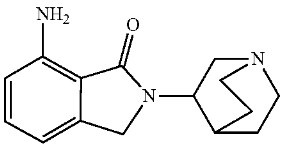

I-37

(R and S)-7-Amino-2-(quinuclidin-3-yl)isoindolin-1-one (1-37)

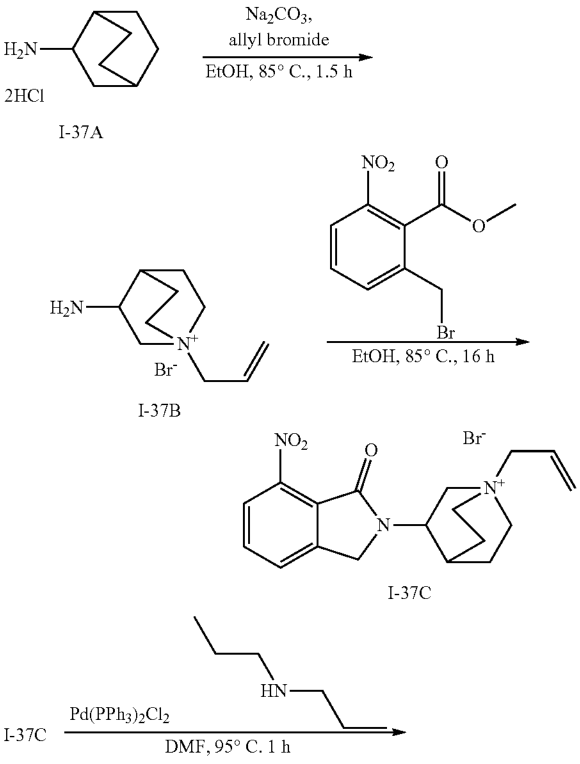

I-37A

I-37B

I-37C

I-37C

-continued

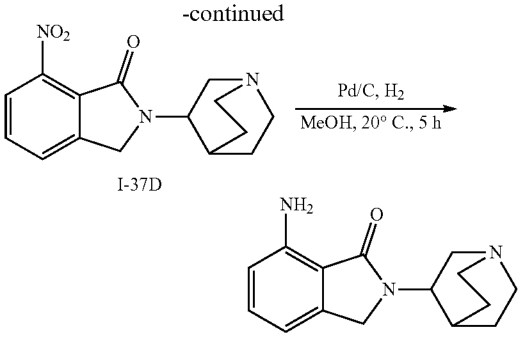

I-37D

I-37

Step A: (R and S)-7-Nitro-2-(quinuclidin-3-yl)isoindolin-1-one (I-37B)

A mixture of (R and S)-quinuclidin-3-amine (1-37A, 1.5 g, 7.5 mmol) in absolute EtOH (ethanol, 25 mL) with anhydrous sodium carbonate (3.2 g, 30 mmol) was heated at 85° C. for 1 h under argon. Then the reaction mixture was cooled to 0-5° C. and 3-bromoprop-1-ene (0.91 g, 7.5 mmol) was added. The reaction mixture was cooled at 0-5° C. for 15 min, at ambient temp for 30 min, and heated to 85° C. for 30 min. To the reaction mixture was added a solution of methyl 2-(bromomethyl)-6-nitrobenzoate (2.1 g, 7.5 mmol) in absolute EtOH (25 mL). The resulting mixture was heated at 85° C. for 16 h. The solvent was removed, and the residue was diluted with hot anhydrous DMF (50.0 mL). The resulting mixture was filtered. To the filtrate were added dipropylamine (4.2 g, 41 mmol) and $Pd(PPh_3)_2Cl_2$ (dichlorobis(triphenylphosphine)palladium(II), 0.26 g, 0.38 mmol). The reaction mixture was deoxygenated and heated at 95° C. for 1 h. The resulting mixture was concentrated, and the residue was partitioned between diethyl ether (50 mL) and 3N aq HCl (40 mL). The pH value of the aqueous solution was adjusted to pH 8 with 50% aq. NaOH solution. The resulting mixture was extracted with EtOAc (3x30 mL) and the combined organic layers were dried over $Na_2SO_4$ and concentrated to afford compound I-37B. MS: m/z=288.0 (M+1).

Step B: (R and S)-7-Amino-2-(quinuclidin-3-yl)isoindolin-1-one (I-37C)

To a deoxygenated solution of (R and S)-7-nitro-2-(quinuclidin-3-yl)isoindolin-1-one (1.2 g, 4.2 mmol) in MeOH (methanol, 20 mL) was added 10 wt % Pd/C (0.44 g, 4.2 mmol). The reaction mixture was degassed with hydrogen (3×) and stirred at ambient temp for 16 h under a balloon of hydrogen gas. The resulting mixture was filtrated over Celite® and the filtrate concentrated. The residue was purified by prep HPLC (19 mm×250 mm C18; 5.5 min, 10-60% ACN/water gradient, 10 mM $NH_4HCO_3$ added) to afford compound I-37. MS: m/z=258.2 (M+1). $^1$H NMR (300 MHz, $CDCl_3$) δ 7.23-7.18 (m, 1H), 6.70 (d, J=7.4 Hz, 1H), 6.57 (d, J=8.1 Hz, 1H), 5.21 (s, 2H), 4.59-4.41 (m, 2H), 4.38-4.30 (m, 1H), 3.39-3.29 (m, 1H), 3.11-2.81 (m, 2.14-2.05 (m, 1H), 1.92-1.62 (m, 3H), 1.61-1.49 (m, 1H).

Intermediate I-38 found in Table 7 was made using an analogous synthesis to that described for Intermediate I-37.

TABLE 7

| Intermediate Number | Structure | Compound Name | Observed Mass (M + 1) |
|---|---|---|---|
| I-38 | 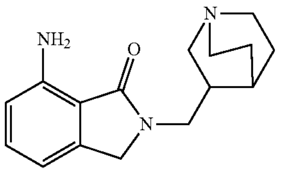 [SMILES: Nc1cccc2c1C(=O)N(CC1CN3CCC1CC3)C2] | (R and S)-7-Amino-2-(quinuclidin-3-ylmethyl) isoindolin-1-one | 272.2 |

Intermediate I-39

I-39

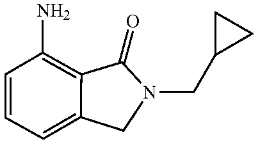

7-Amino-2-(cyclopropylmethyl)isoindolin-1-one (I-39)

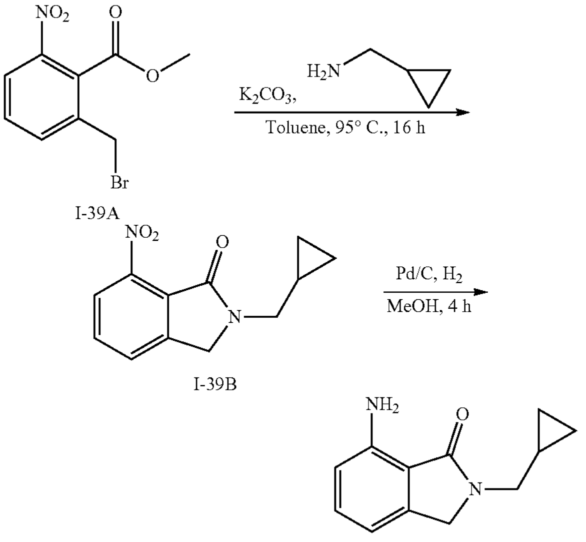

I-39A

I-39B

I-39

Step A: 2-(Cyclopropylmethyl)-7-nitroisoindolin-1-one (I-39B)

A mixture of methyl 2-(bromomethyl)-6-nitrobenzoate (I-39A, 8.0 g, 29 mmol), potassium carbonate (10 g, 73 mmol) and cyclopropylmethanamine (2.1 g, 29 mmol) in toluene (60 mL) was heated at 95° C. for 16 h. The resulting mixture was filtered, and the filtrate was concentrated. The residue was purified by silica gel column chromatography (5-50% EtOAc/PE gradient) to provide compound I-39B. MS: m/z=233.1 (M+1).

Step B: 7-Amino-2-(cyclopropylmethyl)isoindolin-1-one (I-39)

To a deoxygenated solution of 2-(cyclopropylmethyl)-7-nitroisoindolin-1-one (3.0 g, 13 mmol) in MeOH (40 mL) was added 10 wt % Pd/C (0.28 g, 2.6 mmol). The reaction mixture was degassed with hydrogen (3×) and stirred at ambient temp for 16 h under a balloon of hydrogen gas. The resulting mixture was filtrated over Celite® and the filtrate concentrated. The residue was purified by prep HPLC (19 mm×250 mm C18; 5.5 min, 5-50% ACN/water gradient, 10 mM $NH_4HCO_3$ added) to afford compound I-39. MS: m/z=203.3 (M+1). $^1$H NMR (300 MHz, DMSO-$d_6$) δ 7.22-7.18 (m, 1H), 6.65 (d, J=7.3 Hz, 1H), 6.57 (d, J=8.1 Hz, 1H), 6.03 (brs, 2H), 4.41 (s, 2H), 3.30 (d, J=4.2 Hz, 2H), 1.10-0.92 (m, 1H), 0.55-0.46 (m, 2H), 0.32-0.24 (m, 2H).

Intermediate I-40

I-40

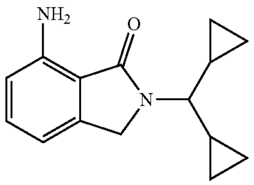

7-Amino-2-(dicyclopropylmethyl)isoindolin-1-one (I-40)

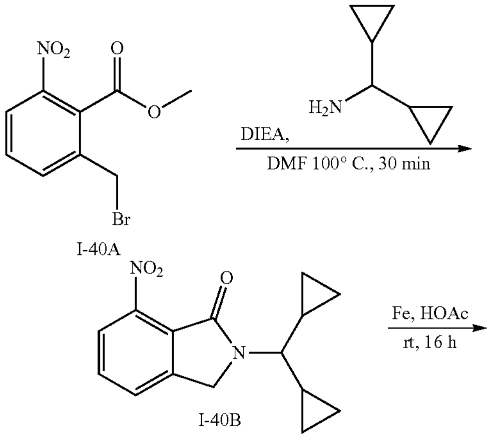

I-40A

I-40B

-continued

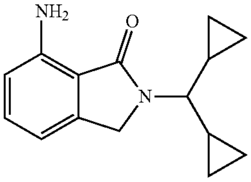

I-40

Step A: 2-(Dicyclopropylmethyl)-7-nitroisoindolin-1-one (I-40B)

In a microwave vial, combined methyl 2-(bromomethyl)-6-nitrobenzoate (800 mg, 2.9 mmol), DIEA (770 μL, 4.4 mmol) and dicyclopropylmethanamine (390 mg, 3.5 mmol) in DMF (0.97 mL). The via was sealed and heated at 100° C. for 40 min in a Biotage® microwave reactor (Biotage, Charlotte, NC, USA). The mixture was cooled, diluted with ethyl acetate and the organic layer was washed with water. The organic layer was dried over $Na_2SO_4$ and concentrated. The residue was purified by silica gel column chromatography (0-85% EtOAc/Hexane gradient) to provide compound I-40. MS: m/z=272.2 (M+1).

Step B: 7-Amino-2-(dicyclopropylmethyl)isoindolin-1-one (I-40)

A mixture of 2-(dicyclopropylmethyl)-7-nitroisoindolin-1-one (I-40B, 390 mg, 1.4 mmol) and iron (400 mg, 7.2 mmol) in acetic acid (2.9 mL) was stirred at ambient temp overnight. The reaction was filtered through a thin pack of Celite® to remove the excess iron, washing with EtOAc. The combined organic layer was washed with sat. aq. $NaHCO_3$ solution, brine, and dried over $Na_2SO_4$. The filtrate was concentrated to a residue to afford compound I-MS: m/z=243.2 (M+1). $^1H$ NMR (400 MHz, DMSO-$d_6$) δ 7.20 (dd, J=8.1, 7.3 Hz, 1H), 6.66 (dd, J=7.2, 0.9 Hz, 1H), 6.56 (dd, J=8.1, 0.8 Hz, 1H), 6.03 (s, 2H), 4.48 (s, 2H), 2.85 (t, J=9.1 Hz, 1H), 1.16-1.07 (m, 2H), 0.65-0.54 (m, 2H), 0.48-0.39 (m, 2H), 0.35-0.28 (m, 2H), (m, 2H).

Intermediates I-41 through I-45 found in Table 8 were prepared in a similar fashion to the condensation procedure conditions described above in intermediate I-40.

TABLE 8

| Intermediate Number | Structure | Compound Name | Observed Mass (M + 1) |
|---|---|---|---|
| I-41 | 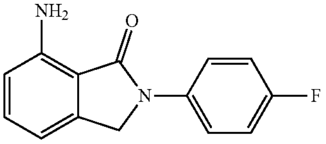 [SMILES: Nc1cccc2c1C(=O)N(c1ccc(F)cc1)C2] | 7-amino-2-(4-fluorophenyl)isoindolin-1-one | 243.2 |
| I-42 | 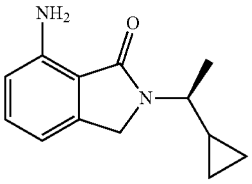 [SMILES: C[C@@H](C1CC1)N1Cc2cccc(N)c2C1=O] | (S)-7-amino-2-(1-cyclopropylethyl)isoindolin-1-one | 217.2 |
| I-43 | 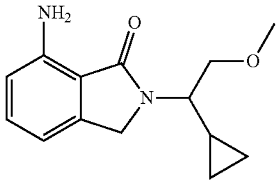 [SMILES: COCC(C1CC1)N1Cc2cccc(N)c2C1=O] | (R and S)-7-amino-2-(1-cyclopropyl-2-methoxyethyl)isoindolin-1-one | 247.2 |
| I-44 | 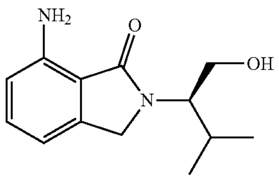 [SMILES: CC(C)[C@H](CO)N1Cc2cccc(N)c2C1=O] | (R)-7-amino-2-(1-hydroxy-3-methylbutan-2-yl)isoindolin-1-one | 235.2 |

TABLE 8-continued

| Intermediate Number | Structure | Compound Name | Observed Mass (M + 1) |
|---|---|---|---|
| I-45 | 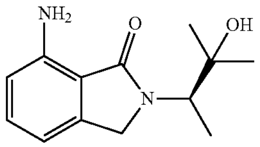 [SMILES: C[C@@H](N1Cc2cccc(N)c2C1=O)C(C)(C)O] | (R)-7-amino-2-(3-hydroxy-3-methylbutan-2-yl)isoindolin-1-one | 235.3 |

Intermediate I-46

I-46

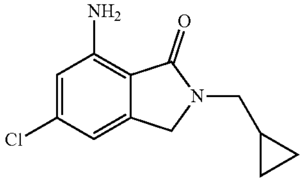

7-Amino-5-chloro-2-(cyclopropylmethyl)isoindolin-1-one (I-46)

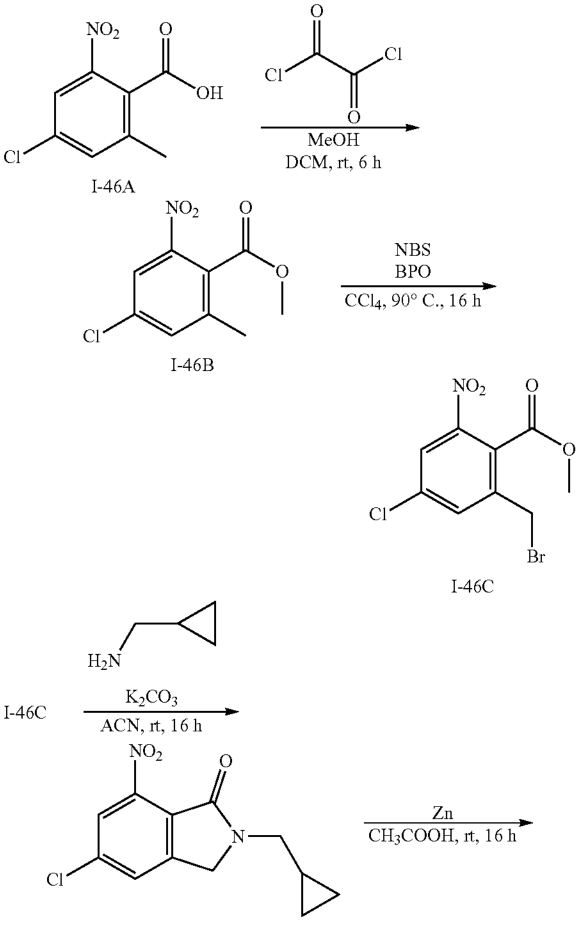

I-46A
I-46B
I-46C
I-46C
I-46D

-continued

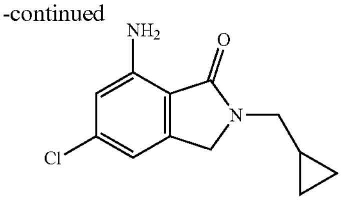

I-46

Step A: Methyl 4-chloro-2-methyl-6-nitrobenzoate (I-46B)

To a solution of 4-chloro-2-methyl-6-nitrobenzoic acid (I-46A, 3.90 g, 18 mmol) in DCM (40 mL) was added oxalyl dichloride (5.7 g, 45 mmol) and the reaction mixture was stirred at ambient temp for 4 h. MeOH (5.8 g, 180 mmol) was added to the reaction mixture at ambient temp and stirred for 2 h. The resulting mixture was concentrated. The residue was diluted with water (80 mL) and extracted with EtOAc (3×80 mL). The combined organic layer was washed with brine (3×80 mL), dried over $Na_2SO_4$ and concentrated. The residue was purified by silica gel column chromatography (0-15% EtOAc/PEe gradient) to provide compound I-46B. $^1H$ NMR (300 MHz, DMSO-$D_6$) δ 8.16 (s, 1H), 8.00-7.93 (m, 1H), 3.89 (s, 3H), 2.38 (s, 3H).

Step B: Methyl 2-(bromomethyl)-4-chloro-6-nitrobenzoate (I-46C)

To a solution of methyl 4-chloro-2-methyl-6-nitrobenzoate (I-46B, 2.0 g, 8.7 mmol) in $CCl_4$ (carbon tetrachloride, 20 mL) were added NBS (2.3 g, 13 mmol) and BPO (1.1 g, 4.4 mmol) and the reaction mixture was heated at 90° C. for 16 h. The resulting mixture was cooled down to ambient temp, diluted with water (30 mL) and extracted with dichloromethane (3×35 mL). The combined organic layers were washed with brine (3×15 mL), dried over $Na_2SO_4$ and concentrated. The residue afforded compound I-46C.

Step C: 5-Chloro-2-(cyclopropylmethyl)-7-nitroisoindolin-1-one (I-46D)

A mixture of methyl 2-(bromomethyl)-4-chloro-6-nitrobenzoate (I-46C, 4.0 g, 13 mmol), $K_2CO_3$ (potassium carbonate, 3.6 g, 26 mmol) and cyclopropylmethanamine (1.4 g, 19 mmol) in ACN (20 mL) was stirred at ambient temp for 16 h. The resulting mixture was filtered, and the filtrate was concentrated. The residue was purified by silica gel column chromatography (5-50% EtOAc/PE gradient) to provide compound I-46D. MS: m/z=267.1 (M+1).

Step D: 7-Amino-5-chloro-2-(cyclopropylmethyl) isoindolin-1-one (I-46)

To a solution of 5-chloro-2-(cyclopropylmethyl)-7-nitroisoindolin-1-one (I-46D, 1.4 g, mmol) in acetic acid (20 mL) was added zinc (3.4 g, 53 mmol) slowly at ambient temp. The reaction mixture was stirred at ambient temp for 16 h. The resulting mixture was filtered, and the filtrate was concentrated. The residue was purified by prep HPLC (19 mm×250 mm C18; 6 min, 55-60% ACN/water gradient, 0.05% TFA added) to afford compound I-46. MS: m/z=237.1 (M+1). $^1$H NMR (300 MHz, DMSO-$d_6$) δ 6.69-6.66 (m, 2H), 6.28 (brs, 2H), 4.43 (s, 2H), 3.29 (d, J=7.1 Hz, 2H), 1.12-0.89 (m, 1H), 0.50-0.47 (m, 2H), 0.31-0.25 (m, 2H).

Intermediate I-47 found in Table 9, was prepared in a similar fashion to the conditions described above in intermediate I-46.

TABLE 9

| Intermediate Number | Structure | Compound Name | Observed Mass (M + 1) |
|---|---|---|---|
| 47 | 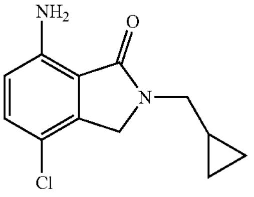 [SMILES: Nc1ccc(Cl)c2c1C(=O)N(CC1CC1)C2] | 7-amino-4-chloro-2-(cyclopropylmethyl)isoindolin-1-one | 237.2 |

Intermediate I-48

I-48

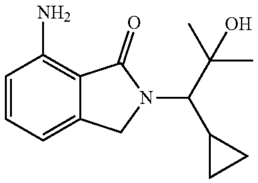

(R or S)-7-Amino-2-(1-cyclopropyl-2-hydroxy-2-methylpropyl)isoindolin-1-one (I-48)

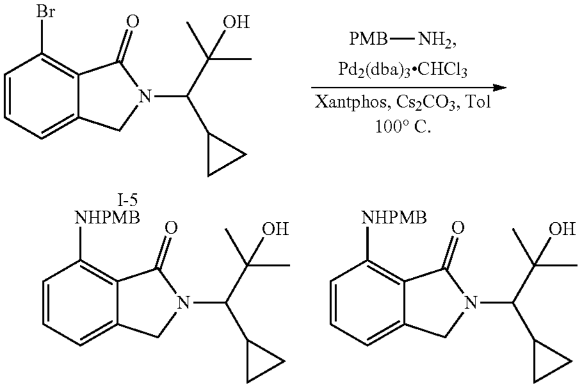

I-5

I-48B

I-48C

-continued

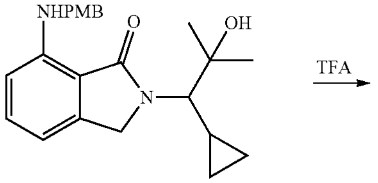

I-48C

-continued

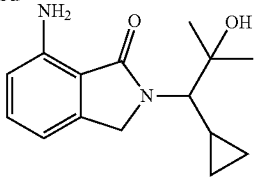

I-48

Step A: (R or S)-2-(1-Cyclopropyl-2-hydroxy-2-methylpropyl)-7-((4-methoxybenzyl)amino)isoindolin-1-one (I-48B, I-48C)

A mixture of 7-bromo-2-(1-cyclopropyl-2-hydroxy-2-methylpropyl)isoindolin-1-one (I-3.2 g, 9.9 mmol), (4-methoxyphenyl)methanamine (1.8 g, 13 mmol), (9,9-dimethyl-9H-xanthene-4,5-diyl)bis(diphenylphosphine) (1.7 g, 3.0 mmol), tris(dibenzylideneacetone)dipalladium-chloroform adduct (1.5 g, 1.5 mmol) and $Cs_2CO_3$ (9.7 g, mmol) in Toluene (18 mL) in a sealed tube was heated at 100° C. for 3 h. The mixture was concentrated, and the residue was purified by silica gel chromatography (0-35% EtOAc/Hexane gradient) to provide the racemic mixture of I-48. The racemic material was separated by SFC (ALPCHIRAK® as-H CHIRALPAK® AS-H (Chiral Technologies, Inc., West Chester, PA USA), 2×25 cm (5 um); Mobile Phase A: $CO_2$ (gas); Mobile Phase B: IPA (isopropyl alcohol) (8 mM $NH_3$ in MeOH); Flow rate: 40 mL/min; Gradient: 30% B hold 4.0 min). The product fractions with longer retention time were concentrated to afford the desired chiral intermediate I-48C. MS: m/z=381.1 (M+1). $^1$H-NMR (400 MHz, DMSO-$d_6$): δ 7.30-7.24 (m, 3H), 7.06-7.03 (m, 1H), 6.93-

6.89 (m, 2H), 6.70 (d, J=7.2 Hz, 1H), 6.53 (d, J=8.0 Hz, 1H), 4.76-4.69 (m, 2H), 4.46 (d, J=18.4 Hz, 1H), 4.34 (d, J=6.0 Hz, 2H), 3.74 (s, 3H), 3.13 (d, J=10.0 Hz, 1H), 1.47-1.37 (m, 1H), 1.32 (s, 3H), 1.03 (s, 3H), 0.76-0.71 (m, 1H), 0.50-0.45 (m, 1H), 0.42-0.36 (m, 1H), −0.10~−0.13 (m, 1H).

Step B: (R or S)-7-Amino-2-(1-cyclopropyl-2-hydroxy-2-methylpropyl)isoindolin-1-one (I-48)

A solution of the desired chiral intermediate 2-(1-cyclopropyl-2-hydroxy-2-methylpropyl)-7-((4-methoxybenzyl)amino)isoindolin-1-one, (I-48C, 2.1 g, 5.5 mmol) in TFA (6.0 mL) was heated at 50° C. for 3 h. The reaction was concentrated, and the residue was purified by silica gel column chromatography (0-45% EtOAc/Hexane gradient) to provide I-48. MS: m/z=261.0 (M+1). $^1$H NMR (400 MHz, DMSO-$d_6$): δ 7.18 (t, J=8.0 Hz, 1H), 8.65 (d, J=7.2 Hz, 1H), 6.54 (d, J=8.0 Hz, 1H), 6.01 (br s, 2H), 4.70 (d, J=18.4 Hz, 1H), 4.67 (s, 1H), 4.43 (d, J=18.4 Hz, 1H), 3.13 (d, J=10.4 Hz, 1H), 1.42-1.34 (m, 1H), 1.31 (s, 3H), 1.02 (s, 3H), 0.76-0.74 (m, 1H), 0.49-0.46 (m, 1H), 0.40-0.36 (m, 1H), −0.10~−0.14 (m, 1H).

Intermediate I-49

I-49

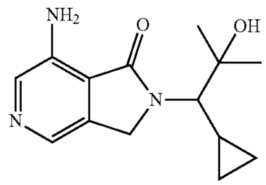

(R or S)-7-Amino-2-(1-cyclopropyl-2-hydroxy-2-methylpropyl)-2,3-dihydro-1H-pyrrolo[3,4-c]pyridin-1-one (I-49)

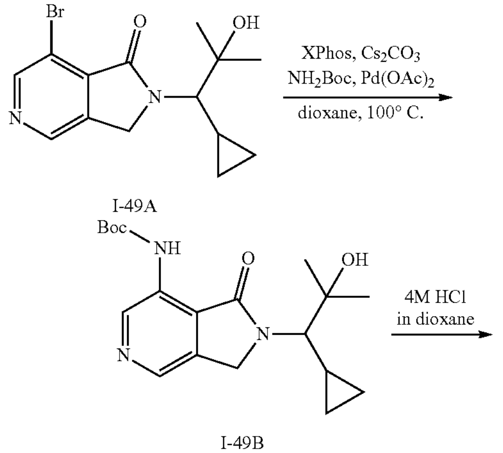

I-49A

I-49B

-continued

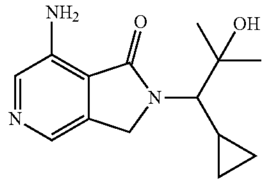

I-49

Step A: (R or S)-tert-butyl(2-(1-cyclopropyl-2-hydroxy-2-methylpropyl)-1-oxo-2,3-dihydro-1H-pyrrolo[3,4-c]pyridin-7-yl)carbamate (I-49B)

A mixture of (R or S)-7-bromo-2-(1-cyclopropyl-2-hydroxy-2-methylpropyl)-2,3-dihydro-1H-pyrrolo[3,4-c]pyridin-1-one (I-49A, 200 mg, 0.62 mmol), tert-butyl carbamate (110 mg, 0.92 mmol), $Cs_2CO_3$ (400 mg, 1.2 mmol), 2-dicyclohexylphosphino-2',4',6'-triisopropylbiphenyl (XPhos, 88 mg, 0.19 mmol) and diacetoxypalladium (14 mg, 0.062 mmol) in 1,4-dioxane (6.0 mL) was heated at 100° C. for 16 h. The reaction was concentrated, and the residue was purified by prep TLC (5% MeOH/DCM gradient) to afford compound I-49B. MS: m/z=362.2 (M+1). $^1$H NMR (300 MHz, DMSO-$d_6$): δ 9.24 (m, 1H), 9.18 (m, 1H), 8.56 (s, 1H), 5.02-4.67 (m, 2H), 4.86 (s, 1H), 3.18 (d, J=10.2 Hz, 1H), 1.51 (s, 9H), 1.50-1.48 (m, 1H), 1.45 (s, 3H), 1.04 (s, 3H), 0.80-0.70 (m, 1H), 0.54-0.41 (m, 2H), −0.07~−0.10 (m, 1H).

Step B: (R or S)-7-Amino-2-(1-cyclopropyl-2-hydroxy-2-methylpropyl)-2,3-dihydro-1H-pyrrolo[3,4-c]pyridin-1-one (I-49)

A solution of (R or S)-tert-butyl(2-(1-cyclopropyl-2-hydroxy-2-methylpropyl)-1-oxo-2,3-dihydro-1H-pyrrolo[3,4-c]pyridin-7-yl)carbamate (I-49B, 130 mg, 0.36 mmol) in 4M HCl in dioxane solution (8 mL) was stirred at ambient temperature for 4 h then concentrated. The residue was partitioned between EtOAc (30 mL) and saturated aq. $NaHCO_3$ (30 mL) and stirred for 10 min. The layers were separated, and the aqueous layer was back-extracted with EtOAc (3×20 mL). The combined organic phase was washed with brine (50 mL), dried over $Na_2SO_4$, and concentrated. The residue obtained afforded compound I-49. MS: m/z=262.1 (M+1). $^1$H NMR (300 MHz, DMSO-$d_6$): δ 8.01-8.00 (m, 2H), 6.06 (s, 2H), 4.87-4.53 (m, 2H), 4.76 (s, 1H), 3.16 (d, J=9.9 Hz, 1H), 1.42-1.40 (m, 1H), 1.34 (s, 3H), 1.04 (s, 3H), 0.80-0.70 (m, 1H), 0.53-0.41 (m, 2H), 0.00~−0.20 (m, 1H).

Intermediate I-50 found in Table 10, was prepared in a similar fashion to the conditions described above in intermediate I-49.

TABLE 10

| Intermediate Number | Structure | Compound Name | Observed Mass (M + 1) |
|---|---|---|---|
| I-50 | 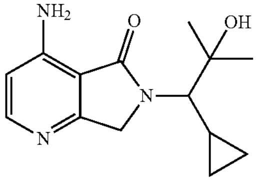 [SMILES: CC(C)(O)C(C1CC1)N1Cc2nccc(N)c2C1=O] | (R or S)-4-amino-6-(1-cyclopropyl-2-hydroxy-2-methylpropyl)-6,7-dihydro-5H-pyrrolo[3,4-b]pyridin-5-one | 262.2 |

Intermediate I-51

I-51

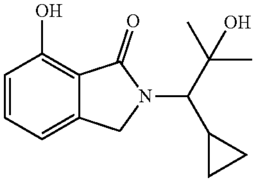

(R or S)-2-(1-Cyclopropyl-2-hydroxy-2-methylpropyl)-7-hydroxyisoindolin-1-one (I-51)

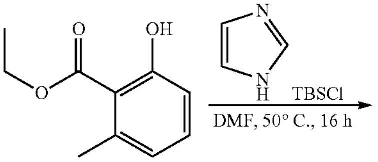

I-51A

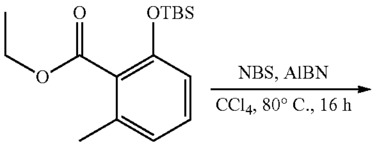

I-51B

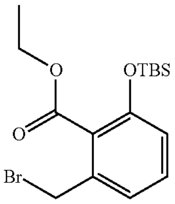

I-51C

I-51C

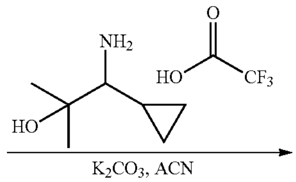

-continued

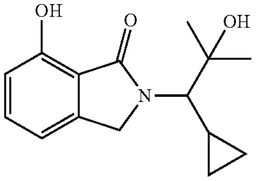

I-51

Step A: Ethyl 2-((tert-butyldimethylsilyl)oxy)-6-methylbenzoate (I-51B)

A mixture of ethyl 2-hydroxy-6-methylbenzoate (5.0 g, 28 mmol), TBS-Cl (tert-butyldimethylsilyl chloride, 5.0 g, 33 mmol) and imidazole (2.5 g, 36 mmol) in DMF (30 mL) were heated at 50° C. for 16 h then concentrated. The residue was diluted with water (100 mL) and extracted with EtOAc (3×100 mL). The combined organic layer was washed with brine (3×100 mL), dried over $Na_2SO_4$ concentrated. The residue was purified by silica gel column chromatography (0-7% EtOAc/PE gradient) to provide compound I-51B. MS: m/z=295.2 (M+1).

Step B: Ethyl 2-(bromomethyl)-6-((tert-butyldimethylsilyl)oxy)benzoate (I-51C)

A mixture of ethyl 2-((tert-butyldimethylsilyl)oxy)-6-methylbenzoate (I-51B, 1.2 g, 4.1 mmol), NBS (0.94 g, 5.3 mmol) and AIBN (0.13 g, 0.82 mmol) in $CCl_4$ (20 mL) was heated at ° C. for 16 h then concentrated. The residue was diluted with water and extracted with EtOAc (3×30 mL). The combined organic layer was washed with brine (3×20 mL), dried over $Na_2SO_4$ and concentrated. The residue obtained afforded compound I-51C. MS: m/z=373, 375 (M+1).

Step C: (R or 5)-2-(1-Cyclopropyl-2-hydroxy-2-methylpropyl)-7-hydroxyisoindolin-1-one (I-51)

The mixture of (R or S)-1-amino-1-cyclopropyl-2-methylpropan-2-ol 2,2,2-trifluoroacetate (I-51C, 200 mg, 0.822 mmol), $K_2CO_3$ (230 mg, 1.6 mmol) and methyl 2-(bromomethyl)-6-((tert-butyldimethylsilyl)oxy)benzoate (420 mg, 0.82 mmol) in acetonitrile (15 mL) was heated at 90° C. overnight. The reaction mixture was cooled to ambient temp and concentrated. The residue was diluted with water (100 mL) and extracted with ethyl acetate (3×100 mL). The combined organic layer was washed with brine (3×100 mL), dried over $Na_2SO_4$ and concentrated. The residue was purified prep HPLC (AQ-C18 Column (40 g, 20-35 μm, from Welch technology (Shanghai) CO., Ltd), 30 min., 0-100% ACN/water gradient) to afford compound I-51. MS: m/z=262.3 (M+1). $^1$H-NMR (400 MHz, Chloroform-d): δ 8.63 (s, 1H), 7.45-7.41 (m, 1H), 6.97-6.96 (m, 1H), 6.89-6.87 (m, 1H), 4.83-4.65 (m, 1H), 3.27 (d, J=10.4 Hz, 1H), 2.37 (s, 1H), 1.46 (s, 3H), 1.41-1.34 (m, 1H), 1.28 (s, 3H), 0.91-0.84 (m, 1H), 0.60-0.50 (m, 2H), 0.22-0.17 (m, 1H).

Intermediate I-52

I-52

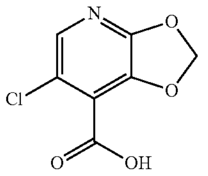

6-Chloro-[1,3]dioxolo[4,5-b]pyridine-7-carboxylic acid (I-52)

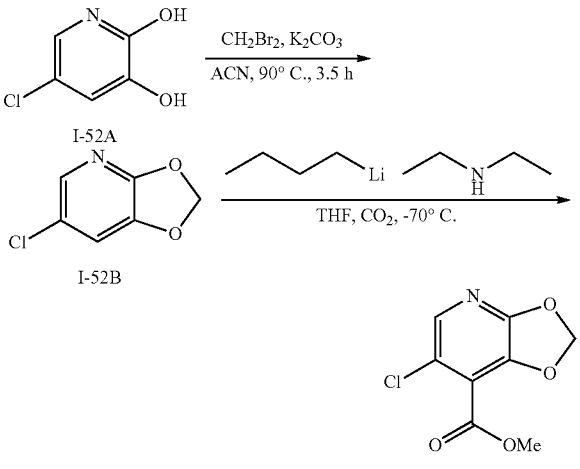

I-52A

I-52B

I-52

Step A: 6-Chloro-[1,3]dioxolo[4,5-b]pyridine (I-52B)

A mixture of dibromomethane (9.0 g, 52 mmol), $K_2CO_3$ (7.1 g, 52 mmol) and 5-chloropyridine-2,3-diol (I-52A, 5.0 g, 34 mmol) in ACN (50 mL) was heated at 90° C. for 3.5 h. The resulting mixture was cooled to ambient temp, filtered, and concentrated. The residue was purified by silica gel chromatography (100% PE isocratic gradient) to provide compound I-52B. MS: m/z=158, 160 (M+1).

Step B: 6-Chloro-[1,3]dioxolo[4,5-b]pyridine-7-carboxylic acid (I-52)

To a solution of diisopropylamine (2.1 mL, 15 mmol) in THF (130 mL) was added 2.5M n-butyllithium in hexanes (5.8 mL, 15 mmol) dropwise at −70° C. The mixture was stirred at −70° C. for an additional 20 minutes. A solution of 6-chloro-[1,3]dioxolo[4,5-b]pyridine (I-52B, 1.3 g, 8.3 mmol) in THF (130 mL) was added over 10 minutes and the reaction mixture was cooled at −78° C. for 1 h. Carbon dioxide gas was bubbled into the reaction mixture for 30 minutes and the resulting reaction mixture was allowed to warm to ambient temp. To the mixture was added water (30 mL) and the organic solvent was evaporated. The residue was acidified to pH=2 by the addition of 1N aq. HCl. The resultant solid collected by vacuum filtration to afford compound I-52. MS=202, 204 (M+1).

Intermediate I-53

I-53

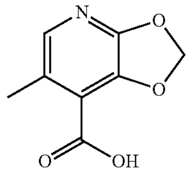

6-Methyl-[1,3]dioxolo[4,5-b]pyridine-7-carboxylic acid (I-53)

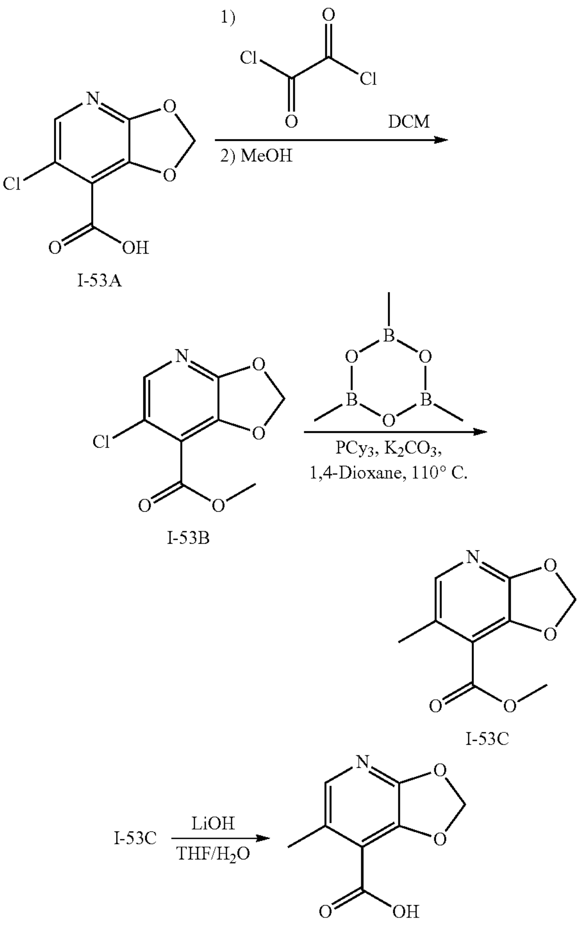

I-53A

I-53B

I-53C

I-53

Step A: Methyl 6-chloro-[1,3]dioxolo[4,5-b]pyridine-7-carboxylate (I-53B)

To a solution of 6-chloro-[1,3]dioxolo[4,5-b]pyridine-7-carboxylic acid (I-53A, 500 mg, 2. mmol) in DCM (5.0 mL)

was added oxalyl dichloride (940 mg, 7.4 mmol) and DMF (one drop) at 0° C. under nitrogen. The reaction mixture was cooled to 0° C. and stirred for 1 h. MeOH (10 mL, 2.5 mmol) was added to the mixture and the mixture was allowed to warm to ambient temp and stirred for 30 min. The reaction was concentrated to a residue, affording compound I-53B. MS: m/z=216.1 (M+1). $^{1}H$ NMR (300 MHz, DMSO-$d_6$): δ 7.97 (s, 1H), 6.33 (s, 2H), 3.91 (s, 3H).

Step B: Methyl 6-methyl-[1,3]dioxolo[4,5-b]pyridine-7-carboxylate (I-53C)

A mixture of methyl 6-chloro-[1,3]dioxolo[4,5-b]pyridine-7-carboxylate (I-53B, 100 mg, 0.46 mmol), 2,4,6-trimethyl-1,3,5,2,4,6-trioxatriborinane (64 mg, 0.510 mmol), $K_2CO_3$ (190 mg, 1.4 mmol) and methanesulfonato (tricyclohexylphosphine) (2'-amino-1,1'-biphenyl-2-yl) palladium (II) dichloromethane adduct (34 mg, 0.046 mmol) in 1,4-Dioxane (1.0 mL) under nitrogen was heated at 110° C. for 16 h. The mixture was cooled, filtered, and the filtrate was concentrated. The residue was purified by prep TLC (20% EtOAc/PE) to afford compound I-53C. MS: m/z=196.2 (M+1). $^{1}H$ NMR (300 MHz, Chloroform-d): δ 7.53 (d, J=0.9 Hz, 1H), 6.16 (s, 2H), 3.96 (s, 3H), 2.41 (d, J=0.9 Hz, 1H).

Step C: 6-Methyl-[1,3]dioxolo[4,5-b]pyridine-7-carboxylic acid (I-53)

To a solution of methyl 6-methyl-[1,3]dioxolo[4,5-b]pyridine-7-carboxylate (I-53C, 60 mg, 0.31 mmol) in THF (0.5 mL)/water (0.5 mL) was added lithium hydroxide (59 mg, 2.5 mmol) at ambient temp. The reaction mixture stirred at ambient temp for 2 h then concentrated. The residue was purified by prep HPLC (AQ-C18 Column, 30 min, 0-45% ACN/10 mM aq. $NH_4HCO_3$ gradient) to afford compound I-53. MS: m/z=182.2 (M+1). $^{1}H$ NMR (300 MHz, DMSO-$d_6$): δ 7.26 (d, J=0.9 Hz, 1H), 5.98 (s, 2H), 2.11 (d, J=0.9 Hz, 1H).

Intermediate I-54

I-54

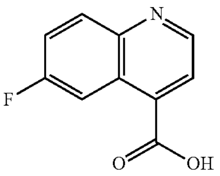

6-Fluoroquinoline-4-carboxylic acid (I-54)

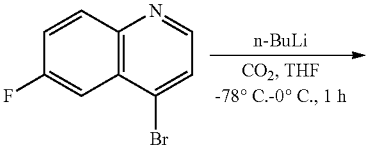

I-54A

-continued

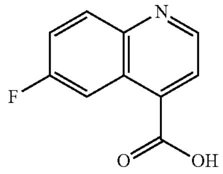

I-54

To a solution of 4-bromo-6-fluoroquinoline (I-54A, 90 mg, 0.40 mmol) in THF (5.0 mL) was added 2.5M n-butyllithium in THF (0.19 mL, 0.48 mmol) at −78° C. The reaction solution was cooled at −78° C. for 15 min then dry ice (5.0 g, 110 mmol) was added at −78° C. with stirring. The reaction mixture was stirred for 1 h then the excess n-butyllithium was quenched by the addition of water (5 mL) at 0° C. The pH value of the resulting mixture was adjusted to pH=6 with 1N aq. HCl (20 mL). The resulting mixture was extracted with EA (ethyl acetate, 3×20 mL). The combined organic layer was washed with brine (20 mL), dried over $Na_2SO_4$ and concentrated. The residue was purified by prep HPLC (19 mm×250 mm C18; 6 min, 10-60% ACN/water, 0.05% TFA added) to afford compound I-54. MS: m/z=192.2 (M+1).

Intermediate I-55

I-55

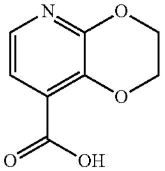

2,3-Dihydro-[1,4]dioxino[2,3-b]pyridine-8-carboxylic acid (I-55)

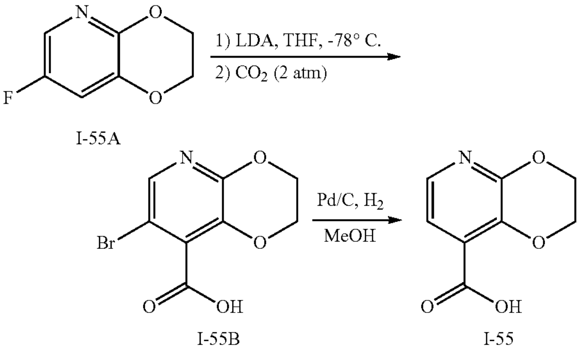

Step A: 7-Bromo-2,3-dihydro-[1,4]dioxino[2,3-b]pyridine-8-carboxylic acid (I-55B)

To a solution of 7-bromo-2,3-dihydro-[1,4]dioxino[2,3-b]pyridine (I-55A, 200 mg, 0.93 mmol) in THF (5.0 ml) was added 2M LDA in THF (0.56 mL, 1.1 mmol) at −78° C. under nitrogen. The reaction was cooled at −78° C. for 1 h then $CO_2$ (gas) was bubbled through the solution for 15 min. The excess LDA was quenched with saturated aq. $NH_4Cl$ (10 mL) and the pH was adjusted to 5 with 2N aq. HCl. The mixture was extracted with EtOAc (3×20 mL) and the organic layer was dried over $Na_2SO_4$ and concentrated. The residue was washed with diethyl ether (4.0 mL) to afford compound I-55B. MS: m/z=260, 262 (M+1). $^1$H NMR (300 MHz, DMSO-$d_6$): δ 14.10 (br s, 1H), 7.93 (s, 1H), 4.46-4.43 (m, 2H), 4.33-4.30 (m, 2H).

Step B: 2,3-Dihydro-[1,4]dioxino[2,3-b]pyridine-8-carboxylic acid (I-55)

The mixture of 7-bromo-2,3-dihydro-[1,4]dioxino[2,3-b]pyridine-8-carboxylic acid (I-55B, 160 mg, 0.60 mmol) and 10 wt % Pd/C (63 mg, 0.060 mmol) in $CH_3OH$ (5 mL) was stirred for 4 h at ambient temp under a balloon of hydrogen gas. The reaction mixture was filtered through a thin pack of Celite® and the filtrate was concentrated. The residue afforded compound I-55. MS: m/z=182.1 (M+1). $^1$H NMR (400 MHz, DMSO-$d_6$): δ 7.78-7.77 (m, 1H), 7.17-7.16 (m, 1H), 4.46-4.43 (m, 2H), 4.33-4.31 (m, 2H).

Intermediate I-56

I-56

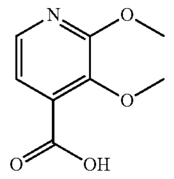

2,3-Dimethoxyisonicotinic acid (I-56)

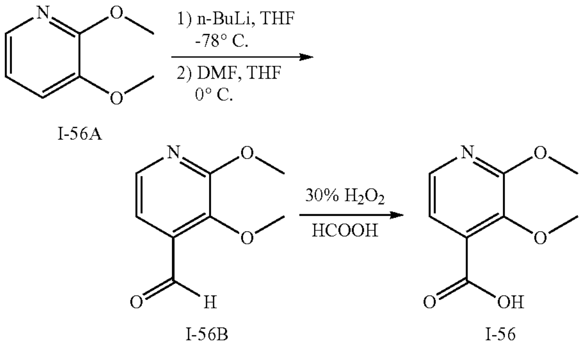

Step A: 2,3-Dimethoxyisonicotinaldehyde (I-56B)

To a stirred solution of 2,3-dimethoxypyridine (I-56A, 5.0 g, 36 mmol) in THF (50 ml) was added 2.5 M n-butyllithium in hexanes (32 ml, 79 mmol) at −78° C. The mixture was cooled at 0° C. for 1 h under nitrogen atmosphere and then anhydrous DMF (12 mL, 160 mmol) was added slowly at −78° C. The mixture was cooled at 0° C. for 1 h and then the excess n-butyllithium was quenched with saturated aq. $NH_4Cl$ (20 mL). The mixture was concentrated. The residue was diluted with EtOAc (500 mL) and washed with water (2×100 mL). The organic layer was dried over anhydrous sodium sulfate and concentrated. The residue was purified by silica gel column chromatography (0-15% EtOAc/PE gradient) to provide I-56B. $^1$H NMR (300 MHz, Chloroform-d): δ 10.49 (s, 1H), 7.99-7.97 (m, 1H), 7.21-7.19 (m, 1H), 4.08-4.01 (m, 6H).

Step B: 2,3-Dimethoxyisonicotinic acid (I-56)

To a stirred solution of 2,3-dimethoxyisonicotinaldehyde (I-56B, 1.6 g, 9.6 mmol) in formic acid (20 mL) was added 33 wt % aq. hydrogen peroxide (2.0 mL, 29 mmol) at 0° C. The mixture was stirred for 16 h at ambient temperature. The excess hydrogen peroxide was quenched with saturated aq. $NaHSO_3$ and concentrated. The residue was diluted with EtOAc (200 mL) and washed with water (3×50 mL). The organic phase was dried over $Na_2SO_4$ and concentrated. The residue was recrystallized from methanol to give compound I-56. MS: m/z=183.9 (M+1). $^1$H NMR (400 MHz, DMSO-$d_6$): δ 13.48 (s, 1H), 7.96 (d, J=5.2 Hz, 1H), 7.11 (d, J=5.2 Hz, 1H), 3.94 (s, 3H), 3.80 (s, 3H).

Intermediate 57

I-57

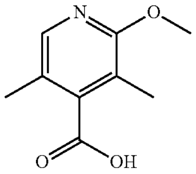

2-Methoxy-3,5-dimethylisonicotinic acid (I-57)

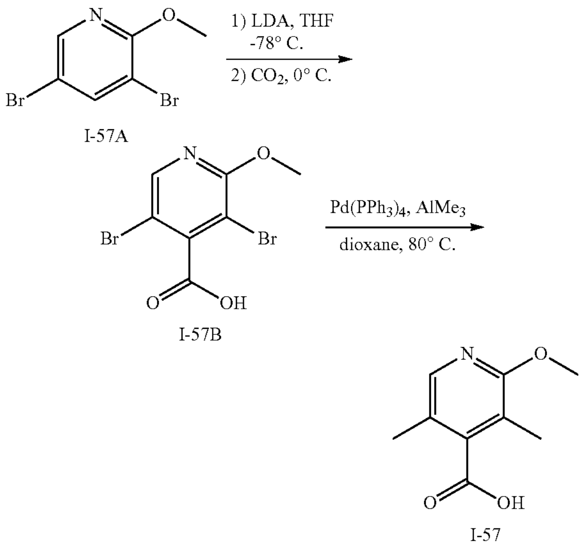

Step A: 3,5-Dibromo-2-methoxyisonicotinic acid (I-57B)

To a mixture of 3,5-dibromo-2-methoxypyridine (I-57A, 2.0 g, 7.5 mmol) in THF (50 mL) was added dropwise 2M LDA in THF (5.6 mL, 11 mmol) at −78° C. under argon. The resulting mixture was cooled at −78° C. for 1 h then $CO_2$ gas was bubbled through the solution for min. The reaction temperature was warmed slowly to 0° C. The excess LDA was quenched with $NH_4Cl$ (30 mL). The mixture was concentrated, and the residue was diluted with water (50 mL). The solids were collected by vacuum filtration and dried to afford compound I-57B. MS: m/z=310, 312 (M+1). $^1$H-NMR (300 MHz, DMSO-$d_6$): δ 8.41 (s, 1H), 3.95 (s, 3H).

Step B: 2-Methoxy-3,5-dimethylisonicotinic acid (I-57)

A mixture of 3,5-dibromo-2-methoxyisonicotinic acid (I-57B, 500 mg, 1.6 mmol), $Pd(Ph_3P)_4$ (93 mg, 0.080 mmol) and 2M trimethylaluminum in toluene (2.0 mL, 4.0 mmol) in 1,4-dioxane (20 mL) under argon was heated at 80° C. overnight. The reaction mixture was cooled to ambient temp and diluted with ice water (20 mL). The pH was adjusted to 4 with 1 N aq. HCl and the mixture was diluted with water (20 mL) and extracted with EtOAc (5×40 mL). The combined organic layer was washed with brine (3×40 mL), dried over $Na_2SO_4$ and concentrated. The residue was purified by prep HPLC (19×150 mm C18, 4.3 min, 15-50% ACN/10 mM aq. TFA gradient) to afford compound I-57. MS: m/z=182.0 (M+1). $^1$H-NMR (300 MHz, DMSO-$d_6$): δ 13.68 (s, 1H), 7.92 (s, 1H), 3.88 (s, 3H), 2.17 (s, 3H), 2.10 (s, 3H).

Intermediate I-58 found in Table 11, was prepared in a similar fashion to the conditions described above in intermediate I-57.

TABLE 11

| Intermediate Number | Structure | Compound Name | Observed Mass (M + 1) |
|---|---|---|---|
| I-58 | 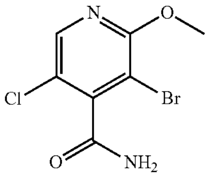 | 3-bromo-5-chloro-2-methoxyiso-nicotinamide | 266.0 |

Intermediate I-59

I-59

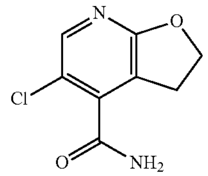

5-Chloro-2,3-dihydrofuro[2,3-b]pyridine-4-carboxamide (I-59)

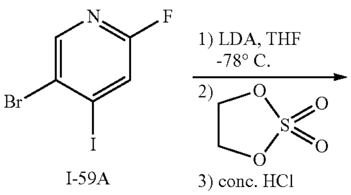

I-59A

-continued

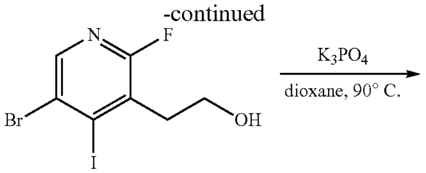

I-59B

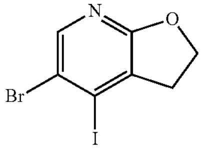

I-59C

I-59C

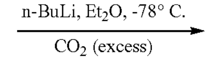

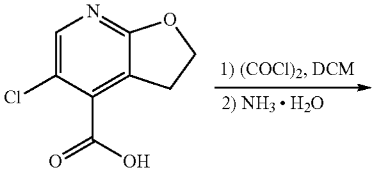

I-59D

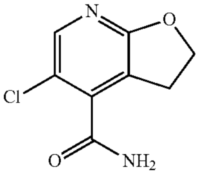

I-59

Step A: 2-(5-Chloro-2-fluoro-4-iodopyridin-3-yl)ethanol (I-59B)

To a solution of 5-chloro-2-fluoro-4-iodopyridine (I-59A, 2.0 g, 7.8 mmol) in THF (30 mL) was added 2M LDA in THF/n-heptane/ethylbenzne (4.7 mL, 9.3 mmol) at −78° C. under argon atmosphere. The resulting mixture was cooled to −78° C. for 90 min then a solution of 1,3,2-dioxathiolane 2,2-dioxide (1.3 g, 10 mmol) in THF (17 mL) was added slowly over a period of 30 min and the solution was stirred for an additional 30 min. The mixture was allowed to warm to ambient temp and stirred for 2 hrs. The mixture was cooled to 0° C. and conc HCl (3.2 mL, 39 mmol) was added. The reaction mixture was allowed to warm to ambient temp and stirred for 3 hrs. The pH of reaction mixture was adjusted to pH=8 with saturated aq. $NaHCO_3$ (sodium bicarbonate) and the mixture was extracted with EtOAc (50 mL×3). The combined organic phase was washed with brine (30 mL), dried over $Na_2SO_4$ and concentrated. The residue was purified by silica gel column chromatography (0-35% EtOAc/PE gradient) to give compound I-59B. MS: m/z=301.9 (M+1).

Step B: 5-Chloro-4-iodo-2,3-dihydrofuro[2,3-b]pyridine (I-59C)

A mixture of 2-(5-chloro-2-fluoro-4-iodopyridin-3-yl)ethanol (I-59B, 2.0 g, 6.6 mmol) and $K_3PO_4$ (5.6 g, 26 mmol) in 1,4-dioxane (50 mL) was heated at reflux for 36 h. The reaction was cooled to ambient temp, filtered and washed with EtOAc (10 mL×5). The filtrate was concentrated, and the residue was purified by silica gel column chromatography (0-30% EtOAc/PE gradient) to afford compound I-59C. MS: m/z=281.9 (M+1). $^1$H-NMR (400 MHz, DMSO-$d_6$): δ 7.98 (s, 1H), 4.67 (t, J=8.8 Hz, 2H), 3.21 (t, J=8.8 Hz, 2H).

Step C: 5-Chloro-2,3-dihydrofuro[2,3-b]pyridine-4-carboxylic acid (I-59D)

To a solution of 5-chloro-4-iodo-2,3-dihydrofuro[2,3-b]pyridine (I-59C, 0.10 g, 0.36 mmol) in THF (2.0 mL) and diethyl ether (2.0 mL) was added dropwise 2.5M n-butyllithium in hexane (0.28 mL, 0.71 mmol) at −78° C. under argon atmosphere. The reaction mixture was cooled at −78° C. for 0.5 h and then $CO_2$ gas was bubbled through the solution for 30 min. The reaction mixture was allowed to warm to ambient temp and 1N aq. NaOH (40 mL) was added. The resulting mixture was washed with EtOAc (50 ml×3). The aqueous fractions were combined and acidified to pH=4 with 1N aq. HCl. The aqueous layer was extracted with EtOAc (20 ml×5) and the combined organic layer was dried over $Na_2SO_4$, and concentrated. The residue obtained afforded compound I-59D. MS: m/z=199.9 (M+1). $^1$H-NMR (400 MHz, Methanol-$d_4$): δ 8.00 (s, 1H), 4.75-4.71 (m, 2H), 3.47-3.43 (m, 2H).

Step D: 5-Chloro-2,3-dihydrofuro[2,3-b]pyridine-4-carboxamide (I-59)

To the mixture of 5-chloro-2,3-dihydrofuro[2,3-b]pyridine-4-carboxylic acid (I-59D, g, 0.25 mmol) in DCM (2.0 mL) and DMF (0.92 mg, 0.013 mmol) was added oxalyl dichloride (95 mg, 0.75 mmol) under argon atmosphere at 0° C. The mixture was stirred for 3 h at ambient temp. The volatiles were removed, and the residue was dissolved in ammonia in water (28% wt, 2 mL) and stirred for 2 h. The solvent was concentrated, and the residue was dissolved in saturate aq. $NaHCO_3$ (10 mL) and extracted with EtOAc (3×10 mL). The organic layer was dried over anhydrous $Na_2SO_4$ and concentrated. The residue obtained afforded compound I-59. MS: m/z=199.1 (M+1).

Intermediates I-60 through I-67 found in Table 12, were prepared in analogous fashion to the conditions described above in intermediate I-59.

TABLE 12

| Intermediate Number | Structure | Compound Name | Observed Mass (M + 1) |
|---|---|---|---|
| I-60 | 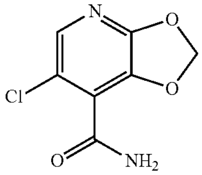 [SMILES: NC(=O)c1c(Cl)cnc2c1OCO2] | 6-chloro-[1,3] dioxolo[4,5-b]pyridine-7-carboxamide | 201.0 |
| I-61 | 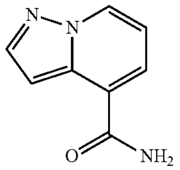 [SMILES: NC(=O)c1cccn2nccc12] | Pyrazolo[1,5-a] pyridine-4-carboxamide | 162.0 |

TABLE 12-continued

| Intermediate Number | Structure | Compound Name | Observed Mass (M + 1) |
|---|---|---|---|
| I-62 | 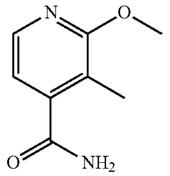 | 2-methoxy-3-methylisonicotinamide | 167.1 |
| I-63 | 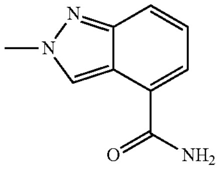 | 2-methyl-2H-indazole-4-carboxamide | 176.2 |
| I-64 | 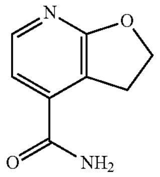 | 2,3-dihydrofuro[2,3-b]pyridine-4-carboxamide | 165.2 |
| I-65 | 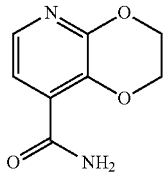 [SMILES: NC(=O)c1ccnc2c1OCCO2] | 2,3-dihydro-[1,4]dioxino [2,3-b]pyridine-8-carboxamide | 181.2 |
| I-66 | 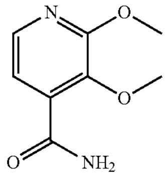 | 2,3-dimethoxy-N-methylisonicotinamide | 183.1 |
| I-67 | 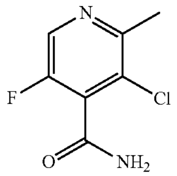 | 3-chloro-5-fluoro-2-methylisonicotinamide | 188.1 |

Intermediate I-68

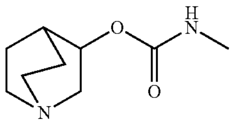

I-68

(R and S)-Quinuclidin-3-yl methylcarbamate (I-68)

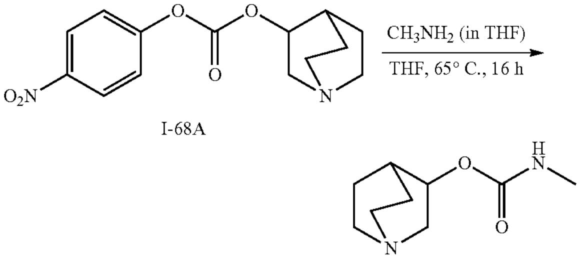

I-68A

I-68

A mixture of 4-nitrophenyl quinuclidin-3-yl carbonate (I-68A, 0.20 g, 0.68 mmol) and methanamine (0.11 g, 3.4 mmol) in THF (4 mL) was heated at 65° C. for 16 h then concentrated. The residue was purified by prep HPLC (19× 250 mm C18, 5.5 min, 5-32% ACN/water, 0.05% TFA added) to afford compound I-68. MS: m/z=185.3 (M+1).

Intermediate I-69

I-69

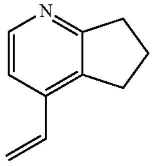

4-Vinyl-6,7-dihydro-5H-cyclopenta[b]pyridine (I-69)

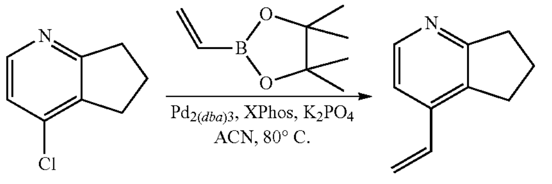

I-69A

I-69

A mixture of 4-chloro-6,7-dihydro-5H-cyclopenta[b]pyridine (I-69A, 0.10 g, 0.65 mmol), vinylboronic acid pinacol ester (0.13 mL, 0.78 mmol), $K_3PO_4$ (0.28 g, 1.3 mmol), 2-dicyclohexylphosphino-2',4',6'-triisopropylbiphenyl (XPhos, 93 mg, 0.20 mmol) and tris(dibenzylideneacetone) dipalladium ($Pd_2(dba)_3$, 53 mg, 0.065 mmol) in acetonitrile (1.0 mL) was heated at 80° C. under nitrogen atmosphere for 16 h. The mixture was diluted with water (15 mL) and extracted with ethyl acetate (3×50 mL). The combined organic fractions were washed with brine (3×50 mL), dried over $Na_2SO_4$ and concentrated. The residue was purified by silica gel column chromatography (0-30% EtOAc/PE gradient) to afford compound I-69. MS: m/z=146.3 (M+1). $^1$H NMR (300 MHz, Chloroform-d): δ 8.30 (d, J=5.1 Hz, 1H), 7.11 (d, J=5.1 Hz, 1H), 6.77-6.68 (m, 1H), 5.92-5.86 (m, 1H), 5.53-5.49 (m, 1H), 3.06-2.96 (m, 4H), 2.19-2.09 (m, 2H).

Intermediate I-70

I-70

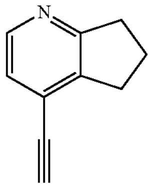

4-ethynyl-6,7-dihydro-5H-cyclopenta[b]pyridine (I-70)

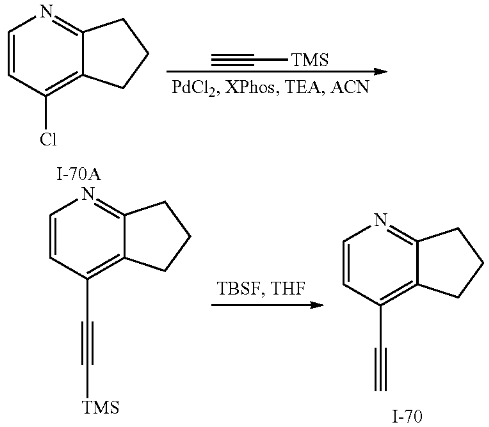

I-70A

I-70B

I-70

Step A: 4-((Trimethylsilyl)ethynyl)-6,7-dihydro-5H-cyclopenta[b]pyridine (I-70B)

A mixture of 4-chloro-6,7-dihydro-5H-cyclopenta[b]pyridine (I-70A, 0.30 g, 2.0 mmol), palladium(II) chloride (3.5 mg, 0.020 mmol), triethylamine (0.89 g, 8.8 mmol) and XPhos (28 mg, 0.059 mmol) in acetonitrile (1.0 mL) under nitrogen atmosphere was stirred for 20 min. then ethynyltrimethylsilane (0.29 g, 2.9 mmol) was added. The reaction mixture was stirred at ambient temperature for 3 h, then diluted with water (20 mL) and extracted with ethyl acetate (3×50 mL). The combined organic phase was washed with brine (3×50 mL), dried over $Na_2SO_4$ and concentrated. The residue was purified by silica gel column chromatography (0-30% EtOAc/PE gradient) to afford compound I-70B. MS: m/z=216.2 (M+1). $^1$H NMR (300 MHz, Chloroform-d): δ 8.29 (d, J=5.2 Hz, 1H), 7.06-7.04 (m, 1H), 3.08-2.99 (m, 4H), 2.16-2.08 (m, 2H), 0.27 (s, 9H).

Step B: 4-Ethynyl-6,7-dihydro-5H-cyclopenta[b]pyridine (I-70)

To a stirred mixture of 4-((trimethylsilyl)ethynyl)-6,7-dihydro-5H-cyclopenta[b]pyridine (I-70B, 370 mg, 1.7 mmol) in THF (3 mL) was added 1M tetrabutylammonium fluoride in THF (2.6 mL, 2.6 mmol) under nitrogen atmosphere. The resulting mixture was stirred for 20 min. then diluted with water (20 mL) and extracted with ethyl acetate (3×50 mL). The combined organic fractions were washed with brine (3×50 mL), dried over $Na_2SO_4$ and concentrated. The residue was purified by silica gel column chromatography (0-30% EtOAc/PE gradient) to afford compound I-70. MS: m/z=144.2 (M+1). $^1$H NMR (300 MHz, Chloroform-d): δ 8.32 (d, J=5.1 Hz, 1H), 7.09 (d, J=5.1 Hz, 1H), 3.39 (s, 1H), 3.09-3.01 (m, 4H), 2.20-2.10 (m, 2H).

Intermediate 71

I-71

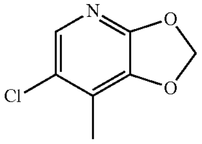

6-Chloro-7-iodo-[1,3]dioxolo[4,5-b]pyridine (I-71)

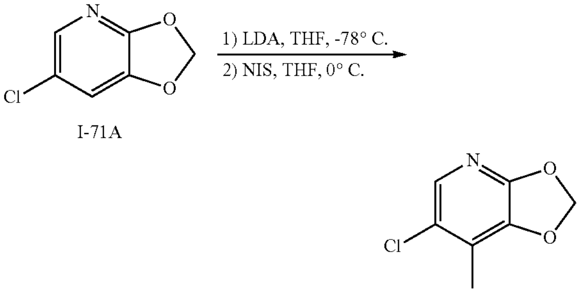

I-71A

I-71

To a stirred solution of 6-chloro-[1,3]dioxolo[4,5-b]pyridine (I-71A, 250 mg, 1.6 mmol) in THF (8.0 mL) was added dropwise 2M LDA in THF/n-heptane/ethylbenzene (1.0 mL, 2.1 mmol) at −78° C. under argon atmosphere over 10 minutes. The resulting mixture was cooled at −78° C. for 30 min. then a solution of NIS (540 mg, 2.4 mmol) in THF (3.0 mL) was added. The reaction mixture was allowed to warm to 0° C. and stirred for 1.5 h. The excess LDA was quenched with 10% aq. $NaHSO_3$ (25 mL) and extracted with EtOAc (3×20 mL). The combined organic phase was washed with $NaHCO_3$ (3×20 mL) and brine (2×20 mL), dried over anhydrous $Na_2SO_4$ and concentrated. The residue was purified by silica gel column chromatography (0-15% EtOAc/PE gradient) to give compound I-71. MS: m/z=283.9 (M+1). $^1$H-NMR (400 MHz, DMSO-$d_6$): δ 7.71 (s, 1H), 6.28 (s, 2H).

Intermediate I-72

I-72

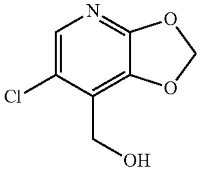

(6-Chloro-[1,3]dioxolo[4,5-b]pyridin-7-yl)methanol (I-72)

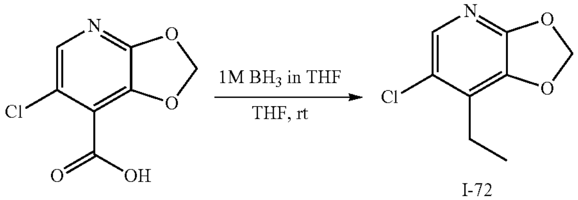

I-72A

I-72

To a solution of 6-chloro-[1,3]dioxolo[4,5-b]pyridine-7-carboxylic acid (I-72A, 140 mg, 0.35 mmol) in THF (3.0 mL) was added 1M $BH_3$-tetrahydrofuran complex in THF (0.35 mL, mmol) at 0° C. The resulting mixture was stirred for 4 h at ambient temp then the excess borane was quenched with MeOH (2.0 mL) and concentrated. The residue was purified by prep HPLC (AQ-C18 Column, 30 min, 0-100% ACN/water gradient) to afford compound I-72. MS: m/z=188.1 (M+1). $^1$H-NMR (300 MHz, Methanol-$d_4$): δ 7.59 (s, 1H), 6.18 (s, 2H), 4.68 (s, 2H).

Intermediate I-73 found in Table 13, was prepared in an analogous fashion to the conditions described above in intermediate I-72.

TABLE 13

| Intermediate Number | Structure | Compound Name | Observed Mass (M + 1) |
|---|---|---|---|
| I-73 | 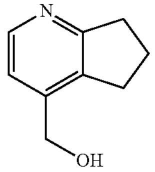 [SMILES: OCc1ccnc2c1CCC2] | (6,7-dihydro-5H-cyclopenta[b]pyridin-4-yl)methanol | 150.1 |

Intermediate I-74

I-74

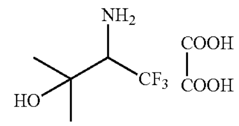

(R and S)-3-amino-4,4,4-trifluoro-2-methylbutan-2-ol oxalate (I-74)

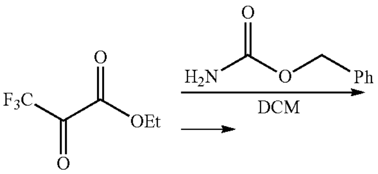

-continued

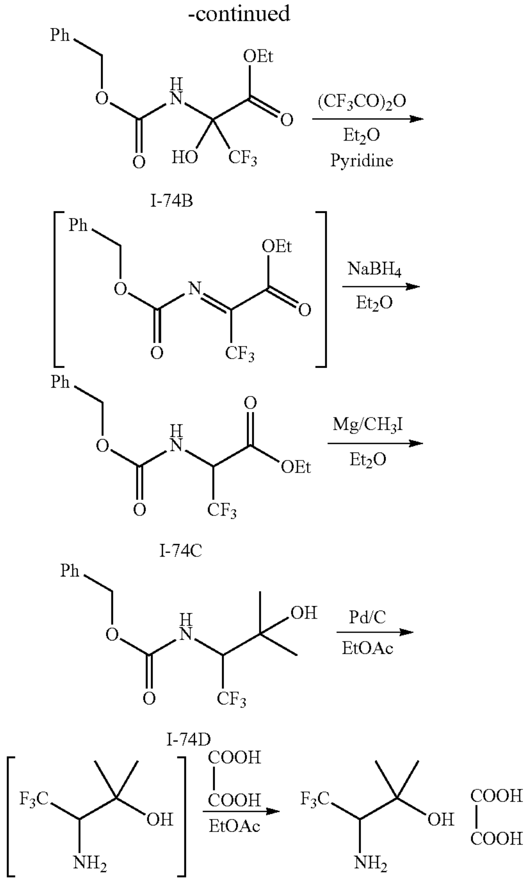

I-74B

I-74C

I-74D

I-74

Intermediate I-74 can be made by process outlined below. Alternatively, intermediate I-74 can be made by the process described in international patent application publication WO2008/086302 A1.

Step A: (R and 5)-Ethyl 2-(((benzyloxy)carbonyl) amino)-3,3,3-trifluoro-2-hydroxypropanoate (I-74B)

A mixture of ethyl 3,3,3-trifluoro-2-oxopropanoate (Matrix Scientific, 5.10 g, 30 mmol) and benzyl carbamate (Acros, 4.0 g, 30 mmol) in DCM (40 mL) is stirred for 2 days at ambient temperature. The precipitates are collected by vacuum filtration to afford compound I-74B.

Step B: (R and 5)-Ethyl 2-(((benzyloxy)carbonyl) amino)-3,3,3-trifluoropropanoate (I-74C)

Into a 100 mL 4-necked, round bottomed flask is placed (R and 5)-ethyl 2-(benzyloxycarbonyl)-3,3,3-trifluoro-2-hydroxypropanoate (I-74B, 4.1 g, 13 mmol), followed by the addition of a solution of trifluoroacetic acid anhydride (3.2 g, 15 mmol) in $Et_2O$ (40 mL). The mixture is stirred for 1 h, then pyridine (2.5 g, 31 mmol) is added and the resulting solution is stirred at ambient temperature overnight. The reaction mixture is cooled to −20° C. and filtered. $NaBH_4$ (790 mg, 21 mmol) is added to the filtrate and the resulting solution is stirred at ambient temperature for 1 h. The reaction mixture is quenched by adding water (50 mL). The separated organic layer is collected. The aqueous layer is extracted with EtOAc (2×20 mL). The combined organic layers are dried with $Na_2SO_4$ and concentrated. The residue is purified by recrystallization from EtOAc:PE in the ratio of 1:8 to afford compound I-74C.

Step C: (R and S)-Benzyl(1,1,1-trifluoro-3-hydroxy-3-methylbutan-2-yl)carbamate (I-74D)

A suspension of magnesium (1.0 g, 42 mmol) in $Et_2O$ (30 mL) is placed into a 50 mL 3-necked, round bottomed flask purged and maintained with an inert atmosphere of nitrogen. To this suspension is added iodomethane (3.1 g, 22 mmol) and (R and 5)-ethyl 2-(((benzyloxy)carbonyl)amino)-3,3,3-trifluoropropanoate (I-74C, 2.0 g, 6.6 mmol). The resulting solution is stirred at ambient temperature for 45 minutes. The reaction mixture is quenched by adding ice water (40 mL) and filtering. The filtrate is extracted with ether (2×16 mL). The combined organic layer is dried over $Na_2SO_4$ and concentrated to afford compound I-74D.

Step D: (R and S)-3-amino-4,4,4-trifluoro-2-methylbutan-2-ol oxalate (I-74)

A 50 mL round bottomed flask is purged, flushed and maintained with a hydrogen atmosphere, then a deoxygenated solution of (R and S)-benzyl 1,1,1-trifluoro-3-hydroxy-3-methylbutan-2-ylcarbamate (I-74D, 1.4 g, 4.8 mmol) in ethyl acetate (10 mL) is added followed by 10 wt % Pd/C (140 mg). The resulting mixture is stirred and is allowed to react, overnight at room temperature. The reaction mixture is filtered while under nitrogen. To the filtrate is added a solution of oxalic acid (390 mg, 4.3 mmol) in ethyl acetate (10 mL) dropwise with stirring. The resulting solution is allowed to react, with stirring for 30 min. The precipitated solid is collected by filtration to afford compound I-74. MS (ESI): m/z=158 (M+1). $^1$H-NMR (400 MHz, $D_2O$): δ 3.91-3.97 (1H, m), 1.31-1.37 (6H, d).

Compounds 1-60 of the current invention were prepared according to general Scheme I.

Example 1

1

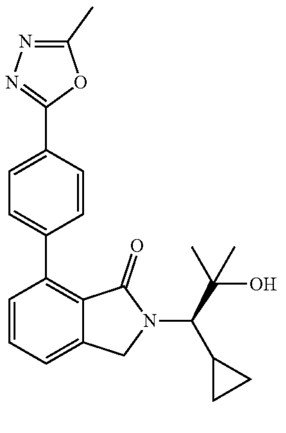

(R)-2-(1-Cyclopropyl-2-hydroxy-2-methylpropyl)-7-(4-(5-methyl-1,3,4-oxadiazol-2-yl)phenyl)isoindolin-1-one (1)

A mixture of (R)-7-bromo-2-(1-cyclopropyl-2-hydroxy-2-methylpropyl)isoindolin-1-one (I-4, 30.0 g, 92 mmol), 2-methyl-5-(4-(4,4,5,5-tetramethyl-1,3,2-dioxaborolan-2- yl)phenyl)-1,3,4-oxadiazole (32 g, 110 mmol), 1,1'-bis(di-t-butylphosphino)ferrocene palladium dichloride (3.0 g, 4.6 mmol) and $K_3PO_4$ (77 mL, 230 mmol) in THF (0.45 L) was heated at 70° C. for 3 h. Reaction mixture poured into water (300 mL) and extracted with ethyl acetate (200 mL, 100 mL, 100 mL). The combine organic layers were washed with brine (200 mL), dried over $Na_2SO_4$, and concentrated. The residue was purified by prep-HPLC (C18 10 um 250×80 mm; 23 min, 30-50% ACN/10 mM aq $NH_4HCO_3$, gradient) to afford compound 1. MS: m/z=404.3 (M+1). $^1$H-NMR (400 MHz, DMSO-$d_6$): δ 7.98 (d, 2H), 7.67-7.72 (m, 4H), 7.43 (t, J=4 Hz, 1H), 4.89 (d, J=18.4 Hz, 1H), 4.74 (s, 1H), 4.62 (d, J=18.4 Hz, 1H), 3.19-3.21 (d, J=10 Hz, 1H) 2.61 (s, 3H), 1.43-1.45 (m, 1H), 1.32 (s, 3H), 1.01 (s, 3H), 0.73-0.74 (m, 1H), 0.38-0.47 (m, 2H), −0.12~−0.09 (m, 1H).

Example 2

(2)

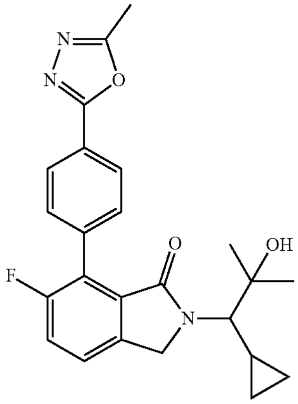

(R or S)-2-(1-Cyclopropyl-2-hydroxy-2-methylpropyl)-6-fluoro-7-(4-(5-methyl-1,3,4-oxadiazol-2-yl)phenyl)isoindolin-1-one (2)

A mixture of (R and S)-2-(1-cyclopropyl-2-hydroxy-2-methylpropyl)-6-fluoro-7-iodoisoindolin-1-one (I-15, 30 mg, 0.08 mmol), 2-methyl-5-(4-(4,4,5,5-tetramethyl-1,3,2-dioxaborolan-2-yl)phenyl)-1,3,4-oxadiazole (26 mg, 0.092 mmol), $K_3PO_4$ (33 mg, 0.15 mmol) and Pd(dppf)$Cl_2$ (5.6 mg, 7.7 μmol) in 1,4-dioxane (1.5 mL) was heated at 80° C. for 16 h. The reaction solution was filtered, and the filtrate directly purified by Prep-HPLC (C-18 19 mm×250 mm; 5.8 min, 70-85% ACN/10 mM aq $NH_4HCO_3$ gradient) to afford the racemic title compound. The racemic mixture was then purified by Chiral-Prep-HPLC (CHIRALPAK® ID, 3×25 cm, 5 um; 25 min, 30% EtOH/Hex (8 mM $NH_3$·MeOH) isocratic gradient). The second product-containing fractions were isolated to give the chiral compound 2. MS: m/z=422.2 (M+1). $^1$H-NMR (400 MHz, Chloroform-d): δ 8.11-8.09 (m, 2H), 7.63-7.60 (m, 2H), 7.47-7.44 (m, 1H), 7.38-7.34 (m, 1H), 4.80-4.64 (m, 1H), 3.32 (d, J=10.4 Hz, 1H), 2.62 (s, 3H), 1.40 (s, 3H), 1.35-1.26 (m, 1H), 1.23 (s, 3H), 0.90-0.84 (m, 1H), 0.58-0.48 (m, 2H), 0.23-0.16 (m, 1H). $^{19}$F-NMR (376 MHz, Chloroform-d): δ −118.69 (s, 1F).

Example 3

(3)

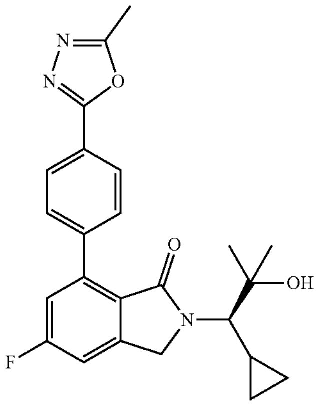

(R)-2-(1-Cyclopropyl-2-hydroxy-2-methylpropyl)-5-fluoro-7-(4-(5-methyl-1,3,4-oxadiazol-2-yl)phenyl)isoindolin-1-one (3)

A mixture of (R)-7-bromo-2-(1-cyclopropyl-2-hydroxy-2-methylpropyl)-5-fluoroisoindolin-1-one (I-20, 18 g, 53 mmol), 2-methyl-5-(4-(4,4,5,5-tetramethyl-1,3,2-dioxaborolan-2-yl)phenyl)-1,3,4-oxadiazole (18 g, 63 mmol), 1,1'-bis(di-t-butylphosphino)ferrocene palladium dichloride (1.7 g, 2.6 mmol) and $K_3PO_4$ (3 M, 44 mL) in THF (270 mL) was heated at 70° C. for 3 h. The reaction mixture poured into water (300 mL) and extracted with ethyl acetate (200 mL, 100 mL, 100 mL). The combine organic layers were washed with brine (200 mL), dried over $Na_2SO_4$, and concentrated. The residue was purified by silica gel chromatography (10-100% EtOAc/PE gradient) to provide compound 3. MS: m/z=422.2 (M+1). $^1$H-NMR (400 MHz, DMSO-$d_6$) δ 7.98 (d, J=8.4 Hz, 2H), 7.74 (d, J=8.4 Hz, 2H), 7.56-7.59 (m, 1H), 7.30-7.34 (m, 1H), 4.90 (d, J=18.8 Hz, 1H), 4.77 (s, 1H), 4.62 (d, J=19.2 Hz, 1H), 3.17 (d, J=10.0 Hz, 1H), 2.61 (s, 3H), 1.43-1.45 (m, 1H), 1.38 (s, 3H), 1.01 (s, 3H), 0.73-0.74 (m, 1H), 0.38-0.47 (m, 2H), −0.12−−0.09 (m, 1H).

Example 4

(4)

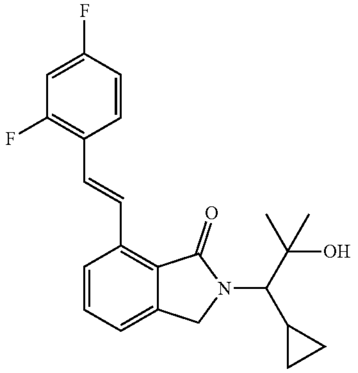

(R and S)-(E)-2-(1-cyclopropyl-2-hydroxy-2-methylpropyl)-7-(2,4-difluorostyryl)isoindolin-1-one (4)

A mixture of (R and S)-7-bromo-2-(1-cyclopropyl-2-hydroxy-2-methylpropyl)isoindolin-1-one (I-4, 9.7 mg, 30 μmol), (E)-2-(2,4-difluorostyryl)-4,4,5,5-tetramethyl-1,3,2-dioxaborolane (45 μmol) in THF (0.30 ml), potassium phosphate (19 mg, 90 μmol), water (75 μL) and bis(di-tert-butyl(4-dimethylaminophenyl)phosphine)dichloropalladium(II) (2.1 mg, 3.0 μmol) was heated at 60° C. for 16 h. The reaction mixture was cooled and concentrated. The residue was purified by prep HPLC (C18 150×25 mm, 52%-82% $ACN/H_2O$, 0.05% $NH_4OH$ and 10 mM $NH_4HCO_3$ added) to give compound 4. MS: m/z=384.1 (M+1). $^1H$ NMR (500 MHz, DMSO-$d_6$) δ 8.58 (d, J=16.8 Hz, 1H), 7.90 (d, J=7.6 Hz, 1H), 7.74 (q, J=8.5 Hz, 1H), 7.59 (t, J=7.5 Hz, 1H), 7.54 (d, J=7.4 Hz, 1H), 7.38 (d, J=16.8 Hz, 1H), 7.30 (t, J=10.2 Hz, 1H), 7.16 (t, J=8.5 Hz, 1H), 4.83 (s, 1H), 4.59 (s, 1H), 3.25 (d, J=10.1 Hz, 1H), 2.55 (s, 1H), 1.43 (s, 1H), 1.34 (s, 4H), 1.03 (s, 4H), 0.76 (s, 1H), 0.51-0.46 (m, 1H), 0.39 (d, J=4.3 Hz, 1H).

Compounds 5 through 62 found in Table 14 were synthesized utilizing analogous methods to those disclosed in Examples 1~4 utilizing the Suzuki coupling reaction shown where the resulting compound may have been synthesized from chiral or racemic material or separated by chiral chromatography. Commercially available reagents were substituted where necessary to produce the compounds 5 through 62. Phenols 58, 59 and 60 were synthesized utilizing a palladium mediated C—O coupling reaction of the corresponding aryl chloride. Compound 61 was afforded after Stille coupling of the corresponding aryl chloride with tetramethyltin. Compound 62 was afforded after SEM deprotection of the corresponding product from the Suzuki coupling with protected intermediate I-24.

TABLE 14

| Compound Number | Structure | Chemical Name | Observed Mass (M + 1) |
|---|---|---|---|
| 5 | 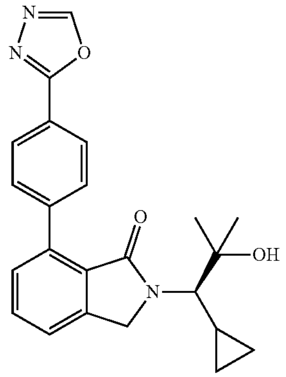 [SMILES: CC(C)(O)[C@@H](C1CC1)N1Cc2cccc(-c3ccc(-c4nnco4)cc3)c2C1=O] | (R)-7-(4-(1,3,4-oxadiazol-2-yl)phenyl)-2-(1-cyclopropyl-2-hydroxy-2-methylpropyl) isoindolin-1-one | 390.3 |
| 6 | 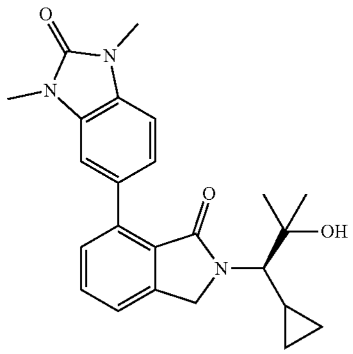 [SMILES: Cn1c(=O)n(C)c2cc(-c3cccc4c3C(=O)N([C@H](C3CC3)C(C)(C)O)C4)ccc21] | (R)-5-(2-(1-cyclopropyl-2-hydroxy-2-methylpropyl)-3-oxoisoindolin-4-yl)-1,3-dimethyl-1,3-dihydro-2H-benzo[d]imidazol-2-one | 406.4 |
| 7 | 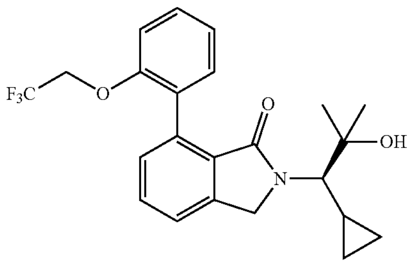 [SMILES: CC(C)(O)[C@@H](C1CC1)N1Cc2cccc(-c3ccccc3OCC(F)(F)F)c2C1=O] | (R)-2-(1-cyclopropyl-2-hydroxy-2-methylpropyl)-7-(2-(2,2,2-trifluoroethoxy) phenyl) isoindolin-1-one | 420.4 |

TABLE 14-continued

| Compound Number | Structure | Chemical Name | Observed Mass (M + 1) |
|---|---|---|---|
| 8 | 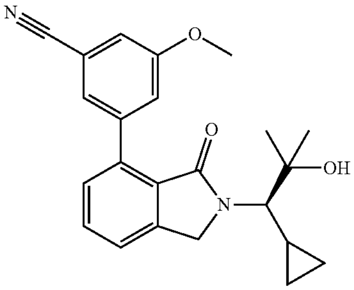 [SMILES: COc1cc(C#N)cc(-c2cccc3c2C(=O)N([C@H](C2CC2)C(C)(C)O)C3)c1] | (R)-3-(2-(1-cyclopropyl-2-hydroxy-2-methylpropyl)-3-oxoisoindolin-4-yl)-5-methoxybenzonitrile | 377.3 |
| 9 | 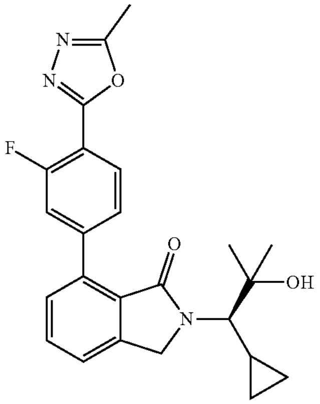 [SMILES: Cc1nnc(-c2ccc(-c3cccc4c3C(=O)N([C@H](C3CC3)C(C)(C)O)C4)cc2F)o1] | (R)-2-(1-cyclopropyl-2-hydroxy-2-methylpropyl)-7-(3-fluoro-4-(5-methyl-1,3,4-oxadiazol-2-yl)phenyl)isoindolin-1-one | 444.3 |
| 10 | 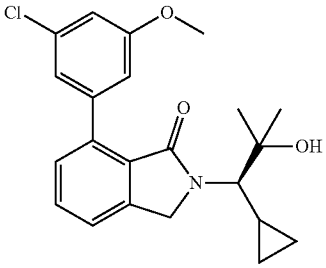 [SMILES: COc1cc(Cl)cc(-c2cccc3c2C(=O)N([C@H](C2CC2)C(C)(C)O)C3)c1] | (R)-7-(3-chloro-5-methoxyphenyl)-2-(1-cyclopropyl-2-hydroxy-2-methylpropyl) isoindolin-1-one | 386.3 |
| 11 | 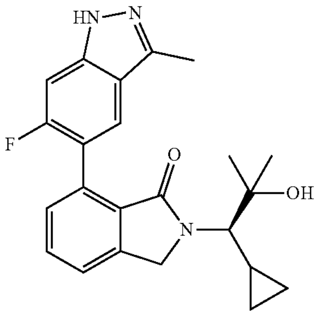 [SMILES: Cc1n[nH]c2cc(F)c(-c3cccc4c3C(=O)N([C@H](C3CC3)C(C)(C)O)C4)cc12] | (R)-2-(1-cyclopropyl-2-hydroxy-2-methylpropyl)-7-(6-fluoro-3-methyl-1H-indazol-5-yl)isoindolin-1-one | 394.3 |

TABLE 14-continued

| Compound Number | Structure | Chemical Name | Observed Mass (M + 1) |
|---|---|---|---|
| 12 | 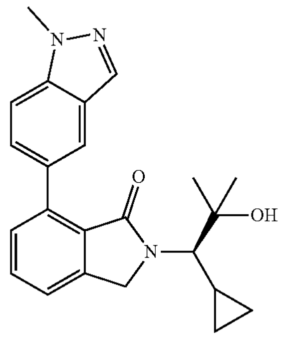 [SMILES: Cn1ncc2cc(-c3cccc4c3C(=O)N([C@H](C3CC3)C(C)(C)O)C4)ccc21] | (R)-2-(1-cyclopropyl-2-hydroxy-2-methylpropyl)-7-(1-methyl-1H-indazol-5-yl)isoindolin-1-one | 376.3 |
| 13 | 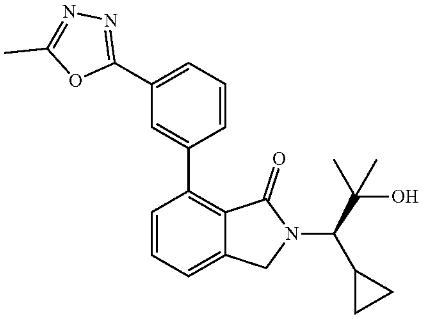 [SMILES: Cc1nnc(-c2cccc(-c3cccc4c3C(=O)N([C@H](C3CC3)C(C)(C)O)C4)c2)o1] | (R)-2-(1-cyclopropyl-2-hydroxy-2-methylpropyl)-7-(3-(5-methyl-1,3,4-oxadiazol-2-yl)phenyl)isoindolin-1-one | 426.2 |
| 14 | 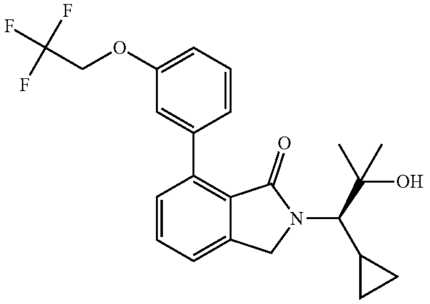 [SMILES: CC(C)(O)[C@@H](C1CC1)N1Cc2cccc(-c3cccc(OCC(F)(F)F)c3)c2C1=O] | (R)-2-(1-cyclopropyl-2-hydroxy-2-methylpropyl)-7-(3-(2,2,2-trifluoroethoxy) phenyl) isoindolin-1-one | 442.2 |
| 15 | 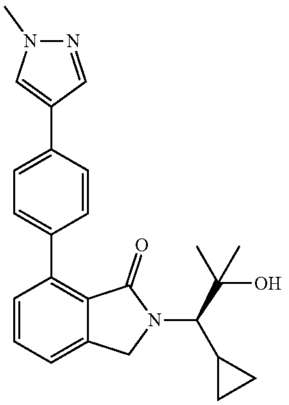 [SMILES: Cn1cc(-c2ccc(-c3cccc4c3C(=O)N([C@H](C3CC3)C(C)(C)O)C4)cc2)cn1] | (R)-2-(1-cyclopropyl-2-hydroxy-2-methylpropyl)-7-(4-(1-methyl-1H-pyrazol-4-yl)phenyl)isoindolin-1-one | 402.3 |

TABLE 14-continued

| Compound Number | Structure | Chemical Name | Observed Mass (M + 1) |
|---|---|---|---|
| 16 | 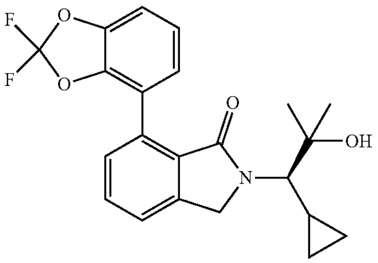 [SMILES: CC(C)(O)[C@@H](C1CC1)N1Cc2cccc(-c3cccc4c3OC(F)(F)O4)c2C1=O] | (R)-2-(1-cyclopropyl-2-hydroxy-2-methylpropyl)-7-(2,2-difluorobenzo[d][1,3]dioxol-4-yl)isoindolin-1-one | 424.2 |
| 17 | 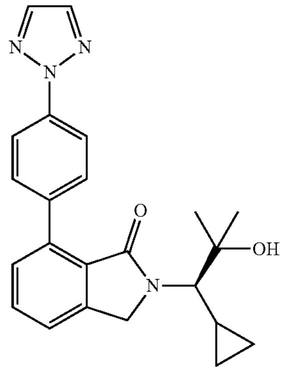 [SMILES: CC(C)(O)[C@@H](C1CC1)N1Cc2cccc(-c3ccc(-n4nccn4)cc3)c2C1=O] | (R)-7-(4-(2H-1,2,3-triazol-2-yl)phenyl)-2-(1-cyclopropyl-2-hydroxy-2-methylpropyl) isoindolin-1-one | 389.4 |
| 18 | 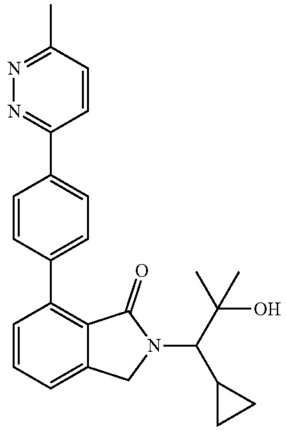 [SMILES: Cc1ccc(-c2ccc(-c3cccc4c3C(=O)N(C(C3CC3)C(C)(C)O)C4)cc2)nn1] | (R and S)-2-(1-cyclopropyl-2-hydroxy-2-methylpropyl)-7-(4-(6-methylpyridazin-3-yl)phenyl)isoindolin-1-one | 414.1 |
| 19 | 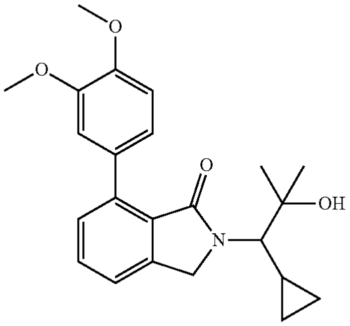 [SMILES: COc1ccc(-c2cccc3c2C(=O)N(C(C2CC2)C(C)(C)O)C3)cc1OC] | (R and S)-2-(1-cyclopropyl-2-hydroxy-2-methylpropyl)-7-(3,4-dimethoxyphenyl) isoindolin-1-one | 382.1 |

TABLE 14-continued

| Compound Number | Structure | Chemical Name | Observed Mass (M + 1) |
|---|---|---|---|
| 20 | 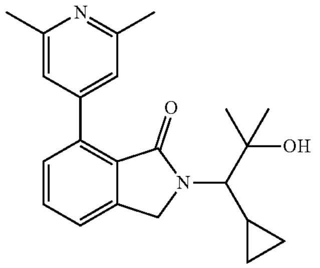 [SMILES: Cc1cc(-c2cccc3c2C(=O)N(C(C2CC2)C(C)(C)O)C3)cc(C)n1] | (R and S)-2-(1-cyclopropyl-2-hydroxy-2-methylpropyl)-7-(2,6-dimethylpyridin-4-yl)isoindolin-1-one | 351.1 |
| 21 | 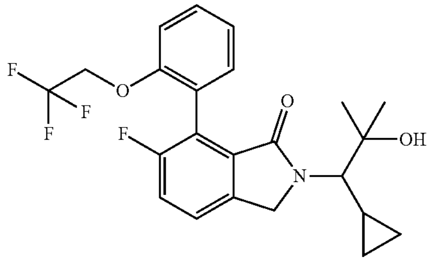 [SMILES: CC(C)(O)C(C1CC1)N1Cc2ccc(F)c(-c3ccccc3OCC(F)(F)F)c2C1=O] | 2-((R or S)-1-cyclopropyl-2-hydroxy-2-methylpropyl)-6-fluoro-7-(2-(2,2,2-trifluoroethoxy) phenyl) isoindolin-1-one | 438.2 |
| 22 | 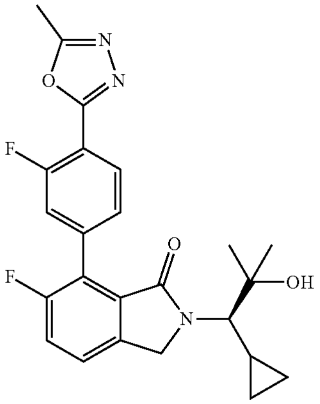 [SMILES: Cc1nnc(-c2ccc(-c3c(F)ccc4c3C(=O)N([C@H](C3CC3)C(C)(C)O)C4)cc2F)o1] | (R)-2-(1-cyclopropyl-2-hydroxy-2-methylpropyl)-6-fluoro-7-(3-fluoro-4-(5-methyl-1,3,4-oxadiazol-2-yl)phenyl) isoindolin-1-one | 440.3 |
| 23 | 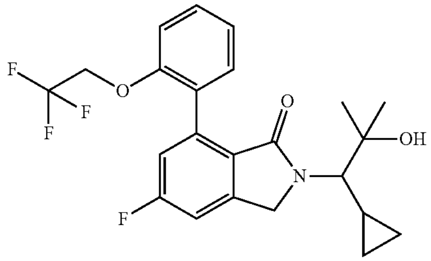 [SMILES: CC(C)(O)C(C1CC1)N1Cc2cc(F)cc(-c3ccccc3OCC(F)(F)F)c2C1=O] | (R or S)-2-(1-cyclopropyl-2-hydroxy-2-methylpropyl)-5-fluoro-7-(2-(2,2,2-trifluoroethoxy) phenyl) isoindolin-1-one | 438.1 |

TABLE 14-continued

| Compound Number | Structure | Chemical Name | Observed Mass (M + 1) |
| --- | --- | --- | --- |
| 24 | 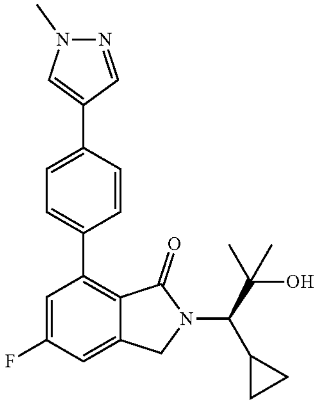 [SMILES: Cn1cc(-c2ccc(-c3cc(F)cc4c3C(=O)N([C@H](C3CC3)C(C)(C)O)C4)cc2)cn1] | (R)-2-(1-cyclopropyl-2-hydroxy-2-methylpropyl)-5-fluoro-7-(4-(1-methyl-1H-pyrazol-4-yl)phenyl)isoindolin-1-one | 420.2 |
| 25 | 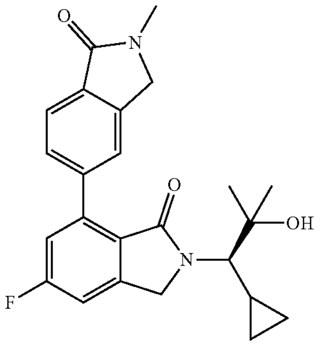 [SMILES: CN1Cc2cc(-c3cc(F)cc4c3C(=O)N([C@H](C3CC3)C(C)(C)O)C4)ccc2C1=O] | (R)-2-(1-cyclopropyl-2-hydroxy-2-methylpropyl)-6-fluoro-2'-methyl-[4,5'-biisoindoline]-1',3-dione | 409.2 |
| 26 | 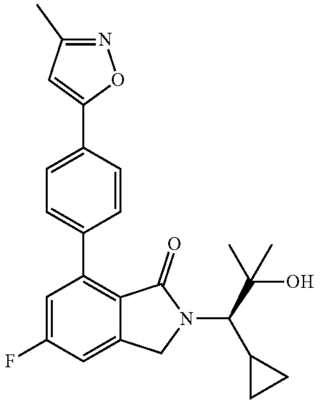 [SMILES: Cc1cc(-c2ccc(-c3cc(F)cc4c3C(=O)N([C@H](C3CC3)C(C)(C)O)C4)cc2)on1] | (R)-2-(1-cyclopropyl-2-hydroxy-2-methylpropyl)-5-fluoro-7-(4-(3-methylisoxazol-5-yl)phenyl)isoindolin-1-one | 421.0 |
| 27 | 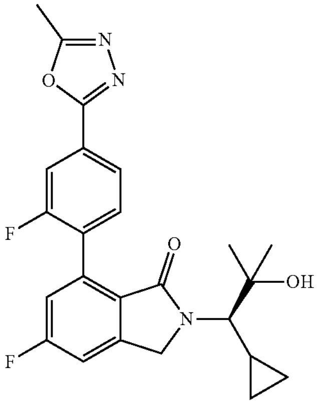 [SMILES: Cc1nnc(-c2ccc(-c3cc(F)cc4c3C(=O)N([C@H](C3CC3)C(C)(C)O)C4)c(F)c2)o1] | (R)-2-(1-cyclopropyl-2-hydroxy-2-methylpropyl)-5-fluoro-7-(2-fluoro-4-(5-methyl-1,3,4-oxadiazol-2-yl)phenyl)isoindolin-1-one | 440.3 |

TABLE 14-continued

| Compound Number | Structure | Chemical Name | Observed Mass (M + 1) |
|---|---|---|---|
| 28 | 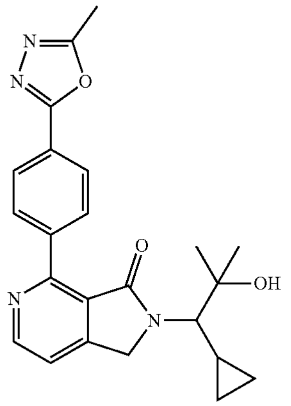 [SMILES: Cc1nnc(-c2ccc(-c3nccc4c3C(=O)N(C(C3CC3)C(C)(C)O)C4)cc2)o1] | (R or S)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one | 405.2 |
| 29 | 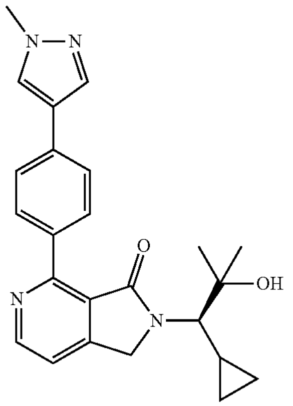 [SMILES: Cn1cc(-c2ccc(-c3nccc4c3C(=O)N([C@H](C3CC3)C(C)(C)O)C4)cc2)cn1] | (R)-2-(1-cyclopropyl-2-hydroxy-2-methylpropyl)-4-(4-(1-methyl-1H-pyrazol-4-yl)phenyl)-1,2-dihydro-3H-pyrrolo[3,4-c]pyridin-3-one | 403.2 |
| 30 | 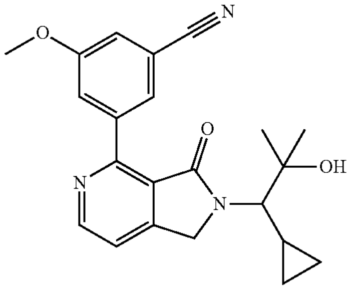 [SMILES: COc1cc(C#N)cc(-c2nccc3c2C(=O)N(C(C2CC2)C(C)(C)O)C3)c1] | (R or S)-3-(2-(1-cyclopropyl-2-hydroxy-2-methylpropyl)-3-oxo-2,3-dihydro-1H-pyrrolo[3,4-c]pyridin-4-yl)-5-methoxybenzonitrile | 378.2 |
| 31 | 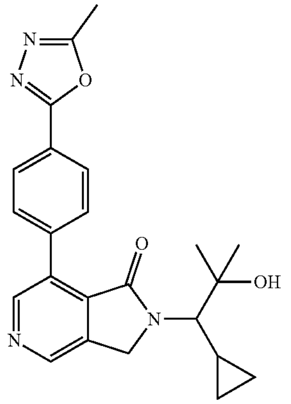 [SMILES: Cc1nnc(-c2ccc(-c3cncc4c3C(=O)N(C(C3CC3)C(C)(C)O)C4)cc2)o1] | (R or S)-2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one | 405.2 |

TABLE 14-continued

| Compound Number | Structure | Chemical Name | Observed Mass (M + 1) |
|---|---|---|---|
| 32 | 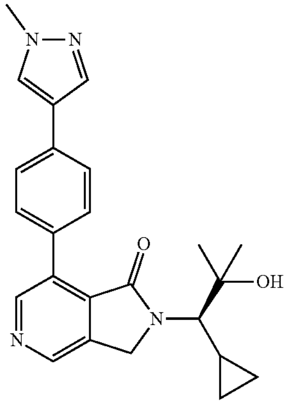 [SMILES: Cn1cc(-c2ccc(-c3cncc4c3C(=O)N([C@H](C3CC3)C(C)(C)O)C4)cc2)cn1] | (R)-2-(1-cyclopropyl-2-hydroxy-2-methylpropyl)-7-(4-(1-methyl-1H-pyrazol-4-yl)phenyl)-2,3-dihydro-1H-pyrrolo[3,4-c]pyridin-1-one | 403.2 |
| 33 | 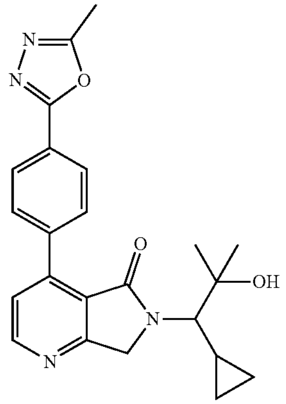 [SMILES: Cc1nnc(-c2ccc(-c3ccnc4c3C(=O)N(C(C3CC3)C(C)(C)O)C4)cc2)o1] | (R or S)-6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one | 405.3 |
| 34 | 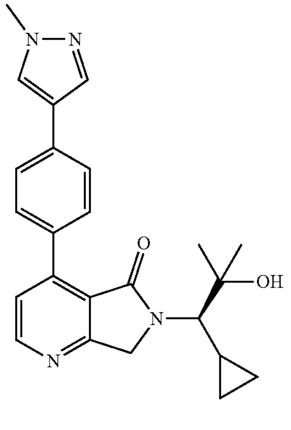 [SMILES: Cn1cc(-c2ccc(-c3ccnc4c3C(=O)N([C@H](C3CC3)C(C)(C)O)C4)cc2)cn1] | (R)-6-(1-cyclopropyl-2-hydroxy-2-methylpropyl)-4-(4-(1-methyl-1H-pyrazol-4-yl)phenyl)-6,7-dihydro-5H-pyrrolo[3,4-b]pyridin-5-one | 403.2 |

TABLE 14-continued
| Compound Number | Structure | Chemical Name | Observed Mass (M + 1) |
|---|---|---|---|
| 35 | 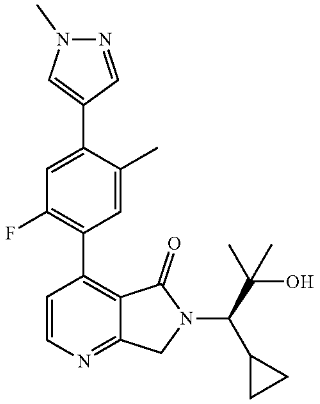 [SMILES: Cc1cc(-c2ccnc3c2C(=O)N([C@H](C2CC2)C(C)(C)O)C3)c(F)cc1-c1cnn(C)c1] | (R)-6-(1-cyclopropyl-2-hydroxy-2-methylpropyl)-4-(2-fluoro-5-methyl-4-(1-methyl-1H-pyrazol-4-yl)phenyl)-6,7-dihydro-5H-pyrrolo[3,4-b]pyridin-5-one | 435.2 |
| 36 | 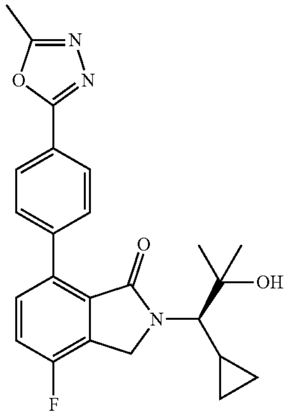 [SMILES: Cc1nnc(-c2ccc(-c3ccc(F)c4c3C(=O)N([C@H](C3CC3)C(C)(C)O)C4)cc2)o1] | (R)-2-(1-cyclopropyl-2-hydroxy-2-methylpropyl)-4-fluoro-7-(4-(5-methyl-1,3,4-oxadiazol-2-yl)phenyl)isoindolin-1-one | 422.2 |
| 37 | 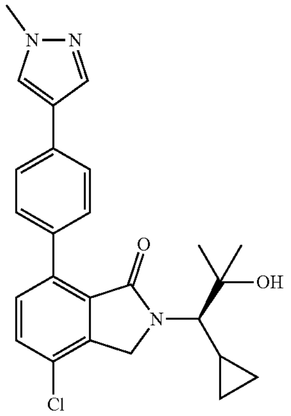 [SMILES: Cn1cc(-c2ccc(-c3ccc(Cl)c4c3C(=O)N([C@H](C3CC3)C(C)(C)O)C4)cc2)cn1] | (R)-4-chloro-2-(1-cyclopropyl-2-hydroxy-2-methylpropyl)-7-(4-(1-methyl-1H-pyrazol-4-yl)phenyl)isoindolin-1-one | 436.2 |

TABLE 14-continued
| Compound Number | Structure | Chemical Name | Observed Mass (M + 1) |
|---|---|---|---|
| 38 | 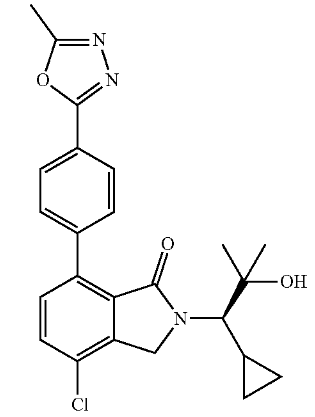 [SMILES: Cc1nnc(-c2ccc(-c3ccc(Cl)c4c3C(=O)N([C@H](C3CC3)C(C)(C)O)C4)cc2)o1] | (R)-4-chloro-2-(1-cyclopropyl-2-hydroxy-2-methylpropyl)-7-(4-(5-methyl-1,3,4-oxadiazol-2-yl)phenyl)isoindolin-1-one | 438.2 |
| 39 | 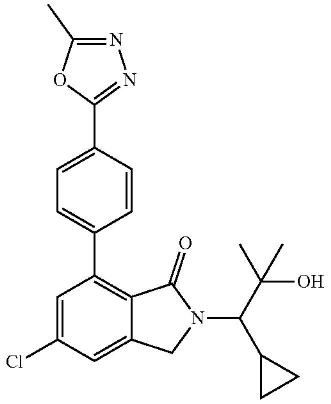 [SMILES: Cc1nnc(-c2ccc(-c3cc(Cl)cc4c3C(=O)N(C(C3CC3)C(C)(C)O)C4)cc2)o1] | (R or S)-5-chloro-2-(1-cyclopropyl-2-hydroxy-2-methylpropyl)-7-(4-(5-methyl-1,3,4-oxadiazol-2-yl)phenyl)isoindolin-1-one | 438.2 |
| 40 | 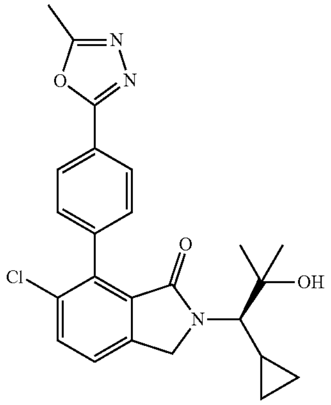 [SMILES: Cc1nnc(-c2ccc(-c3c(Cl)ccc4c3C(=O)N([C@H](C3CC3)C(C)(C)O)C4)cc2)o1] | (R)-6-chloro-2-(1-cyclopropyl-2-hydroxy-2-methylpropyl)-7-(4-(5-methyl-1,3,4-oxadiazol-2-yl)phenyl)isoindolin-1-one | 438.2 |

TABLE 14-continued
| Compound Number | Structure | Chemical Name | Observed Mass (M + 1) |
|---|---|---|---|
| 41 | 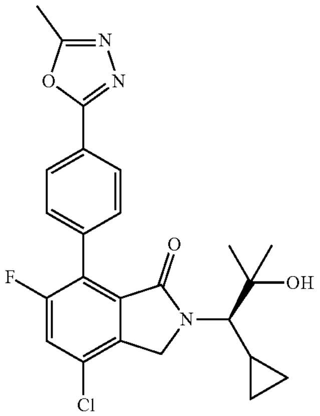 [SMILES: Cc1nnc(-c2ccc(-c3c(F)cc(Cl)c4c3C(=O)N([C@H](C3CC3)C(C)(C)O)C4)cc2)o1] | (R)-4-chloro-2-(1-cyclopropyl-2-hydroxy-2-methylpropyl)-6-fluoro-7-(4-(5-methyl-1,3,4-oxadiazol-2-yl)phenyl)isoindolin-1-one | 456.0 |
| 42 | 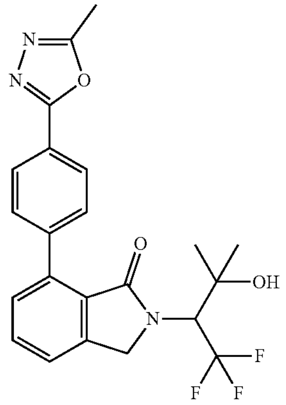 [SMILES: Cc1nnc(-c2ccc(-c3cccc4c3C(=O)N(C(C(C)(C)O)C(F)(F)F)C4)cc2)o1] | (R or S)-7-(4-(5-methyl-1,3,4-oxadiazol-2-yl)phenyl)-2-(1,1,1-trifluoro-3-hydroxy-3-methylbutan-2-yl)isoindolin-1-one | 432.1 |
| 43 | 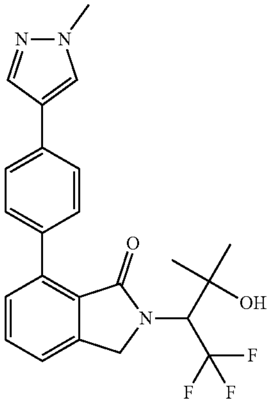 [SMILES: Cn1cc(-c2ccc(-c3cccc4c3C(=O)N(C(C(C)(C)O)C(F)(F)F)C4)cc2)cn1] | (R or S)-7-(4-(1-methyl-1H-pyrazol-4-yl)phenyl)-2-(1,1,1-trifluoro-3-hydroxy-3-methylbutan-2-yl)isoindolin-1-one | 430.2 |

TABLE 14-continued

| Compound Number | Structure | Chemical Name | Observed Mass (M + 1) |
|---|---|---|---|
| 44 | 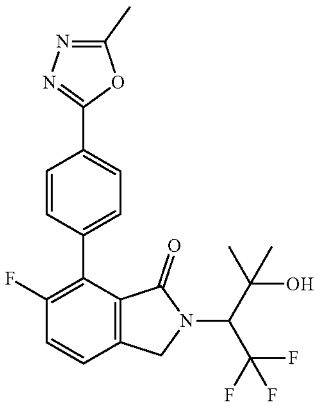 [SMILES: Cc1nnc(-c2ccc(-c3c(F)ccc4c3C(=O)N(C(C(C)(C)O)C(F)(F)F)C4)cc2)o1] | (R or S)-6-fluoro-7-(4-(5-methyl-1,3,4-oxadiazol-2-yl)phenyl)-2-(1,1,1-trifluoro-3-hydroxy-3-methylbutan-2-yl)isoindolin-1-one | 450.2 |
| 45 | 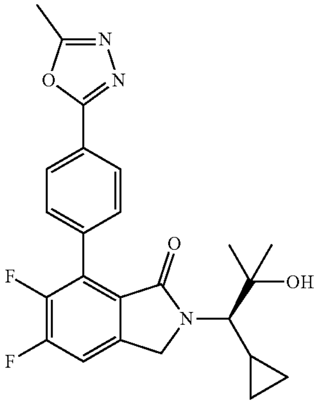 [SMILES: Cc1nnc(-c2ccc(-c3c(F)c(F)cc4c3C(=O)N([C@H](C3CC3)C(C)(C)O)C4)cc2)o1] | (R)-2-(1-cyclopropyl-2-hydroxy-2-methylpropyl)-5,6-difluoro-7-(4-(5-methyl-1,3,4-oxadiazol-2-yl)phenyl)isoindolin-1-one | 440.1 |
| 46 | 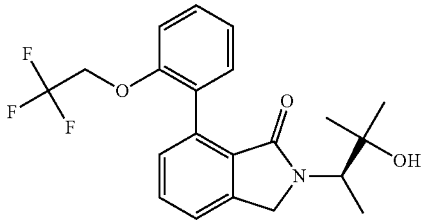 [SMILES: C[C@@H](N1Cc2cccc(-c3ccccc3OCC(F)(F)F)c2C1=O)C(C)(C)O] | (R)-2-(3-hydroxy-3-methylbutan-2-yl)-7-(2-(2,2,2-trifluoroethoxy) phenyl) isoindolin-1-one | 416.1 |
| 47 | 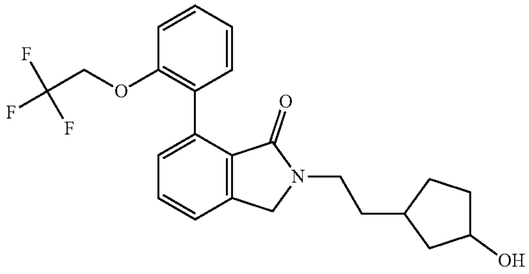 [SMILES: O=C1c2c(cccc2-c2ccccc2OCC(F)(F)F)CN1CCC1CCC(O)C1] | (cis and trans racemic)-2-(2-(3-hydroxycyclopentyl) ethyl)-7-(2-(2,2,2-trifluoroethoxy) phenyl) isoindolin-1-one | 442.3 |

TABLE 14-continued

| Compound Number | Structure | Chemical Name | Observed Mass (M + 1) |
|---|---|---|---|
| 48 | 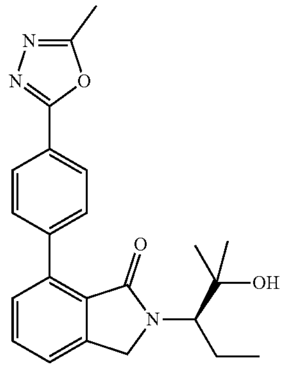 [SMILES: CC[C@@H](N1Cc2cccc(-c3ccc(-c4nnc(C)o4)cc3)c2C1=O)C(C)(C)O] | 2-[(1R)-1-ethyl-2-hydroxy-2-methyl-propyl]-7-[4-(5-methyl-1,3,4-oxadiazol-2-yl)phenyl]isoindolin-1-one | 392.1 |
| 49 | 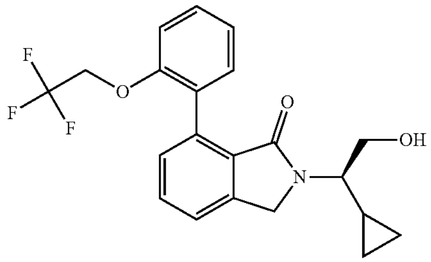 [SMILES: O=C1c2c(cccc2-c2ccccc2OCC(F)(F)F)CN1[C@@H](CO)C1CC1] | (R)-2-(1-cyclopropyl-2-hydroxyethyl)-7-(2-(2,2,2-trifluoroethoxy) phenyl) isoindolin-1-one | 414.2 |
| 50 | 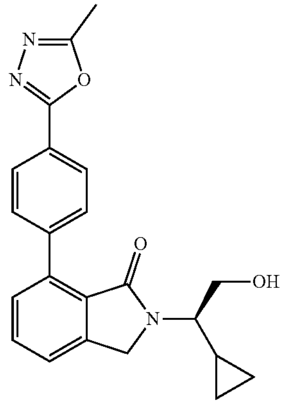 [SMILES: Cc1nnc(-c2ccc(-c3cccc4c3C(=O)N([C@@H](CO)C3CC3)C4)cc2)o1] | (R)-2-(1-cyclopropyl-2-hydroxyethyl)-7-(4-(5-methyl-1,3,4-oxadiazol-2-yl)phenyl)isoindolin-1-one | 376.3 |
| 51 | 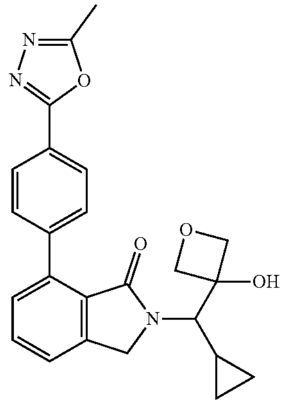 [SMILES: Cc1nnc(-c2ccc(-c3cccc4c3C(=O)N(C(C3CC3)C3(O)COC3)C4)cc2)o1] | (R or S)-2-(cyclopropyl(3-hydroxyoxetan-3-yl)methyl)-7-(4-(5-methyl-1,3,4-oxadiazol-2-yl)phenyl)isoindolin-1-one | 418.3 |

TABLE 14-continued

| Compound Number | Structure | Chemical Name | Observed Mass (M + 1) |
|---|---|---|---|
| 52 | 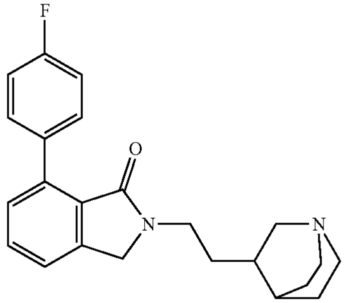 [SMILES: O=C1c2c(cccc2-c2ccc(F)cc2)CN1CCC1CN2CCC1CC2] | (R and S)-7-(4-fluorophenyl)-2-(2-(quinuclidin-3-yl)ethyl)isoindolin-1-one | 365.4 |
| 53 | 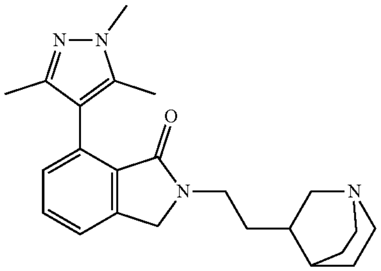 [SMILES: Cc1nn(C)c(C)c1-c1cccc2c1C(=O)N(CCC1CN3CCC1CC3)C2] | (R and S)-2-(2-(quinuclidin-3-yl)ethyl)-7-(1,3,5-trimethyl-1H-pyrazol-4-yl)isoindolin-1-one | 379.5 |
| 54 | 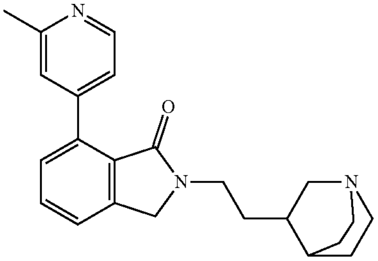 [SMILES: Cc1cc(-c2cccc3c2C(=O)N(CCC2CN4CCC2CC4)C3)ccn1] | (R and S)-7-(2-methylpyridin-4-yl)-2-(2-(quinuclidin-3-yl)ethyl)isoindolin-1-one | 362.4 |
| 55 | 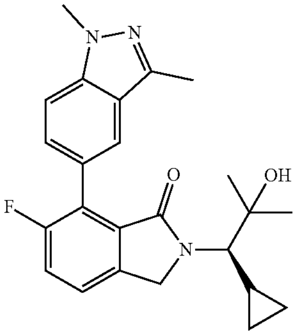 [SMILES: Cc1nn(C)c2ccc(-c3c(F)ccc4c3C(=O)N([C@H](C3CC3)C(C)(C)O)C4)cc12] | (R)-2-(1-cyclopropyl-2-hydroxy-2-methylpropyl)-7-(1,3-dimethyl-1H-indazol-5-yl)-6-fluoroisoindolin-1-one | 408.1 |
| 56 | 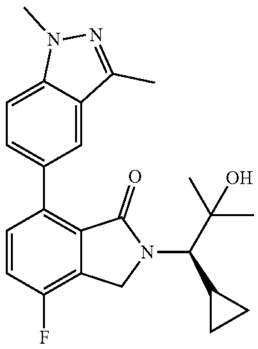 [SMILES: Cc1nn(C)c2ccc(-c3ccc(F)c4c3C(=O)N([C@H](C3CC3)C(C)(C)O)C4)cc12] | (R)-2-(1-cyclopropyl-2-hydroxy-2-methylpropyl)-7-(1,3-dimethyl-1H-indazol-5-yl)-4-fluoroisoindolin-1-one | 408.2 |

TABLE 14-continued

| Compound Number | Structure | Chemical Name | Observed Mass (M + 1) |
|---|---|---|---|
| 57 | 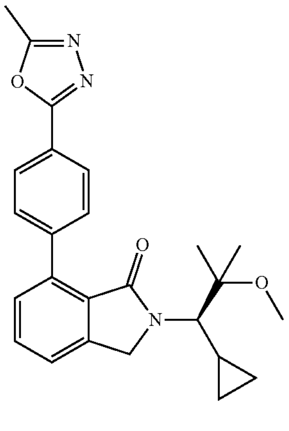 | (R)-2-(1-cyclopropyl-2-methoxy-2-methylpropyl)-7-(4-(5-methyl-1,3,4-oxadiazol-2-yl)phenyl)isoindolin-1-one | 418.2 |
| 58 | 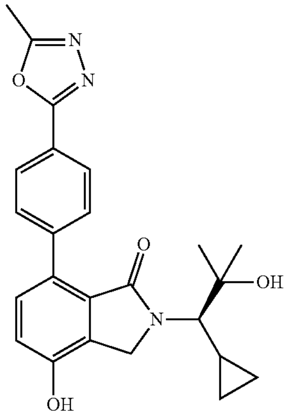 [SMILES: Cc1nnc(-c2ccc(-c3ccc(O)c4c3C(=O)N([C@H](C3CC3)C(C)(C)O)C4)cc2)o1] | (R)-2-(1-cyclopropyl-2-hydroxy-2-methylpropyl)-4-hydroxy-7-(4-(5-methyl-1,3,4-oxadiazol-2-yl)phenyl)isoindolin-1-one | 420.2 |

-continued

| | | | |
|---|---|---|---|
| 59 | 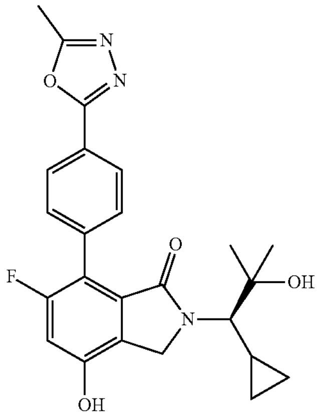 [SMILES: Cc1nnc(-c2ccc(-c3c(F)cc(O)c4c3C(=O)N([C@H](C3CC3)C(C)(C)O)C4)cc2)o1] | (R)-2-(1-cyclopropyl-2-hydroxy-2-methylpropyl)-6-fluoro-4-hydroxy-7-(4-(5-methyl-1,3,4-oxadiazol-2-yl)phenyl) isoindolin-1-one | 438.2 |
| 60 | 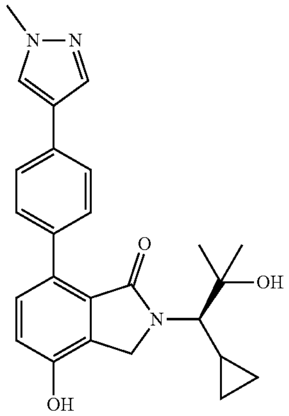 [SMILES: Cn1cc(-c2ccc(-c3ccc(O)c4c3C(=O)N([C@H](C3CC3)C(C)(C)O)C4)cc2)cn1] | (R)-2-(1-cyclopropyl-2-hydroxy-2-methylpropyl)-4-hydroxy-7-(4-(1-methyl-1H-pyrazol-4-yl)phenyl) isoindolin-1-one | 436.2 |

-continued

| | | | |
|---|---|---|---|
| 61 | 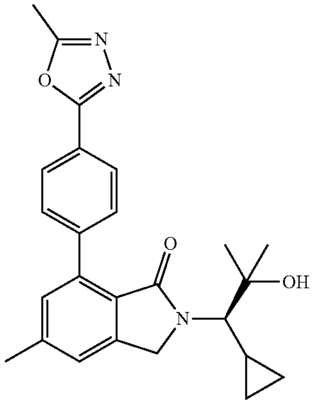 [SMILES: Cc1cc2c(c(-c3ccc(-c4nnc(C)o4)cc3)c1)C(=O)N([C@H](C1CC1)C(C)(C)O)C2] | (R)-2-(1-cyclopropyl-2-hydroxy-2-methylpropyl)-5-methyl-7-(4-(5-methyl-1,3,4-oxadiazol-2-yl)phenyl) isoindolin-1-one | 418.3 |
| 62 | 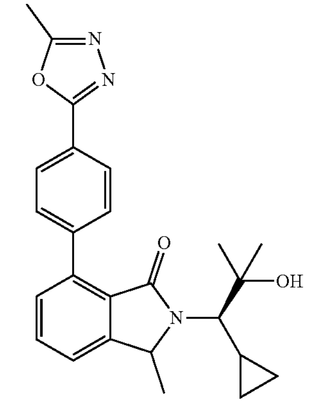 [SMILES: Cc1nnc(-c2ccc(-c3cccc4c3C(=O)N([C@H](C3CC3)C(C)(C)O)C4C)cc2)o1] | (R or S)-2-((R)-1-cyclopropyl-2-hydroxy-2-methylpropyl)-3-methyl-7-(4-(5-methyl-1,3,4-oxadiazol-2-yl)phenyl) isoindolin-1-one | 418.3 |

Example 5

(58)

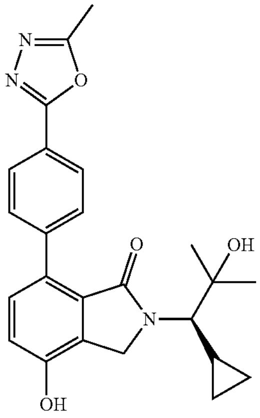

(R)-2-(1-Cyclopropyl-2-hydroxy-2-methylpropyl)-4-hydroxy-7-(4-(5-methyl-1,3,4-oxadiazol-2-yl)phenyl)isoindolin-1-one (58)

A mixture of (R)-4-chloro-2-(1-cyclopropyl-2-hydroxy-2-methylpropyl)-7-(4-(5-methyl-1,3,4-oxadiazol-2-yl)phenyl)isoindolin-1-one (30 mg, 0.069 mmol), $Cs_2CO_3$ (49 mg, 0.15 mmol), Rock Phos Pd G3 (1.7 mg, 2.1 μmol) and (E)-benzaldehyde oxime (11 mg, 0.089 mmol) in DMF (200

μL) under nitrogen was heated at 80° C. for 16 h. The reaction solution was filtered, and the filtrate was purified by prep HPLC (C-18 19×150 mm; 4.3 min, 15-50% ACN/10 mM aq FA gradient) to afford compound 58. MS: m/z=420.25 (M+1). $^1$H-NMR (400 MHz, DMSO-$d_6$): δ 10.28 (s, 1H), 7.95-7.93 (m, 2H), 7.67-7.65 (m, 2H), 7.29 (d, J=8.8 Hz, 1H), 7.07 (d, J=8.0 Hz, 1H), 4.82-4.45 (m, 2H), 4.74 (s, 1H), 3.19 (d, J=10.0 Hz, 1H), 2.61 (s, 3H), 1.47-1.42 (m, 1H), 1.33 (s, 3H), 1.02 (s, 3H), 0.78-0.72 (m, 1H), 0.49-0.40 (m, 2H), −0.19-−0.13 (m, 1H).

Example 6

(61)

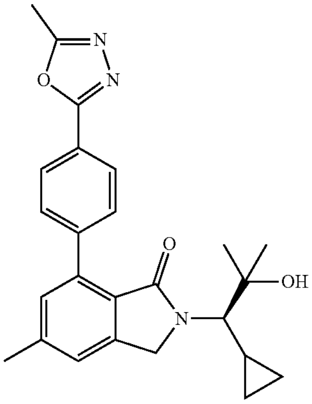

(R)-2-(1-Cyclopropyl-2-hydroxy-2-methylpropyl)-5-methyl-7-(4-(5-methyl-1,3,4-oxadiazol-2-yl)phenyl) isoindolin-1-one (61)

A mixture of (R)-5-chloro-2-(1-cyclopropyl-2-hydroxy-2-methylpropyl)-7-(4-(5-methyl-1,3,4-oxadiazol-2-yl)phenyl)isoindolin-1-one (7.4 mg, 0.017 mmol), tetramethyltin (12 μl, 0.084 mmol), tripotassium phosphate (18 mg, 0.084 mmol), and chloro[(tri-tert-butylphosphine)-2-(2-aminobiphenyl)]palladium(II) (4.3 mg, 8.4 μmol) in DMF (340 μl) was heated at 100° C. for 16 h. The mixture was cooled, diluted with ethyl acetate (20 mL), washed with water (20 mL), dried ($MgSO_4$), and concentrated. The residue was purified by silica gel chromatography (35-100% EtOAc/Hexane gradient) to provide compound 61. MS: m/z=418.3 (M+1). $^1$H-NMR (500 MHz, Chloroform-d): δ 8.07 (d, J=8.4 Hz, 1H), 7.69 (d, J=8.4 Hz, 1H), 7.35-7.15 (m, 4H), 4.81-4.62 (m, 2H), 3.33 (d, J=10.3 Hz, 1H), 2.63 (s, 3H), 2.51 (s, 3H), 1.46-1.38 (m, 3H), 1.37-1.30 (m, 1H), 1.29-1.20 (m, 3H), 0.84 (dt, J=7.8, 3.6 Hz, 1H), 0.51 (ddt, J=21.2, 8.3, 4.6 Hz, 2H), 0.17 (dd, J=9.5, 4.8 Hz, 1H).

Example 7

(62)

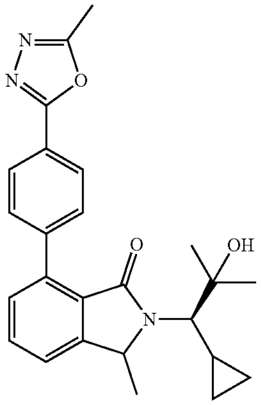

(R or S)-2-((R)-1-Cyclopropyl-2-hydroxy-2-methylpropyl)-3-methyl-7-(4-(5-methyl-1,3,4-oxadiazol-2-yl)phenyl)isoindolin-1-one (62)

Step A: (R or S)-2-((R)-1-Cyclopropyl-2-methyl-2-((2-(trimethylsilyl)ethoxy)methoxy)propyl)-3-methyl-7-(4-(5-methyl-L3,4-oxadiazol-2-yl)phenyl)isoindolin-1-one (62A)

A deoxygenated mixture of (R or S)-7-bromo-2-((R)-1-cyclopropyl-2-methyl-2-((2-(trimethylsilyl)ethoxy)methoxy)propyl)-3-methylisoindolin-1-one (I-24, 80 mg, 0.17 mmol), 2-methyl-5-(4-(4,4,5,5-tetramethyl-1,3,2-dioxaborolan-2-yl)phenyl)-1,3,4-oxadiazole (59 mg, 0.20 mmol), potassium phosphate (72 mg, 0.34 mmol), and [1,1'-bis(diphenylphosphino)ferrocene]dichloropalladium (II) (12 mg, 0.017 mmol) in 1,4-dioxane (0.50 mL) was heated at 80° C. in a sealed tube for 16 h. The reaction mixture was diluted with water (5 mL) and extracted with ethyl acetate (3×10 mL). The combined organic phase was washed with brine (3×10 mL), dried over $Na_2SO_4$ and concentrated. The residue was purified by silica gel column chromatography (0-60% EtOAc/PE gradient) to provide compound 62a. MS: m/z=548.3 (M+1).

Step B: (R or S)-2-((R)-1-Cyclopropyl-2-hydroxy-2-methylpropyl)-3-methyl-7-(4-(5-methyl-1,3,4-oxadiazol-2-yl)phenyl)isoindolin-1-one (62B)

Hydrogen fluoride (5.5 mg, 0.19 mmol) was added to a solution of (R or S)-2-((R)-1-cyclopropyl-2-methyl-2-((2-(trimethyl silyl)ethoxy)methoxy)propyl)-3-methyl-7-(4-(5-methyl-1,3,4-oxadiazol-2-yl)phenyl)isoindolin-1-one (62A, 35 mg, 0.064 mmol) in THF (0.5 mL) cooled at 0° C. The reaction was stirred for 1 h at ambient temp. The reaction mixture was diluted by water (10 mL) and extracted with ethyl acetate (3×20 mL). The combined organic phase was washed with brine (3×20 mL), dried over $Na_2SO_4$ and concentrated. The residue was purified by prep HPLC (C18 19 mm×250 mm; 5.8 min, 30-60% ACN/10 mM aq. $NH_4HCO_3$ gradient) to give compound 62. MS: m/z=418.3 (M+1). $^1$H-NMR (400 MHz, Chloroform-d): δ 8.11-8.09 (m, 2H), 7.72-7.70 (m, 2H), 7.65-7.61 (m, 1H), 7.45-7.40 (m, 2H), 4.79-4.78 (m, 1H), 2.83-2.80 (m, 1H), 2.63 (s, 3H), 1.77-1.76 (m, 1H), 1.57 (d, J=6.4 Hz, 3H), 1.45 (s, 3H), 1.22 (s, 3H), 0.86-0.81 (m, 1H), 0.46-0.43 (m, 2H), 0.35-0.29 (m, 1H).

Compounds 63 through 97 of the current invention were prepared according to general Scheme J.

Example 8

(63)

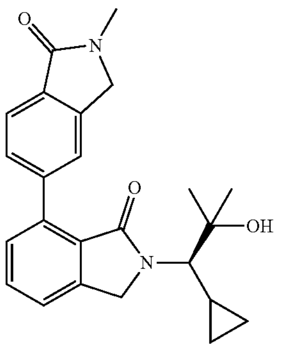

(R)-2-(1-Cyclopropyl-2-hydroxy-2-methylpropyl)-2'-methyl-[4,5'-biisoindoline]-1',3-dione (63)

A mixture of (R)-(2-(1-cyclopropyl-2-hydroxy-2-methylpropyl)-3-oxoisoindolin-4-yl)boronic acid (1-26, 8.0 mg, 0.028 mmol), methyl 2-bromo-6-(bromomethyl)benzoate (9.4 mg, mmol), $PdCl_2$ (dtbpf) (1.1 mg, 0.001 mmol) and $K_3PO_4$ (15 mg, 0.069 mmol) in water (75 μL) was combined in THF (0.50 mL) was heated at 65° C. for 15 h. The reaction was cooled and concentrated. The residue was purified by prep HPLC (C18 19 mm×100 mm; 10 min, 25-60% ACN/aq. $NH_4OH$ pH 10 gradient) to afford compound 63. MS: m/z=391.3 (M+1). $^1$H NMR (500 MHz, DMSO-$d_6$) δ 7.70-7.64 (m, 4H), 7.56 (d, J=7.8 Hz, 1H), 7.43-7.38 (m, 1H), 4.85 (d, J=8.7 Hz, 1H), 4.62 (d, J=18.6 Hz, 1H), 4.50 (s, 2H), 3.18 (d, J=10.1 Hz, 1H), 3.10 (s, 3H), 2.55 (s, 2H), 1.42 (s, 0.5H), 1.31 (s, 3H), 0.99 (s, 3H), 0.74 (s, 0.5H), 0.47-0.42 (m, 0.5H), (d, J=4.4 Hz, 0.5H).

Example 9

(64)

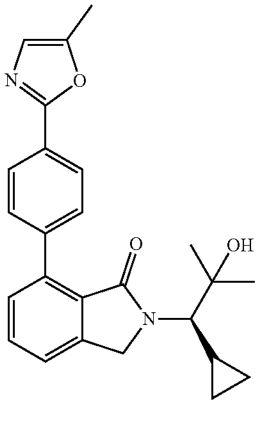

(R)-2-(1-Cyclopropyl-2-hydroxy-2-methylpropyl)-7-(4-(5-methyloxazol-2-yl)phenyl)isoindolin-1-one (64)

A deoxygenated mixture of 2-(4-bromophenyl)-5-methyloxazole (I-28, 71 mg, 0.30 mmol), (R)-(2-(1-cyclopropyl-2-hydroxy-2-methylpropyl)-3-oxoisoindolin-4-yl) boronic acid (58 mg, 0.20 mmol), [1,1'-bis(diphenylphosphino)ferrocene]dichloropalladium (II) (15 mg, 0.02 mmol) and cesium carbonate (160 mg, 0.50 mmol) in 1,4-dioxane (1.0 mL) was heated at 90° C. for 16 h. The reaction mixture was diluted with ethyl acetate (30 mL), then washed with brine (3×5 mL) dried over $Na_2SO_4$ and concentrated. The residue was purified by prep HPLC (C18 19 mm×250 mm; 5.8 min, 40-70% ACN/10 mM aq. $NH_4HCO_3$, gradient) to afford compound 64. MS: m/z=403.1 (M+1). $^1$H-NMR (400 MHz, Chloroform-d): δ 8.07-8.05 (m, 2H), 7.66-7.57 (m, 3H), 7.48-7.41 (m, 2H), 6.85 (s, 1H), 4.81-4.69 (m, 2H), 3.35 (d, J=10.4 Hz, 1H), 2.40 (s, 3H), 1.41 (s, 3H), 1.38-1.30 (m, 1H), 1.26 (s, 3H), 0.87-0.81 (m, 1H) 0.59-0.43 (m, 2H), 0.23-0.13 (m, 1H).

Compounds 65 through 97 found in Table 15 were synthesized by analogous methods from synthetic sequences disclosed in Examples 6 and 7 for compounds 61 and 62 utilizing analogous Suzuki coupling reactions to that shown. Commercially available reagents were substituted where necessary to produce compounds 65 through 97.

TABLE 15

| Compound Number | Structure | Chemical Name | Observed Mass (M + 1) |
| --- | --- | --- | --- |
| 65 | 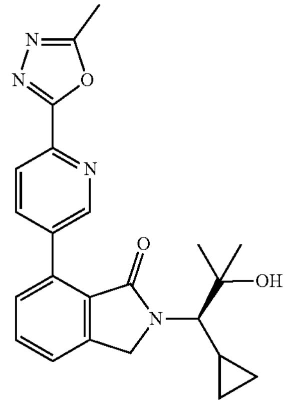 [SMILES: Cc1nnc(-c2ccc(-c3cccc4c3C(=O)N([C@H](C3CC3)C(C)(C)O)C4)cn2)o1] | (R)-2-(1-cyclopropyl-2-hydroxy-2-methylpropyl)-7-(6-(5-methyl-1,3,4-oxadiazol-2-yl)pyridin-3-yl)isoindolin-1-one | 405.3 |
| 66 | 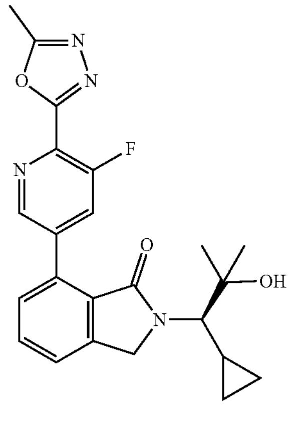 [SMILES: Cc1nnc(-c2ncc(-c3cccc4c3C(=O)N([C@H](C3CC3)C(C)(C)O)C4)cc2F)o1] | (R)-2-(1-cyclopropyl-2-hydroxy-2-methylpropyl)-7-(5-fluoro-6-(5-methyl-1,3,4-oxadiazol-2-yl)pyridin-3-yl)isoindolin-1-one | 423.3 |

TABLE 15-continued
| Compound Number | Structure | Chemical Name | Observed Mass (M + 1) |
|---|---|---|---|
| 67 | 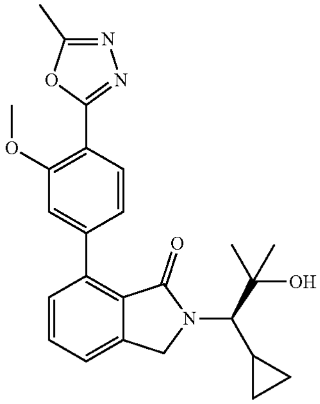 [SMILES: COc1cc(-c2cccc3c2C(=O)N([C@H](C2CC2)C(C)(C)O)C3)ccc1-c1nnc(C)o1] | (R)-2-(1-cyclopropyl-2-hydroxy-2-methylpropyl)-7-(3-methoxy-4-(5-methyl-1,3,4-oxadiazol-2-yl)phenyl)isoindolin-1-one | 432.4 |
| 68 | 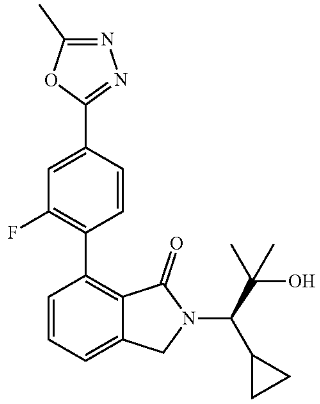 [SMILES: Cc1nnc(-c2ccc(-c3cccc4c3C(=O)N([C@H](C3CC3)C(C)(C)O)C4)c(F)c2)o1] | (R)-2-(1-cyclopropyl-2-hydroxy-2-methylpropyl)-7-(2-fluoro-4-(5-methyl-1,3,4-oxadiazol-2-yl)phenyl)isoindolin-1-one | 422.2 |
| 69 | 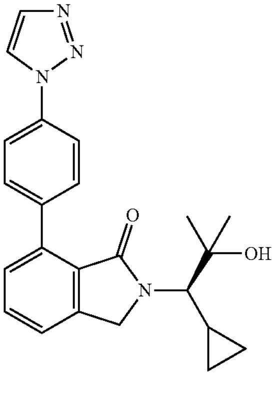 [SMILES: CC(C)(O)[C@@H](C1CC1)N1Cc2cccc(-c3ccc(-n4ccnn4)cc3)c2C1=O] | (R)-7-(4-(1H-1,2,3-triazol-1-yl)phenyl)-2-(1-cyclopropyl-2-hydroxy-2-methylpropyl)isoindolin-1-one | 389.3 |

TABLE 15-continued

| Compound Number | Structure | Chemical Name | Observed Mass (M + 1) |
|---|---|---|---|
| 70 | 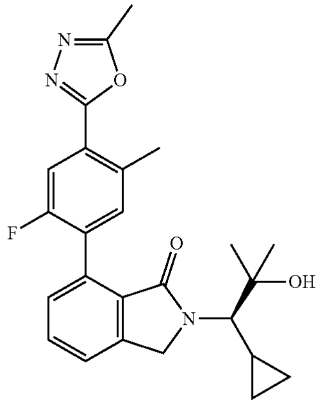 [SMILES: Cc1nnc(-c2cc(F)c(-c3cccc4c3C(=O)N([C@H](C3CC3)C(C)(C)O)C4)cc2C)o1] | (R)-2-(1-cyclopropyl-2-hydroxy-2-methylpropyl)-7-(2-fluoro-5-methyl-4-(5-methyl-1,3,4-oxadiazol-2-yl)phenyl)isoindolin-1-one | 436.3 |
| 71 | 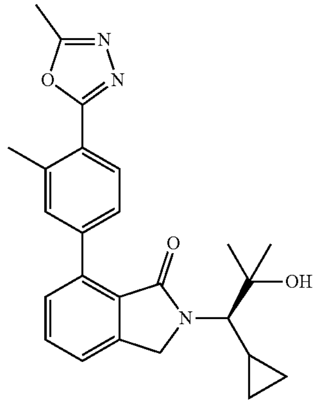 [SMILES: Cc1nnc(-c2ccc(-c3cccc4c3C(=O)N([C@H](C3CC3)C(C)(C)O)C4)cc2C)o1] | (R)-2-(1-cyclopropyl-2-hydroxy-2-methylpropyl)-7-(3-methyl-4-(5-methyl-1,3,4-oxadiazol-2-yl)phenyl)isoindolin-1-one | 418.3 |
| 72 | 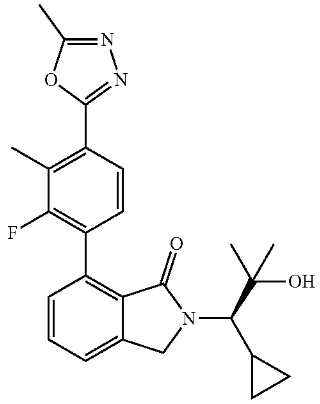 [SMILES: Cc1nnc(-c2ccc(-c3cccc4c3C(=O)N([C@H](C3CC3)C(C)(C)O)C4)c(F)c2C)o1] | (R)-2-(1-cyclopropyl-2-hydroxy-2-methylpropyl)-7-(2-fluoro-3-methyl-4-(5-methyl-1,3,4-oxadiazol-2-yl)phenyl)isoindolin-1-one | 436.2 |
| 73 | 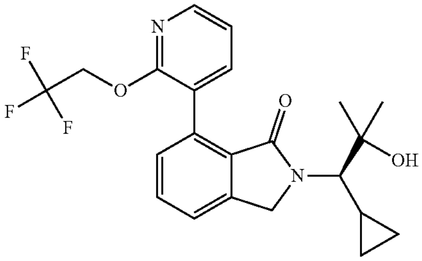 [SMILES: CC(C)(O)[C@@H](C1CC1)N1Cc2cccc(-c3cccnc3OCC(F)(F)F)c2C1=O] | (R)-2-(1-cyclopropyl-2-hydroxy-2-methylpropyl)-7-(2-(2,2,2-trifluoroethoxy)pyridin-3-yl)isoindolin-1-one | 443.0 |

TABLE 15-continued
| Compound Number | Structure | Chemical Name | Observed Mass (M + 1) |
|---|---|---|---|
| 74 | 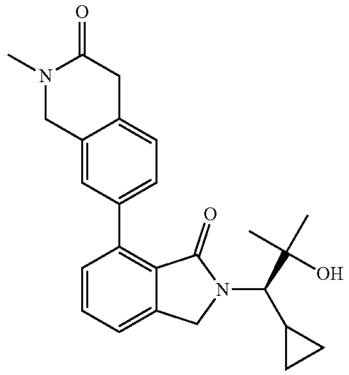 [SMILES: CN1Cc2cc(-c3cccc4c3C(=O)N([C@H](C3CC3)C(C)(C)O)C4)ccc2CC1=O] | (R)-7-(2-(1-cyclopropyl-2-hydroxy-2-methylpropyl)-3-oxoisoindolin-4-yl)-2-methyl-1,4-dihydroisoquinolin-3(2H)-one | 427.3 |
| 75 | 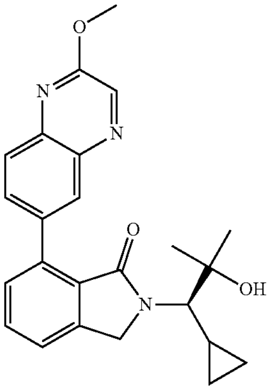 [SMILES: COc1cnc2cc(-c3cccc4c3C(=O)N([C@H](C3CC3)C(C)(C)O)C4)ccc2n1] | (R)-2-(1-cyclopropyl-2-hydroxy-2-methylpropyl)-7-(2-methoxyquinoxalin-6-yl)isoindolin-1-one | 426.2 |
| 76 | 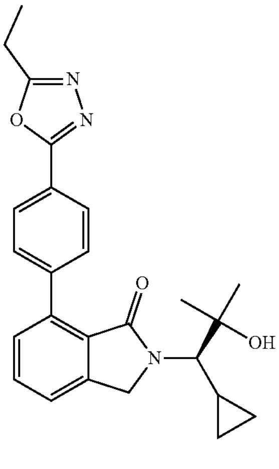 [SMILES: CCc1nnc(-c2ccc(-c3cccc4c3C(=O)N([C@H](C3CC3)C(C)(C)O)C4)cc2)o1] | (R)-2-(1-cyclopropyl-2-hydroxy-2-methylpropyl)-7-(4-(5-ethyl-1,3,4-oxadiazol-2-yl)phenyl)isoindolin-1-one | 418.3 |

TABLE 15-continued

| Compound Number | Structure | Chemical Name | Observed Mass (M + 1) |
|---|---|---|---|
| 77 | 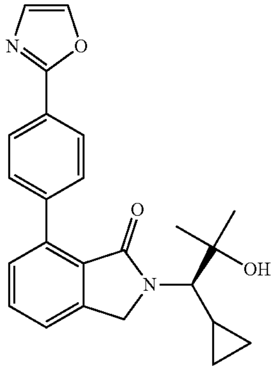 [SMILES: CC(C)(O)[C@@H](C1CC1)N1Cc2cccc(-c3ccc(-c4ncco4)cc3)c2C1=O] | (R)-2-(1-cyclopropyl-2-hydroxy-2-methylpropyl)-7-(4-(oxazol-2-yl)phenyl)isoindolin-1-one | 389.3 |
| 78 | 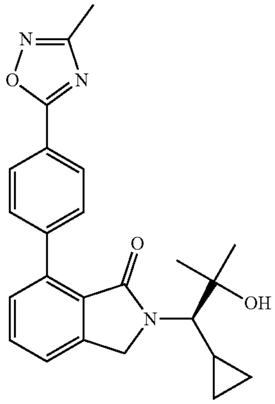 [SMILES: Cc1noc(-c2ccc(-c3cccc4c3C(=O)N([C@H](C3CC3)C(C)(C)O)C4)cc2)n1] | (R)-2-(1-cyclopropyl-2-hydroxy-2-methylpropyl)-7-(4-(3-methyl-1,2,4-oxadiazol-5-yl)phenyl)isoindolin-1-one | 404.3 |
| 79 | 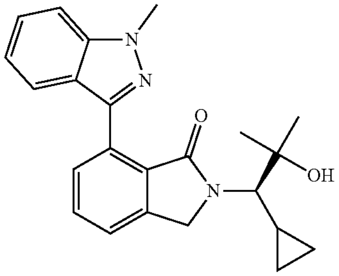 [SMILES: Cn1nc(-c2cccc3c2C(=O)N([C@H](C2CC2)C(C)(C)O)C3)c2ccccc21] | (R)-2-(1-cyclopropyl-2-hydroxy-2-methylpropyl)-7-(1-methyl-1H-indazol-3-yl)isoindolin-1-one | 376.4 |
| 80 | 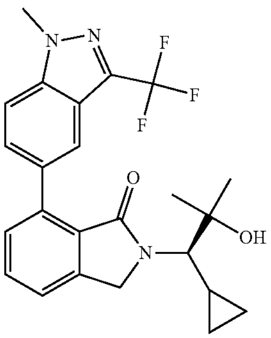 [SMILES: Cn1nc(C(F)(F)F)c2cc(-c3cccc4c3C(=O)N([C@H](C3CC3)C(C)(C)O)C4)ccc21] | (R)-2-(1-cyclopropyl-2-hydroxy-2-methylpropyl)-7-(1-methyl-3-(trifluoromethyl)-1H-indazol-5-yl)isoindolin-1-one | 466.2 |

TABLE 15-continued

| Compound Number | Structure | Chemical Name | Observed Mass (M + 1) |
|---|---|---|---|
| 81 | 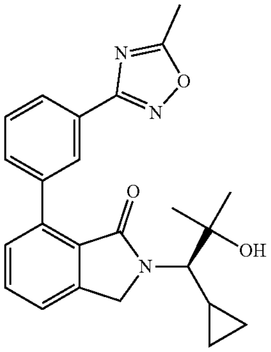 [SMILES: Cc1nc(-c2cccc(-c3cccc4c3C(=O)N([C@H](C3CC3)C(C)(C)O)C4)c2)no1] | (R)-2-(1-cyclopropyl-2-hydroxy-2-methylpropyl)-7-(3-(5-methyl-1,2,4-oxadiazol-3-yl)phenyl)isoindolin-1-one | 426.2 |
| 82 | 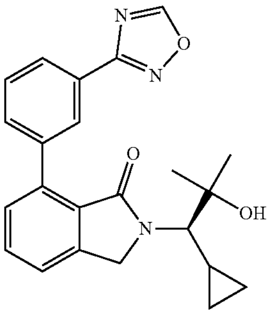 [SMILES: CC(C)(O)[C@@H](C1CC1)N1Cc2cccc(-c3cccc(-c4ncon4)c3)c2C1=O] | (R)-7-(3-(1,2,4-oxadiazol-3-yl)phenyl)-2-(1-cyclopropyl-2-hydroxy-2-methylpropyl)isoindolin-1-one | 412.2 |
| 83 | 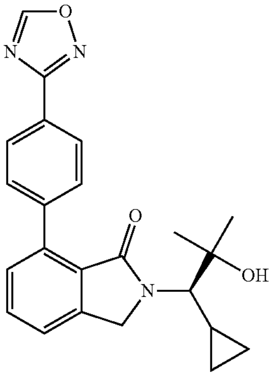 [SMILES: CC(C)(O)[C@@H](C1CC1)N1Cc2cccc(-c3ccc(-c4ncon4)cc3)c2C1=O] | (R)-7-(4-(1,2,4-oxadiazol-3-yl)phenyl)-2-(1-cyclopropyl-2-hydroxy-2-methylpropyl)isoindolin-1-one | 390.3 |
| 84 | 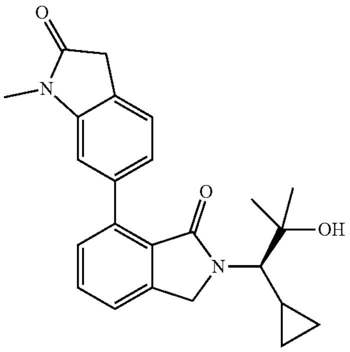 [SMILES: CN1C(=O)Cc2ccc(-c3cccc4c3C(=O)N([C@H](C3CC3)C(C)(C)O)C4)cc21] | (R)-6-(2-(1-cyclopropyl-2-hydroxy-2-methylpropyl)-3-oxoisoindolin-4-yl)-1-methylindolin-2-one | 391.2 |

TABLE 15-continued

| Compound Number | Structure | Chemical Name | Observed Mass (M + 1) |
|---|---|---|---|
| 85 | 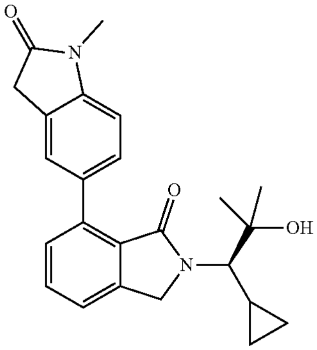 [SMILES: CN1C(=O)Cc2cc(-c3cccc4c3C(=O)N([C@H](C3CC3)C(C)(C)O)C4)ccc21] | (R)-5-(2-(1-cyclopropyl-2-hydroxy-2-methylpropyl)-3-oxoisoindolin-4-yl)-1-methylindolin-2-one | 391.2 |
| 86 | 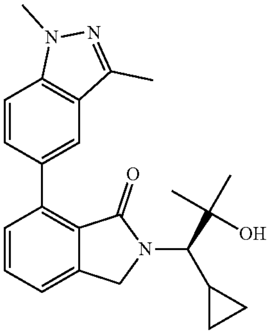 [SMILES: Cc1nn(C)c2ccc(-c3cccc4c3C(=O)N([C@H](C3CC3)C(C)(C)O)C4)cc12] | (R)-2-(1-cyclopropyl-2-hydroxy-2-methylpropyl)-7-(1,3-dimethyl-1H-indazol-5-yl)isoindolin-1-one | 390.5 |
| 87 | 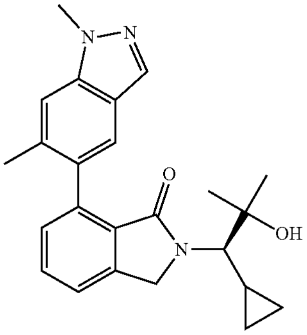 [SMILES: Cc1cc2c(cnn2C)cc1-c1cccc2c1C(=O)N([C@H](C1CC1)C(C)(C)O)C2] | (R)-2-(1-cyclopropyl-2-hydroxy-2-methylpropyl)-7-(1,6-dimethyl-1H-indazol-5-yl)isoindolin-1-one | 390.4 |
| 88 | 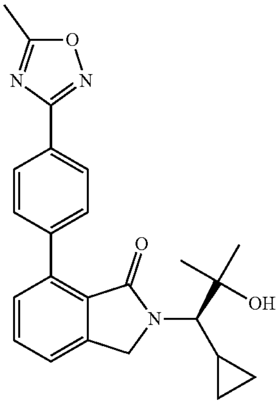 [SMILES: Cc1nc(-c2ccc(-c3cccc4c3C(=O)N([C@H](C3CC3)C(C)(C)O)C4)cc2)no1] | (R)-2-(1-cyclopropyl-2-hydroxy-2-methylpropyl)-7-(4-(5-methyl-1,2,4-oxadiazol-3-yl)phenyl)isoindolin-1-one | 404.3 |

TABLE 15-continued

| Compound Number | Structure | Chemical Name | Observed Mass (M + 1) |
| --- | --- | --- | --- |
| 89 | 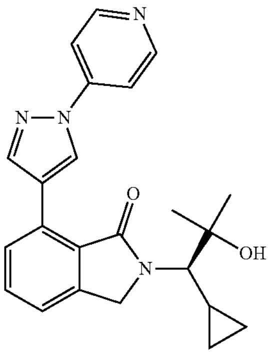 [SMILES: CC(C)(O)[C@@H](C1CC1)N1Cc2cccc(-c3cnn(-c4ccncc4)c3)c2C1=O] | (R)-2-(1-cyclopropyl-2-hydroxy-2-methylpropyl)-7-(1-(pyridin-4-yl)-1H-pyrazol-4-yl)isoindolin-1-one | 389.3 |
| 90 | 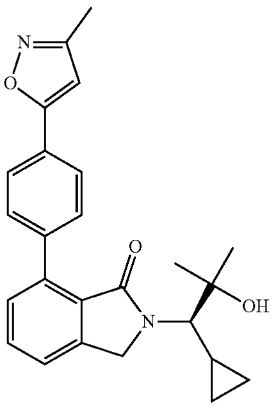 [SMILES: Cc1cc(-c2ccc(-c3cccc4c3C(=O)N([C@H](C3CC3)C(C)(C)O)C4)cc2)on1] | (R)-2-(1-cyclopropyl-2-hydroxy-2-methylpropyl)-7-(4-(3-methylisoxazol-5-yl)phenyl)isoindolin-1-one | 403.2 |
| 91 | 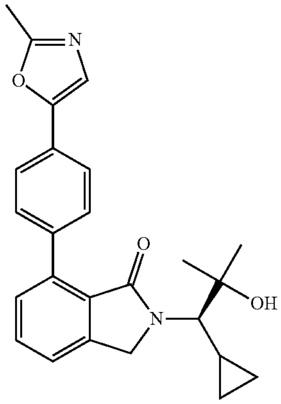 [SMILES: Cc1ncc(-c2ccc(-c3cccc4c3C(=O)N([C@H](C3CC3)C(C)(C)O)C4)cc2)o1] | 2-[(1R)-1-cyclopropyl-2-hydroxy-2-methyl-propyl]-7-[4-(2-methyloxazol-5-yl)phenyl]isoindolin-1-one | 403.2 |
| 92 | 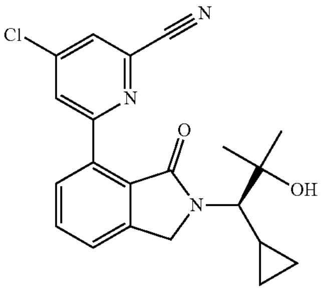 [SMILES: CC(C)(O)[C@@H](C1CC1)N1Cc2cccc(-c3cc(Cl)cc(C#N)n3)c2C1=O] | 4-chloro-6-[2-[(1R)-1-cyclopropyl-2-hydroxy-2-methyl-propyl]-3-oxo-isoindolin-4-yl]pyridine-2-carbonitrile | 382.2 |

TABLE 15-continued

| Compound Number | Structure | Chemical Name | Observed Mass (M + 1) |
|---|---|---|---|
| 93 | 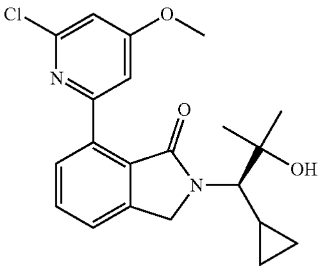 [SMILES: COc1cc(Cl)nc(-c2cccc3c2C(=O)N([C@H](C2CC2)C(C)(C)O)C3)c1] | (R)-7-(6-chloro-4-methoxypyridin-2-yl)-2-(1-cyclopropyl-2-hydroxy-2-methylpropyl)isoindolin-1-one | 409.2 |
| 94 | 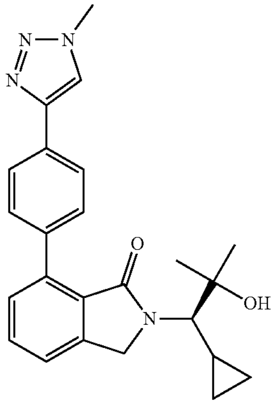 [SMILES: Cn1cc(-c2ccc(-c3cccc4c3C(=O)N([C@H](C3CC3)C(C)(C)O)C4)cc2)nn1] | 2-[(1R)-1-cyclopropyl-2-hydroxy-2-methyl-propyl]-7-[4-(1-methyltriazol-4-yl)phenyl]isoindolin-1-one | 403.3 |
| 95 | 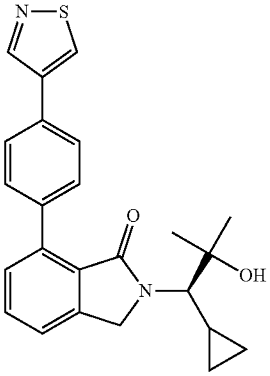 [SMILES: CC(C)(O)[C@@H](C1CC1)N1Cc2cccc(-c3ccc(-c4cnsc4)cc3)c2C1=O] | (R)-2-(1-cyclopropyl-2-hydroxy-2-methylpropyl)-7-(4-(isothiazol-4-yl)phenyl)isoindolin-1-one | 405.3 |
| 96 | 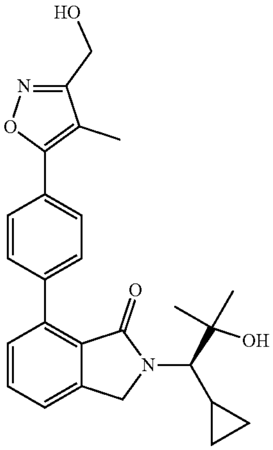 [SMILES: Cc1c(CO)noc1-c1ccc(-c2cccc3c2C(=O)N([C@H](C2CC2)C(C)(C)O)C3)cc1] | 2-[(1R)-1-cyclopropyl-2-hydroxy-2-methyl-propyl]-7-[4-[3-(hydroxymethyl)-4-methyl-isoxazol-5-yl]phenyl]isoindolin-1-one | 433.3 |

TABLE 15-continued

| Compound Number | Structure | Chemical Name | Observed Mass (M + 1) |
| --- | --- | --- | --- |
| 97 | 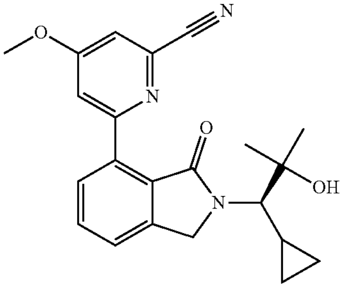 [SMILES: COc1cc(C#N)nc(-c2cccc3c2C(=O)N([C@H](C2CC2)C(C)(C)O)C3)c1] | (R)-6-(2-(1-cyclopropyl-2-hydroxy-2-methylpropyl)-3-oxoisoindolin-4-yl)-4-methoxypicolinonitrile | 378.2 |

Compounds 98-106 of the current invention were prepared according to general Scheme K.

Example 10

98

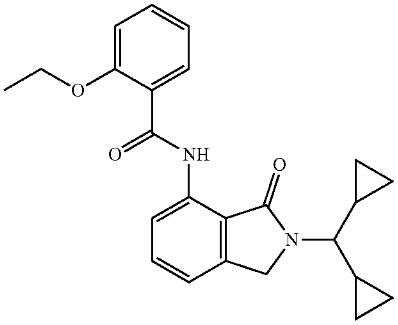

N-(2-(Dicyclopropylmethyl)-3-oxoisoindolin-4-yl)-2-ethoxybenzamide (98)

A mixture of ethyl 2-(bromomethyl)-6-(2-ethoxybenzamido)benzoate, (I-35, 8.0 mg, 0.020 mmol), dicyclopropylmethanamine (3.2 mg, 0.030 mmol) and DIEA (3.8 mg, 0.030 mmol) in DMF (0.50 ml) was heated at 60° C. for 16 h. The reaction was concentrated, and the residue was by prep HPLC (19 mm×100 mm C18; 6 min, 55-100% ACN/water gradient, 0.1% TFA added) to afford compound 98. MS: m/z=391.3 (M+1). 1 EINMR (500 MHz, DMSO-$d_6$) δ 11.58 (s, 3H), 8.57 (d, J=8.2 Hz, 1H), 7.87 (d, J=7.7 Hz, 1H), 7.62-7.51 (m, 4H), 7.32 (d, J=7.5 Hz, 2H), 7.20 (d, J=8.5 Hz, 2H), 7.09 (t, J=7.5 Hz, 1H), 4.65 (s, 8H), 4.26 (q, J=7.1 Hz, 6H), 2.86 (s, 1H), 2.55 (s, 13H), 1.35 (t, J=6.9 Hz, 13H), 1.21 (s, 5H), 0.61 (s, 6H), 0.52-0.46 (m, 7H), 0.37 (s, 6H), 0.18-0.13 (m, 7H).

Example 11

99

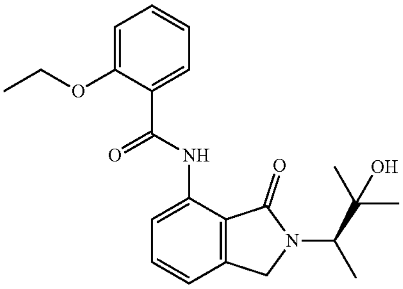

(R)-2-Ethoxy-N-(2-(3-hydroxy-3-methylbutan-2-yl)-3-oxoisoindolin-4-yl)benzamide (99)

A mixture of methyl 2-(bromomethyl)-6-(2-ethoxybenzamido)benzoate, (I-36, 17 mg, 0.043 mmol) and (R)-3-amino-2-methylbutan-2-ol HCl (15 mg, 0.11 mmol) in THF (330 μl) and ethanol (110 μl) was stirred for 30 h. The reaction was directly purified by prep HPLC (30×150 mm C18, 20 min, 30-70% ACN/$H_2O$ gradient, 0.1% TFA added) to give compound 99. MS: m/z=383.4 (M+1). $^1H$ NMR (500 MHz, Chloroform-d) δ 11.72 (s, 1H), 8.83 (d, J=8.3 Hz, 1H), 8.14 (dd, J=7.8, 1.8 Hz, 1H), 7.56 (t, J=7.9 Hz, 1H), 7.47 (ddd, J=8.4, 7.3, 1.8 Hz, 1H), 7.13 (d, J=7.5 Hz, 1H), 7.11-7.00 (m, 2H), 4.59 (d, J=17.5 Hz, 1H), 4.45 (d, J=17.5 Hz, 1H), 4.39 (q, J=7.0 Hz, 2H), 3.86 (q, J=7.0 Hz, 1H), 1.53-1.42 (m, 6H), 1.33 (s, 3H), 1.28 (s, 3H).

Compounds 100 through 106 found in Table 16, were synthesized by analogous methods from synthetic sequences disclosed Examples 10 and 11 for compounds 98 and 99 utilizing the condensations reactions analogous to that shown. Commercially available reagents were substituted where necessary to produce compounds 100 to 106.

TABLE 16
| Compound Number | Structure | Chemical Name | Observed Mass (M + 1) |
|---|---|---|---|
| 100 | 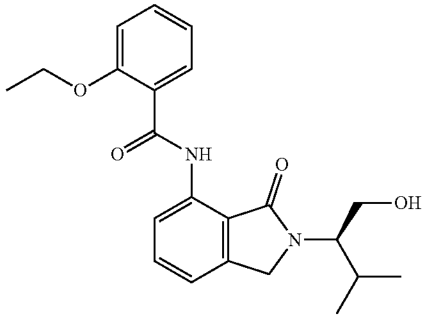 [SMILES: CCOc1ccccc1C(=O)Nc1cccc2c1C(=O)N([C@@H](CO)C(C)C)C2] | (R)-2-ethoxy-N-(2-(1-hydroxy-3-methylbutan-2-yl)-3-oxoisoindolin-4-yl)benzamide | 383.4 |
| 101 | 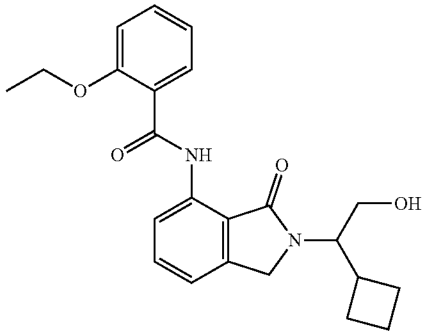 [SMILES: CCOc1ccccc1C(=O)Nc1cccc2c1C(=O)N(C(CO)C1CCC1)C2] | (R and S)-N-(2-(1-cyclobutyl-2-hydroxyethyl)-3-oxoisoindolin-4-yl)-2-ethoxybenzamide | 395.4 |
| 102 | 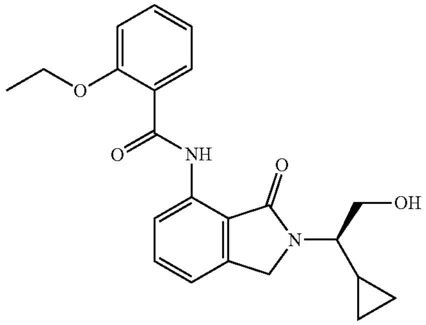 [SMILES: CCOc1ccccc1C(=O)Nc1cccc2c1C(=O)N([C@@H](CO)C1CC1)C2] | (R)-N-(2-(1-cyclopropyl-2-hydroxyethyl)-3-oxoisoindolin-4-yl)-2-ethoxybenzamide | 381.4 |
| 103 | 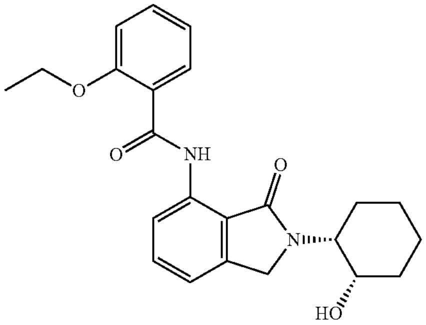 [SMILES: CCOc1ccccc1C(=O)Nc1cccc2c1C(=O)N([C@@H]1CCCC[C@@H]1O)C2] | 2-ethoxy-N-(2-((1R,2S)-2-hydroxycyclohexyl)-3-oxoisoindolin-4-yl)benzamide | 395.2 |

TABLE 16-continued
| Compound Number | Structure | Chemical Name | Observed Mass (M + 1) |
| --- | --- | --- | --- |
| 104 | 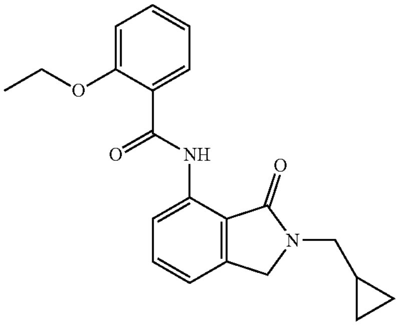 [SMILES: CCOc1ccccc1C(=O)Nc1cccc2c1C(=O)N(CC1CC1)C2] | N-(2-(cyclopropylmethyl)-3-oxoisoindolin-4-yl)-2-ethoxybenzamide | 351.3 |
| 105 | 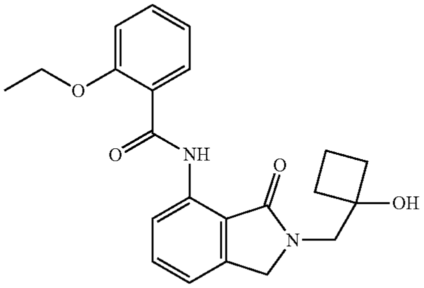 [SMILES: CCOc1ccccc1C(=O)Nc1cccc2c1C(=O)N(CC1(O)CCC1)C2] | 2-ethoxy-N-(2-((1-hydroxycyclobutyl)methyl)-3-oxoisoindolin-4-yl)benzamide | 381.3 |
| 106 | 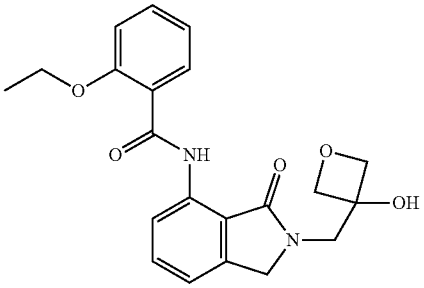 [SMILES: CCOc1ccccc1C(=O)Nc1cccc2c1C(=O)N(CC1(O)COC1)C2] | 2-ethoxy-N-(2-((3-hydroxyoxetan-3-yl)methyl)-3-oxoisoindolin-4-yl)benzamide | 383.3 |

Compounds 107-154 of the current invention were prepared according to general Scheme L.

Example 12

(107)

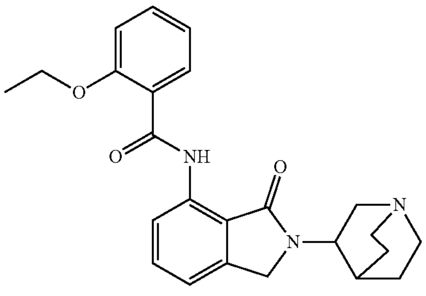

(R and S)-2-Ethoxy-N-(3-oxo-2-(quinuclidin-3-yl)isoindolin-4-yl)benzamide (107)

To a suspension of 2-ethoxybenzoic acid (23 mg, 0.14 mmol) in DCM (580 μl) was added 1-chloro-N,N,2-trimethylpropenylamine (47 mg, 0.35 mmol). The reaction was stirred for 30 min, at which point pyridine (28 μl, 0.35 mmol), (R and S)-7-amino-2-(quinuclidin-3-yl)isoindolin-1-one (I-37, 30 mg, 0.117 mmol) and DMAP (14 mg, 0.12 mmol) were added. The reaction was stirred 30 min and concentrated. The residue was purified by prep HPLC purification (19 cm×150 cm C18, 30 min, 0-95% acetonitrile-water gradient, 0.05% TFA added) to give compound 107. MS: m/z=406.5 (M+1). $^1$H NMR (600 MHz, Chloroform-d) δ 12.25 (s, 1H), 11.59 (s, 1H), 8.80 (d, J=8.3 Hz, 1H), 8.11 (dd, J=7.8, 1.7 Hz, 1H), 7.56 (t, J=7.9 Hz, 1H), 7.48-7.42 (m, 1H), 7.11 (d, J=7.4 Hz, 1H), 7.07-6.99 (m, 2H), 4.55 (d, J=15.9 Hz, 1H), 4.45 (d, J=16.1 Hz, 1H), 4.37 (dt, J=11.4, 5.7 Hz, 3H), 4.11-4.00 (m, 1H), 3.81-3.60 (m, 2H), 3.44-3.23 (m, 3H), 2.51-2.47 (m, 1H), 2.28 (s, 1H), 2.07 (d, J=24.0 Hz, 2H), 1.93 (s, 1H), 1.44 (t, J=7.0 Hz, 3H).

Example 13

108

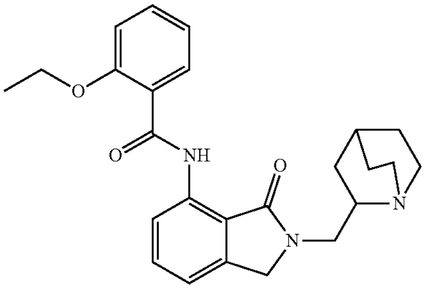

(R and S)-2-Ethoxy-N-(3-oxo-2-(quinuclidin-2-ylmethyl)isoindolin-4-yl)benzamide (108)

To a solution of 2-ethoxybenzoic acid (61 mg, 0.37 mmol) in DCM (5 mL) cooled to 0° C. were added oxalyl dichloride (94 mg, 0.74 mmol) and one drop of DMF. The reaction mixture was stirred at ambient temp for 1 h. The resulting mixture was concentrated, and residue was dissolved DCM (5 mL). To this mixture was added (R and S)-7-amino-2-(quinuclidin-3-ylmethyl)isoindolin-1-one, (I-38, 0.10 g, 0.37 mmol) and triethylamine (0.26 mL, 1.8 mmol). The reaction mixture was stirred at ambient temp for 3 h and concentrated. The residue was purified by prep HPLC (C18 19 mm×250 mm; 6 min., 33-38% ACN/water gradient, 0.05% TFA added) to afford compound 108. MS: m/z=420.2 (M+1). $^1$H NMR (400 MHz, CD 3 OD) δ 8.66 (d, J=8.4 Hz, 1H), 8.06-7.96 (m, 1H), 7.67-7.52 (m, 2H), 7.30 (d, J=7.5 Hz, 1H), 7.26-7.17 (m, 1H), 7.15-7.08 (m, 1H), 4.56 (d, J=5.6 Hz, 2H), 4.47-4.35 (m, 2H), 3.93-3.79 (m, 1H), 3.78-3.65 (m, 1H), 3.59-3.48 (m, 1H), 3.44-3.35 (m, 4H), 3.11-2.99 (m, 1H), 2.74-2.57 (m, 1H), 2.49-2.33 (m, 1H), 2.13-1.84 (m, 4H), 1.49 (t, J=7.0 Hz, 3H).

Example 14

109

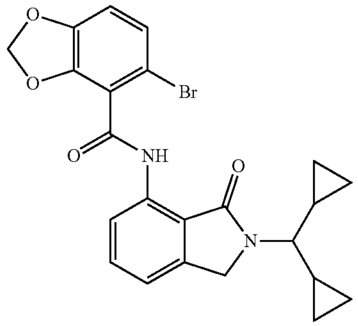

5-Bromo-N-(2-(dicyclopropylmethyl)-3-oxoisoindolin-4-yl)-benzo[d][1,3]dioxole-4-carboxamide (109)

To a solution of $POCl_3$ (4.2 μL, 0.045 mmol) in DCM (0.50 mL) and pyridine (17 μL, 0.21 mmol) cooled to 0° C. was added 5-bromobenzo[d][1,3]dioxole-4-carboxylic acid (15 mg, 0.062 mmol) and the mixture was stirred for 20 min. A solution of 7-amino-2-(dicyclopropylmethyl)isoindolin-1-one (I-40, 10 mg, 0.041 mmol) in DCM (0.50 mL) was added at 0° C. and the reaction was stirred for 1 h. The excess $POCl_3$ (phosphoryl chloride) was quenched with one drop of water and concentrated. The residue was purified by prep HPLC (20×50 mm C18; 20 min, 40-90% ACN-water gradient, 0.1% TFA added) to afford compound 109. MS: m/z=469.1, 471.1 (M+1). $^1$H NMR (500 MHz, DMSO-$d_6$) δ 10.84 (s, 1H), 8.41 (d, J=8.2 Hz, 1H), 7.64 (t, J=7.9 Hz, 1H), 7.39 (d, J=7.5 Hz, 1H), 7.21 (d, J=8.3 Hz, 1H), 7.04 (d, J=8.3 Hz, 1H), 6.16 (s, 2H), 4.69 (s, 2H), 2.87 (t, J=9.0 Hz, 1H), 1.20 (tq, J=8.6, 5.0, 4.5 Hz, 2H), 0.60 (dq, J=8.7, 4.5, 3.9 Hz, 2H), 0.47 (dt, J=9.0, 4.5 Hz, 2H), 0.37 (tt, J=9.3, 5.1 Hz, 2H), 0.18 (dt, J=9.3, 4.8 Hz, 2H).

Compounds 110 through 149 found in Table 17 were synthesized by analogous methods from synthetic sequences disclosed in Examples 12 through 14 for compounds 107 through 109 utilizing analogous reactions conditions. Commercially available reagents were substituted where necessary to produce compounds 110 through 149. Compound 148 was synthesized via a palladium catalyzed Suzuki coupling reaction with compound 143 using potassium methyltrifluoroborate. Compound 149 was synthesized via a palladium catalyzed Suzuki coupling reaction with Compound 147 using KOH.

TABLE 17

| Compound Number | Structure | Chemical Name | Observed Mass (M + 1) |
|---|---|---|---|
| 110 | 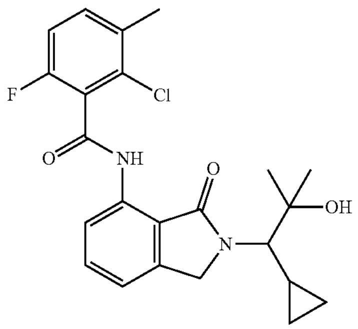 [SMILES: Cc1ccc(F)c(C(=O)Nc2cccc3c2C(=O)N(C(C2CC2)C(C)(C)O)C3)c1Cl] | (R or S)-2-chloro-N-(2-(1-cyclopropyl-2-hydroxy-2-methylpropyl)-3-oxoisoindolin-4-yl)-6-fluoro-3-methylbenzamide | 431.2 |
| 111 | 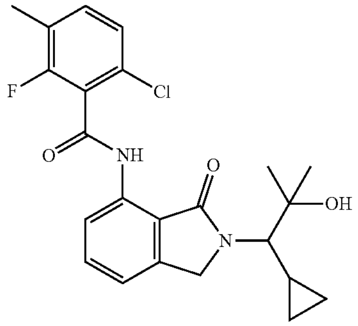 [SMILES: Cc1ccc(Cl)c(C(=O)Nc2cccc3c2C(=O)N(C(C2CC2)C(C)(C)O)C3)c1F] | (R or S)-6-chloro-N-(2-(1-cyclopropyl-2-hydroxy-2-methylpropyl)-3-oxoisoindolin-4-yl)-2-fluoro-3-methylbenzamide | 431.2 |
| 112 | 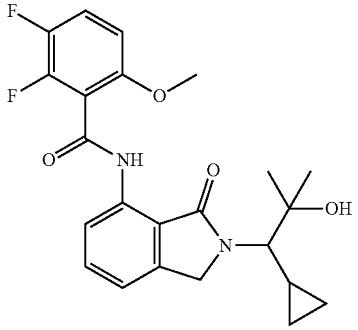 [SMILES: COc1ccc(F)c(F)c1C(=O)Nc1cccc2c1C(=O)N(C(C1CC1)C(C)(C)O)C2] | (R or S)-N-(2-(1-cyclopropyl-2-hydroxy-2-methylpropyl)-3-oxoisoindolin-4-yl)-2,3-difluoro-6-methoxybenzamide | 431.1 |
| 113 | 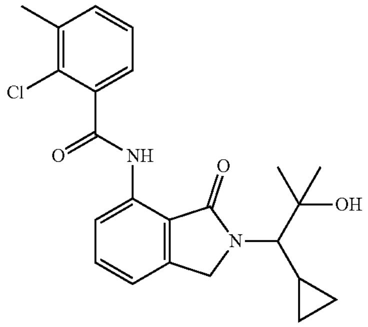 [SMILES: Cc1cccc(C(=O)Nc2cccc3c2C(=O)N(C(C2CC2)C(C)(C)O)C3)c1Cl] | (R or S)-2-chloro-N-(2-(1-cyclopropyl-2-hydroxy-2-methylpropyl)-3-oxoisoindolin-4-yl)-3-methylbenzamide | 413.1 |

TABLE 17-continued

| Compound Number | Structure | Chemical Name | Observed Mass (M + 1) |
|---|---|---|---|
| 114 | 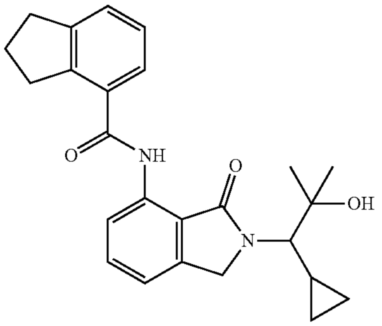 [SMILES: CC(C)(O)C(C1CC1)N1Cc2cccc(NC(=O)c3cccc4c3CCC4)c2C1=O] | (R or S)-N-(2-(1-cyclopropyl-2-hydroxy-2-methylpropyl)-3-oxoisoindolin-4-yl)-2,3-dihydro-1H-indene-4-carboxamide | 405.1 |
| 115 | 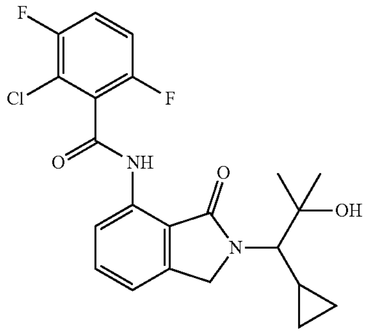 [SMILES: CC(C)(O)C(C1CC1)N1Cc2cccc(NC(=O)c3c(F)ccc(F)c3Cl)c2C1=O] | (R or S)-2-chloro-N-(2-(1-cyclopropyl-2-hydroxy-2-methylpropyl)-3-oxoisoindolin-4-yl)-3,6-difluorobenzamide | 435.0 |
| 116 | 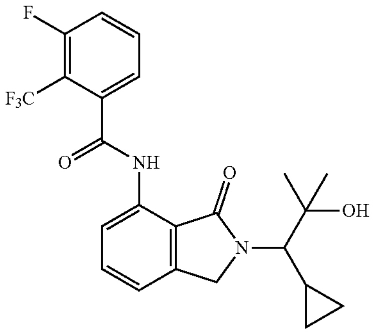 [SMILES: CC(C)(O)C(C1CC1)N1Cc2cccc(NC(=O)c3cccc(F)c3C(F)(F)F)c2C1=O] | (R or S)-N-(2-(1-cyclopropyl-2-hydroxy-2-methylpropyl)-3-oxoisoindolin-4-yl)-3-fluoro-2-(trifluoromethyl)benzamide | 451.1 |
| 117 | 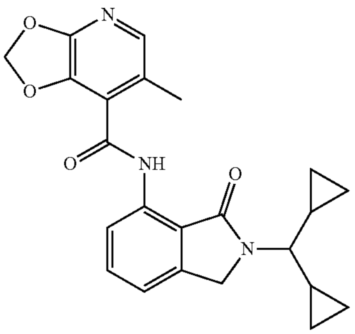 [SMILES: Cc1cnc2c(c1C(=O)Nc1cccc3c1C(=O)N(C(C1CC1)C1CC1)C3)OCO2] | N-(2-(dicyclopropylmethyl)-3-oxoisoindolin-4-yl)-6-methyl-[1,3]dioxolo[4,5-b]pyridine-7-carboxamide | 406.2 |

TABLE 17-continued

| Compound Number | Structure | Chemical Name | Observed Mass (M + 1) |
|---|---|---|---|
| 118 | 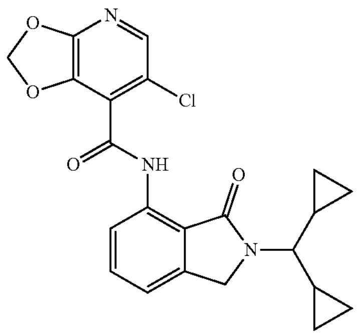 [SMILES: O=C(Nc1cccc2c1C(=O)N(C(C1CC1)C1CC1)C2)c1c(Cl)cnc2c1OCO2] | 6-chloro-N-(2-(dicyclopropylmethyl)-3-oxoisoindolin-4-yl)-[1,3]dioxolo[4,5-b]pyridine-7-carboxamide | 426.6 |
| 119 | 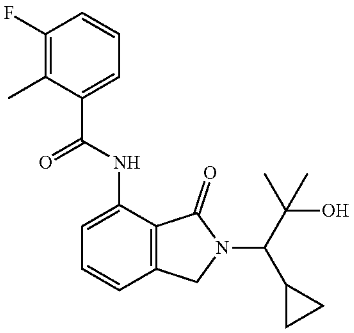 [SMILES: Cc1c(F)cccc1C(=O)Nc1cccc2c1C(=O)N(C(C1CC1)C(C)(C)O)C2] | (R or S)-N-(2-(1-cyclopropyl-2-hydroxy-2-methylpropyl)-3-oxoisoindolin-4-yl)-3-fluoro-2-methylbenzamide | 397.2 |
| 120 | 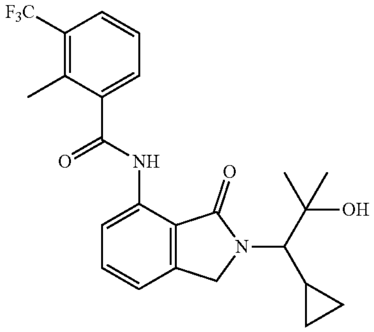 [SMILES: Cc1c(C(=O)Nc2cccc3c2C(=O)N(C(C2CC2)C(C)(C)O)C3)cccc1C(F)(F)F] | (R or S)-N-(2-(1-cyclopropyl-2-hydroxy-2-methylpropyl)-3-oxoisoindolin-4-yl)-2-methyl-3-(trifluoromethyl)benzamide | 447.2 |
| 121 | 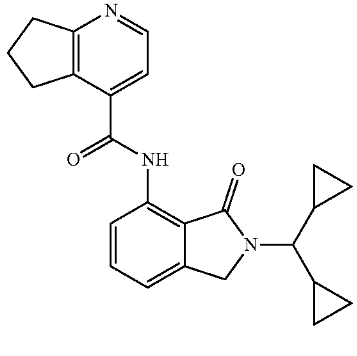 [SMILES: O=C(Nc1cccc2c1C(=O)N(C(C1CC1)C1CC1)C2)c1ccnc2c1CCC2] | N-(2-(dicyclopropylmethyl)-3-oxoisoindolin-4-yl)-6,7-dihydro-5H-cyclopenta[b]pyridine-4-carboxamide | 388.3 |

TABLE 17-continued

| Compound Number | Structure | Chemical Name | Observed Mass (M + 1) |
|---|---|---|---|
| 122 | 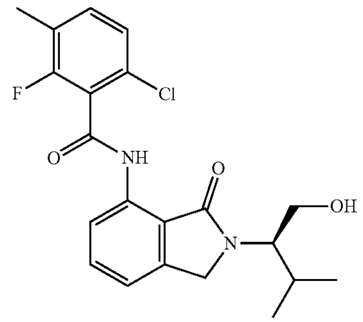 [SMILES: Cc1ccc(Cl)c(C(=O)Nc2cccc3c2C(=O)N([C@@H](CO)C(C)C)C3)c1F] | (R)-6-chloro-2-fluoro-N-(2-(1-hydroxy-3-methylbutan-2-yl)-3-oxoisoindolin-4-yl)-3-methylbenzamide | 405.3 |
| 123 | 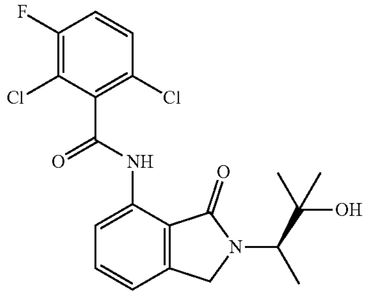 [SMILES: C[C@@H](N1Cc2cccc(NC(=O)c3c(Cl)ccc(F)c3Cl)c2C1=O)C(C)(C)O] | (R)-2,6-dichloro-3-fluoro-N-(2-(3-hydroxy-3-methylbutan-2-yl)-3-oxoisoindolin-4-yl)benzamide | 425.2 |
| 124 | 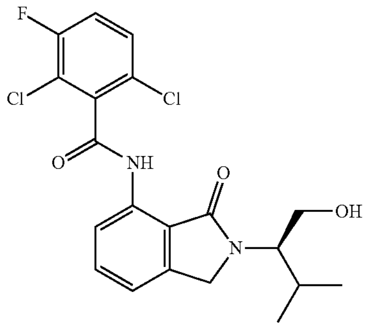 [SMILES: CC(C)[C@H](CO)N1Cc2cccc(NC(=O)c3c(Cl)ccc(F)c3Cl)c2C1=O] | (R)-2,6-dichloro-3-fluoro-N-(2-(1-hydroxy-3-methylbutan-2-yl)-3-oxoisoindolin-4-yl)benzamide | 425.2 |
| 125 | 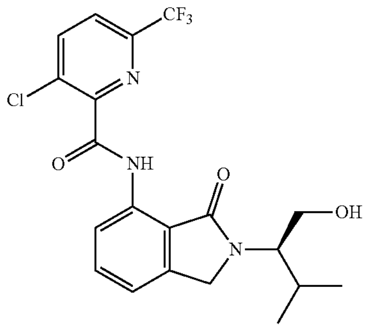 [SMILES: CC(C)[C@H](CO)N1Cc2cccc(NC(=O)c3nc(C(F)(F)F)ccc3Cl)c2C1=O] | (R)-3-chloro-N-(2-(1-hydroxy-3-methylbutan-2-yl)-3-oxoisoindolin-4-yl)-6-(trifluoromethyl)picolinamide | 442.3 |

TABLE 17-continued

| Compound Number | Structure | Chemical Name | Observed Mass (M + 1) |
|---|---|---|---|
| 126 | 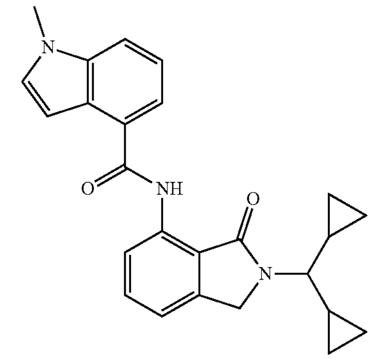 [SMILES: Cn1ccc2c(C(=O)Nc3cccc4c3C(=O)N(C(C3CC3)C3CC3)C4)cccc21] | N-(2-(dicyclopropylmethyl)-3-oxoisoindolin-4-yl)-1-methyl-1H-indole-4-carboxamide | 400.3 |
| 127 | 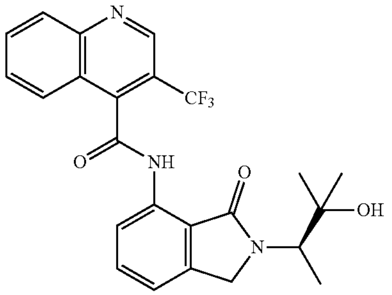 [SMILES: C[C@@H](N1Cc2cccc(NC(=O)c3c(C(F)(F)F)cnc4ccccc34)c2C1=O)C(C)(C)O] | (R)-N-(2-(3-hydroxy-3-methylbutan-2-yl)-3-oxoisoindolin-4-yl)-3-(trifluoromethyl)quinoline-4-carboxamide | 458.2 |
| 128 | 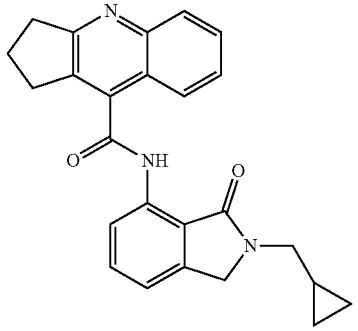 [SMILES: O=C(Nc1cccc2c1C(=O)N(CC1CC1)C2)c1c2c(nc3ccccc13)CCC2] | N-(2-(cyclopropylmethyl)-3-oxoisoindolin-4-yl)-2,3-dihydro-1H-cyclopenta[b]quinoline-9-carboxamide | 398.4 |
| 129 | 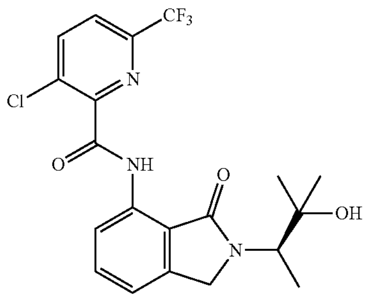 [SMILES: C[C@@H](N1Cc2cccc(NC(=O)c3nc(C(F)(F)F)ccc3Cl)c2C1=O)C(C)(C)O] | (R)-3-chloro-N-(2-(3-hydroxy-3-methylbutan-2-yl)-3-oxoisoindolin-4-yl)-6-(trifluoromethyl)picolinamide | 442.2 |

TABLE 17-continued

| Compound Number | Structure | Chemical Name | Observed Mass (M + 1) |
|---|---|---|---|
| 130 | 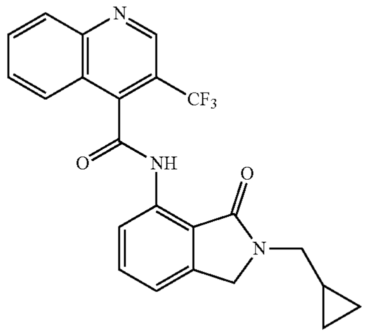 [SMILES: O=C(Nc1cccc2c1C(=O)N(CC1CC1)C2)c1c(C(F)(F)F)cnc2ccccc12] | N-(2-(cyclopropylmethyl)-3-oxoisoindolin-4-yl)-3-(trifluoromethyl)quinoline-4-carboxamide | 426.3 |
| 131 | 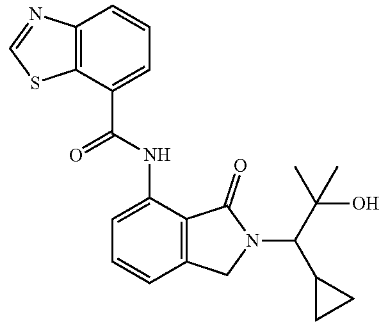 [SMILES: CC(C)(O)C(C1CC1)N1Cc2cccc(NC(=O)c3cccc4ncsc34)c2C1=O] | (R or S)-N-(2-(1-cyclopropyl-2-hydroxy-2-methylpropyl)-3-oxoisoindolin-4-yl)benzo[d]thiazole-7-carboxamide | 422.0 |
| 132 | 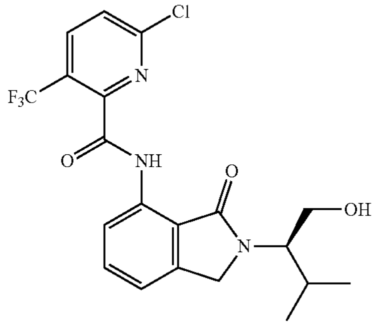 [SMILES: CC(C)[C@H](CO)N1Cc2cccc(NC(=O)c3nc(Cl)ccc3C(F)(F)F)c2C1=O] | (R)-6-chloro-N-(2-(1-hydroxy-3-methylbutan-2-yl)-3-oxoisoindolin-4-yl)-3-(trifluoromethyl)picolinamide | 442.3 |
| 133 | 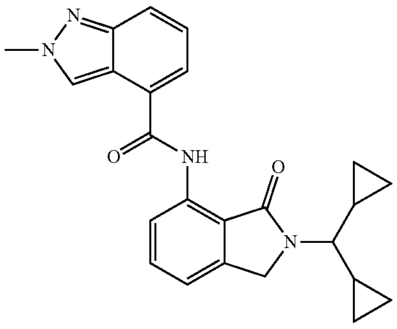 [SMILES: Cn1cc2c(C(=O)Nc3cccc4c3C(=O)N(C(C3CC3)C3CC3)C4)cccc2n1] | N-(2-(dicyclopropylmethyl)-3-oxoisoindolin-4-yl)-2-methyl-2H-indazole-4-carboxamide | 401.3 |

TABLE 17-continued

| Compound Number | Structure | Chemical Name | Observed Mass (M + 1) |
| --- | --- | --- | --- |
| 134 | 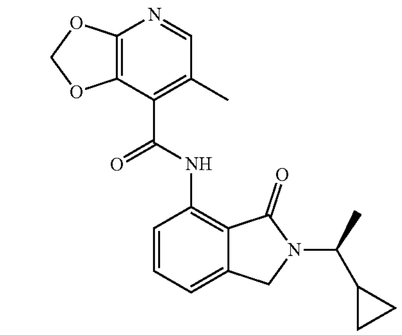 [SMILES: Cc1cnc2c(c1C(=O)Nc1cccc3c1C(=O)N([C@@H](C)C1CC1)C3)OCO2] | (S)-N-(2-(1-cyclopropylethyl)-3-oxoisoindolin-4-yl)-6-methyl-[1,3]dioxolo[4,5-b]pyridine-7-carboxamide | 380.3 |
| 135 | 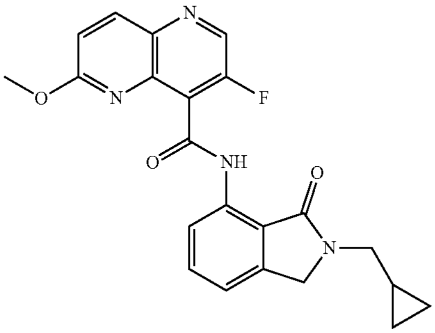 [SMILES: COc1ccc2ncc(F)c(C(=O)Nc3cccc4c3C(=O)N(CC3CC3)C4)c2n1] | N-(2-(cyclopropylmethyl)-3-oxoisoindolin-4-yl)-3-fluoro-6-methoxy-1,5-naphthyridine-4-carboxamide | 407.3 |
| 136 | 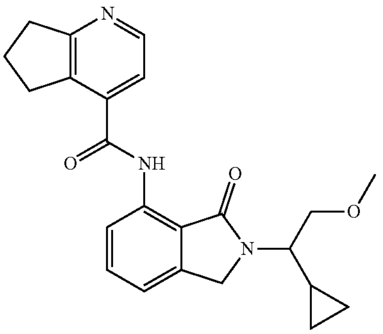 [SMILES: COCC(C1CC1)N1Cc2cccc(NC(=O)c3ccnc4c3CCC4)c2C1=O] | (R or S)-N-(2-(1-cyclopropyl-2-methoxyethyl)-3-oxoisoindolin-4-yl)-6,7-dihydro-5H-cyclopenta[b]pyridine-4-carboxamide | 392.3 |
| 137 | 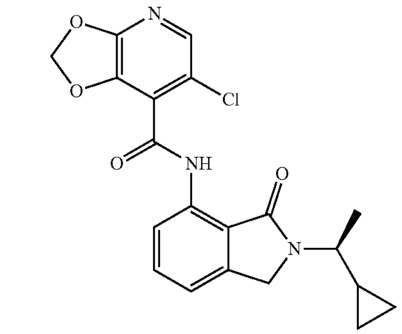 [SMILES: C[C@@H](C1CC1)N1Cc2cccc(NC(=O)c3c(Cl)cnc4c3OCO4)c2C1=O] | (S)-6-chloro-N-(2-(1-cyclopropylethyl)-3-oxoisoindolin-4-yl)-[1,3]dioxolo[4,5-b]pyridine-7-carboxamide | 400.3 |

TABLE 17-continued

| Compound Number | Structure | Chemical Name | Observed Mass (M + 1) |
|---|---|---|---|
| 138 | 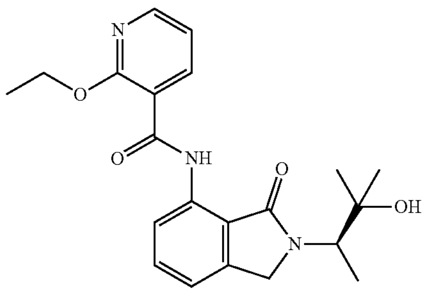 [SMILES: CCOc1ncccc1C(=O)Nc1cccc2c1C(=O)N([C@H](C)C(C)(C)O)C2] | (R)-2-ethoxy-N-(2-(3-hydroxy-3-methylbutan-2-yl)-3-oxoisoindolin-4-yl)nicotinamide | 384.2 |
| 139 | 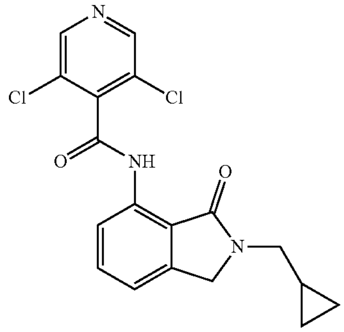 [SMILES: O=C(Nc1cccc2c1C(=O)N(CC1CC1)C2)c1c(Cl)cncc1Cl] | 3,5-dichloro-N-(2-(cyclopropylmethyl)-3-oxoisoindolin-4-yl)isonicotinamide | 376.0 |
| 140 | 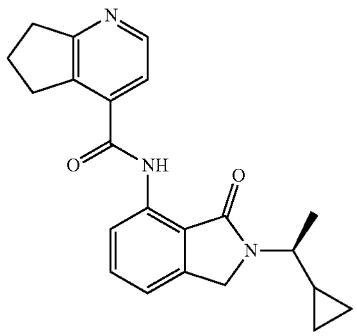 [SMILES: C[C@@H](C1CC1)N1Cc2cccc(NC(=O)c3ccnc4c3CCC4)c2C1=O] | (S)-N-(2-(1-cyclopropylethyl)-3-oxoisoindolin-4-yl)-6,7-dihydro-5H-cyclopenta[b]pyridine-4-carboxamide | 362.2 |
| 141 | 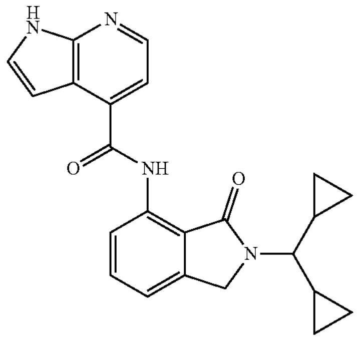 [SMILES: O=C(Nc1cccc2c1C(=O)N(C(C1CC1)C1CC1)C2)c1ccnc2[nH]ccc12] | N-(2-(dicyclopropylmethyl)-3-oxoisoindolin-4-yl)-1H-pyrrolo[2,3-b]pyridine-4-carboxamide | 387.3 |

TABLE 17-continued

| Compound Number | Structure | Chemical Name | Observed Mass (M + 1) |
| --- | --- | --- | --- |
| 142 | 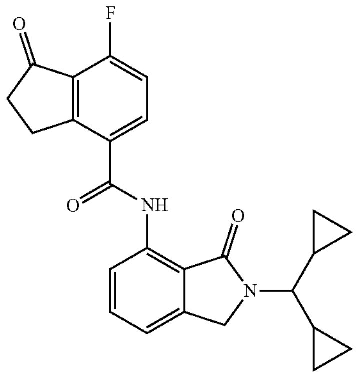 [SMILES: O=C(Nc1cccc2c1C(=O)N(C(C1CC1)C1CC1)C2)c1ccc(F)c2c1CCC2=O] | N-(2-(dicyclopropylmethyl)-3-oxoisoindolin-4-yl)-7-fluoro-1-oxo-2,3-dihydro-1H-indene-4-carboxamide | 419.4 |
| 143 | 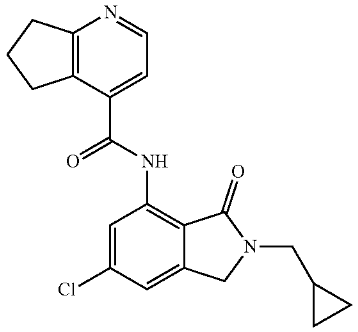 [SMILES: O=C(Nc1cc(Cl)cc2c1C(=O)N(CC1CC1)C2)c1ccnc2c1CCC2] | N-(6-chloro-2-(cyclopropylmethyl)-3-oxoisoindolin-4-yl)-6,7-dihydro-5H-cyclopenta[b]pyridine-4-carboxamide | 382.2 |
| 144 | 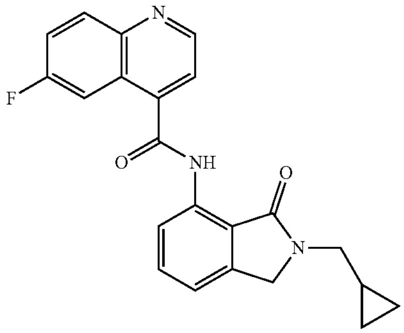 [SMILES: O=C(Nc1cccc2c1C(=O)N(CC1CC1)C2)c1ccnc2ccc(F)cc12] | N-(2-(cyclopropylmethyl)-3-oxoisoindolin-4-yl)-6-fluoroquinoline-4-carboxamide | 376.2 |
| 145 | 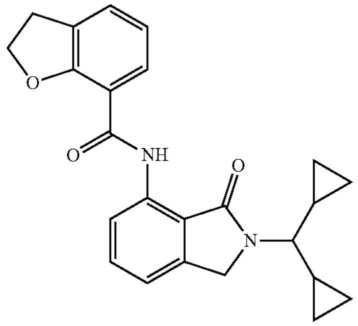 [SMILES: O=C(Nc1cccc2c1C(=O)N(C(C1CC1)C1CC1)C2)c1cccc2c1OCC2] | N-(2-(dicyclopropylmethyl)-3-oxoisoindolin-4-yl)-2,3-dihydrobenzofuran-7-carboxamide | 389.4 |

TABLE 17-continued

| Compound Number | Structure | Chemical Name | Observed Mass (M + 1) |
|---|---|---|---|
| 146 | 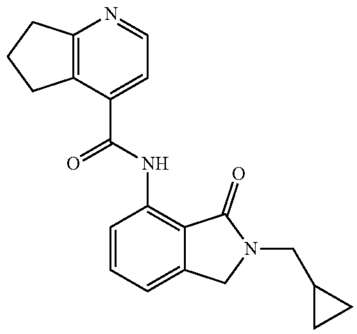 [SMILES: O=C(Nc1cccc2c1C(=O)N(CC1CC1)C2)c1ccnc2c1CCC2] | N-(2-(cyclopropylmethyl)-3-oxoisoindolin-4-yl)-6,7-dihydro-5H-cyclopenta[b]pyridine-4-carboxamide | 348.5 |
| 147 | 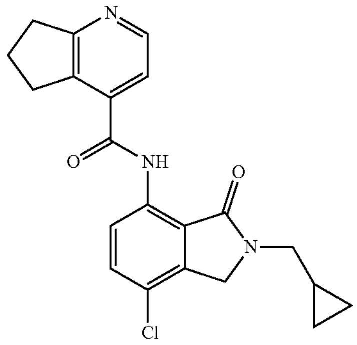 [SMILES: O=C(Nc1ccc(Cl)c2c1C(=O)N(CC1CC1)C2)c1ccnc2c1CCC2] | N-(7-chloro-2-(cyclopropylmethyl)-3-oxoisoindolin-4-yl)-6,7-dihydro-5H-cyclopenta[b]pyridine-4-carboxamide | 382.2 |
| 148 | 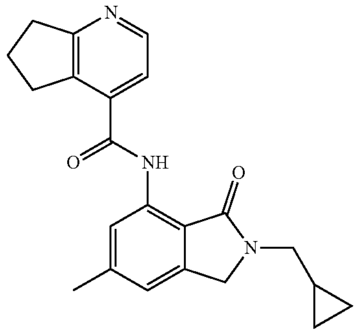 [SMILES: Cc1cc2c(c(NC(=O)c3ccnc4c3CCC4)c1)C(=O)N(CC1CC1)C2] | N-(2-(Cyclopropylmethyl)-6-methyl-3-oxoisoindolin-4-yl)-6,7-dihydro-5H-cyclopenta[b]pyridine-4-carboxamide | 362.3 |
| 149 | 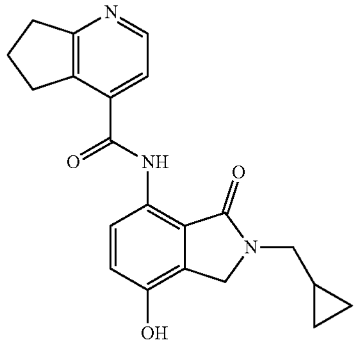 [SMILES: O=C(Nc1ccc(O)c2c1C(=O)N(CC1CC1)C2)c1ccnc2c1CCC2] | N-(2-(cyclopropylmethyl)-7-hydroxy-3-oxoisoindolin-4-yl)-6,7-dihydro-5H-cyclopenta[b]pyridine-4-carboxamide | 364.3 |

Example 15

148

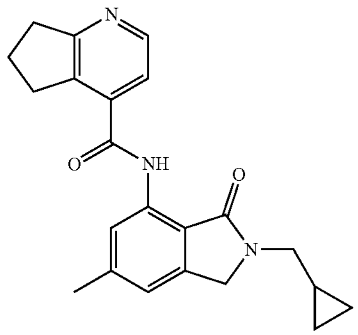

N-(2-(Cyclopropylmethyl)-6-methyl-3-oxoisoindolin-4-yl)-6,7-dihydro-5H-cyclopenta[b]pyridine-4-carboxamide (148)

A deoxygenated mixture of N-(6-chloro-2-(cyclopropylmethyl)-3-oxoisoindolin-4-yl)-6,7-dihydro-5H-cyclopenta[b]pyridine-4-carboxamide, (Compound 143, 15 mg, 0.039 mmol), potassium methyltrifluoroborate (9.6 mg, 0.079 mmol), $Cs_2CO_3$ (38 mg, 0.12 mmol) and chloro[(di(1-adamantyl)-N-butylphosphine)-2-(2-aminobiphenyl)]palladium(II) (5.3 mg, 7.9 μmol) in dioxane (360 μl) and water (36 μl) was irradiated for 1 h in a Biotage® microwave reactor at 100° C. The reaction was filtered and concentrated and the residue was purified by prep HPLC (21×100 mm C18, 20 min, 10-50% ACN/water gradient, 0.1% TFA added) to afford compound 148. MS: m/z=362.3 (M+1). $^1H$ NMR (500 MHz, DMSO-$d_6$) δ 11.10 (s, 1H), 8.54 (d, J=5.2 Hz, 1H), 8.29 (s, 1H), 7.45 (d, J=5.1 Hz, 1H), 7.17 (s, 1H), 4.57 (s, 2H), 3.37 (d, J=7.2 Hz, 2H), 3.26 (t, J=7.5 Hz, 2H), 3.00 (t, J=7.8 Hz, 2H), 2.45 (s, 3H), 2.10 (p, J=7.6 Hz, 2H), 1.06 (s, 1H), 0.55-0.48 (m, 2H), 0.34-0.27 (m, 2H).

Example 16

149

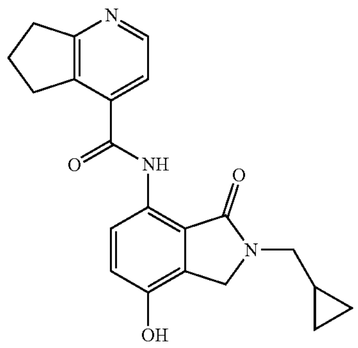

N-(2-(Cyclopropylmethyl)-7-hydroxy-3-oxoisoindolin-4-yl)-6,7-dihydro-5H-cyclopenta[b]pyridine-4-carboxamide (149)

To a microwave vial containing N-(7-chloro-2-(cyclopropylmethyl)-3-oxoisoindolin-4-yl)-6,7-dihydro-5H-cyclopenta[b]pyridine-4-carboxamide (compound 147, 15 mg, 0.039 mmol), KOH (6.6 mg, 0.12 mmol), $Pd_2(dba)_3$ (3.6 mg, 3.9 μmol) and 2-di-t-butylphosphino-3,4,5,6-tetramethyl-2',4',6'-tri-i-propylbiphenyl (1.9 mg, 3.9 μmol) under nitrogen was added dioxane (200 μL) and water (200 μL). The sealed vial was heated at 100° C. overnight. The reaction was filtered and concentrated and the residue was purified by prep HPLC (21×100 mm C18; 25 min., 5-50% ACN/water gradient, 0.1% TFA added) to afford compound 149. MS: m/z=364.3 (M+1). $^1H$ NMR (500 MHz, DMSO-$d_6$) δ 10.91 (s, 1H), 8.51 (d, J=5.3 Hz, 1H), 8.28 (d, J=8.4 Hz, 1H), 7.43 (d, J=5.3 Hz, 1H), 7.01 (d, J=8.7 Hz, 1H), 4.50 (s, 2H), 3.38 (m, 2H), 3.24 (d, J=7.1 Hz, 2H), 2.99 (t, J=7.7 Hz, 2H), 2.10 (q, J=7.5 Hz, 2H), 1.07 (m, 1H), 0.56-0.49 (m, 2H), 0.34-0.28 (m, 2H).

Example 17

150

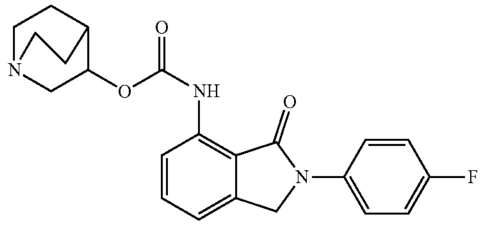

Quinuclidin-3-yl(2-(4-fluorophenyl)-3-oxoisoindolin-4-yl)carbamate (150)

To a solution of triphosgene (26 mg, 0.088 mmol) in DCM (340 μl) was added quinuclidin-3-ol (26 mg, 0.21 mmol) and DMAP (17 mg, 0.14 mmol). The reaction was stirred at ambient temp for 30 min at which point 7-amino-2-(4-fluorophenyl)isoindolin-1-one (25 mg, 0.10 mmol) and DMAP (17 mg, 0.14 mmol) were added. The reaction was sealed and heated at 80° C. for 12 h and then concentrated. The residue was purified by prep HPLC (19 cm×150 cm C18, 30 min, 0-95% ACN/water gradient, 0.05% TFA added) to afford compound 150. MS: m/z=396.5 (M+1). $^1H$ NMR (600 MHz, Chloroform-d) δ 9.95 (s, 1H), 8.15 (d, J=8.1 Hz, 1H), 7.73-7.68 (m, 2H), 7.56 (t, J=7.9 Hz, 1H), 7.18-7.09 (m, 3H), 5.15-5.11 (m, 1H), 4.82 (s, 2H), 3.75 (dd, J=14.0, 9.0 Hz, 1H), 3.39 (t, J=8.4 Hz, 2H), 3.35-3.28 (m, 3H), 2.50 (s, 1H), 2.33 (s, 1H), 2.13-2.04 (m, 1H), 2.00-1.92 (m, 1H), 1.90-1.80 (m, 1H).

Example 18

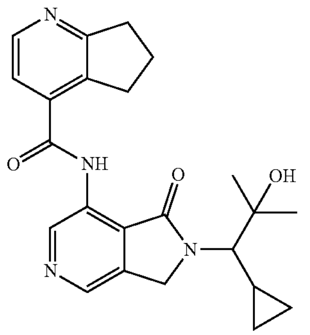

151

(R or S)—N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide (151)

A mixture of 6,7-dihydro-5H-cyclopenta[b]pyridine-4-carboxylic acid (31 mg, 0.19 mmol), 1-methyl-1H-imidazole (55 mg, 0.67 mmol), N-(chloro(dimethylamino)methylene)-N-methylmethanaminium hexafluorophosphate (V) (110 mg, 0.38 mmol) and (R or S)-7-amino-2-(1-cyclopropyl-2-hydroxy-2-methylpropyl)-2,3-dihydro-1H-pyrrolo[3,4-c]pyridin-1-one (I-49, mg, 0.19 mmol) in acetonitrile (2.5 mL) was stirred at ambient temperature for 3 h then concentrated. The residue was purified by prep HPLC (C18 19 mm×250 mm; 4.3 min, 20-60% ACN/10 mM aq. $NH_4HCO_3$, gradient) to afford compound 151. MS: m/z=407.1 (M+1). $^1$H NMR (300 MHz, Chloroform-d): δ 10.79 (s, 1H), 9.95 (s, 1H), 8.63 (s, 1H), 8.53 (d, J=5.4 Hz, 1H), 7.50 (d, J=5.4 Hz, 1H), 4.99-4.75 (m, 2H), 3.41-3.34 (m, 3H), 3.16-3.10 (m, 2H), 2.27-2.10 (m, 2H), 1.49 (s, 3H), 1.46-1.40 (m, 1H), 1.24 (s, 3H), 0.95-0.86 (m, 1H), 0.64-0.51 (m, 2H), 0.19-0.11 (m, 1H).

Compound 152 through 154 found in Table 18, were synthesized by analogous methods from the synthetic sequences described in Examples 151. Commercially available reagents were substituted where necessary to produce compound 152 through 154. Compound 154 was synthesized via palladium catalyzed borylation.

TABLE 18

| Compound Number | Structure | Chemical Name | Observed Mass (M + 1) |
| --- | --- | --- | --- |
| 152 | 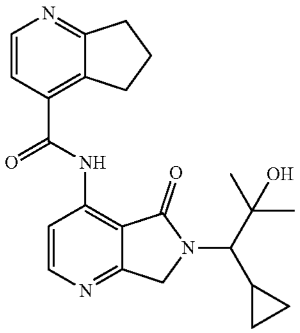 [SMILES: CC(C)(O)C(C1CC1)N1Cc2nccc(NC(=O)c3ccnc4c3CCC4)c2C1=O] | (R or S)-N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide | 407.2 |
| 153 | 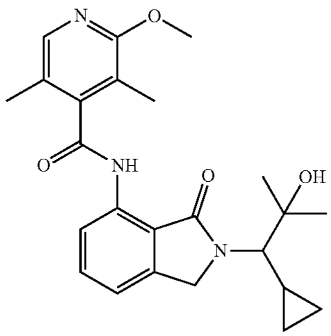 [SMILES: COc1ncc(C)c(C(=O)Nc2cccc3c2C(=O)N(C(C2CC2)C(C)(C)O)C3)c1C] | (R or S)-N-(2-(1-cyclopropyl-2-hydroxy-2-methylpropyl)-3-oxoisoindolin-4-yl)-2-methoxy-3,5-dimethylisonicotinamide | 424.2 |

TABLE 18-continued

| Compound Number | Structure | Chemical Name | Observed Mass (M + 1) |
|---|---|---|---|
| 154 | 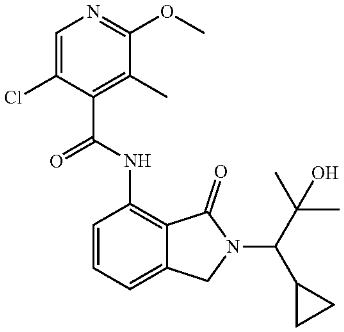 [SMILES: COc1ncc(Cl)c(C(=O)Nc2cccc3c2C(=O)N(C(C2CC2)C(C)(C)O)C3)c1C] | (R or S)-5-chloro-N-(2-(1-cyclopropyl-2-hydroxy-2-methylpropyl)-3-oxoisoindolin-4-yl)-2-methoxy-3-methylisonicotinamide | 444.1 |

Example 19

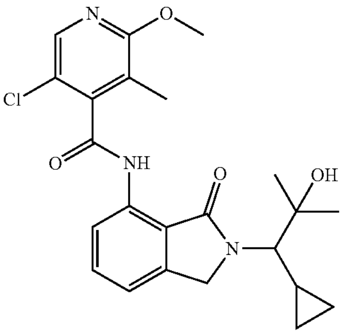

154

(R or S)-5-Chloro-N-(2-(1-cyclopropyl-2-hydroxy-2-methylpropyl)-3-oxoisoindolin-4-yl)-2-methoxy-3-methylisonicotinamide (154)

A deoxygenated mixture of 3-bromo-5-chloro-N-(2-(1-cyclopropyl-2-hydroxy-2-methylpropyl)-3-oxoisoindolin-4-yl)-2-methoxyisonicotinamide (40 mg, 0.079 mmol, made in a similar manner to compound 151 shown in Example 18), 2,4,6-trimethyl-1,3,5,2,4,6-trioxatriborinane (15 mg, 0.12 mmol), $K_2CO_3$ (22 mg, 0.16 mmol), and bis(di-tert-butyl(4-dimethylaminophenyl)phosphine)dichloropalladium(II) (5.6 mg, 7.9 μmol) in 1,4-dioxane (0.5 mL) was heated at 80° C. for 3 h. The reaction was cooled, diluted with water (20 mL), and extracted with EtOAc (3×20 mL). The combined organic phase was washed with brine (3×20 mL), dried over $Na_2SO_4$ and concentrated. The residue was purified by prep TLC (1:1.2 EtOAc/PE) to afford the racemic compound 154. The isomers were separated by Chiral-Prep-HPLC (CHIRALPAK® IF, 2×25 cm, 5 μm; 19 min., 10% EtOH/Hex (8 mM $NH_3$·MeOH) isocratic gradient. The second product-containing fractions were isolated to give the desired isomer of compound 154. m/z=444.1 (M+1). $^1$H-NMR (400 MHz, DMSO-$d_6$): δ 10.80 (s, 1H), 8.32 (d, J=8.4 Hz, 1H), 8.24 (s, 1H), 7.65 (t, J=8.0 Hz, 1H), 7.42 (d, J=7.2 Hz, 1H), 4.93-4.61 (m, 2H), 4.80 (s, 1H), 3.94 (s, 3H), 3.13 (d, J=10.0 Hz, 1H), 2.17 (s, 3H), 1.43-1.40 (m, 1H), 1.31 (s, 3H), 1.01 (s, 3H), 0.76-0.72 (m, 1H), 0.49-0.40 (m, 2H), −0.12-−0.13 (m, 1H).

Compounds 155 through 170 of the current invention were prepared according to general Scheme M.

Example 20

155

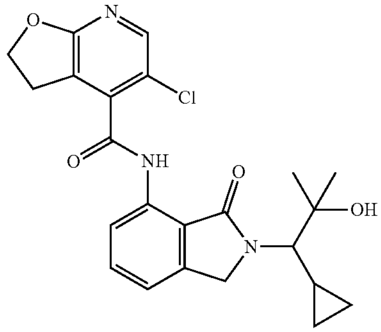

(R or S)-5-Chloro-N-(2-(1-cyclopropyl-2-hydroxy-2-methylpropyl)-3-oxoisoindolin-4-yl)-2,3-dihydrofuro[2,3-b]pyridine-4-carboxamide (155)

A mixture of t-BuONa (sodium-tert butoxide, 97 mg, 1.0 mmol), t-BuXPhos Pd G3 ([(2-di-tert-butylphosphino-2',4',6'-triisopropyl-1,1'-biphenyl)-2-(2'-amino-1,1'-biphenyl)] palladium(II) methanesulfonate, 80 mg, 0.10 mmol), 5-chloro-2,3-dihydrofuro[2,3-b]pyridine-4-carboxamide (100 mg, 0.00 mmol), and (R and S)-7-bromo-2-(1-cyclopropyl-2-hydroxy-2-methylpropyl)isoindolin-1-one (I-5, 130 mg, 0.40 mmol) in tert-Amyl alcohol (2.0 mL) was heated at 40° C. for 16 h. The reaction was concentrated, and the residue was purified by Prep HPLC (AQ-C18 Column; 30 min., 0-45% ACN/10 mM aq. $NH_4HCO_3$, gradient) to afford the racemic compound 155. The mixture of isomers was separated by prep Chiral HPLC (CHIRALPAK IF, 2×25 cm, 5 μm; 19 min., 22% EtOH/Hex (8 mM $NH_3$·MeOH) isocratic gradient). The second product-containing fractions isolated to give the desired isomer of compound 155. MS: m/z=442.2 (M+1). $^1$H-NMR (400 MHz, DMSO-$d_6$): δ 10.96 (s, 1H), 8.34 (d, J=8.0 Hz, 1H), 8.13 (s, 1H), 7.64 (t, J=8.0 Hz, 1H), 7.41 (d, J=7.6 Hz, 1H), 4.93-4.61 (m, 4H), 4.79 (s, 1H), 3.39 (t, J=8.8 Hz, 2H), 3.17 (d, J=10.0 Hz, 1H), 1.43-1.41 (m, 1H), 1.33 (s, 3H), 1.02 (s, 3H), 0.76-0.71 (m, 1H), 0.51-0.47 (m, 1H), 0.43-0.37 (m, 1H), −0.10-−0.14 (m, 1H).

Example 21

156

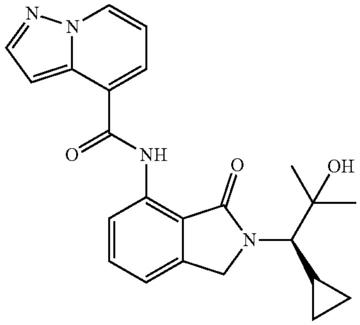

(R)-N-(2-(1-cyclopropyl-2-hydroxy-2-methylpropyl)-3-oxoisoindolin-4-yl)pyrazolo[1,5-a]pyridine-4-carboxamide (156)

A mixture of (R)-7-bromo-2-(1-cyclopropyl-2-hydroxy-2-methylpropyl)isoindolin-1-one (I-4, 25 mg, 0.077 mmol), XantPhos (7.4 mg, 7.7 μmol), XantPhos Pd $G_2$ (chloro[(4,5-bis(diphenylphosphino)-9,9-dimethylxanthene)-2-(2'-amino-1,1'-biphenyl)]palladium(II), 7.5 mg, 7.7 μmol), pyrazolo[1,5-α]pyridine-4-carboxamide (12 mg, 0.077 mmol) and $Cs_2CO_3$ (50 mg, 0.15 mmol) in dioxane (2.0 mL) was heated at 80° C. for 16 h under argon and then concentrated. The residue was purified by prep HPLC (C-18 19 mm×250 mm; 5 min, 40-80% ACN/10 mM aq. $NH_4HCO_3$, gradient) to give compound 156. MS: m/z=405.1 (M+1). $^1$H-NMR (400 MHz, DMSO-$d_6$): δ 11.49 (s, 1H), 8.97 (d, J=7.2 Hz, 1H), 8.49 (d, J=8.0 Hz, 1H), 8.18 (d, J=2.4 Hz, 1H), 7.84 (d, J=7.2 Hz, 1H), 7.67-7.61 (m, 1H), 7.38 (d, J=7.6 Hz, 1H), 7.18-7.16 (m, 1H), 7.14-7.08 (m, 1H), 4.99-4.61 (m, 3H), 3.25-3.22 (m, 1H), 1.50-1.40 (m, 1H), 1.35 (s, 3H), 1.05 (s, 3H), 0.81-0.72 (m, 1H), 0.58-0.50 (m, 1H), 0.45-0.39 (m, 1H), −0.03-−0.10 (m, 1H).

Compounds 157 through 170 found in Table 19, were synthesized by analogous methods from synthetic sequences disclosed in Examples 20 and 21 for compounds 155 and 156. Commercially available reagents were substituted where necessary to produce compounds 157 through 170. Compounds 168 and 169 were synthesized via palladium catalyzed borylation. Compound 170 was synthesized via palladium catalyzed Suzuki coupling with quinuclidin-3-yl methylcarbamate.

TABLE 19

| Compound Number | Structure | Chemical Name | Observed Mass (M + 1) |
|---|---|---|---|
| 157 | 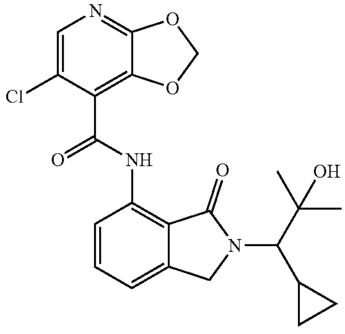 [SMILES: CC(C)(O)C(C1CC1)N1Cc2cccc(NC(=O)c3c(Cl)cnc4c3OCO4)c2C1=O] | (R or S)-6-chloro-N-(2-(1-cyclopropyl-2-hydroxy-2-methylpropyl)-3-oxoisoindolin-4-yl)-[1,3]dioxolo[4,5-b]pyridine-7-carboxamide | 444.2 |
| 158 | 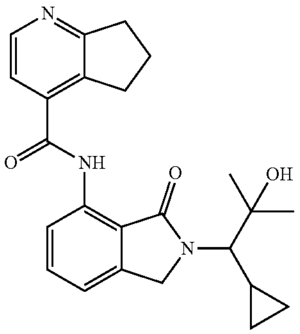 [SMILES: CC(C)(O)C(C1CC1)N1Cc2cccc(NC(=O)c3ccnc4c3CCC4)c2C1=O] | (R or S)-N-(2-(1-cyclopropyl-2-hydroxy-2-methylpropyl)-3-oxoisoindolin-4-yl)-6,7-dihydro-5H-cyclopenta[b]pyridine-4-carboxamide | 406.3 |

TABLE 19-continued

| Compound Number | Structure | Chemical Name | Observed Mass (M + 1) |
| --- | --- | --- | --- |
| 159 | 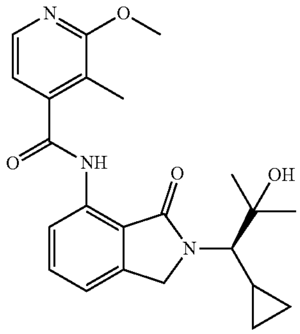 [SMILES: COc1nccc(C(=O)Nc2cccc3c2C(=O)N([C@H](C2CC2)C(C)(C)O)C3)c1C] | (R)-N-(2-(1-cyclopropyl-2-hydroxy-2-methylpropyl)-3-oxoisoindolin-4-yl)-2-methoxy-3-methylisonicotinamide | 410.2 |
| 160 | 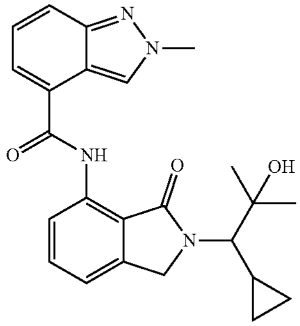 [SMILES: Cn1cc2c(C(=O)Nc3cccc4c3C(=O)N(C(C3CC3)C(C)(C)O)C4)cccc2n1] | (R or S)-N-(2-(1-cyclopropyl-2-hydroxy-2-methylpropyl)-3-oxoisoindolin-4-yl)-2-methyl-2H-indazole-4-carboxamide | 419.2 |
| 161 | 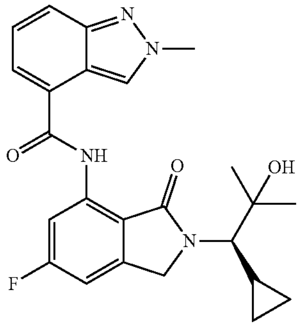 [SMILES: Cn1cc2c(C(=O)Nc3cc(F)cc4c3C(=O)N([C@H](C3CC3)C(C)(C)O)C4)cccc2n1] | (R)-N-(2-(1-cyclopropyl-2-hydroxy-2-methylpropyl)-6-fluoro-3-oxoisoindolin-4-yl)-2-methyl-2H-indazole-4-carboxamide | 437.2 |
| 162 | 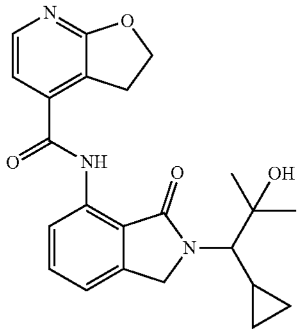 [SMILES: CC(C)(O)C(C1CC1)N1Cc2cccc(NC(=O)c3ccnc4c3CCO4)c2C1=O] | (R or S)-N-(2-(1-cyclopropyl-2-hydroxy-2-methylpropyl)-3-oxoisoindolin-4-yl)-2,3-dihydrofuro[2,3-b]pyridine-4-carboxamide | 408.5 |

TABLE 19-continued

| Compound Number | Structure | Chemical Name | Observed Mass (M + 1) |
|---|---|---|---|
| 163 | 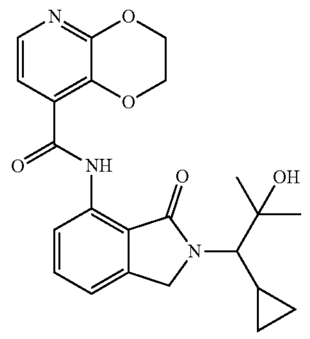 [SMILES: CC(C)(O)C(C1CC1)N1Cc2cccc(NC(=O)c3ccnc4c3OCCO4)c2C1=O] | (R or S)-N-(2-(1-cyclopropyl-2-hydroxy-2-methylpropyl)-3-oxoisoindolin-4-yl)-2,3-dihydro-[1,4]dioxino[2,3-b]pyridine-8-carboxamide | 424.1 |
| 164 | 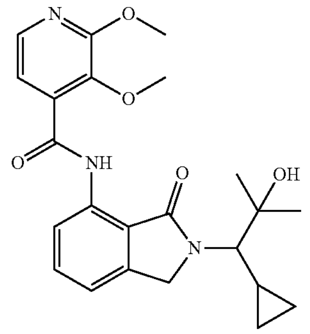 [SMILES: COc1nccc(C(=O)Nc2cccc3c2C(=O)N(C(C2CC2)C(C)(C)O)C3)c1OC] | (R or S)-N-(2-(1-cyclopropyl-2-hydroxy-2-methylpropyl)-3-oxoisoindolin-4-yl)-2,3-dimethoxyisonicotinamide | 426.2 |
| 165 | 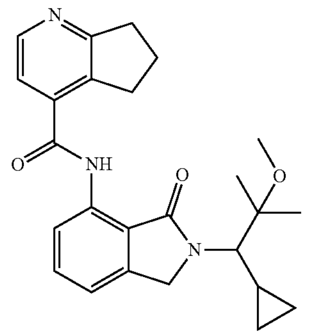 [SMILES: COC(C)(C)C(C1CC1)N1Cc2cccc(NC(=O)c3ccnc4c3CCC4)c2C1=O] | (R or S)-N-(2-(1-cyclopropyl-2-methoxy-2-methylpropyl)-3-oxoisoindolin-4-yl)-6,7-dihydro-5H-cyclopenta[b]pyridine-4-carboxamide | 420.2 |
| 166 | 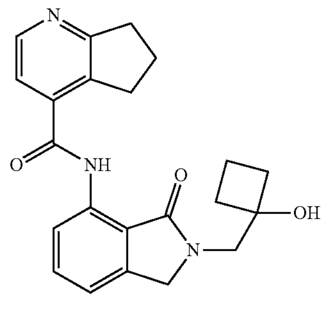 [SMILES: O=C(Nc1cccc2c1C(=O)N(CC1(O)CCC1)C2)c1ccnc2c1CCC2] | N-(2-((1-hydroxycyclobutyl)methyl)-3-oxoisoindolin-4-yl)-6,7-dihydro-5H-cyclopenta[b]pyridine-4-carboxamide | 378.3 |

TABLE 19-continued

| Compound Number | Structure | Chemical Name | Observed Mass (M + 1) |
|---|---|---|---|
| 167 | 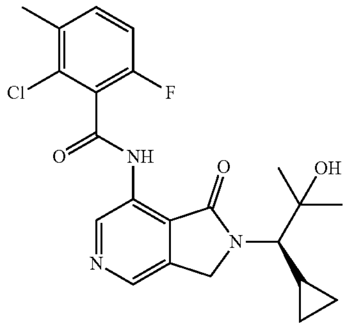 [SMILES: Cc1ccc(F)c(C(=O)Nc2cncc3c2C(=O)N([C@H](C2CC2)C(C)(C)O)C3)c1Cl] | (R)-2-chloro-N-(2-(1-cyclopropyl-2-hydroxy-2-methylpropyl)-1-oxo-2,3-dihydro-1H-pyrrolo[3,4-c]pyridin-7-yl)-6-fluoro-3-methylbenzamide | 432.1 |
| 168 | 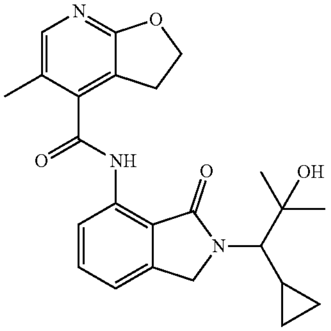 [SMILES: Cc1cnc2c(c1C(=O)Nc1cccc3c1C(=O)N(C(C1CC1)C(C)(C)O)C3)CCO2] | (R or S)-N-(2-(1-cyclopropyl-2-hydroxy-2-methylpropyl)-3-oxoisoindolin-4-yl)-5-methyl-2,3-dihydrofuro[2,3-b]pyridine-4-carboxamide | 422.2 |
| 169 | 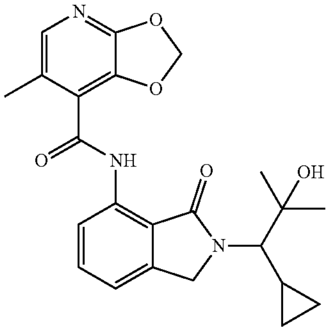 [SMILES: Cc1cnc2c(c1C(=O)Nc1cccc3c1C(=O)N(C(C1CC1)C(C)(C)O)C3)OCO2] | (R or S)-N-(2-(1-cyclopropyl-2-hydroxy-2-methylpropyl)-3-oxoisoindolin-4-yl)-6-methyl-[1,3]dioxolo[4,5-b]pyridine-7-carboxamide | 424.3 |
| 170 | 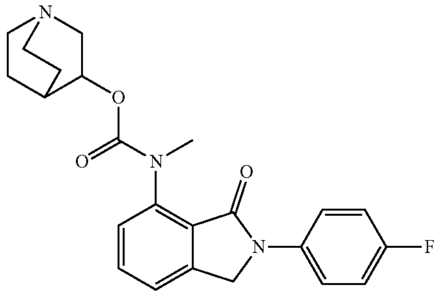 | (R and S)-quinuclidin-3-yl (2-(4-fluorophenyl)-3-oxoisoindolin-4-yl)(methyl)carbamate | 410.1 |

Example 22

168

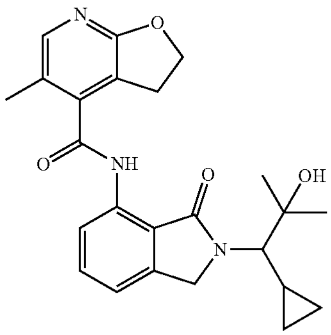

(R or S)—N-(2-(1-Cyclopropyl-2-hydroxy-2-methylpropyl)-3-oxoisoindolin-4-yl)-5-methyl-2,3-dihydrofuro[2,3-b]pyridine-4-carboxamide (168)

A deoxygenated mixture of (R or S)-5-chloro-N-(2-(1-cyclopropyl-2-hydroxy-2-methylpropyl)-3-oxoisoindolin-4-yl)-2,3-dihydrofuro[2,3-b]pyridine-4-carboxamide (compound 155, 40 mg, 0.09 mmol), 2,4,6-trimethyl-1,3,5,2,4,6-trioxatriborinane (50% wt in THF, 34 mg, mmol), a solution of $Cs_2CO_3$ (59 mg, 0.18 mmol) in water (0.2 mL) and 1,1'-bis(di-tert-butylphosphino)ferrocene palladium dichloride (5.9 mg, 9.1 μmol) in 1,4-dioxane (1.0 mL) was heated at 100° C. for 16 h. The reaction was concentrated, and the residue was purified by prep TLC (1:1 EtOAc/PE) to give the racemic compound 168. The mixture of isomers was separated by prep Chiral-HPLC (CHIRALPAK® IF-3, 4.6×50 cm, 3 μm; 18 min., 20% EtOH/Hex (0.1% DEA) isocratic gradient). The second product-containing fractions were isolated to give the desired isomer of compound 168. MS: m/z=422.2 (M+1). $^1$H-NMR (400 MHz, Chloroform-d): δ 10.79 (s, 1H), 8.67-8.65 (m, 1H), 7.92 (s, 1H), 7.63-7.59 (m, 1H), 7.25-7.23 (m, 1H), 4.88-4.65 (m, 4H), 3.48-3.42 (m, 2H), 3.30 (d, J=10.4 Hz, 1H), 2.40 (s, 3H), 2.06 (s, 1H), 1.47 (s, 3H), 1.39-1.35 (m, 1H), 1.26 (s, 3H), 0.91-0.87 (m, 1H), 0.61-0.52 (m, 2H), 0.18-0.15 (m, 1H).

Example 23

169

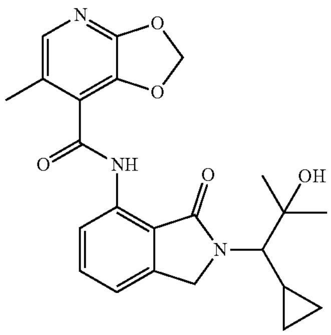

(R or S)—N-(2-(1-Cyclopropyl-2-hydroxy-2-methylpropyl)-3-oxoisoindolin-4-yl)-6-methyl-[1,3]dioxolo[4,5-b]pyridine-7-carboxamide (169)

A mixture of (R or S)-6-chloro-N-(2-(1-cyclopropyl-2-hydroxy-2-methylpropyl)-3-oxoisoindolin-4-yl)-[1,3]dioxolo[4,5-b]pyridine-7-carboxamide (compound 157, 100 mg, 0.23 mmol), 2,4,6-trimethyl-1,3,5,2,4,6-trioxatriborinane (50% wt in THF, 55 mg, 0.44 mmol), bis(di-tert-butyl(4-dimethylaminophenyl)phosphine)dichloropalladium (II) (70 mg, 0.099 mmol) and potassium carbonate (70 mg, 0.51 mmol) in DMF (1.5 mL) was heated at 110° C. for 3 h then filtered. The filtrate was purified by prep HPLC (C18-Column, 30 min., 0-100% ACN/5 mM aq. $NH_4CO_3$; gradient) to afford the racemic compound 169. The mixture of isomers was separated by Chiral-Prep-HPLC (CHIRALPAK® IF, 2×25 cm, 5 μm; 19 min, 30% B EtOH/Hexane (8 mM ammonia in methanol) isocratic gradient). The second product-containing fractions were isolated to afford the desired isomer of compound 169. MS: m/z=424.3 (M+1). $^1$H NMR (400 MHz, Methanol-$d_4$): δ 8.54 (d, J=8.4 Hz, 1H), 7.60 (t, J=7.6 Hz, 1H), 7.50 (s, 1H), 7.33 (d, J=7.6 Hz, 1H), 6.23 (d, J=4.8 Hz, 2H), 4.96-4.70 (m, 2H), 3.31-3.25 (m, 1H), 2.39 (s, 3H), 1.49-1.41 (m, 4H), 1.14 (s, 3H), 0.89-0.84 (m, 1H), 0.60-0.48 (m, 2H), 0.10-0.01 (m, 1H).

Example 24

170

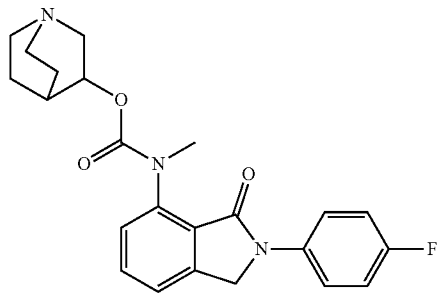 [SMILES: CN(C(=O)OC1CN2CCC1CC2)c1cccc2c1C(=O)N(c1ccc(F)cc1)C2]

(R and S)-Quinuclidin-3-yl(2-(4-fluorophenyl)-3-oxoisoindolin-4-yl)(methyl)carbamate (170)

A deoxygenated mixture of 7-bromo-2-(4-fluorophenyl)isoindolin-1-one (0.10 g, 0.33 mmol), (R and S)-quinuclidin-3-yl methylcarbamate, (90 mg, 0.49 mmol), (2-(2-aminoethyl)phenyl)(6-(dicyclohexylphosphino)-2',6'-diisopropoxy-[1,1'-biphenyl]-3-yl)palladium(III) chloride (24 mg, 0.033 mmol) and $Cs_2CO_3$ (0.32 g, 0.98 mmol) in tert-amyl alcohol (3 mL) was heated at 100° C. for 16 h. The resulting mixture was diluted with water (20 mL) and extracted with EtOAc (3×20 mL). The aqueous phase was concentrated, and the residue was purified by Prep-HPLC (C18 19 mm×250 mm; 6 min., 51-55% ACN/water gradient, 0.05% $NH_4OH$ added) to afford compound 170. MS: m/z=410.1 (M+1). $^1$H NMR (400 MHz, $CD_3OD$) δ 7.92-7.81 (m, 2H), 7.72-7.68 (m, 1H), 7.61 (d, J=7.6 Hz, 1H), 7.4-7.36 (m, 1H), 7.19-7.15 (m, 2H), 5.06-4.98 (m, 2H), 4.77-4.66 (m, 1H), 3.37-3.34 (m, 1H), 3.23-2.84 (m, 3H), 2.64-2.60 (m, 2H), 2.53-2.44 (m, 2H), 1.82-1.76 (m, 1H), 1.63-1.55 (m, 3H), 1.17-1.13 (m, 2H).

Compounds 171 through 176 of the current invention were prepared according to general Scheme N.

Example 25

171

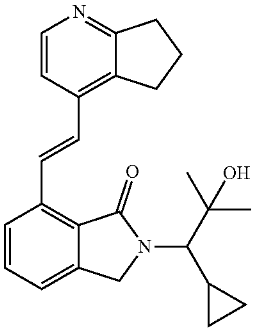

(R or S)-(E)-2-(1-Cyclopropyl-2-hydroxy-2-methylpropyl)-7-(2-(6,7-dihydro-5H-cyclopenta[b]pyridin-4-yl)vinyl)isoindolin-1-one (171)

A deoxygenated mixture of (R or S)-7-bromo-2-(1-cyclopropyl-2-hydroxy-2-methylpropyl)isoindolin-1-one (I-4, 30 mg, 0.093 mmol), triethylamine (33 mg, 0.32 mmol), diacetoxypalladium (0.21 mg, 0.93 μmol), tris(2-methoxyphenyl)phosphine (1.3 mg, 3.7 μmol) and 4-vinyl-6,7-dihydro-5H-cyclopenta[b]pyridine (16 mg, 0.11 mmol) in acetonitrile (1.0 mL) was heated at 100° C. for 2 h. The reaction was diluted with water (20 mL) and extracted with ethyl acetate (3×50 mL). The combined organic phase was washed with brine (3×50 mL), dried over $Na_2SO_4$ and concentrated. The residue was purified by prep-HPLC (C18 19 mm×250 mm; 5 min, 15-45% ACN/10 mM aq. $NH_4HCO_3$ gradient) to afford compound 171. MS: m/z=389.3 (M+1). $^1$H-NMR (300 MHz, Chloroform-d): δ 8.80 (d, J=16.5 Hz, 1H), 8.33 (d, J=5.7 Hz, 1H), 7.82 (d, J=7.8 Hz, 1H), 7.56 (t, J=10.5 Hz, 1H), 7.42-7.35 (m, 2H), 7.24 (d, J=5.1 Hz, 1H), 4.83-4.64 (m, 2H), 3.41 (d, J=10.2 Hz, 1H), 3.19-3.05 (m, 4H), 2.48-2.46 (m, 1H), 2.25-2.14 (m, 2H), 1.46 (s, 3H), 1.44-1.30 (m, 1H), 1.27 (s, 3H), 0.89-0.85 (m, 1H), 0.62-0.49 (m, 2H), 0.22-0.17 (m, 1H).

Example 26

172

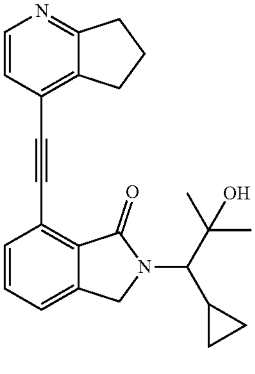

(R or S)-2-(1-Cyclopropyl-2-hydroxy-2-methylpropyl)-7-((6,7-dihydro-5H-cyclopenta[b]pyridin-4-yl)ethynyl)isoindolin-1-one (172)

A deoxygenated mixture of (R or S)-7-bromo-2-(1-cyclopropyl-2-hydroxy-2-methylpropyl)isoindolin-1-one (I-4, 35 mg, 0.12 mmol), palladium(II) chloride (0.19 mg, 1.1 triethylamine (0.068 mL, 0.49 mmol) and 2-dicyclohexylphosphino-2',4',6'-triisopropylbiphenyl (XPhos, 1.5 mg, 3.2 μmol) in acetonitrile (1.0 mL) was stirred for 20 min then 4-ethynyl-6,7-dihydro-5H-cyclopenta[b]pyridine (23 mg, 0.16 mmol) was added. The reaction mixture was stirred for 2 h then diluted with water (20 mL) and extracted with ethyl acetate (3×50 mL). The combined organic phase was washed with brine (3×50 mL), dried over $Na_2SO_4$ and concentrated. The residue was purified by silica gel column chromatography (0-30% EtOAc/HEXANE gradient) to afford compound 172. MS: m/z=387.20 (M+1). $^1$H NMR (300 MHz, Chloroform-d): δ 8.33-8.31 (m, 1H), 7.64-7.45 (m, 3H), 7.26-7.24 (m, 1H), 4.82-4.63 (m, 2H), 3.42 (d, J=10.2 Hz, 1H), 3.22-3.19 (m, 2H), 3.09-3.04 (m, 2H), 2.71 (s, 1H), 2.21-2.14 (m, 2H), 1.45 (s, 3H), 1.44-1.31 (m, 1H), 1.30 (s, 3H), 0.89-0.84 (m, 1H), 0.60-0.49 (m, 2H), 0.24-0.21 (m, 1H).

Example 27

173

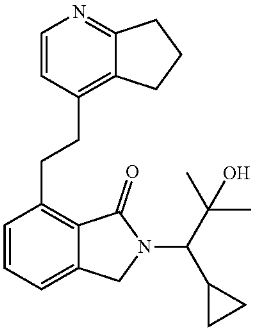 [SMILES: CC(C)(O)C(C1CC1)N1Cc2cccc(OCc3ccnc4c3CCC4)c2C1=O]

(R or S)-2-(1-Cyclopropyl-2-hydroxy-2-methylpropyl)-7-(2-(6,7-dihydro-5H-cyclopenta[b]pyridin-4-yl)ethyl)isoindolin-1-one (173)

To a stirred mixture of (R or S)-2-(1-cyclopropyl-2-hydroxy-2-methylpropyl)-7-((6,7-dihydro-5H-cyclopenta[b]pyridin-4-yl)ethynyl)isoindolin-1-one (compound 172, 22 mg, 0.057 mmol) in MeOH (3 mL) was added 20 wt % $Pd(OH)_2/C$ (22 mg, 0.029 mmol) at ambient temp under nitrogen atmosphere. The mixture was then purged with hydrogen then stirred for 24 h at ambient temp under a balloon of hydrogen gas. The reaction mixture was filtered through a pad of Celite® and the filtrate was concentrated. The residue was purified by Prep-HPLC (C18 19×250 mm; 5 min., 15-45% ACN/10 mM aq. $NH_4HCO_3$ gradient) to afford compound 173. MS: m/z=391.3 (M+1). $^1$H NMR (300 MHz, Chloroform-d): δ 8.24 (d, J=4.8 Hz, 1H), 7.45-7.42 (m, 1H), 7.33 (d, J=7.6 Hz, 1H), 7.15 (d, J=7.6 Hz, 1H), 6.99 (d, J=4.8 Hz, 1H), 4.76-4.64 (m, 2H), 3.47-3.43 (m, 2H), 3.35 (d, J=10.4 Hz, 1H), 3.05-2.81 (m, 7H), 2.13-2.06 (m, 2H), 1.45 (s, 3H), 1.39-1.36 (m, 1H), 1.29 (s, 3H), 0.90-0.86 (m, 1H), 0.62-0.51 (m, 2H), 0.21-0.17 (m, 1H).

Example 28

174

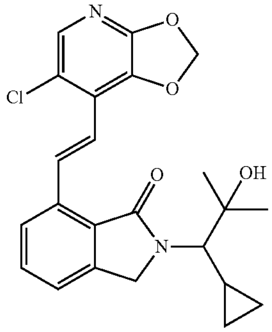

(R or S)-(E)-7-(2-(6-Chloro-[1,3]dioxolo[4,5-b]pyridin-7-yl)vinyl)-2-(1-cyclopropyl-2-hydroxy-2-methylpropyl)isoindolin-1-one (174)

Step A: (R or S)-2-(1-Cyclopropyl-2-hydroxy-2-methylpropyl)-7-vinylisoindolin-1-one (28-a)

A deoxygenated mixture of (R or S)-7-bromo-2-(1-cyclopropyl-2-hydroxy-2-methylpropyl)isoindolin-1-one (I-4, 120 mg, 0.37 mmol), vinylboronic acid pinacol ester (0.075 mL, 0.44 mmol), $K_3PO_4$ (160 mg, 0.74 mmol) and [1,1'-bis(diphenylphosphino)ferrocene]dichloropalladium(II) (27 mg, 0.037 mmol) in acetonitrile (5 mL) was heated at 90° C. for 16 h. The reaction was diluted with water (5.0 mL) and extracted with ethyl acetate (3×50 mL). The combined organic phase was washed with brine (3×50 mL), dried over $Na_2SO_4$ and concentrated. The residue was purified by silica gel column chromatography (0-30% EtOAc/hexanes gradient) to afford compound 28-a. MS: m/z=272.2 (M+1). $^1$H-NMR (300 MHz, Chloroform-d): δ 8.16-8.06 (m, 1H), 7.71-7.68 (m, 1H), 7.54-7.49 (m, 1H), 7.37-7.29 (m, 1H), 5.93-5.87 (m, 1H), 5.47-5.43 (m, 1H), 4.72-4.69 (m, 2H), 3.35 (d, J=10.5 Hz, 1H), 1.46 (s, 3H), 1.41-1.34 (m, 1H), 1.30 (s, 3H), 0.96-0.83 (m, 1H), 0.62-0.49 (m, 2H), 0.22-0.18 (m, 1H).

Step B: (R or S)-(E)-7-(2-(6-Chloro-[1,3]dioxolo[4,5-b]pyridin-7-yl)vinyl)-2-(1-cyclopropyl-2-hydroxy-2-methylpropyl)isoindolin-1-one (174)

A deoxygenated mixture of (R or S)-2-(1-cyclopropyl-2-hydroxy-2-methylpropyl)-7-vinylisoindolin-1-one (28-a, 30 mg, 0.11 mmol), triethylamine (39 mg, 0.39 mmol), diacetoxypalladium (0.25 mg, 1.1 μmol), tris(2-methoxyphenyl) phosphine (1.6 mg, 4.4 μmol) and 6-chloro-7-iodo-[1,3]dioxolo[4,5-b]pyridine (38 mg, 0.13 mmol) in acetonitrile (1.0 mL) was heated at 100° C. for 16 h. The reaction was diluted with water (2.0 mL) and extracted with ethyl acetate (3×50 mL). The combined organic phase was washed with brine (3×50 mL), dried over $Na_2SO_4$ and concentrated. The residue was purified by Prep-HPLC (C18 19×250 mm; 5 min, 15-45% ACN/10 mM aq. $NH_4HCO_3$ gradient) to afford compound 174. MS: m/z=427.2 (M+1). $^1$H-NMR (400 MHz, Chloroform-d): δ 9.05 (d, J=16.8 Hz, 1H), 7.87 (d, J=7.6 Hz, 1H), 7.70 (s, 1H), 7.59 (t, J=7.6 Hz, 1H), 7.45-7.38 (m, 2H), 6.30-6.29 (m, 2H), 4.82-4.67 (m, 2H), 3.41 (d, J=10.4 Hz, 1H), 1.46 (s, 3H), 1.42-1.35 (m, 1H), 1.30 (s, 3H), 0.90-0.85 (m, 1H), 0.62-0.49 (m, 2H), 0.23-0.19 (m, 1H).

Example 29

175

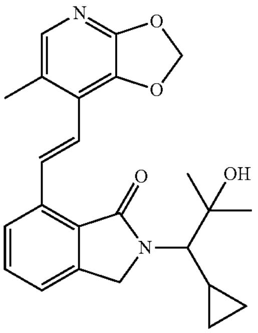

(R or S)-(E)-2-(1-Cyclopropyl-2-hydroxy-2-methylpropyl)-7-(2-(6-methyl-[1,3]dioxolo[4,5-b]pyridin-7-yl)vinyl)isoindolin-1-one (175)

A solution of (R or S)-(E)-7-(2-(6-chloro-[1,3]dioxolo[4,5-b]pyridin-7-yl)vinyl)-2-(1-cyclopropyl-2-hydroxy-2-methylpropyl)isoindolin-1-one (compound 174, 30 mg, 0.070 mmol), 2,4,6-trimethyl-1,3,5,2,4,6-trioxatriborinane (50% wt in THF, 13 mg, 0.11 mmol), $K_2CO_3$ (19 mg, 0.14 mmol) and $PdCl_2$ (dppf) (5.1 mg, 7.0 μmol) in dioxane (2.0 mL) was heated at 90° C. for 4 h. The reaction mixture was cooled, diluted with water (10 mL), and extracted with ethyl acacate (3×10 mL). The combined organic phase was washed with brine (3×10 mL), dried over $Na_2SO_4$ and concentrated. The residue was purified by Prep-HPLC (C18 19×250 mm; 5.8 min., 65-80% ACN/10 mM aq. $NH_4HCO_3$ gradient) to afford compound 175. MS: m/z=407.3 (M+1). $^1$H-NMR (400 MHz, Chloroform-d): δ 8.93 (d, J=16.8 Hz, 1H), 7.81 (d, J=8.0 Hz, 1H), 7.57 (t, J=7.6 Hz, 1H), 7.49 (s, 1H), 7.42 (d, J=7.6 Hz, 1H), 7.19 (d, J=16.4 Hz, 1H), 6.21 (s, 2H), 4.81-4.66 (m, 1H), 3.42 (d, J=10.4 Hz, 1H), 2.37 (s, 3H), 1.46 (s, 3H), 1.41-1.35 (m, 1H), 1.31 (s, 3H), 0.90-0.86 (m, 1H), 0.62-0.49 (m, 2H), 0.23-0.20 (m, 1H).

Example 30

176

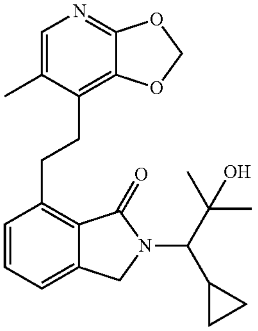

(R or S)-2-(1-Cyclopropyl-2-hydroxy-2-methylpropyl)-7-(2-(6-methyl-[1,3]dioxolo[4,5-b]pyridin-7-yl)ethyl)isoindolin-1-one (176)

To a deoxygenated solution of (R or S)-2-(1-cyclopropyl-2-hydroxy-2-methylpropyl)-7-(2-(6-methyl-[1,3]dioxolo[4,5-b]pyridin-7-yl)vinyl)isoindolin-1-one (25 mg, 0.062 mmol) in $CH_3OH$ (3.0 mL) was added 10 wt % Pd/C (22 mg, 0.19 mmol). The resulting mixture was stirred for 24 h at ambient temp under a balloon of hydrogen gas. The reaction was filtered through a pad of Celite®) and the filtrate was concentrated. The residue was purified by Prep-HPLC (C18 19×150 mm 5 μm 10 nm; 6 min, 35-75% ACN/10 mM aq. FA gradient) to afford compound 176. MS: m/z=409.3 (M+1). $^1$H-NMR (400 MHz, Chloroform-d): δ 7.43-7.39 (m, 2H), 7.32-7.28 (m, 1H), 7.15 (d, J=7.6 Hz, 1H), 5.95 (s, 2H), 4.74-4.62 (m, 2H), 3.47-3.43 (m, 2H), 3.35 (d, J=10.4 Hz, 1H), 3.01-2.97 (m, 2H), 2.13 (s, 3H), 1.44 (s, 3H), 1.39-1.35 (m, 1H), 1.28 (s, 3H), 0.90-0.86 (m, 1H), 0.62-0.50 (m, 2H), 0.20-0.17 (m, 1H).

Compounds 177 through 178 of the current invention were prepared according to general Scheme O.

Example 31

177

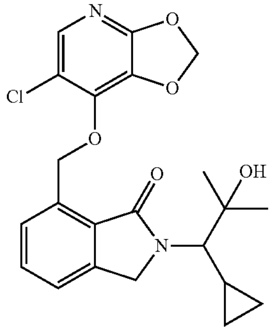

(R or S)-7-(((6-chloro-[1,3]dioxolo[4,5-b]pyridin-7-yl)oxy)methyl)-2-(1-cyclopropyl-2-hydroxy-2-methylpropyl)isoindolin-1-one (177)

Step A: (R or S)-2-(1-Cyclopropyl-2-hydroxy-2-methylpropyl)-7-((2-(trimethylsilyl)ethoxy)methyl)isoindolin-1-one (31-A)

A deoxygenated mixture of (R or S)-7-bromo-2-(1-cyclopropyl-2-hydroxy-2-methylpropyl)isoindolin-1-one (I-4, 200 mg, 0.62 mmol), methanesulfonato (2-dicyclohexylphosphino-2',6'-di-1-propoxy-1,1'-biphenyl)(2'-amino-1,1'-biphenyl-2-yl)palladium (II) (52 mg, 0.062 mmol), potassium trifluoro((2-(trimethylsilyl)ethoxy)methyl)borate (180 mg, 0.74 mmol) and cesium carbonate (720 mg, 2.2 mmol) in toluene (6.0 mL) and water (0.60 mL) was stirred for 2 h then diluted with water (5 mL) and extracted with ethyl acetate (3×100 mL). The combined organic extracts were washed with brine (3×100 mL), dried over $Na_2SO_4$ and concentrated. The residue was purified by silica gel column chromatography (0-30% EtOAc/hexanes gradient) to afford compound 31-A. MS: m/z=376.4 (M+1). $^1$H-NMR (300 MHz, Chloroform-d): δ 7.65-7.62 (m, 1H), 7.56-7.51 (m, 1H), 7.36-7.33 (m, 1H), 5.14-5.13 (m, 2H), 4.77-4.62 (m, 2H), 3.75-3.69 (m, 2H), 3.31 (d, J=10.2 Hz, 1H), 1.43 (s, 3H), 1.38-1.35 (m, 1H), 1.28 (s, 3H), 1.09-1.04 (m, 2H), 0.88-0.84 (m, 1H), 0.59-0.49 (m, 2H), 0.20-0.16 (m, 1H), 0.05 (s, 9H).

Step B: (R or S)-2-(1-Cyclopropyl-2-hydroxy-2-methylpropyl)-7-(hydroxymethyl)isoindolin-1-one (31-B)

To a solution of (R or S)-2-(1-cyclopropyl-2-hydroxy-2-methylpropyl)-7-((2-(trimethylsilyl)ethoxy)methyl)isoindolin-1-one (31-a, 180 mg, 0.48 mmol) in THF (5.0 mL) was added pyridine hydrofluoride (1.4 g, 14 mmol) at 0° C. The reaction mixture was heated at 50° C. for 16 h and then the mixture was diluted with ethyl acetate (100 mL), washed with water (2×50 mL) and brine (50 mL), the organic layer was dried over $MgSO_4$ and concentrated. The residue was purified by prep HPLC (AQ-C18 Column; 30 min., 0-80% ACN/water gradient) to give compound 31-b. MS: m/z=276.2 (M+1). $^1$H-NMR (300 MHz, Chloroform-d): δ 7.57-7.31 (m, 3H), 4.93-4.76 (m, 4H), 4.33 (t, J=6.6 Hz, 1H), 3.40 (d, J=10.2 Hz, 1H), 1.48 (s, 3H), 1.45-1.31 (m, 1H), 1.28 (s, 3H), 0.91-0.84 (m, 1H), 0.62-0.45 (m, 2H), 0.23-0.18 (m, 1H).

Step C: (R or S)-7-(((6-Chloro-[1,3]dioxolo[4,5-b]pyridin-7-yl)amino)methyl)-2-(1-cyclopropyl-2-hydroxy-2-methylpropyl)isoindolin-1-one (177)

A deoxygenated mixture of (R or S)-2-(1-cyclopropyl-2-hydroxy-2-methylpropyl)-7-(hydroxymethyl)isoindolin-1-one (31-B, 40 mg, 0.15 mmol), brunopalladacycle (13 mg, 0.015 mmol), (R)-(S)-Josiphos (8.6 mg, 0.015 mmol), cesium carbonate (95 mg, 0.29 mmol) and 6-chloro-7-iodo-[1,3]dioxolo[4,5-b]pyridine (41 mg, 0.15 mmol) in 1,4-dioxane (3.0 mL) was stirred for 16 hrs, diluted with water (10 mL) and extracted with ethyl acetate (3×20 mL). The combined organic phase was washed with brine (3×20 mL), dried over $Na_2SO_4$ and concentrated. The residue was purified by Prep-HPLC (C18 19×250 mm; 5.8 min, 70-85%: ACN/10 mM aq. $NH_4HCO_3$ gradient) to afford compound 177. MS: m/z=431.2 (M+1). $^1$H-NMR (300 MHz, Chloroform-d): δ 7.75-7.72 (m, 1H), 7.63-7.56 (m, 2H), 7.44-7.41 (m, 1H), 6.18 (d, J=5.7 Hz, 2H), 6.03 (s, 2H), 4.83-4.65 (m, 1H), 3.33 (d, J=10.5 Hz, 1H), 2.45 (s, 1H), 1.47 (s, 3H), 1.43-1.31 (m, 1H), 1.29 (s, 3H), 0.91-0.82 (m, 1H), 0.59-0.46 (m 2H), 0.20-0.12 (m, 1H).

Example 32

178

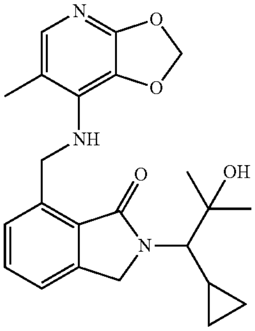

(R or S)-2-(1-Cyclopropyl-2-hydroxy-2-methylpropyl)-7-0(6-methyl-[1,3]dioxolo[4,5-b]pyridin-7-yl) amino)methyl)isoindolin-1-one (178)

Step A: (R or S)-tert-Butyl ((2-(1-cyclopropyl-2-hydroxy-2-methylpropyl)-3-oxoisoindolin-4-yl) methyl)carbamate (32-A)

Using an analogous procedure to that described in Example 31, Step A, potassium (((tert-butoxycarbonyl) amino)methyl)trifluoroborate was used in place potassium trifluoro((2-(trimethylsilyl)ethoxy)methyl)borate to afford compound 32-A. MS: m/z=375.20 (M+1).

Step B: (R or S)-7-(Aminomethyl)-2-(1-cyclopropyl-2-hydroxy-2-methylpropyl)isoindolin-1-one (32-B)

A solution of (R or S)-tert-butyl ((2-(1-cyclopropyl-2-hydroxy-2-methylpropyl)-3-oxoisoindolin-4-yl)methyl)carbamate (180 mg, 0.29 mmol) and 4M HCl in dioxane (2.0 mL, 8.0 mmol) in DCM (5 mL) was stirred at ambient temp for 1 h then concentrated. The residue was purified by prep HPLC (AQ-C18; 20 min., 10-80% ACN/10 mM aq. $NH_4HCO_3$ gradient) to afford compound 32-B. MS: m/z=275.2 (M+1). $^1$H NMR (300 MHz, Chloroform-d): δ 7.53-7.48 (m, 1H), 7.41-7.37 (m, 2H), 4.85-4.67 (m, 2H), 4.28 (s, 2H), 3.39-3.34 (m, 1H), 1.45 (s, 3H), 1.40-1.28 (m, 1H), 1.27 (s, 3H), 0.90-0.85 (m, 1H), 0.61-0.50 (m, 2H), 0.21-0.15 (m, 1H).

Step C: (R or S)-7-(((6-Chloro-[1,3]dioxolo[4,5-b] pyridin-7-yl)amino)methyl)-2-(1-cyclopropyl-2-hydroxy-2-methylpropyl)isoindolin-1-one (32-C)

A deoxygenated mixture of (R or S)-7-(aminomethyl)-2-(1-cyclopropyl-2-hydroxy-2-methylpropyl)isoindolin-1-one (32-B, 120 mg, 0.44 mmol), brunopalladacycle (40 mg, 0.044 mmol), (R)-(S)-Josiphos (26 mg, 0.044 mmol), cesium carbonate (290 mg, 0.88 mmol) and 6-chloro-7-iodo-[1,3]dioxolo[4,5-b]pyridine (120 mg, 0.44 mmol) in 1,4-dioxane (3.0 mL) was stirred for 16 h, diluted with water (10 mL) and extracted with ethyl acetate (3×20 mL). The combined organic phase was washed with brine (3×20 mL), dried over $Na_2SO_4$ and concentrated. The residue was purified by silica gel column chromatography (0-70% EtOAc/hexanes gradient) to afford the impure compound 32-C. The impure product was purified by Prep-HPLC (C18 19×250 mm; 5.8 min, 60-80% ACN/10 mM aq. $NH_4HCO_3$ gradient) to afford compound 32-C. MS: m/z=430.2 (M+1). $^1$H-NMR (400 MHz, Chloroform-d): δ 7.49-7.38 (m, 4H), 6.81 (s, 1H), 6.04 (s, 2H), 4.97-4.96 (m, 2H), 4.85-4.67 (m, 2H), 3.42 (d, J=Hz, 1H), 1.49 (s, 3H), 1.45-1.37 (m, 1H), 1.29 (s, 3H), 0.93-0.86 (m, 1H), 0.64-0.48 (m, 2H), 0.22-0.16 (m, 1H).

Step D: (R or S)-2-(1-Cyclopropyl-2-hydroxy-2-methylpropyl)-7-(((6-methyl-[1,3]dioxolo[4,5-b] pyridin-7-yl)amino)methyl)isoindolin-1-one (178)

A deoxygenated solution of (R or S)-7-(((6-chloro-[1,3] dioxolo[4,5-b]pyridin-7-yl)amino)methyl)-2-(1-cyclopropyl-2-hydroxy-2-methylpropyl)isoindolin-1-one (32-C, 30 mg, mmol), 2,4,6-trimethyl-1,3,5,2,4,6-trioxatriborinane (50% wt in THF, 13 mg, 0.11 mmol), $K_2CO_3$ (19 mg, 0.14 mmol) and $PdCl_2$(dppf) (5.1 mg, 7.0 μmol) in dioxane (1.0 mL) was heated at 90° C. for 4 h. The reaction mixture was cooled, diluted with water (10 mL), and extracted with ethyl acetate (3×10 mL). The combined organic phase was washed with brine (3×10 mL), dried over $Na_2SO_4$ and concentrated. The residue was purified by Prep-HPLC (C18 19×250 mm; 5.8 min, 60-80% ACN/10 mM aq. $NH_4HCO_3$ gradient) to afford compound 178. MS: m/z=410.3 (M+1). $^1$H-NMR (400 MHz, Chloroform-d): δ 7.48-7.37 (m, 3H), 7.20 (s, 1H), 6.39 (s, 1H), 5.96 (s, 2H), 4.91-4.90 (m, 2H), 4.85-4.66 (m, 2H), 3.39 (d, J=10.4 Hz, 1H), 1.98 (s, 3H), 1.48 (s, 3H), 1.44-1.38 (m, 1H), 1.28 (s, 3H), 0.92-0.87 (m, 1H), 0.64-0.57 (m, 1H), 0.55-0.49 (m, 1H), 0.17-0.10 (m, 1H).

Compounds 179 through 181 of the current invention were prepared according to general Scheme P.

Example 33

179

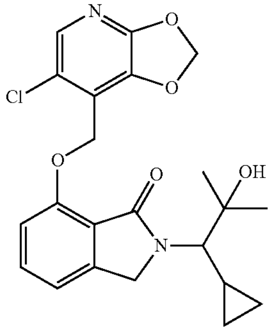

(R or S)-7-((6-chloro-[1,3]dioxolo[4,5-b]pyridin-7-yl)methoxy)-2-(1-cyclopropyl-2-hydroxy-2-methylpropyl)isoindolin-1-one (179)

Step A: (6-chloro-[1,3]dioxolo[4,5-b]pyridin-7-yl) methanol (33-A)

To a solution of 6-chloro-[1,3]dioxolo[4,5-b]pyridine-7-carboxylic acid (I-52, 140 mg, mmol) in THF (3.0 mL) was added borane-tetrahydrofuran complex (0.35 mL, 0.35 mmol) at 0° C. The resulted mixture was stirred for 4 h at room temperature. The reaction mixture was quenched with $CH_3OH$ (2.0 mL), concentrated, and the residue was purified by Prep-HPLC (AQ-C18 Column, 40 g, 60 Å, 40-60 μm, flow rate: 50 mL/min, 0-100% ACN/water gradient) to afford compound 33-A. MS: m/z=188.0 (M+1). $^1$H-NMR (300 MHz, Methanol-$d_4$): δ 7.59 (s, 1H), 6.18 (s, 2H), 4.68 (s, 2H).

Step B: (R or S)-7-((6-chloro-[1,3]dioxolo[4,5-b] pyridin-7-yl)methoxy)-2-(1-cyclopropyl-2-hydroxy-2-methylpropyl)isoindolin-1-one (179)

To a stirred mixture of (R or S)-2-(1-cyclopropyl-2-hydroxy-2-methylpropyl)-7-hydroxyisoindolin-1-one (35 mg, 0.13 mmol) in acetonitrile (2.0 mL) were added 1,1'-(azodicarbonyl)dipiperidine (67 mg, 0.27 mmol), tributylphosphine (81 mg, 0.40 mmol) and (6-chloro-[1,3] dioxolo[4,5-b]pyridin-7-yl)methanol (25 mg, 0.13 mmol) at room temperature under nitrogen atmosphere. The resulting mixture was warmed to ambient temp and stirred for 1 h. The reaction mixture was concentrated, and the residue was purified by Prep-HPLC (C18 OBD Prep Column 100 Å, 10 μm, 19 mm×250 mm; 5.8 min, 60-80% ACN/10 mM aq. $NH_4HCO_3$ gradient) to afford compound 179. MS: m/z=431.2 (M+1). $^1$H-NMR (400 MHz, Chloroform-d): δ 7.68 (s, 1H), 7.49-7.45 (m, 1H), 7.12-7.10 (m, 1H), 7.00-6.98 (m, 1H), 6.12 (s, 2H), 5.45-5.38 (m, 2H), 4.76-4.63 (m, 2H), 3.35 (d, J=10.4 Hz, 1H), 1.43 (s, 3H), 1.39-1.31 (m, 1H), 1.30 (s, 3H), 1.28 (s, 1H), 0.90-0.84 (m, 1H), 0.60-0.48 (m, 2H), 0.22-0.17 (m, 1H).

Compound 180 was synthesized by analogous methods from the disclosed synthetic sequence in Example 33, compound 179. Commercially available reagents were substituted where necessary to produce compound 180.

TABLE 20

| Example Number | Structure | Chemical Name | Observed Mass (M + 1) |
|---|---|---|---|
| 180 | 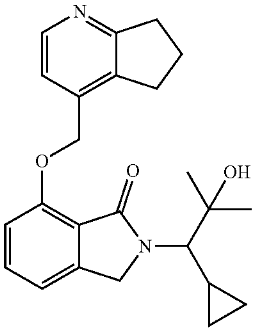 | (R or S)-2-(1-cyclopropyl-2-hydroxy-2-methylpropyl)-7-((6,7-dihydro-5H-cyclopenta[b]pyridin-4-yl)methoxy)isoindolin-1-one | 393.2 |

Example 34

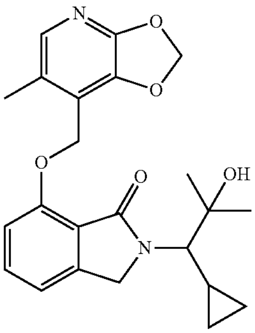

181

(R or S)-2-(1-Cyclopropyl-2-hydroxy-2-methylpropyl)-7-(2-(6-methyl-[1,3]dioxolo[4,5-b]pyridin-7-yl)ethyl)isoindolin-1-one (181)

To a deoxygenated solution of 7-((6-chloro-[1,3]dioxolo[4,5-b]pyridin-7-yl)methoxy)-2-(1-cyclopropyl-2-hydroxy-2-methylpropyl)isoindolin-1-one (179, 25 mg, 0.058 mmol), 2,4,6-trimethyl-1,3,5,2,4,6-trioxatriborinane (11 mg, 0.087 mmol), $K_2CO_3$ (16 mg, 0.12 mmol) and [1,1'-bis(diphenylphosphino)ferrocene]dichloropalladium (II) (4.2 mg, 5.8 μmol) in dioxane (2.0 mL) was stirred for 4 h at 90° C. The reaction mixture was cooled, diluted with water (10 mL), and extracted with ethyl acetate (3×10 mL). The combined organic phase was washed with brine (3×10 mL), dried over $Na_2SO_4$ and concentrated. The residue was purified by prep-HPLC (C18 19×250 mm; 5.8 min, 60-80% ACN/10 mM aq. $NH_4HCO_3$ gradient) to afford compound 181. MS: m/z=411.2 (M+1). $^1$H-NMR (400 MHz, Chloroform-d): δ 7.49-7.45 (m, 2H), 7.08-7.01 (m, 2H), 6.08 (s, 2H), 5.32-5.25 (m, 2H), 4.75-4.61 (m, 1H), 4.63 (d, J=17.9 Hz, 1H), 3.35 (d, J=10.4 Hz, 1H), 2.63 (s, 1H), 2.41 (s, 3H), 1.43 (s, 3H), 1.37-1.31 (m, 1H), 1.29 (s, 3H), 0.88-0.83 (m, 1H), 0.59-0.47 (m, 2H), 0.21-0.17 (m, 1H).

Example 35

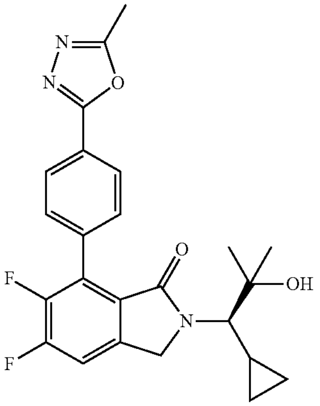

45

(R)-2-(1-cyclopropyl-2-hydroxy-2-methylpropyl)-5,6-difluoro-7-(4-(5-methyl-1,3,4-oxadiazol-2-yl)phenyl)isoindolin-1-one (45)

A mixture of $Cs_2CO_3$ (80 mg, 0.25 mmol), (R)-2-(1-cyclopropyl-2-hydroxy-2-methylpropyl)-5,6-difluoro-7-iodoisoindolin-1-one (I-16, 50 mg, 0.12 mmol), 2-methyl-5-(4-(4,4,5,5-tetramethyl-1,3,2-dioxaborolan-2-yl)phenyl)-1,3,4-oxadiazole (PharmaBlock (USA), Inc., Hatfield, PA, USA, 46 mg, 0.16 mmol) and methanesulfonato (2-dicyclohexylphosphino-2',4',6'-tri-i-propyl-1,1'-biphenyl)(2'- amino-1,1'-biphenyl-2-yl)palladium (II) (10 mg, 0.012 mmol) in 1,4-dioxane (2.0 mL) and water (0.4 mL) was heated at 80° C. for 4 h under argon. The reaction was diluted with water (20 mL) and extracted with ethyl acetate (2×20 mL). The combined organic layers was washed with brine (2×20 mL), dried over $Na_2SO_4$ and concentrated. The residue was purified by prep HPLC (C18, 30-50% ACN/10 mM aq. $NH_4HCO_3$, gradient) to afford compound 45. MS: m/z=440.1 (M+1). $^1$H-NMR (400 MHz, Chloroform-d): δ 8.15-8.13 (m, 2H), 7.65-7.63 (d, J=8.0 Hz, 2H), 7.35-7.29 (m, 1H), 4.84-4.65 (m, 2H), 3.34 (d, J=10.4 Hz, 1H), 2.65 (s, 3H), 1.43 (s, 3H), 1.37-1.27 (m, 1H), 1.24 (s, 3H), 0.90-0.87 (m, 1H), 0.61-0.49 (m, 2H), 0.21-0.14 (m, 1H).

Example 36

182

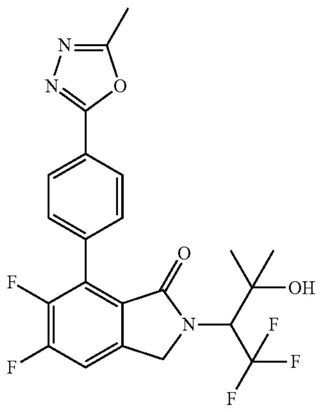

(R or S)-5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one (182)

A mixture of (R or S)-5,6-difluoro-7-iodo-2-(1,1,1-trifluoro-3-hydroxy-3-methylbutan-2-yl)isoindolin-1-one (I-14, 11 mg, 0.024 mmol), 2-methyl-5-(4-(4,4,5,5-tetramethyl-1,3,2-dioxaborolan-2-yl)phenyl)-1,3,4-oxadiazole (PharmaBlock (USA, 8.4 mg, 0.029 mmol), $PdCl_2$ (dppf) (3.6 mg, 5.0 μmol), and 1M aq $K_3PO_4$ (49 μL, 0.049 mmol) in THF (240 μL) was heated at 65° C. for 16 h. The reaction was filtered through a syringe filter (0.45 μm pore size) and the filtrate was purified by preparative HPLC (C18, 35-70% ACN/0.1% $NH_4OH$ in water gradient) to afford compound 182. MS: m/z=467.1 (M+1). $^1$H-NMR (500 MHz, DMSO-$d_6$): δ 8.06 (d, J=8.3 Hz, 2H), 7.90-7.82 (m, 1H), 7.67 (d, J=8.2 Hz, 2H), 5.03 (d, J=18.6 Hz, 1H), 4.69 (m, 1H), 4.54 (d, J=18.6 Hz, 1H), 2.62 (s, 3H), 1.38 (s, 3H), 1.10 (s, 3H).

Example 37

183

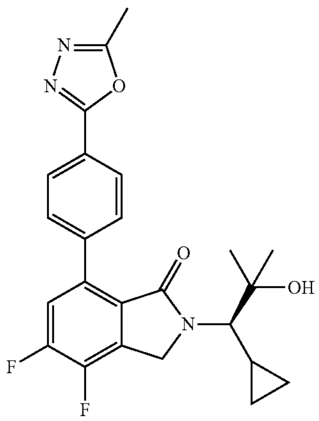

(R)-2-(1-cyclopropyl-2-hydroxy-2-methylpropyl)-4,5-difluoro-7-(4-(5-methyl-1,3,4-oxadiazol-2-yl)phenyl)isoindolin-1-one (183)

A mixture of (R)-2-(1-cyclopropyl-2-hydroxy-2-methylpropyl)-4,5-difluoro-7-iodoisoindolin-1-one (I-75, 35 mg, 0.086 mmol), potassium phosphate tribasic (37 mg, 0.17 mmol), $PdCl_2$ (dppf) (6.3 mg, 8.6 μmol), and 2-methyl-5-(4-(4,4,5,5-tetramethyl-1,3,2-dioxaborolan-2-yl)phenyl)-1,3,4-oxadiazole (PharmaBlock (USA), 30 mg, 0.10 mmol) in 1,4-dioxane (1.0 ml) was heated at 80° C. for 16 h. The cooled reaction mixture was filtered through a Celite® pad, and the filtrate was concentrated. The residue was purified by prep HPLC (C18, 0-30% ACN/10 mM aq. $NH_4HCO_3$, gradient) to afford compound 183. MS: m/z=440.3 (M+1). $^1$H-NMR (300 MHz, Chloroform-d): δ 8.10-8.07 (m, 2H), 7.66-7.61 (m, 2H), 7.29-7.23 (m, 1H), 4.95-4.72 (m, 2H), 3.35 (d, J=10.2, 1H), 2.63 (s, 3H), 1.43-1.24 (m, 4H), 1.20 (s, 3H), 0.91-0.78 (m, 1H), 0.60-0.42 (m, 2H), 0.21-0.11 (m, 1H). $^{19}$F-NMR (282 MHz, Chloroform-d): δ −133.84, −133.92 (m, 1F), −145.27, −145.35 (m, 1F).

UDP-Glo™ Glucosylceramide Synthase Biochemical Assay

A UDP-Glo™ glucosylceramide synthase biochemical assay was utilized to evaluate the effect of test compounds on the activity of endogenous levels of GCS enzyme contained within Golgi preparations isolated from human A375 malignant melanoma skin cells. The UDP-Glo™ glucosylceramide synthase assay uses UDP-Glucose as a nucleotide-glycosyl donor and ceramide as substrate acceptor molecules. In the reaction, glucosylceramide synthase (GCS) transfers glucose from UDP-Glucose to ceramide. Glucosylceramide and UDP are released as products.

Using Promega's UDP-Glo™ Glycosyltransferase assay kit (Promega Corporation, Madison, WI, USA (Promega)), GCS activity was indirectly measured by detecting the amount of UDP produced. An aliquot of GCS enzyme (1.5 μg crude golgi preparation, total protein) and titrated test compound were aliquoted to each well and incubated for 30 minutes at room temperature. Substrate mixture was prepared by mixing $C_6$ ceramide (Avanti Polar Lipids, Alabaster, AL USA (Avanti)) (micelles prepared at 0.6 mM in 0.6 mM DOPC) and UDP-glucose (20 μM; Promega), at concentrations equivalent to 2× Km, in assay buffer (25 mM HEPES (pH 7.5), 50 mM KCl, 5 mM MgCl2). An equivalent volume of substrate mixture was then added to each well. Following a 20 h incubation at room temperature to allow for GCS turnover of substrate, an equal volume of UDP detection reagent (Promega) was added to each well and incubated for an additional 75 minutes at room temperature to simultaneously convert the accumulated UDP product into ATP and generate light in a luciferase reaction. The generated light was detected using a luminometer. Random luminescence values (RLUs) were normalized to mean "min" and "max" effects, as determined on each plate. "Min" was defined as the mean of the values of the wells treated with vehicle (DMSO) and which represent 0% inhibition; "max" was defined as the mean of the values of the wells treated with a reference inhibitor and which represent the 100% effect. Values for % Emax and EC50 were determined by best-fitting the normalized data to a curve in Activity Base along a four-parameter logistic non-linear regression (4PL) model (based on the Levenberg-Marquardt algorithm and defined by the equation below):

$$y = n + \frac{m - n}{1 + \left(\frac{i}{x}\right)^p}$$

where: n is 4 PMin (bottom of the curve); m is 4 PMax (top of the curve); i is IP (inflection point of curve); and p is slope. See Levenberg, K., "A Method for the Solution of Certain Problems in Least Squares", *Quart. Appl. Math.* 2, (1944), pp 164-168 and Marquardt, D., "An Algorithm for Least Squares Estimation on Nonlinear Parameters", *SIAM J. Appl. Math.* 11, (1963) pp 431-441.

$EC_{50}$ values from the aforementioned assay for the compounds of this invention range between 0.02 nM to 5000 nM. $EC_{50}$ values for particular embodiments of this invention are provided in Table 21 below.

TABLE 21

| Compound | GCS $EC_{50}$ (nM) |
|---|---|
| 1 | 7.9 |
| 2 | 2.6 |
| 3 | 2.0 |
| 4 | 290 |
| 5 | 52 |
| 6 | 4.5 |
| 7 | 3.6 |
| 8 | 7.5 |
| 9 | 24 |
| 10 | 2.8 |
| 11 | 4.9 |
| 12 | 13 |
| 13 | 260 |
| 14 | 48 |
| 15 | 6.4 |
| 16 | 39 |
| 17 | 580 |
| 18 | 45 |
| 19 | 28 |
| 20 | 67 |
| 21 | 0.91 |
| 22 | 6.9 |
| 23 | 0.41 |
| 24 | 0.93 |
| 25 | 9.2 |
| 26 | 1.0 |
| 27 | 1.4 |

TABLE 21-continued

| Compound | GCS $EC_{50}$ (nM) |
|---|---|
| 28 | 540 |
| 29 | 200 |
| 30 | 95 |
| 31 | 180 |
| 32 | 57 |
| 33 | 350 |
| 34 | 48 |
| 35 | 6.8 |
| 36 | 14 |
| 37 | 0.24 |
| 38 | 0.55 |
| 39 | 0.80 |
| 40 | 0.98 |
| 41 | 0.25 |
| 42 | 72 |
| 43 | 24 |
| 44 | 18 |
| 45 | 0.68 |
| 46 | 140 |
| 47 | 380 |
| 48 | 81 |
| 49 | 92 |
| 50 | 630 |
| 51 | 5.9 |
| 52 | 160 |
| 53 | 48 |
| 54 | 97 |
| 55 | 0.18 |
| 56 | 0.43 |
| 57 | 260 |
| 58 | 28 |
| 59 | 9.9 |
| 60 | 9.4 |
| 61 | 8.9 |
| 62 | 53 |
| 63 | 44 |
| 64 | 180 |
| 65 | 150 |
| 66 | 500 |
| 67 | 12 |
| 68 | 3.5 |
| 69 | 110 |
| 70 | 0.81 |
| 71 | 0.84 |
| 72 | 0.59 |
| 73 | 55 |
| 74 | 40 |
| 75 | 8.8 |
| 76 | 26 |
| 77 | 39 |
| 78 | 59 |
| 79 | 2.1 |
| 80 | 0.39 |
| 81 | 31 |
| 82 | 46 |
| 83 | 100 |
| 84 | 4.8 |
| 85 | 8.2 |
| 86 | 0.58 |
| 87 | 9.5 |
| 88 | 90 |
| 89 | 420 |
| 90 | 2.0 |
| 91 | 520 |
| 92 | 33 |
| 93 | 55 |
| 94 | 24 |
| 95 | 83 |
| 96 | 1.4 |
| 97 | 12 |
| 98 | 43 |
| 99 | 140 |
| 100 | 150 |
| 101 | 160 |
| 102 | 260 |
| 103 | 450 |
| 104 | 590 |

TABLE 21-continued

| Compound | GCS $EC_{50}$ (nM) |
|---|---|
| 105 | 650 |
| 106 | 720 |
| 107 | 550 |
| 108 | 270 |
| 109 | 2 |
| 110 | 0.21 |
| 111 | 0.26 |
| 112 | 0.41 |
| 113 | 1.2 |
| 114 | 1.3 |
| 115 | 1.5 |
| 116 | 3.1 |
| 117 | 5.2 |
| 118 | 5.7 |
| 119 | 7.2 |
| 120 | 10 |
| 121 | 15 |
| 122 | 18 |
| 123 | 26 |
| 124 | 26 |
| 125 | 30 |
| 126 | 35 |
| 127 | 38 |
| 128 | 38 |
| 129 | 38 |
| 130 | 40 |
| 131 | 45 |
| 132 | 46 |
| 133 | 49 |
| 134 | 59 |
| 135 | 64 |
| 136 | 80 |
| 137 | 77 |
| 138 | 88 |
| 139 | 120 |
| 140 | 120 |
| 141 | 140 |
| 142 | 140 |
| 143 | 180 |
| 144 | 190 |
| 145 | 260 |
| 146 | 390 |
| 147 | 560 |
| 148 | 500 |
| 149 | 900 |
| 150 | 740 |
| 151 | 61 |
| 152 | 96 |
| 153 | 29 |
| 154 | 0.1 |
| 155 | 0.19 |
| 156 | 0.97 |
| 157 | 0.49 |
| 158 | 1 |
| 159 | 2.5 |
| 160 | 5.9 |
| 161 | 9.1 |
| 162 | 23 |
| 163 | 61 |
| 164 | 77 |
| 165 | 200 |
| 166 | 360 |
| 167 | 2.1 |
| 168 | 0.3 |
| 169 | 0.4 |
| 170 | 130 |
| 171 | 230 |
| 172 | 9.7 |
| 173 | 120 |
| 174 | 6.8 |
| 175 | 27 |
| 176 | 14 |
| 177 | 28 |
| 178 | 21 |
| 179 | 16 |
| 180 | 35 |
| 181 | 54 |
| 182 | 8.7 |
| 183 | 8.4 |

What is claimed is:

1. A compound of the formula I:

I

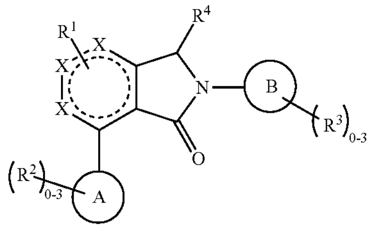

or a pharmaceutically acceptable salt thereof, wherein $R^1$ is hydrogen, C1-C4 alkyl, C1-C4 fluoroalkyl, hydroxy, —C1-C4alkylOH, or halo;

Each X is independently —$CR^a$—, or N;

$R^a$ is hydrogen, C1-C4 alkyl, C1-C4 fluoroalkyl, hydroxy, or halo;

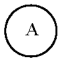

is phenyl, 2,3-dihydro-1H-benzo[d]imidazolyl, benzo[d][1,3]dioxolyl, 1,2,3,4-tetrahydroisoquinolinyl, quinoxalinyl, phenylcarbonylamino, isoindolinyl, (benzo[d][1,3]dioxolyl)carbonylamino, quinuclidinyloxycarbonylamino, pyridylcarbonylamino, quinolinylcarbonylamino, (2,3-dihydro-1H-cyclopenta[b]quinolinyl)carbonylamino, (2,3-dihydrofuro[2,3-b]pyridinyl)carbonylamino, (dihydrobenzofuranyl)carbonylamino, (indolyl)carbonylamino, (indazolyl)carbonylamino, (2,3-dihydrobenzofuranyl)cabonylamino, (1H-pyrrolo[2,3-b]pyridinyl)carbonylamino, (2,3-dihydro[1,4]dioxino[2,3-b]pyridinyl)carbonylamino, (2,3-dihydro-1H-indenyl)carbonylamino, (6,7-dihydro-5H-cyclopenta[b]pyridyl)ethenyl, (6,7-dihydro-5H-cyclopenta[b]pyridyl)carbonylamino, (benzo[d]thiazolyl)carbonylamino, (6,7-dihydro-5H-cyclopenta[b]pyridyl)ethenyl, (6,7-dihydro-5H-cyclopenta[b]pyridyl)ethyl, (6,7-dihydro-5H-cyclopenta[b]pyridyl)oxymethyl, (6,7-dihydro-5H-cyclopenta[b]pyridyl)methoxy, (6,7-dihydro-5H-cyclopenta[b]pyridyl)ethynyl, phenylethenyl, ([1,3]dioxolo[4,5-b]pyridyl)ethenyl, ([1,3]dioxolo[4,5-b]pyridyl)ethyl, ([1,3]dioxolo[4,5-b]pyridyl)carbonylamino, ([1,3]dioxolo[4,5-b]pyridyl)oxymethyl, ([1,3]dioxolo[4,5-b]pyridyl)methoxy, ([1,3]dioxolo[4,5-b]pyridyl)aminomethyl, (pyrazolo[1,5-a]pyridyl)carbonylamino, (pyrazolo[4,3-b]pyridyl)carbonylamino, or naphthyridinylcarbonylamino;

each $R^2$ is independently selected from fluoro, chloro, bromo, cyano, trifluromethyl, 2,2,2-trifluroethyl, methoxy, ethoxy, propoxy, hydroxy, methyl, ethyl, propyl, isopropyl, butyl, oxo, phenyl, azaindolyl, benzoimidazolyl, benzisoxazolyl, benzofuranyl, benzofurazanyl, benzopyrazolyl, benzotriazolyl, benzothiophenyl, benzothiazolyl, benzo[d]isothiazole, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyrrolyl, pyrazolopyrimidinyl, pyridazinyl, pyridyl, pyrimidyl, pyrimidinyl, pyrrolyl, quinazolinyl, quinolyl, quinoxalinyl, tetrazolyl, tetrazolopyridyl, thiadiazolyl, 5H-pyrrolo[3,4-b]pyridine, thiazolyl, thienyl, triazolyl, triazinyl, benzothiazolyl, benzothienyl, quinolinyl, quinazolinyl, isoquinolinyl, and oxazolyl, —(C0-C4 alkyl)O(C1-C4 fluoroalkyl), wherein each $R^2$ is substituted with 0, 1, or 2 $R^5$ substituents, each $R^5$ is independently C1-C6alkyl, halo, hydroxy, or —(C1-C4 alkyl)OH;

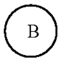

is 2-hydroxy-2-methylpropyl, 1-methyl-2-hydroxy-2-methylpropyl, cyclopentylethyl, 1-ethyl-2-hydroxy-2-methylpropyl, 2-hydroxyethyl, oxetanylmethyl, quinuclidinylethyl, cyclopropyl-2-methylpropyl, cyclopropylmethyl, methylisobutyl, cyclobutylmethyl, 1-cyclopropylethyl, cyclohexyl, phenyl, isobutyl, or oxetanylmethyl;

each $R^3$ is independently selected from trifluoromethyl, methyl, ethyl, hydroxy, methoxy, 2-hydroxy-propyl, hydroxymethyl, cyclopropyl, methoxymethyl and fluoro; and $R^4$ is hydrogen, C1-C4 alkyl, or hydroxy.

2. The compound of claim 1 or a pharmaceutically acceptable salt thereof, wherein $R^1$ is hydrogen, C1-C4 alkyl, C1-C4 fluoroalkyl, C1-C4 alkoxy, hydroxy, or halo.

3. The compound of claim 1 or a pharmaceutically acceptable salt thereof, wherein $R^1$ is methyl, ethyl, propyl, isopropyl, trifluoromethyl, —OH, fluoro, chloro, or bromo.

4. The compound of claim 1 or a pharmaceutically acceptable salt thereof, wherein each $R^2$ independently is selected from fluoro, chloro, bromo, cyano, trifluromethyl, methoxy, ethoxy, 2,2,2-trifluoroethoxy, trifluoroethoxy, hydroxy, methyl, oxo, isothiazolyl, isoxazolyl, oxadiazolyl, oxazolyl, pyrazolyl, pyridazinyl, pyridyl, triazolyl, and oxazolyl, wherein each $R^2$ is substituted with 0, 1, or 2 $R^5$ substituents.

5. The compound of claim 4 or a pharmaceutically acceptable salt thereof, wherein $R^5$ independently is selected from methyl, ethyl, propyl, isopropyl, butyl, hydroxymethyl, hydroxyethyl, hydroxypropyl, methoxy, ethoxy, and propoxy.

6. The compound of claim 1 or a pharmaceutically acceptable salt thereof, wherein at least one X is N.

7. The compound of claim 1 or a pharmaceutically acceptable salt thereof, wherein each X is —$CR^a$—.

8. The compound of claim 1 or a pharmaceutically acceptable salt thereof, wherein $R^a$ is hydrogen, methyl, hydroxy, F, or Cl.

9. A compound of claim 1, or a pharmaceutically acceptable salt thereof, selected from:

(R)-2-(1-Cyclopropyl-2-hydroxy-2-methylpropyl)-7-(4-(5-methyl-1,3,4-oxadiazol-2-yl)phenyl)isoindolin-1-one;

2-(1-Cyclopropyl-2-hydroxy-2-methylpropyl)-7-(4-(5-methyl-1,3,4-oxadiazol-2-yl)phenyl)isoindolin-1-one;

(R)-2-(1-Cyclopropyl-2-hydroxy-2-methylpropyl)-6-fluoro-7-(4-(5-methyl-1,3,4-oxadiazol-2-yl)phenyl) isoindolin-1-one;

(S)-2-(1-Cyclopropyl-2-hydroxy-2-methylpropyl)-6-fluoro-7-(4-(5-methyl-1,3,4-oxadiazol-2-yl)phenyl) isoindolin-1-one;

2-(1-Cyclopropyl-2-hydroxy-2-methylpropyl)-6-fluoro-7-(4-(5-methyl-1,3,4-oxadiazol-2-yl)phenyl)isoindolin-1-one;

2-(1-Cyclopropyl-2-hydroxy-2-methylpropyl)-5-fluoro-7-(4-(5-methyl-1,3,4-oxadiazol-2-yl)phenyl)isoindolin-1-one;

(R)-2-(1-Cyclopropyl-2-hydroxy-2-methylpropyl)-5-fluoro-7-(4-(5-methyl-1,3,4-oxadiazol-2-yl)phenyl) isoindolin-1-one;

2-(1-cyclopropyl-2-hydroxy-2-methylpropyl)-7-(2,4-difluorostyryl)isoindolin-1-one;

(R)-(E)-2-(1-cyclopropyl-2-hydroxy-2-methylpropyl)-7-(2,4-difluorostyryl)isoindolin-1-one;

(S)-(E)-2-(1-cyclopropyl-2-hydroxy-2-methylpropyl)-7-(2,4-difluorostyryl)isoindolin-1-one;

7-(4-(1,3,4-oxadiazol-2-yl)phenyl)-2-(1-cyclopropyl-2-hydroxy-2-methylpropyl)isoindolin-1-one;

(R)-7-(4-(1,3,4-oxadiazol-2-yl)phenyl)-2-(1-cyclopropyl-2-hydroxy-2-methylpropyl)isoindolin-1-one;

(R)-5-(2-(1-cyclopropyl-2-hydroxy-2-methylpropyl)-3-oxoisoindolin-4-yl)-1,3-dimethyl-1,3-dihydro-2H-benzo[d]imidazol-2-one;

5-(2-(1-cyclopropyl-2-hydroxy-2-methylpropyl)-3-oxoisoindolin-4-yl)-1,3-dimethyl-1,3-dihydro-2H-benzo[d] imidazol-2-one;

(R)-2-(1-cyclopropyl-2-hydroxy-2-methylpropyl)-7-(2-(2,2,2-trifluoroethoxy)phenyl)isoindolin-1-one;

2-(1-cyclopropyl-2-hydroxy-2-methylpropyl)-7-(2-(2,2,2-trifluoroethoxy)phenyl)isoindolin-1-one;

3-(2-(1-cyclopropyl-2-hydroxy-2-methylpropyl)-3-oxoisoindolin-4-yl)-5-methoxybenzonitrile;

(R)-3-(2-(1-cyclopropyl-2-hydroxy-2-methylpropyl)-3-oxoisoindolin-4-yl)-5-methoxybenzonitrile;

2-(1-cyclopropyl-2-hydroxy-2-methylpropyl)-7-(3-fluoro-4-(5-methyl-1,3,4-oxadiazol-2-yl)phenyl)isoindolin-1-one;

(R)-2-(1-cyclopropyl-2-hydroxy-2-methylpropyl)-7-(3-fluoro-4-(5-methyl-1,3,4-oxadiazol-2-yl)phenyl)isoindolin-1-one;

7-(3-chloro-5-methoxyphenyl)-2-(1-cyclopropyl-2-hydroxy-2-methylpropyl)isoindolin-1-one;

(R)-7-(3-chloro-5-methoxyphenyl)-2-(1-cyclopropyl-2-hydroxy-2-methylpropyl)isoindolin-1-one;

(R)-2-(1-cyclopropyl-2-hydroxy-2-methylpropyl)-7-(6-fluoro-3-methyl-1H-indazol-5-yl)isoindolin-1-one;

2-(1-cyclopropyl-2-hydroxy-2-methylpropyl)-7-(6-fluoro-3-methyl-1H-indazol-5-yl)isoindolin-1-one;

(R)-2-(1-cyclopropyl-2-hydroxy-2-methylpropyl)-7-(1-methyl-1H-indazol-5-yl)isoindolin-1-one;

2-(1-cyclopropyl-2-hydroxy-2-methylpropyl)-7-(1-methyl-1H-indazol-5-yl)isoindolin-1-one;

(R)-2-(1-cyclopropyl-2-hydroxy-2-methylpropyl)-7-(3-(5-methyl-1,3,4-oxadiazol-2-yl)phenyl)isoindolin-1-one;

2-(1-cyclopropyl-2-hydroxy-2-methylpropyl)-7-(3-(5-methyl-1,3,4-oxadiazol-2-yl)phenyl)isoindolin-1-one;

(R)-2-(1-cyclopropyl-2-hydroxy-2-methylpropyl)-7-(3-(2,2,2-trifluoroethoxy)phenyl)isoindolin-1-one;

2-(1-cyclopropyl-2-hydroxy-2-methylpropyl)-7-(3-(2,2,2-trifluoroethoxy)phenyl)isoindolin-1-one;

(R)-2-(1-cyclopropyl-2-hydroxy-2-methylpropyl)-7-(4-(1-methyl-1H-pyrazol-4-yl)phenyl)isoindolin-1-one;

2-(1-cyclopropyl-2-hydroxy-2-methylpropyl)-7-(4-(1-methyl-1H-pyrazol-4-yl)phenyl)isoindolin-1-one;

(R)-2-(1-cyclopropyl-2-hydroxy-2-methylpropyl)-7-(2,2-difluorobenzo[d][1,3]dioxol-4-yl)isoindolin-1-one;
2-(1-cyclopropyl-2-hydroxy-2-methylpropyl)-7-(2,2-difluorobenzo[d][1,3]dioxol-4-yl)isoindolin-1-one;
(R)-7-(4-(2H-1,2,3-triazol-2-yl)phenyl)-2-(1-cyclopropyl-2-hydroxy-2-methylpropyl)isoindolin-1-one;
7-(4-(2H-1,2,3-triazol-2-yl)phenyl)-2-(1-cyclopropyl-2-hydroxy-2-methylpropyl)isoindolin-1-one;
(R)-2-(1-cyclopropyl-2-hydroxy-2-methylpropyl)-7-(4-(6-methylpyridazin-3-yl)phenyl)isoindolin-1-one;
2-(1-cyclopropyl-2-hydroxy-2-methylpropyl)-7-(4-(6-methylpyridazin-3-yl)phenyl)isoindolin-1-one;
(S)-2-(1-cyclopropyl-2-hydroxy-2-methylpropyl)-7-(4-(6-methylpyridazin-3-yl)phenyl)isoindolin-1-one;
2-(1-cyclopropyl-2-hydroxy-2-methylpropyl)-7-(4-(6-methylpyridazin-3-yl)phenyl)isoindolin-1-one;
(R)-2-(1-cyclopropyl-2-hydroxy-2-methylpropyl)-7-(3,4-dimethoxyphenyl)isoindolin-1-one;
(S)-2-(1-cyclopropyl-2-hydroxy-2-methylpropyl)-7-(3,4-dimethoxyphenyl)isoindolin-1-one;
2-(1-cyclopropyl-2-hydroxy-2-methylpropyl)-7-(3,4-dimethoxyphenyl)isoindolin-1-one;
(R)-2-(1-cyclopropyl-2-hydroxy-2-methylpropyl)-7-(2,6-dimethylpyridin-4-yl)isoindolin-1-one;
(S)-2-(1-cyclopropyl-2-hydroxy-2-methylpropyl)-7-(2,6-dimethylpyridin-4-yl)isoindolin-1-one;
2-(1-cyclopropyl-2-hydroxy-2-methylpropyl)-7-(2,6-dimethylpyridin-4-yl)isoindolin-1-one;
2-((R)-1-cyclopropyl-2-hydroxy-2-methylpropyl)-6-fluoro-7-(2-(2,2,2-trifluoroethoxy)phenyl)isoindolin-1-one;
2-((S)-1-cyclopropyl-2-hydroxy-2-methylpropyl)-6-fluoro-7-(2-(2,2,2-trifluoroethoxy)phenyl)isoindolin-1-one;
2-(1-cyclopropyl-2-hydroxy-2-methylpropyl)-6-fluoro-7-(2-(2,2,2-trifluoroethoxy)phenyl)isoindolin-1-one;
(R)-2-(1-cyclopropyl-2-hydroxy-2-methylpropyl)-6-fluoro-7-(3-fluoro-4-(5-methyl-1,3,4-oxadiazol-2-yl)phenyl)isoindolin-1-one;
2-(1-cyclopropyl-2-hydroxy-2-methylpropyl)-6-fluoro-7-(3-fluoro-4-(5-methyl-1,3,4-oxadiazol-2-yl)phenyl)isoindolin-1-one;
(R)-2-(1-cyclopropyl-2-hydroxy-2-methylpropyl)-5-fluoro-7-(2-(2,2,2-trifluoroethoxy)phenyl)isoindolin-1-one;
(S)-2-(1-cyclopropyl-2-hydroxy-2-methylpropyl)-5-fluoro-7-(2-(2,2,2-trifluoroethoxy)phenyl)isoindolin-1-one;
2-(1-cyclopropyl-2-hydroxy-2-methylpropyl)-5-fluoro-7-(2-(2,2,2-trifluoroethoxy)phenyl)isoindolin-1-one;
(R)-2-(1-cyclopropyl-2-hydroxy-2-methylpropyl)-5-fluoro-7-(4-(1-methyl-1H-pyrazol-4-yl)phenyl)isoindolin-1-one;
2-(1-cyclopropyl-2-hydroxy-2-methylpropyl)-5-fluoro-7-(4-(1-methyl-1H-pyrazol-4-yl)phenyl)isoindolin-1-one;
(R)-2-(1-cyclopropyl-2-hydroxy-2-methylpropyl)-6-fluoro-2'-methyl-[4,5'-biisoindoline]-1',3-dione;
2-(1-cyclopropyl-2-hydroxy-2-methylpropyl)-6-fluoro-2'-methyl-[4,5'-biisoindoline]-1',3-dione;
(R)-2-(1-cyclopropyl-2-hydroxy-2-methylpropyl)-5-fluoro-7-(4-(3-methylisoxazol-5-yl)phenyl)isoindolin-1-one;
2-(1-cyclopropyl-2-hydroxy-2-methylpropyl)-5-fluoro-7-(4-(3-methylisoxazol-5-yl)phenyl)isoindolin-1-one;
(R)-2-(1-cyclopropyl-2-hydroxy-2-methylpropyl)-5-fluoro-7-(2-fluoro-4-(5-methyl-1,3,4-oxadiazol-2-yl)phenyl)isoindolin-1-one;
2-(1-cyclopropyl-2-hydroxy-2-methylpropyl)-5-fluoro-7-(2-fluoro-4-(5-methyl-1,3,4-oxadiazol-2-yl)phenyl)isoindolin-1-one;
(R)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one;
(S)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one;
(R)-2-(1-cyclopropyl-2-hydroxy-2-methylpropyl)-4-(4-(5-methyl-1,3,4-oxadiazol-2-yl)phenyl)-1,2-dihydro-3H-pyrrolo[3,4-c]pyridin-3-one;
(R)-2-(1-cyclopropyl-2-hydroxy-2-methylpropyl)-4-(4-(1-methyl-1H-pyrazol-4-yl)phenyl)-1,2-dihydro-3H-pyrrolo[3,4-c]pyridin-3-one;
2-(1-cyclopropyl-2-hydroxy-2-methylpropyl)-4-(4-(1-methyl-1H-pyrazol-4-yl)phenyl)-1,2-dihydro-3H-pyrrolo[3,4-c]pyridin-3-one;
(R)-3-(2-(1-cyclopropyl-2-hydroxy-2-methylpropyl)-3-oxo-2,3-dihydro-1H-pyrrolo[3,4-c]pyridin-4-yl)-5-methoxybenzonitrile;
(S)-3-(2-(1-cyclopropyl-2-hydroxy-2-methylpropyl)-3-oxo-2,3-dihydro-1H-pyrrolo[3,4-c]pyridin-4-yl)-5-methoxybenzonitrile;
3-(2-(1-cyclopropyl-2-hydroxy-2-methylpropyl)-3-oxo-2,3-dihydro-1H-pyrrolo[3,4-c]pyridin-4-yl)-5-methoxybenzonitrile;
(R)-2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one;
(S)-2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one;
2-(1-cyclopropyl-2-hydroxy-2-methylpropyl)-7-(4-(5-methyl-1,3,4-oxadiazol-2-yl)phenyl)-2,3-dihydro-1H-pyrrolo[3,4-c]pyridin-1-one;
(R)-2-(1-cyclopropyl-2-hydroxy-2-methylpropyl)-7-(4-(1-methyl-1H-pyrazol-4-yl)phenyl)-2,3-dihydro-1H-pyrrolo[3,4-c]pyridin-1-one;
2-(1-cyclopropyl-2-hydroxy-2-methylpropyl)-7-(4-(1-methyl-1H-pyrazol-4-yl)phenyl)-2,3-dihydro-1H-pyrrolo[3,4-c]pyridin-1-one;
(R)-6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one;
(S)-6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one;
6-(1-cyclopropyl-2-hydroxy-2-methylpropyl)-4-(4-(5-methyl-1,3,4-oxadiazol-2-yl)phenyl)-6,7-dihydro-5H-pyrrolo[3,4-b]pyridin-5-one;
(R)-6-(1-cyclopropyl-2-hydroxy-2-methylpropyl)-4-(4-(1-methyl-1H-pyrazol-4-yl)phenyl)-6,7-dihydro-5H-pyrrolo[3,4-b]pyridin-5-one;
6-(1-cyclopropyl-2-hydroxy-2-methylpropyl)-4-(4-(1-methyl-1H-pyrazol-4-yl)phenyl)-6,7-dihydro-5H-pyrrolo[3,4-b]pyridin-5-one;
(R)-6-(1-cyclopropyl-2-hydroxy-2-methylpropyl)-4-(2-fluoro-5-methyl-4-(1-methyl-1H-pyrazol-4-yl)phenyl)-6,7-dihydro-5H-pyrrolo[3,4-b]pyridin-5-one;
6-(1-cyclopropyl-2-hydroxy-2-methylpropyl)-4-(2-fluoro-5-methyl-4-(1-methyl-1H-pyrazol-4-yl)phenyl)-6,7-dihydro-5H-pyrrolo[3,4-b]pyridin-5-one;

(R)-2-(1-cyclopropyl-2-hydroxy-2-methylpropyl)-4-fluoro-7-(4-(5-methyl-1,3,4-oxadiazol-2-yl)phenyl)isoindolin-1-one;
2-(1-cyclopropyl-2-hydroxy-2-methylpropyl)-4-fluoro-7-(4-(5-methyl-1,3,4-oxadiazol-2-yl)phenyl)isoindolin-1-one;
(R)-4-chloro-2-(1-cyclopropyl-2-hydroxy-2-methylpropyl)-7-(4-(1-methyl-1H-pyrazol-4-yl)phenyl)isoindolin-1-one;
4-chloro-2-(1-cyclopropyl-2-hydroxy-2-methylpropyl)-7-(4-(1-methyl-1H-pyrazol-4-yl)phenyl)isoindolin-1-one;
(R)-4-chloro-2-(1-cyclopropyl-2-hydroxy-2-methylpropyl)-7-(4-(5-methyl-1,3,4-oxadiazol-2-yl)phenyl)isoindolin-1-one;
4-chloro-2-(1-cyclopropyl-2-hydroxy-2-methylpropyl)-7-(4-(5-methyl-1,3,4-oxadiazol-2-yl)phenyl)isoindolin-1-one;
(R)-5-chloro-2-(1-cyclopropyl-2-hydroxy-2-methylpropyl)-7-(4-(5-methyl-1,3,4-oxadiazol-2-yl)phenyl)isoindolin-1-one;
(S)-5-chloro-2-(1-cyclopropyl-2-hydroxy-2-methylpropyl)-7-(4-(5-methyl-1,3,4-oxadiazol-2-yl)phenyl)isoindolin-1-one;
5-chloro-2-(1-cyclopropyl-2-hydroxy-2-methylpropyl)-7-(4-(5-methyl-1,3,4-oxadiazol-2-yl)phenyl)isoindolin-1-one;
(R)-6-chloro-2-(1-cyclopropyl-2-hydroxy-2-methylpropyl)-7-(4-(5-methyl-1,3,4-oxadiazol-2-yl)phenyl)isoindolin-1-one;
6-chloro-2-(1-cyclopropyl-2-hydroxy-2-methylpropyl)-7-(4-(5-methyl-1,3,4-oxadiazol-2-yl)phenyl)isoindolin-1-one;
(R)-4-chloro-2-(1-cyclopropyl-2-hydroxy-2-methylpropyl)-6-fluoro-7-(4-(5-methyl-1,3,4-oxadiazol-2-yl)phenyl)isoindolin-1-one;
4-chloro-2-(1-cyclopropyl-2-hydroxy-2-methylpropyl)-6-fluoro-7-(4-(5-methyl-1,3,4-oxadiazol-2-yl)phenyl)isoindolin-1-one;
(R)-7-(4-(5-methyl-1,3,4-oxadiazol-2-yl)phenyl)-2-(1,1,1-trifluoro-3-hydroxy-3-methylbutan-2-yl)isoindolin-1-one;
(S)-7-(4-(5-methyl-1,3,4-oxadiazol-2-yl)phenyl)-2-(1,1,1-trifluoro-3-hydroxy-3-methylbutan-2-yl)isoindolin-1-one;
7-(4-(5-methyl-1,3,4-oxadiazol-2-yl)phenyl)-2-(1,1,1-trifluoro-3-hydroxy-3-methylbutan-2-yl)isoindolin-1-one;
(R)-7-(4-(1-methyl-1H-pyrazol-4-yl)phenyl)-2-(1,1,1-trifluoro-3-hydroxy-3-methylbutan-2-yl)isoindolin-1-one;
(S)-7-(4-(1-methyl-1H-pyrazol-4-yl)phenyl)-2-(1,1,1-trifluoro-3-hydroxy-3-methylbutan-2-yl)isoindolin-1-one;
7-(4-(1-methyl-1H-pyrazol-4-yl)phenyl)-2-(1,1,1-trifluoro-3-hydroxy-3-methylbutan-2-yl)isoindolin-1-one;
(R)-6-fluoro-7-(4-(5-methyl-1,3,4-oxadiazol-2-yl)phenyl)-2-(1,1,1-trifluoro-3-hydroxy-3-methylbutan-2-yl)isoindolin-1-one;
(S)-6-fluoro-7-(4-(5-methyl-1,3,4-oxadiazol-2-yl)phenyl)-2-(1,1,1-trifluoro-3-hydroxy-3-methylbutan-2-yl)isoindolin-1-one;
6-fluoro-7-(4-(5-methyl-1,3,4-oxadiazol-2-yl)phenyl)-2-(1,1,1-trifluoro-3-hydroxy-3-methylbutan-2-yl)isoindolin-1-one;
(R)-2-(1-cyclopropyl-2-hydroxy-2-methylpropyl)-5,6-difluoro-7-(4-(5-methyl-1,3,4-oxadiazol-2-yl)phenyl)isoindolin-1-one;
2-(1-cyclopropyl-2-hydroxy-2-methylpropyl)-5,6-difluoro-7-(4-(5-methyl-1,3,4-oxadiazol-2-yl)phenyl)isoindolin-1-one;
(R)-2-(3-hydroxy-3-methylbutan-2-yl)-7-(2-(2,2,2-trifluoroethoxy)phenyl)isoindolin-1-one;
2-(3-hydroxy-3-methylbutan-2-yl)-7-(2-(2,2,2-trifluoroethoxy)phenyl)isoindolin-1-one;
(cis)-2-(2-(3-hydroxycyclopentyl)ethyl)-7-(2-(2,2,2-trifluoroethoxy)phenyl)isoindolin-1-one;
(trans)-2-(2-(3-hydroxycyclopentyl)ethyl)-7-(2-(2,2,2-trifluoroethoxy)phenyl)isoindolin-1-one;
2-(2-(3-hydroxycyclopentyl)ethyl)-7-(2-(2,2,2-trifluoroethoxy)phenyl)isoindolin-1-one;
2-[(1R)-1-ethyl-2-hydroxy-2-methyl-propyl]-7-[4-(5-methyl-1,3,4-oxadiazol-2-yl)phenyl]isoindolin-1-one;
2-[(1-ethyl-2-hydroxy-2-methyl-propyl]-7-[4-(5-methyl-1,3,4-oxadiazol-2-yl)phenyl]isoindolin-1-one;
(R)-2-(1-cyclopropyl-2-hydroxyethyl)-7-(2-(2,2,2-trifluoroethoxy)phenyl)isoindolin-1-one;
2-(1-cyclopropyl-2-hydroxyethyl)-7-(2-(2,2,2-trifluoroethoxy)phenyl)isoindolin-1-one;
(R)-2-(1-cyclopropyl-2-hydroxyethyl)-7-(4-(5-methyl-1,3,4-oxadiazol-2-yl)phenyl)isoindolin-1-one;
2-(1-cyclopropyl-2-hydroxyethyl)-7-(4-(5-methyl-1,3,4-oxadiazol-2-yl)phenyl)isoindolin-1-one;
(R)-2-(cyclopropyl(3-hydroxyoxetan-3-yl)methyl)-7-(4-(5-methyl-1,3,4-oxadiazol-2-yl)phenyl)isoindolin-1-one;
(S)-2-(cyclopropyl(3-hydroxyoxetan-3-yl)methyl)-7-(4-(5-methyl-1,3,4-oxadiazol-2-yl)phenyl)isoindolin-1-one;
2-(cyclopropyl(3-hydroxyoxetan-3-yl)methyl)-7-(4-(5-methyl-1,3,4-oxadiazol-2-yl)phenyl)isoindolin-1-one;
(R)-7-(4-fluorophenyl)-2-(2-(quinuclidin-3-yl)ethyl)isoindolin-1-one;
(S)-7-(4-fluorophenyl)-2-(2-(quinuclidin-3-yl)ethyl)isoindolin-1-one;
7-(4-fluorophenyl)-2-(2-(quinuclidin-3-yl)ethyl)isoindolin-1-one;
(R)-2-(2-(quinuclidin-3-yl)ethyl)-7-(1,3,5-trimethyl-1H-pyrazol-4-yl)isoindolin-1-one;
(S)-2-(2-(quinuclidin-3-yl)ethyl)-7-(1,3,5-trimethyl-1H-pyrazol-4-yl)isoindolin-1-one;
2-(2-(quinuclidin-3-yl)ethyl)-7-(1,3,5-trimethyl-1H-pyrazol-4-yl)isoindolin-1-one;
(R)-7-(2-methylpyridin-4-yl)-2-(2-(quinuclidin-3-yl)ethyl)isoindolin-1-one;
(S)-7-(2-methylpyridin-4-yl)-2-(2-(quinuclidin-3-yl)ethyl)isoindolin-1-one;
7-(2-methylpyridin-4-yl)-2-(2-(quinuclidin-3-yl)ethyl)isoindolin-1-one;
(R)-2-(1-cyclopropyl-2-hydroxy-2-methylpropyl)-7-(1,3-dimethyl-1H-indazol-5-yl)-6-fluoroisoindolin-1-one;
2-(1-cyclopropyl-2-hydroxy-2-methylpropyl)-7-(1,3-dimethyl-1H-indazol-5-yl)-6-fluoroisoindolin-1-one;
2-(1-cyclopropyl-2-hydroxy-2-methylpropyl)-7-(1,3-dimethyl-1H-indazol-5-yl)-4-fluoroisoindolin-1-one;
(R)-2-(1-cyclopropyl-2-hydroxy-2-methylpropyl)-7-(1,3-dimethyl-1H-indazol-5-yl)-4-fluoroisoindolin-1-one;
2-(1-cyclopropyl-2-methoxy-2-methylpropyl)-7-(4-(5-methyl-1,3,4-oxadiazol-2-yl)phenyl)isoindolin-1-one;
(R)-2-(1-cyclopropyl-2-methoxy-2-methylpropyl)-7-(4-(5-methyl-1,3,4-oxadiazol-2-yl)phenyl)isoindolin-1-one;

2-(1-cyclopropyl-2-hydroxy-2-methylpropyl)-4-hydroxy-7-(4-(5-methyl-1,3,4-oxadiazol-2-yl)phenyl)isoindolin-1-one;

(R)-2-(1-cyclopropyl-2-hydroxy-2-methylpropyl)-4-hydroxy-7-(4-(5-methyl-1,3,4-oxadiazol-2-yl)phenyl) isoindolin-1-one;

2-(1-cyclopropyl-2-hydroxy-2-methylpropyl)-6-fluoro-4-hydroxy-7-(4-(5-methyl-1,3,4-oxadiazol-2-yl)phenyl) isoindolin-1-one;

(R)-2-(1-cyclopropyl-2-hydroxy-2-methylpropyl)-6-fluoro-4-hydroxy-7-(4-(5-methyl-1,3,4-oxadiazol-2-yl)phenyl)isoindolin-1-one;

2-(1-cyclopropyl-2-hydroxy-2-methylpropyl)-4-hydroxy-7-(4-(1-methyl-1H-pyrazol-4-yl)phenyl)isoindolin-1-one;

(R)-2-(1-cyclopropyl-2-hydroxy-2-methylpropyl)-4-hydroxy-7-(4-(1-methyl-1H-pyrazol-4-yl)phenyl)isoindolin-1-one;

2-(1-cyclopropyl-2-hydroxy-2-methylpropyl)-5-methyl-7-(4-(5-methyl-1,3,4-oxadiazol-2-yl)phenyl)isoindolin-1-one;

(R)-2-(1-cyclopropyl-2-hydroxy-2-methylpropyl)-5-methyl-7-(4-(5-methyl-1,3,4-oxadiazol-2-yl)phenyl) isoindolin-1-one;

2-(1-cyclopropyl-2-hydroxy-2-methylpropyl)-3-methyl-7-(4-(5-methyl-1,3,4-oxadiazol-2-yl)phenyl)isoindolin-1-one;

(R)-2-((R)-1-cyclopropyl-2-hydroxy-2-methylpropyl)-3-methyl-7-(4-(5-methyl-1,3,4-oxadiazol-2-yl)phenyl) isoindolin-1-one;

(S)-2-((R)-1-cyclopropyl-2-hydroxy-2-methylpropyl)-3-methyl-7-(4-(5-methyl-1,3,4-oxadiazol-2-yl)phenyl) isoindolin-1-one;

2-(1-Cyclopropyl-2-hydroxy-2-methylpropyl)-4-hydroxy-7-(4-(5-methyl-1,3,4-oxadiazol-2-yl)phenyl) isoindolin-1-one;

(R)-2-(1-Cyclopropyl-2-hydroxy-2-methylpropyl)-4-hydroxy-7-(4-(5-methyl-1,3,4-oxadiazol-2-yl)phenyl) isoindolin-1-one;

2-(1-Cyclopropyl-2-hydroxy-2-methylpropyl)-5-methyl-7-(4-(5-methyl-1,3,4-oxadiazol-2-yl)phenyl)isoindolin-1-one;

(R)-2-(1-Cyclopropyl-2-hydroxy-2-methylpropyl)-5-methyl-7-(4-(5-methyl-1,3,4-oxadiazol-2-yl)phenyl) isoindolin-1-one;

2-(1-Cyclopropyl-2-hydroxy-2-methylpropyl)-3-methyl-7-(4-(5-methyl-1,3,4-oxadiazol-2-yl)phenyl)isoindolin-1-one;

(R)-2-((R)-1-Cyclopropyl-2-hydroxy-2-methylpropyl)-3-methyl-7-(4-(5-methyl-1,3,4-oxadiazol-2-yl)phenyl) isoindolin-1-one;

(S)-2-((R)-1-Cyclopropyl-2-hydroxy-2-methylpropyl)-3-methyl-7-(4-(5-methyl-1,3,4-oxadiazol-2-yl)phenyl) isoindolin-1-one;

2-(1-Cyclopropyl-2-hydroxy-2-methylpropyl)-2'-methyl-[4,5'-biisoindoline]-1',3-dione;

(R)-2-(1-Cyclopropyl-2-hydroxy-2-methylpropyl)-2'-methyl-[4,5'-biisoindoline]-1',3-dione;

2-(1-Cyclopropyl-2-hydroxy-2-methylpropyl)-7-(4-(5-methyloxazol-2-yl)phenyl)isoindolin-1-one;

(R)-2-(1-Cyclopropyl-2-hydroxy-2-methylpropyl)-7-(4-(5-methyloxazol-2-yl)phenyl)isoindolin-1-one;

2-(1-cyclopropyl-2-hydroxy-2-methylpropyl)-7-(6-(5-methyl-1,3,4-oxadiazol-2-yl)pyridin-3-yl)isoindolin-1-one;

(R)-2-(1-cyclopropyl-2-hydroxy-2-methylpropyl)-7-(6-(5-methyl-1,3,4-oxadiazol-2-yl)pyridin-3-yl)isoindolin-1-one;

2-(1-cyclopropyl-2-hydroxy-2-methylpropyl)-7-(5-fluoro-6-(5-methyl-1,3,4-oxadiazol-2-yl)pyridin-3-yl) isoindolin-1-one;

(R)-2-(1-cyclopropyl-2-hydroxy-2-methylpropyl)-7-(5-fluoro-6-(5-methyl-1,3,4-oxadiazol-2-yl)pyridin-3-yl) isoindolin-1-one;

2-(1-cyclopropyl-2-hydroxy-2-methylpropyl)-7-(3-methoxy-4-(5-methyl-1,3,4-oxadiazol-2-yl)phenyl) isoindolin-1-one;

(R)-2-(1-cyclopropyl-2-hydroxy-2-methylpropyl)-7-(3-methoxy-4-(5-methyl-1,3,4-oxadiazol-2-yl)phenyl) isoindolin-1-one;

2-(1-cyclopropyl-2-hydroxy-2-methylpropyl)-7-(2-fluoro-4-(5-methyl-1,3,4-oxadiazol-2-yl)phenyl)isoindolin-1-one;

(R)-2-(1-cyclopropyl-2-hydroxy-2-methylpropyl)-7-(2-fluoro-4-(5-methyl-1,3,4-oxadiazol-2-yl)phenyl)isoindolin-1-one;

7-(4-(1H-1,2,3-triazol-1-yl)phenyl)-2-(1-cyclopropyl-2-hydroxy-2-methylpropyl)isoindolin-1-one;

(R)-7-(4-(1H-1,2,3-triazol-1-yl)phenyl)-2-(1-cyclopropyl-2-hydroxy-2-methylpropyl)isoindolin-1-one;

2-(1-cyclopropyl-2-hydroxy-2-methylpropyl)-7-(2-fluoro-5-methyl-4-(5-methyl-1,3,4-oxadiazol-2-yl) phenyl)isoindolin-1-one;

(R)-2-(1-cyclopropyl-2-hydroxy-2-methylpropyl)-7-(2-fluoro-5-methyl-4-(5-methyl-1,3,4-oxadiazol-2-yl) phenyl)isoindolin-1-one;

2-(1-cyclopropyl-2-hydroxy-2-methylpropyl)-7-(3-methyl-4-(5-methyl-1,3,4-oxadiazol-2-yl)phenyl) isoindolin-1-one;

(R)-2-(1-cyclopropyl-2-hydroxy-2-methylpropyl)-7-(3-methyl-4-(5-methyl-1,3,4-oxadiazol-2-yl)phenyl) isoindolin-1-one;

2-(1-cyclopropyl-2-hydroxy-2-methylpropyl)-7-(2-fluoro-3-methyl-4-(5-methyl-1,3,4-oxadiazol-2-yl) phenyl)isoindolin-1-one;

(R)-2-(1-cyclopropyl-2-hydroxy-2-methylpropyl)-7-(2-fluoro-3-methyl-4-(5-methyl-1,3,4-oxadiazol-2-yl) phenyl)isoindolin-1-one;

2-(1-cyclopropyl-2-hydroxy-2-methylpropyl)-7-(2-(2,2,2-trifluoroethoxy)pyridin-3-yl)isoindolin-1-one;

(R)-2-(1-cyclopropyl-2-hydroxy-2-methylpropyl)-7-(2-(2,2,2-trifluoroethoxy)pyridin-3-yl)isoindolin-1-one;

7-(2-(1-cyclopropyl-2-hydroxy-2-methylpropyl)-3-oxoisoindolin-4-yl)-2-methyl-1,4-dihydroisoquinolin-3 (2H)-one;

(R)-7-(2-(1-cyclopropyl-2-hydroxy-2-methylpropyl)-3-oxoisoindolin-4-yl)-2-methyl-1,4-dihydroisoquinolin-3 (2H)-one;

2-(1-cyclopropyl-2-hydroxy-2-methylpropyl)-7-(2-methoxyquinoxalin-6-yl)isoindolin-1-one;

(R)-2-(1-cyclopropyl-2-hydroxy-2-methylpropyl)-7-(2-methoxyquinoxalin-6-yl)isoindolin-1-one;

2-(1-cyclopropyl-2-hydroxy-2-methylpropyl)-7-(4-(5-ethyl-1,3,4-oxadiazol-2-yl)phenyl)isoindolin-1-one;

(R)-2-(1-cyclopropyl-2-hydroxy-2-methylpropyl)-7-(4-(5-ethyl-1,3,4-oxadiazol-2-yl)phenyl)isoindolin-1-one;

2-(1-cyclopropyl-2-hydroxy-2-methylpropyl)-7-(4-(oxazol-2-yl)phenyl)isoindolin-1-one;

(R)-2-(1-cyclopropyl-2-hydroxy-2-methylpropyl)-7-(4-(oxazol-2-yl)phenyl)isoindolin-1-one;

2-(1-cyclopropyl-2-hydroxy-2-methylpropyl)-7-(4-(3-methyl-1,2,4-oxadiazol-5-yl)phenyl)isoindolin-1-one;

(R)-2-(1-cyclopropyl-2-hydroxy-2-methylpropyl)-7-(4-(3-methyl-1,2,4-oxadiazol-5-yl)phenyl)isoindolin-1-one;

2-(1-cyclopropyl-2-hydroxy-2-methylpropyl)-7-(1-methyl-1H-indazol-3-yl)isoindolin-1-one;

(R)-2-(1-cyclopropyl-2-hydroxy-2-methylpropyl)-7-(1-methyl-1H-indazol-3-yl)isoindolin-1-one;

2-(1-cyclopropyl-2-hydroxy-2-methylpropyl)-7-(1-methyl-3-(trifluoromethyl)-1H-indazol-5-yl)isoindolin-1-one;

(R)-2-(1-cyclopropyl-2-hydroxy-2-methylpropyl)-7-(1-methyl-3-(trifluoromethyl)-1H-indazol-5-yl)isoindolin-1-one;

2-(1-cyclopropyl-2-hydroxy-2-methylpropyl)-7-(3-(5-methyl-1,2,4-oxadiazol-3-yl)phenyl)isoindolin-1-one;

(R)-2-(1-cyclopropyl-2-hydroxy-2-methylpropyl)-7-(3-(5-methyl-1,2,4-oxadiazol-3-yl)phenyl)isoindolin-1-one;

7-(3-(1,2,4-oxadiazol-3-yl)phenyl)-2-(1-cyclopropyl-2-hydroxy-2-methylpropyl)isoindolin-1-one;

(R)-7-(3-(1,2,4-oxadiazol-3-yl)phenyl)-2-(1-cyclopropyl-2-hydroxy-2-methylpropyl)isoindolin-1-one;

7-(4-(1,2,4-oxadiazol-3-yl)phenyl)-2-(1-cyclopropyl-2-hydroxy-2-methylpropyl)isoindolin-1-one;

(R)-7-(4-(1,2,4-oxadiazol-3-yl)phenyl)-2-(1-cyclopropyl-2-hydroxy-2-methylpropyl)isoindolin-1-one;

6-(2-(1-cyclopropyl-2-hydroxy-2-methylpropyl)-3-oxoisoindolin-4-yl)-1-methylindolin-2-one;

(R)-6-(2-(1-cyclopropyl-2-hydroxy-2-methylpropyl)-3-oxoisoindolin-4-yl)-1-methylindolin-2-one;

5-(2-(1-cyclopropyl-2-hydroxy-2-methylpropyl)-3-oxoisoindolin-4-yl)-1-methylindolin-2-one;

(R)-5-(2-(1-cyclopropyl-2-hydroxy-2-methylpropyl)-3-oxoisoindolin-4-yl)-1-methylindolin-2-one;

2-(1-cyclopropyl-2-hydroxy-2-methylpropyl)-7-(1,3-dimethyl-1H-indazol-5-yl)isoindolin-1-one;

(R)-2-(1-cyclopropyl-2-hydroxy-2-methylpropyl)-7-(1,3-dimethyl-1H-indazol-5-yl)isoindolin-1-one;

2-(1-cyclopropyl-2-hydroxy-2-methylpropyl)-7-(1,6-dimethyl-1H-indazol-5-yl)isoindolin-1-one;

(R)-2-(1-cyclopropyl-2-hydroxy-2-methylpropyl)-7-(1,6-dimethyl-1H-indazol-5-yl)isoindolin-1-one;

2-(1-cyclopropyl-2-hydroxy-2-methylpropyl)-7-(4-(5-methyl-1,2,4-oxadiazol-3-yl)phenyl)isoindolin-1-one;

(R)-2-(1-cyclopropyl-2-hydroxy-2-methylpropyl)-7-(4-(5-methyl-1,2,4-oxadiazol-3-yl)phenyl)isoindolin-1-one;

2-(1-cyclopropyl-2-hydroxy-2-methylpropyl)-7-(1-(pyridin-4-yl)-1H-pyrazol-4-yl)isoindolin-1-one;

(R)-2-(1-cyclopropyl-2-hydroxy-2-methylpropyl)-7-(1-(pyridin-4-yl)-1H-pyrazol-4-yl)isoindolin-1-one;

2-(1-cyclopropyl-2-hydroxy-2-methylpropyl)-7-(4-(3-methylisoxazol-5-yl)phenyl)isoindolin-1-one;

(R)-2-(1-cyclopropyl-2-hydroxy-2-methylpropyl)-7-(4-(3-methylisoxazol-5-yl)phenyl)isoindolin-1-one;

2-[(1-cyclopropyl-2-hydroxy-2-methyl-propyl]-7-[4-(2-methyloxazol-5-yl)phenyl]isoindolin-1-one;

2-[(1R)-1-cyclopropyl-2-hydroxy-2-methyl-propyl]-7-[4-(2-methyloxazol-5-yl)phenyl]isoindolin-1-one;

4-chloro-6-[2-[1-cyclopropyl-2-hydroxy-2-methyl-propyl]-3-oxo-isoindolin-4-yl]pyridine-2-carbonitrile;

4-chloro-6-[2-[(1R)-1-cyclopropyl-2-hydroxy-2-methyl-propyl]-3-oxo-isoindolin-4-yl]pyridine-2-carbonitrile;

7-(6-chloro-4-methoxypyridin-2-yl)-2-(1-cyclopropyl-2-hydroxy-2-methylpropyl)isoindolin-1-one;

(R)-7-(6-chloro-4-methoxypyridin-2-yl)-2-(1-cyclopropyl-2-hydroxy-2-methylpropyl)isoindolin-1-one;

2-[(1R)-1-cyclopropyl-2-hydroxy-2-methyl-propyl]-7-[4-(1-methyltriazol-4-yl)phenyl]isoindolin-1-one;

2-[1-cyclopropyl-2-hydroxy-2-methyl-propyl]-7-[4-(1-methyltriazol-4-yl)phenyl]isoindolin-1-one;

(R)-2-(1-cyclopropyl-2-hydroxy-2-methylpropyl)-7-(4-(isothiazol-4-yl)phenyl)isoindolin-1-one;

2-(1-cyclopropyl-2-hydroxy-2-methylpropyl)-7-(4-(isothiazol-4-yl)phenyl)isoindolin-1-one;

2-[(1R)-1-cyclopropyl-2-hydroxy-2-methyl-propyl]-7-[4-[3-(hydroxymethyl)-4-methyl-isoxazol-5-yl]phenyl]isoindolin-1-one;

2-[(1-cyclopropyl-2-hydroxy-2-methyl-propyl]-7-[4-[3-(hydroxymethyl)-4-methyl-isoxazol-5-yl]phenyl]isoindolin-1-one;

6-(2-(1-cyclopropyl-2-hydroxy-2-methylpropyl)-3-oxoisoindolin-4-yl)-4-methoxypicolinonitrile;

(R)-6-(2-(1-cyclopropyl-2-hydroxy-2-methylpropyl)-3-oxoisoindolin-4-yl)-4-methoxypicolinonitrile;

N-(2-(Dicyclopropylmethyl)-3-oxoisoindolin-4-yl)-2-ethoxybenzamide;

2-Ethoxy-N-(2-(3-hydroxy-3-methylbutan-2-yl)-3-oxoisoindolin-4-yl)benzamide;

(R)-2-Ethoxy-N-(2-(3-hydroxy-3-methylbutan-2-yl)-3-oxoisoindolin-4-yl)benzamide;

2-ethoxy-N-(2-(1-hydroxy-3-methylbutan-2-yl)-3-oxoisoindolin-4-yl)benzamide;

(R)-2-ethoxy-N-(2-(1-hydroxy-3-methylbutan-2-yl)-3-oxoisoindolin-4-yl)benzamide;

N-(2-(1-cyclobutyl-2-hydroxyethyl)-3-oxoisoindolin-4-yl)-2-ethoxybenzamide;

(S)-N-(2-(1-cyclobutyl-2-hydroxyethyl)-3-oxoisoindolin-4-yl)-2-ethoxybenzamide;

(R)-N-(2-(1-cyclobutyl-2-hydroxyethyl)-3-oxoisoindolin-4-yl)-2-ethoxybenzamide;

N-(2-(1-cyclopropyl-2-hydroxyethyl)-3-oxoisoindolin-4-yl)-2-ethoxybenzamide;

(R)-N-(2-(1-cyclopropyl-2-hydroxyethyl)-3-oxoisoindolin-4-yl)-2-ethoxybenzamide;

2-ethoxy-N-(2-(2-hydroxycyclohexyl)-3-oxoisoindolin-4-yl)benzamide;

2-ethoxy-N-(2-((1R,2S)-2-hydroxycyclohexyl)-3-oxoisoindolin-4-yl)benzamide;

N-(2-(cyclopropylmethyl)-3-oxoisoindolin-4-yl)-2-ethoxybenzamide;

2-ethoxy-N-(2-((1-hydroxycyclobutyl)methyl)-3-oxoisoindolin-4-yl)benzamide;

2-ethoxy-N-(2-((3-hydroxyoxetan-3-yl)methyl)-3-oxoisoindolin-4-yl)benzamide;

2-Ethoxy-N-(3-oxo-2-(quinuclidin-3-yl)isoindolin-4-yl)benzamide;

(R)-2-Ethoxy-N-(3-oxo-2-(quinuclidin-3-yl)isoindolin-4-yl)benzamide;

(S)-2-Ethoxy-N-(3-oxo-2-(quinuclidin-3-yl)isoindolin-4-yl)benzamide;

2-Ethoxy-N-(3-oxo-2-(quinuclidin-2-ylmethyl)isoindolin-4-yl)benzamide; (108)

(R)-2-Ethoxy-N-(3-oxo-2-(quinuclidin-2-ylmethyl)isoindolin-4-yl)benzamide;

(S)-2-Ethoxy-N-(3-oxo-2-(quinuclidin-2-ylmethyl)isoindolin-4-yl)benzamide;

5-Bromo-N-(2-(dicyclopropylmethyl)-3-oxoisoindolin-4-yl)benzo[d][1,3]dioxole-4-carboxamide;

2-chloro-N-(2-(1-cyclopropyl-2-hydroxy-2-methylpropyl)-3-oxoisoindolin-4-yl)-6-fluoro-3-methylbenzamide;

(R)-2-chloro-N-(2-(1-cyclopropyl-2-hydroxy-2-methylpropyl)-3-oxoisoindolin-4-yl)-6-fluoro-3-methylbenzamide;

(S)-2-chloro-N-(2-(1-cyclopropyl-2-hydroxy-2-methylpropyl)-3-oxoisoindolin-4-yl)-6-fluoro-3-methylbenzamide;

6-chloro-N-(2-(1-cyclopropyl-2-hydroxy-2-methylpropyl)-3-oxoisoindolin-4-yl)-2-fluoro-3-methylbenzamide;

(R)-6-chloro-N-(2-(1-cyclopropyl-2-hydroxy-2-methylpropyl)-3-oxoisoindolin-4-yl)-2-fluoro-3-methylbenzamide;

(S)-6-chloro-N-(2-(1-cyclopropyl-2-hydroxy-2-methylpropyl)-3-oxoisoindolin-4-yl)-2-fluoro-3-methylbenzamide;

N-(2-(1-cyclopropyl-2-hydroxy-2-methylpropyl)-3-oxoisoindolin-4-yl)-2,3-difluoro-6-methoxybenzamide;

(R)-N-(2-(1-cyclopropyl-2-hydroxy-2-methylpropyl)-3-oxoisoindolin-4-yl)-2,3-difluoro-6-methoxybenzamide;

(S)-N-(2-(1-cyclopropyl-2-hydroxy-2-methylpropyl)-3-oxoisoindolin-4-yl)-2,3-difluoro-6-methoxybenzamide;

2-chloro-N-(2-(1-cyclopropyl-2-hydroxy-2-methylpropyl)-3-oxoisoindolin-4-yl)-3-methylbenzamide;

(R)-2-chloro-N-(2-(1-cyclopropyl-2-hydroxy-2-methylpropyl)-3-oxoisoindolin-4-yl)-3-methylbenzamide;

(S)-2-chloro-N-(2-(1-cyclopropyl-2-hydroxy-2-methylpropyl)-3-oxoisoindolin-4-yl)-3-methylbenzamide;

N-(2-(1-cyclopropyl-2-hydroxy-2-methylpropyl)-3-oxoisoindolin-4-yl)-2,3-dihydro-1H-indene-4-carboxamide;

(R)-N-(2-(1-cyclopropyl-2-hydroxy-2-methylpropyl)-3-oxoisoindolin-4-yl)-2,3-dihydro-1H-indene-4-carboxamide;

(S)-N-(2-(1-cyclopropyl-2-hydroxy-2-methylpropyl)-3-oxoisoindolin-4-yl)-2,3-dihydro-1H-indene-4-carboxamide;

2-chloro-N-(2-(1-cyclopropyl-2-hydroxy-2-methylpropyl)-3-oxoisoindolin-4-yl)-3,6-difluorobenzamide;

(R)-2-chloro-N-(2-(1-cyclopropyl-2-hydroxy-2-methylpropyl)-3-oxoisoindolin-4-yl)-3,6-difluorobenzamide;

(S)-2-chloro-N-(2-(1-cyclopropyl-2-hydroxy-2-methylpropyl)-3-oxoisoindolin-4-yl)-3,6-difluorobenzamide;

N-(2-(1-cyclopropyl-2-hydroxy-2-methylpropyl)-3-oxoisoindolin-4-yl)-3-fluoro-2-(trifluoromethyl)benzamide;

(R)-N-(2-(1-cyclopropyl-2-hydroxy-2-methylpropyl)-3-oxoisoindolin-4-yl)-3-fluoro-2-(trifluoromethyl)benzamide;

(S)-N-(2-(1-cyclopropyl-2-hydroxy-2-methylpropyl)-3-oxoisoindolin-4-yl)-3-fluoro-2-(trifluoromethyl)benzamide;

N-(2-(dicyclopropylmethyl)-3-oxoisoindolin-4-yl)-6-methyl-[1,3]dioxolo[4,5-b]pyridine-7-carboxamide;

6-chloro-N-(2-(dicyclopropylmethyl)-3-oxoisoindolin-4-yl)-[1,3]dioxolo[4,5-b]pyridine-7-carboxamide;

N-(2-(1-cyclopropyl-2-hydroxy-2-methylpropyl)-3-oxoisoindolin-4-yl)-3-fluoro-2-methylbenzamide;

(R)-N-(2-(1-cyclopropyl-2-hydroxy-2-methylpropyl)-3-oxoisoindolin-4-yl)-3-fluoro-2-methylbenzamide;

(S)-N-(2-(1-cyclopropyl-2-hydroxy-2-methylpropyl)-3-oxoisoindolin-4-yl)-3-fluoro-2-methylbenzamide;

N-(2-(1-cyclopropyl-2-hydroxy-2-methylpropyl)-3-oxoisoindolin-4-yl)-2-methyl-3-(trifluoromethyl)benzamide;

(R)-N-(2-(1-cyclopropyl-2-hydroxy-2-methylpropyl)-3-oxoisoindolin-4-yl)-2-methyl-3-(trifluoromethyl)benzamide;

(S)-N-(2-(1-cyclopropyl-2-hydroxy-2-methylpropyl)-3-oxoisoindolin-4-yl)-2-methyl-3-(trifluoromethyl)benzamide;

N-(2-(dicyclopropylmethyl)-3-oxoisoindolin-4-yl)-6,7-dihydro-5H-cyclopenta[b]pyridine-4-carboxamide;

6-chloro-2-fluoro-N-(2-(1-hydroxy-3-methylbutan-2-yl)-3-oxoisoindolin-4-yl)-3-methylbenzamide;

(R)-6-chloro-2-fluoro-N-(2-(1-hydroxy-3-methylbutan-2-yl)-3-oxoisoindolin-4-yl)-3-methylbenzamide;

2,6-dichloro-3-fluoro-N-(2-(3-hydroxy-3-methylbutan-2-yl)-3-oxoisoindolin-4-yl)benzamide;

(R)-2,6-dichloro-3-fluoro-N-(2-(3-hydroxy-3-methylbutan-2-yl)-3-oxoisoindolin-4-yl)benzamide;

2,6-dichloro-3-fluoro-N-(2-(1-hydroxy-3-methylbutan-2-yl)-3-oxoisoindolin-4-yl)benzamide;

(R)-2,6-dichloro-3-fluoro-N-(2-(1-hydroxy-3-methylbutan-2-yl)-3-oxoisoindolin-4-yl)benzamide;

3-chloro-N-(2-(1-hydroxy-3-methylbutan-2-yl)-3-oxoisoindolin-4-yl)-6-(trifluoromethyl)picolinamide;

(R)-3-chloro-N-(2-(1-hydroxy-3-methylbutan-2-yl)-3-oxoisoindolin-4-yl)-6-(trifluoromethyl)picolinamide;

N-(2-(dicyclopropylmethyl)-3-oxoisoindolin-4-yl)-1-methyl-1H-indole-4-carboxamide;

N-(2-(3-hydroxy-3-methylbutan-2-yl)-3-oxoisoindolin-4-yl)-3-(trifluoromethyl)quinoline-4-carboxamide;

(R)-N-(2-(3-hydroxy-3-methylbutan-2-yl)-3-oxoisoindolin-4-yl)-3-(trifluoromethyl)quinoline-4-carboxamide;

N-(2-(cyclopropylmethyl)-3-oxoisoindolin-4-yl)-2,3-dihydro-1H-cyclopenta[b]quinoline-9-carboxamide;

3-chloro-N-(2-(3-hydroxy-3-methylbutan-2-yl)-3-oxoisoindolin-4-yl)-6-(trifluoromethyl)picolinamide;

(R)-3-chloro-N-(2-(3-hydroxy-3-methylbutan-2-yl)-3-oxoisoindolin-4-yl)-6-(trifluoromethyl)picolinamide;

N-(2-(cyclopropylmethyl)-3-oxoisoindolin-4-yl)-3-(trifluoromethyl)quinoline-4-carboxamide;

N-(2-(1-cyclopropyl-2-hydroxy-2-methylpropyl)-3-oxoisoindolin-4-yl)benzo[d]thiazole-7-carboxamide;

(R)-N-(2-(1-cyclopropyl-2-hydroxy-2-methylpropyl)-3-oxoisoindolin-4-yl)benzo[d]thiazole-7-carboxamide;

(S)-N-(2-(1-cyclopropyl-2-hydroxy-2-methylpropyl)-3-oxoisoindolin-4-yl)benzo[d]thiazole-7-carboxamide;

6-chloro-N-(2-(1-hydroxy-3-methylbutan-2-yl)-3-oxoisoindolin-4-yl)-3-(trifluoromethyl)picolinamide;

(R)-6-chloro-N-(2-(1-hydroxy-3-methylbutan-2-yl)-3-oxoisoindolin-4-yl)-3-(trifluoromethyl)picolinamide;

N-(2-(dicyclopropylmethyl)-3-oxoisoindolin-4-yl)-2-methyl-2H-indazole-4-carboxamide;

(S)-N-(2-(1-cyclopropylethyl)-3-oxoisoindolin-4-yl)-6-methyl-[1,3]dioxolo[4,5-b]pyridine-7-carboxamide;

N-(2-(1-cyclopropylethyl)-3-oxoisoindolin-4-yl)-6-methyl-[1,3]dioxolo[4,5-b]pyridine-7-carboxamide;

N-(2-(cyclopropylmethyl)-3-oxoisoindolin-4-yl)-3-fluoro-6-methoxy-1,5-naphthyridine-4-carboxamide;

N-(2-(1-cyclopropyl-2-methoxyethyl)-3-oxoisoindolin-4-yl)-6,7-dihydro-5H-cyclopenta[b]pyridine-4-carboxamide;

(R)-N-(2-(1-cyclopropyl-2-methoxyethyl)-3-oxoisoindolin-4-yl)-6,7-dihydro-5H-cyclopenta[b]pyridine-4-carboxamide;

(S)-N-(2-(1-cyclopropyl-2-methoxyethyl)-3-oxoisoindolin-4-yl)-6,7-dihydro-5H-cyclopenta[b]pyridine-4-carboxamide;

6-chloro-N-(2-(1-cyclopropylethyl)-3-oxoisoindolin-4-yl)-[1,3]dioxolo[4,5-b]pyridine-7-carboxamide;

(S)-6-chloro-N-(2-(1-cyclopropylethyl)-3-oxoisoindolin-4-yl)-[1,3]dioxolo[4,5-b]pyridine-7-carboxamide;

(R)-2-ethoxy-N-(2-(3-hydroxy-3-methylbutan-2-yl)-3-oxoisoindolin-4-yl)nicotinamide;

2-ethoxy-N-(2-(3-hydroxy-3-methylbutan-2-yl)-3-oxoisoindolin-4-yl)nicotinamide;

3,5-dichloro-N-(2-(cyclopropylmethyl)-3-oxoisoindolin-4-yl)isonicotinamide;

(S)-N-(2-(1-cyclopropylethyl)-3-oxoisoindolin-4-yl)-6,7-dihydro-5H-cyclopenta[b]pyridine-4-carboxamide;

N-(2-(1-cyclopropylethyl)-3-oxoisoindolin-4-yl)-6,7-dihydro-5H-cyclopenta[b]pyridine-4-carboxamide;

N-(2-(dicyclopropylmethyl)-3-oxoisoindolin-4-yl)-1H-pyrrolo[2,3-b]pyridine-4-carboxamide;

N-(2-(dicyclopropylmethyl)-3-oxoisoindolin-4-yl)-7-fluoro-1-oxo-2,3-dihydro-1H-indene-4-carboxamide;

N-(6-chloro-2-(cyclopropylmethyl)-3-oxoisoindolin-4-yl)-6,7-dihydro-5H-cyclopenta[b]pyridine-4-carboxamide;

N-(2-(cyclopropylmethyl)-3-oxoisoindolin-4-yl)-6-fluoroquinoline-4-carboxamide;

N-(2-(dicyclopropylmethyl)-3-oxoisoindolin-4-yl)-2,3-dihydrobenzofuran-7-carboxamide;

N-(2-(cyclopropylmethyl)-3-oxoisoindolin-4-yl)-6,7-dihydro-5H-cyclopenta[b]pyridine-4-carboxamide;

N-(7-chloro-2-(cyclopropylmethyl)-3-oxoisoindolin-4-yl)-6,7-dihydro-5H-cyclopenta[b]pyridine-4-carboxamide;

N-(2-(Cyclopropylmethyl)-6-methyl-3-oxoisoindolin-4-yl)-6,7-dihydro-5H-cyclopenta[b]pyridine-4-carboxamide;

N-(2-(cyclopropylmethyl)-7-hydroxy-3-oxoisoindolin-4-yl)-6,7-dihydro-5H-cyclopenta[b]pyridine-4-carboxamide;

N-(2-(Cyclopropylmethyl)-6-methyl-3-oxoisoindolin-4-yl)-6,7-dihydro-5H-cyclopenta[b]pyridine-4-carboxamide;

N-(2-(Cyclopropylmethyl)-7-hydroxy-3-oxoisoindolin-4-yl)-6,7-dihydro-5H-cyclopenta[b]pyridine-4-carboxamide;

Quinuclidin-3-yl(2-(4-fluorophenyl)-3-oxoisoindolin-4-yl)carbamate;

N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide;

(R)-N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide;

(S)-N-(2-(1-Cyclopropyl-2-hydroxy-2-methylpropyl)-1-oxo-2,3-dihydro-1H-pyrrolo[3,4-c]pyridin-7-yl)-6,7-dihydro-5H-cyclopenta[b]pyridine-4-carboxamide;

N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide;

(R)-N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide;

(S)-N-(6-(1-cyclopropyl-2-hydroxy-2-methylpropyl)-5-oxo-6,7-dihydro-5H-pyrrolo[3,4-b]pyridin-4-yl)-6,7-dihydro-5H-cyclopenta[b]pyridine-4-carboxamide;

N-(2-(1-cyclopropyl-2-hydroxy-2-methylpropyl)-3-oxoisoindolin-4-yl)-2-methoxy-3,5-dimethylisonicotinamide;

(R)-N-(2-(1-cyclopropyl-2-hydroxy-2-methylpropyl)-3-oxoisoindolin-4-yl)-2-methoxy-3,5-dimethylisonicotinamide;

(S)-N-(2-(1-cyclopropyl-2-hydroxy-2-methylpropyl)-3-oxoisoindolin-4-yl)-2-methoxy-3,5-dimethylisonicotinamide;

5-chloro-N-(2-(1-cyclopropyl-2-hydroxy-2-methylpropyl)-3-oxoisoindolin-4-yl)-2-methoxy-3-methylisonicotinamide;

(R)-5-chloro-N-(2-(1-cyclopropyl-2-hydroxy-2-methylpropyl)-3-oxoisoindolin-4-yl)-2-methoxy-3-methylisonicotinamide;

(S)-5-Chloro-N-(2-(1-cyclopropyl-2-hydroxy-2-methylpropyl)-3-oxoisoindolin-4-yl)-2-methoxy-3-methylisonicotinamide;

5-Chloro-N-(2-(1-cyclopropyl-2-hydroxy-2-methylpropyl)-3-oxoisoindolin-4-yl)-2,3-dihydrofuro[2,3-b]pyridine-4-carboxamide;

(R)-5-Chloro-N-(2-(1-cyclopropyl-2-hydroxy-2-methylpropyl)-3-oxoisoindolin-4-yl)-2,3-dihydrofuro[2,3-b]pyridine-4-carboxamide;

(S)-5-Chloro-N-(2-(1-cyclopropyl-2-hydroxy-2-methylpropyl)-3-oxoisoindolin-4-yl)-2,3-dihydrofuro[2,3-b]pyridine-4-carboxamide;

N-(2-(1-cyclopropyl-2-hydroxy-2-methylpropyl)-3-oxoisoindolin-4-yl)pyrazolo[1,5-a]pyridine-4-carboxamide;

(R)-N-(2-(1-cyclopropyl-2-hydroxy-2-methylpropyl)-3-oxoisoindolin-4-yl)pyrazolo[1,5-a]pyridine-4-carboxamide;

6-chloro-N-(2-(1-cyclopropyl-2-hydroxy-2-methylpropyl)-3-oxoisoindolin-4-yl)-[1,3]dioxolo[4,5-b]pyridine-7-carboxamide;

(R)-6-chloro-N-(2-(1-cyclopropyl-2-hydroxy-2-methylpropyl)-3-oxoisoindolin-4-yl)-[1,3]dioxolo[4,5-b]pyridine-7-carboxamide;

(S)-6-chloro-N-(2-(1-cyclopropyl-2-hydroxy-2-methylpropyl)-3-oxoisoindolin-4-yl)-[1,3]dioxolo[4,5-b]pyridine-7-carboxamide;

N-(2-(1-cyclopropyl-2-hydroxy-2-methylpropyl)-3-oxoisoindolin-4-yl)-6,7-dihydro-5H-cyclopenta[b]pyridine-4-carboxamide;

(R)-N-(2-(1-cyclopropyl-2-hydroxy-2-methylpropyl)-3-oxoisoindolin-4-yl)-6,7-dihydro-5H-cyclopenta[b]pyridine-4-carboxamide;

(S)-N-(2-(1-cyclopropyl-2-hydroxy-2-methylpropyl)-3-oxoisoindolin-4-yl)-6,7-dihydro-5H-cyclopenta[b]pyridine-4-carboxamide;

N-(2-(1-cyclopropyl-2-hydroxy-2-methylpropyl)-3-oxoisoindolin-4-yl)-2-methoxy-3-methylisonicotinamide;

(R)-N-(2-(1-cyclopropyl-2-hydroxy-2-methylpropyl)-3-oxoisoindolin-4-yl)-2-methoxy-3-methylisonicotinamide;

N-(2-(1-cyclopropyl-2-hydroxy-2-methylpropyl)-3-oxoisoindolin-4-yl)-2-methyl-2H-indazole-4-carboxamide;

(R)-N-(2-(1-cyclopropyl-2-hydroxy-2-methylpropyl)-3-oxoisoindolin-4-yl)-2-methyl-2H-indazole-4-carboxamide;

(S)-N-(2-(1-cyclopropyl-2-hydroxy-2-methylpropyl)-3-oxoisoindolin-4-yl)-2-methyl-2H-indazole-4-carboxamide;

N-(2-(1-cyclopropyl-2-hydroxy-2-methylpropyl)-6-fluoro-3-oxoisoindolin-4-yl)-2-methyl-2H-indazole-4-carboxamide;

(R)-N-(2-(1-cyclopropyl-2-hydroxy-2-methylpropyl)-6-fluoro-3-oxoisoindolin-4-yl)-2-methyl-2H-indazole-4-carboxamide;

N-(2-(1-cyclopropyl-2-hydroxy-2-methylpropyl)-3-oxoisoindolin-4-yl)-2,3-dihydrofuro[2,3-b]pyridine-4-carboxamide;

(R)-N-(2-(1-cyclopropyl-2-hydroxy-2-methylpropyl)-3-oxoisoindolin-4-yl)-2,3-dihydrofuro[2,3-b]pyridine-4-carboxamide;

(S)-N-(2-(1-cyclopropyl-2-hydroxy-2-methylpropyl)-3-oxoisoindolin-4-yl)-2,3-dihydrofuro[2,3-b]pyridine-4-carboxamide;

N-(2-(1-cyclopropyl-2-hydroxy-2-methylpropyl)-3-oxoisoindolin-4-yl)-2,3-dihydro-[1,4]dioxino[2,3-b]pyridine-8-carboxamide;

(R)-N-(2-(1-cyclopropyl-2-hydroxy-2-methylpropyl)-3-oxoisoindolin-4-yl)-2,3-dihydro-[1,4]dioxino[2,3-b]pyridine-8-carboxamide;

(S)-N-(2-(1-cyclopropyl-2-hydroxy-2-methylpropyl)-3-oxoisoindolin-4-yl)-2,3-dihydro-[1,4]dioxino[2,3-b]pyridine-8-carboxamide;

N-(2-(1-cyclopropyl-2-hydroxy-2-methylpropyl)-3-oxoisoindolin-4-yl)-2,3-dimethoxyisonicotinamide;

(R)-N-(2-(1-cyclopropyl-2-hydroxy-2-methylpropyl)-3-oxoisoindolin-4-yl)-2,3-dimethoxyisonicotinamide;

(S)-N-(2-(1-cyclopropyl-2-hydroxy-2-methylpropyl)-3-oxoisoindolin-4-yl)-2,3-dimethoxyisonicotinamide;

N-(2-(1-cyclopropyl-2-methoxy-2-methylpropyl)-3-oxoisoindolin-4-yl)-6,7-dihydro-5H-cyclopenta[b]pyridine-4-carboxamide;

(R)-N-(2-(1-cyclopropyl-2-methoxy-2-methylpropyl)-3-oxoisoindolin-4-yl)-6,7-dihydro-5H-cyclopenta[b]pyridine-4-carboxamide;

(S)-N-(2-(1-cyclopropyl-2-methoxy-2-methylpropyl)-3-oxoisoindolin-4-yl)-6,7-dihydro-5H-cyclopenta[b]pyridine-4-carboxamide;

N-(2-((1-hydroxycyclobutyl)methyl)-3-oxoisoindolin-4-yl)-6,7-dihydro-5H-cyclopenta[b]pyridine-4-carboxamide;

2-chloro-N-(2-(1-cyclopropyl-2-hydroxy-2-methylpropyl)-1-oxo-2,3-dihydro-1H-pyrrolo[3,4-c]pyridin-7-yl)-6-fluoro-3-methylbenzamide;

(R)-2-chloro-N-(2-(1-cyclopropyl-2-hydroxy-2-methylpropyl)-1-oxo-2,3-dihydro-1H-pyrrolo[3,4-c]pyridin-7-yl)-6-fluoro-3-methylbenzamide;

N-(2-(1-cyclopropyl-2-hydroxy-2-methylpropyl)-3-oxoisoindolin-4-yl)-5-methyl-2,3-dihydrofuro[2,3-b]pyridine-4-carboxamide;

(R)-N-(2-(1-cyclopropyl-2-hydroxy-2-methylpropyl)-3-oxoisoindolin-4-yl)-5-methyl-2,3-dihydrofuro[2,3-b]pyridine-4-carboxamide;

(S)-N-(2-(1-cyclopropyl-2-hydroxy-2-methylpropyl)-3-oxoisoindolin-4-yl)-5-methyl-2,3-dihydrofuro[2,3-b]pyridine-4-carboxamide;

N-(2-(1-cyclopropyl-2-hydroxy-2-methylpropyl)-3-oxoisoindolin-4-yl)-6-methyl-[1,3]dioxolo[4,5-b]pyridine-7-carboxamide;

(R)-N-(2-(1-cyclopropyl-2-hydroxy-2-methylpropyl)-3-oxoisoindolin-4-yl)-6-methyl-[1,3]dioxolo[4,5-b]pyridine-7-carboxamide;

(S)-N-(2-(1-cyclopropyl-2-hydroxy-2-methylpropyl)-3-oxoisoindolin-4-yl)-6-methyl-[1,3]dioxolo[4,5-b]pyridine-7-carboxamide;

quinuclidin-3-yl(2-(4-fluorophenyl)-3-oxoisoindolin-4-yl)(methyl)carbamate;

(R)-quinuclidin-3-yl(2-(4-fluorophenyl)-3-oxoisoindolin-4-yl)(methyl)carbamate;

(S)-quinuclidin-3-yl(2-(4-fluorophenyl)-3-oxoisoindolin-4-yl)(methyl)carbamate;

N-(2-(1-Cyclopropyl-2-hydroxy-2-methylpropyl)-3-oxoisoindolin-4-yl)-5-methyl-2,3-dihydrofuro[2,3-b]pyridine-4-carboxamide;

(R)-N-(2-(1-Cyclopropyl-2-hydroxy-2-methylpropyl)-3-oxoisoindolin-4-yl)-5-methyl-2,3-dihydrofuro[2,3-b]pyridine-4-carboxamide;

(S)-N-(2-(1-Cyclopropyl-2-hydroxy-2-methylpropyl)-3-oxoisoindolin-4-yl)-5-methyl-2,3-dihydrofuro[2,3-b]pyridine-4-carboxamide;

N-(2-(1-Cyclopropyl-2-hydroxy-2-methylpropyl)-3-oxoisoindolin-4-yl)-6-methyl-[1,3]dioxolo[4,5-b]pyridine-7-carboxamide;

(R)-N-(2-(1-Cyclopropyl-2-hydroxy-2-methylpropyl)-3-oxoisoindolin-4-yl)-6-methyl-[1,3]dioxolo[4,5-b]pyridine-7-carboxamide;

(S)-N-(2-(1-Cyclopropyl-2-hydroxy-2-methylpropyl)-3-oxoisoindolin-4-yl)-6-methyl-[1,3]dioxolo[4,5-b]pyridine-7-carboxamide;

Quinuclidin-3-yl(2-(4-fluorophenyl)-3-oxoisoindolin-4-yl)(methyl)carbamate;

(R)-Quinuclidin-3-yl(2-(4-fluorophenyl)-3-oxoisoindolin-4-yl)(methyl)carbamate;

(S)-Quinuclidin-3-yl(2-(4-fluorophenyl)-3-oxoisoindolin-4-yl)(methyl)carbamate;

2-(1-Cyclopropyl-2-hydroxy-2-methylpropyl)-7-(2-(6,7-dihydro-5H-cyclopenta[b]pyridin-4-yl)vinyl)isoindolin-1-one;

(R)-(E)-2-(1-Cyclopropyl-2-hydroxy-2-methylpropyl)-7-(2-(6,7-dihydro-5H-cyclopenta[b]pyridin-4-yl)vinyl)isoindolin-1-one;

(S)-(E)-2-(1-Cyclopropyl-2-hydroxy-2-methylpropyl)-7-(2-(6,7-dihydro-5H-cyclopenta[b]pyridin-4-yl)vinyl)isoindolin-1-one;

2-(1-Cyclopropyl-2-hydroxy-2-methylpropyl)-7-((6,7-dihydro-5H-cyclopenta[b]pyridin-4-yl)ethynyl)isoindolin-1-one;

(R)-2-(1-Cyclopropyl-2-hydroxy-2-methylpropyl)-7-((6,7-dihydro-5H-cyclopenta[b]pyridin-4-yl)ethynyl)isoindolin-1-one;

(S)-2-(1-Cyclopropyl-2-hydroxy-2-methylpropyl)-7-((6,7-dihydro-5H-cyclopenta[b]pyridin-4-yl)ethynyl)isoindolin-1-one;

2-(1-Cyclopropyl-2-hydroxy-2-methylpropyl)-7-(2-(6,7-dihydro-5H-cyclopenta[b]pyridin-4-yl)ethyl)isoindolin-1-one;

(R)-2-(1-Cyclopropyl-2-hydroxy-2-methylpropyl)-7-(2-(6,7-dihydro-5H-cyclopenta[b]pyridin-4-yl)ethyl)isoindolin-1-one;

(S)-2-(1-Cyclopropyl-2-hydroxy-2-methylpropyl)-7-(2-(6,7-dihydro-5H-cyclopenta[b]pyridin-4-yl)ethyl)isoindolin-1-one;

7-(2-(6-Chloro-[1,3]dioxolo[4,5-b]pyridin-7-yl)vinyl)-2-(1-cyclopropyl-2-hydroxy-2-methylpropyl)isoindolin-1-one;

(R)-(E)-7-(2-(6-Chloro-[1,3]dioxolo[4,5-b]pyridin-7-yl)vinyl)-2-(1-cyclopropyl-2-hydroxy-2-methylpropyl)isoindolin-1-one;

(S)-(E)-7-(2-(6-Chloro-[1,3]dioxolo[4,5-b]pyridin-7-yl)vinyl)-2-(1-cyclopropyl-2-hydroxy-2-methylpropyl)isoindolin-1-one;

2-(1-Cyclopropyl-2-hydroxy-2-methylpropyl)-7-(2-(6-methyl-[1,3]dioxolo[4,5-b]pyridin-7-yl)vinyl)isoindolin-1-one;

(R)-(E)-2-(1-Cyclopropyl-2-hydroxy-2-methylpropyl)-7-(2-(6-methyl-[1,3]dioxolo[4,5-b]pyridin-7-yl)vinyl)isoindolin-1-one;

(S)-(E)-2-(1-Cyclopropyl-2-hydroxy-2-methylpropyl)-7-(2-(6-methyl-[1,3]dioxolo[4,5-b]pyridin-7-yl)vinyl)isoindolin-1-one;

2-(1-Cyclopropyl-2-hydroxy-2-methylpropyl)-7-(2-(6-methyl-[1,3]dioxolo[4,5-b]pyridin-7-yl)ethyl)isoindolin-1-one;
(R)-2-(1-Cyclopropyl-2-hydroxy-2-methylpropyl)-7-(2-(6-methyl-[1,3]dioxolo[4,5-b]pyridin-7-yl)ethyl)isoindolin-1-one;
(S)-2-(1-Cyclopropyl-2-hydroxy-2-methylpropyl)-7-(2-(6-methyl-[1,3]dioxolo[4,5-b]pyridin-7-yl)ethyl)isoindolin-1-one;
7-(((6-chloro-[1,3]dioxolo[4,5-b]pyridin-7-yl)oxy)methyl)-2-(1-cyclopropyl-2-hydroxy-2-methylpropyl)isoindolin-1-one;
(R)-7-(((6-chloro-[1,3]dioxolo[4,5-b]pyridin-7-yl)oxy)methyl)-2-(1-cyclopropyl-2-hydroxy-2-methylpropyl)isoindolin-1-one;
(S)-7-(((6-chloro-[1,3]dioxolo[4,5-b]pyridin-7-yl)oxy)methyl)-2-(1-cyclopropyl-2-hydroxy-2-methylpropyl)isoindolin-1-one;
2-(1-Cyclopropyl-2-hydroxy-2-methylpropyl)-7-(((6-methyl-[1,3]dioxolo[4,5-b]pyridin-7-yl)amino)methyl)isoindolin-1-one;
(R)-2-(1-Cyclopropyl-2-hydroxy-2-methylpropyl)-7-(((6-methyl-[1,3]dioxolo[4,5-b]pyridin-7-yl)amino)methyl)isoindolin-1-one;
(S)-2-(1-Cyclopropyl-2-hydroxy-2-methylpropyl)-7-(((6-methyl-[1,3]dioxolo[4,5-b]pyridin-7-yl)amino)methyl)isoindolin-1-one;
7-((6-chloro-[1,3]dioxolo[4,5-b]pyridin-7-yl)methoxy)-2-(1-cyclopropyl-2-hydroxy-2-methylpropyl)isoindolin-1-one;
(R)-7-((6-chloro-[1,3]dioxolo[4,5-b]pyridin-7-yl)methoxy)-2-(1-cyclopropyl-2-hydroxy-2-methylpropyl)isoindolin-1-one;
(S)-7-((6-chloro-[1,3]dioxolo[4,5-b]pyridin-7-yl)methoxy)-2-(1-cyclopropyl-2-hydroxy-2-methylpropyl)isoindolin-1-one;
2-(1-cyclopropyl-2-hydroxy-2-methylpropyl)-7-((6,7-dihydro-5H-cyclopenta[b]pyridin-4-yl)methoxy)isoindolin-1-one;
(R)-2-(1-cyclopropyl-2-hydroxy-2-methylpropyl)-7-((6,7-dihydro-5H-cyclopenta[b]pyridin-4-yl)methoxy)isoindolin-1-one;
(S)-2-(1-cyclopropyl-2-hydroxy-2-methylpropyl)-7-((6,7-dihydro-5H-cyclopenta[b]pyridin-4-yl)methoxy)isoindolin-1-one;
2-(1-Cyclopropyl-2-hydroxy-2-methylpropyl)-7-(2-(6-methyl-[1,3]dioxolo[4,5-b]pyridin-7-yl)ethyl)isoindolin-1-one;
(R)-2-(1-Cyclopropyl-2-hydroxy-2-methylpropyl)-7-(2-(6-methyl-[1,3]dioxolo[4,5-b]pyridin-7-yl)ethyl)isoindolin-1-one;
(S)-2-(1-Cyclopropyl-2-hydroxy-2-methylpropyl)-7-(2-(6-methyl-[1,3]dioxolo[4,5-b]pyridin-7-yl)ethyl)isoindolin-1-one;
5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one;
(R)-5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one;
(S)-5,6-difluoro-7-(4-(5-methyl-1,3,4-oxadiazol-2-yl)phenyl)-2-(1,1,1-trifluoro-3-hydroxy-3-methylbutan-2-yl)isoindolin-1-one;
2-(1-cyclopropyl-2-hydroxy-2-methylpropyl)-4,5-difluoro-7-(4-(5-methyl-1,3,4-oxadiazol-2-yl)phenyl)isoindolin-1-one; and
(R)-2-(1-cyclopropyl-2-hydroxy-2-methylpropyl)-4,5-difluoro-7-(4-(5-methyl-1,3,4-oxadiazol-2-yl)phenyl)isoindolin-1-one.

10. A pharmaceutical composition comprising an effective amount of a compound of claim 1, or a pharmaceutically acceptable salt thereof, and a pharmaceutically acceptable carrier.

11. The pharmaceutical composition of claim 10, further comprising one or more additional therapeutic agents.

12. A method for treatment of lysosomal storage diseases, kidney disease, neurodegenerative disease, diabetes related diseases, or cancers where GSL synthesis is abnormal or overexpression GCS disrupts ceramide-induced apoptosis, which comprises administering to a subject in need of such treatment a therapeutically effective amount of a compound according to claim 1.

13. A method of treatment of Parkinson's Disease, which comprises administering to a subject in need of such treatment a therapeutically effective amount of a compound according to claim 1, or a pharmaceutically acceptable salt thereof.

14. A method of treatment of a disease, which comprises administering to a subject in need of such treatment a therapeutically effective amount of a compound of claim 1, wherein said disease is selected from dementia with Lewy bodies, polycystic kidney disease, renal hypertrophy, diabetes mellitus, obesity, hyperglycemia, hyperinsulemia, leukemia, papillary renal cancer, and thyroid carcinomas.

* * * * *